(12) United States Patent
Regev et al.

(10) Patent No.: US 12,060,412 B2
(45) Date of Patent: Aug. 13, 2024

(54) METHODS FOR DETERMINING SPATIAL AND TEMPORAL GENE EXPRESSION DYNAMICS IN SINGLE CELLS

(71) Applicants: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

(72) Inventors: Aviv Regev, Cambridge, MA (US); Feng Zhang, Cambridge, MA (US); Naomi Habib, Cambridge, MA (US); Yinqing Li, Cambridge, MA (US); Matthias Heidenreich, Cambridge, MA (US); Lukasz Swiech, Cambridge, MA (US); Anindita Basu, Cambridge, MA (US); David Weitz, Cambridge, MA (US); Inbal Avraham Davidi, Cambridge, MA (US)

(73) Assignees: The Broad Institute, Inc., Cambridge, MA (US); Massachusetts Institute of Technology, Cambridge, MA (US); President and Fellows of Harvard College, MA, Cambridge, MA (US)

( * ) Notice: Subject to any disclaimer, the term of this patent is extended or adjusted under 35 U.S.C. 154(b) by 1419 days.

(21) Appl. No.: 16/087,036

(22) PCT Filed: Oct. 27, 2016

(86) PCT No.: PCT/US2016/059239
§ 371 (c)(1),
(2) Date: Sep. 20, 2018

(87) PCT Pub. No.: WO2017/164936
PCT Pub. Date: Sep. 28, 2017

(65) Prior Publication Data
US 2019/0218276 A1  Jul. 18, 2019

Related U.S. Application Data

(60) Provisional application No. 62/311,129, filed on Mar. 21, 2016.

(51) Int. Cl.
*C07K 16/10* (2006.01)
*C12N 15/10* (2006.01)
*C12Q 1/686* (2018.01)
*C12Q 1/6869* (2018.01)

(52) U.S. Cl.
CPC ...... *C07K 16/1036* (2013.01); *C12N 15/1093* (2013.01); *C12N 15/1096* (2013.01); *C12Q 1/686* (2013.01); *C12Q 1/6869* (2013.01); *C12Q 2537/165* (2013.01); *C12Q 2563/179* (2013.01); *C12Q 2565/514* (2013.01); *C12Q 2565/629* (2013.01)

(58) Field of Classification Search
CPC ............ C12N 15/1093; C12N 15/1096; C12Q 1/6869; C12Q 2537/165; C12Q 2563/179; C12Q 2565/514; C12Q 2565/629
See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 5,843,657 A | 12/1998 | Liotta et al. | |
| 5,859,699 A | 1/1999 | Baer et al. | |
| 5,985,085 A | 11/1999 | Baer et al. | |

(Continued)

FOREIGN PATENT DOCUMENTS

| EP | 2 047 910 A2 | 4/2009 |
|---|---|---|
| WO | 01/89788 A2 | 11/2001 |

(Continued)

OTHER PUBLICATIONS

Satija, Rahul, et al. "Spatial reconstruction of single-cell gene expression data." Nature biotechnology 33.5 (2015): 495-502. (Year: 2015).*

(Continued)

*Primary Examiner* — Sahana S Kaup
(74) *Attorney, Agent, or Firm* — F. Brent Nix, Esq.; Johnson, Marcou, Isaacs & Nix, LLC; Drew P. Harding

(57) ABSTRACT

Transcriptomes of individual neurons provide rich information about cell types and dynamic states. However, it is difficult to capture rare dynamic processes, such as adult neurogenesis, because isolation from dense adult tissue is challenging, and markers for each phase are limited. Here, Applicants developed Nuc-seq, Div-Seq, and Dronc-Seq. Div-seq combines Nuc-Seq, a scalable single nucleus RNA-Seq method, with EdU-mediated labeling of proliferating cells. Nuc-Seq can sensitively identify closely related cell types within the adult hippocampus. Div-Seq can track transcriptional dynamics of newborn neurons in an adult neurogenic region in the hippocampus. Dronc-Seq uses a microfluidic device to co-encapsulate individual nuclei in reverse emulsion aqueous droplets in an oil medium together with one uniquely barcoded mRNA-capture bead. Finally, Applicants found rare adult newborn GABAergic neurons in the spinal cord, a non-canonical neurogenic region. Taken together, Nuc-Seq, Div-Seq and Dronc-Seq allow for unbiased analysis of any complex tissue.

54 Claims, 41 Drawing Sheets
Specification includes a Sequence Listing.

(56) References Cited

U.S. PATENT DOCUMENTS

| | | | |
|---|---|---|---|
| 7,041,481 | B2 | 5/2006 | Anderson et al. |
| 7,708,949 | B2 | 5/2010 | Stone et al. |
| RE41,780 | E | 9/2010 | Anderson et al. |
| 2005/0172476 | A1 | 8/2005 | Stone et al. |
| 2006/0163385 | A1 | 7/2006 | Link et al. |
| 2007/0003442 | A1 | 1/2007 | Link et al. |
| 2007/0184489 | A1 | 8/2007 | Griffiths et al. |
| 2007/0195127 | A1 | 8/2007 | Ahn et al. |
| 2008/0003142 | A1 | 1/2008 | Link et al. |
| 2008/0014589 | A1 | 1/2008 | Link et al. |
| 2009/0005254 | A1 | 1/2009 | Griffiths et al. |
| 2009/0131543 | A1 | 5/2009 | Weitz et al. |
| 2010/0002241 | A1 | 1/2010 | Hirose et al. |
| 2010/0022414 | A1 | 1/2010 | Link et al. |
| 2010/0137163 | A1 | 6/2010 | Link et al. |
| 2010/0172803 | A1 | 7/2010 | Stone et al. |
| 2012/0122714 | A1 | 5/2012 | Samuels et al. |
| 2012/0219947 | A1 | 8/2012 | Yurkovetsky et al. |
| 2014/0256595 | A1 | 9/2014 | Link et al. |
| 2014/0295414 | A1 * | 10/2014 | Salic .............. G01N 33/582 536/23.1 |

FOREIGN PATENT DOCUMENTS

| | | | | |
|---|---|---|---|---|
| WO | 2004/002627 | A2 | 1/2004 | |
| WO | 2004/091763 | A2 | 10/2004 | |
| WO | 2005/021151 | A1 | 3/2005 | |
| WO | 2006/040551 | A2 | 4/2006 | |
| WO | 2006/040554 | A1 | 4/2006 | |
| WO | 2006/096571 | A2 | 9/2006 | |
| WO | 2007/081385 | A2 | 7/2007 | |
| WO | 2007/089541 | A2 | 8/2007 | |
| WO | 2007/133710 | A2 | 11/2007 | |
| WO | 2008/063227 | A2 | 5/2008 | |
| WO | 2011/079176 | A2 | 6/2011 | |
| WO | 2014/047561 | A1 | 3/2014 | |
| WO | 2014/085802 | A1 | 6/2014 | |
| WO | 2014/143157 | A1 | 9/2014 | |
| WO | WO-2014204728 | A1 * | 12/2014 | ......... A01K 67/0275 |
| WO | WO-2016040476 | A1 * | 3/2016 | ......... C12N 15/1096 |
| WO | 2017/164936 | A1 | 9/2017 | |

OTHER PUBLICATIONS

Satija 2015 supplemetnary materials (Year: 2015).*

Grindberg et al. ("RNA-sequencing from single nuclei." Proceedings of the National Academy of Sciences 110.49 (2013): 19802-19807.) (Year: 2013).*

Grindberg (2013) supplementary materials (Year: 2013).*

Wang et al. ("Clonal evolution in breast cancer revealed by single nucleus genome sequencing." Nature 512.7513 (2014): 155-160; including supplementary methods and figures: 15 pages). (Year: 2014).*

The Broad Institute, Inc., International Search Report and Written Opinion for PCT International Patent Application No. PCT/US2016/059239, Mar. 2, 2017, 15.

The Broad Institute, Inc., Invitation to Pay Additional Fees for PCT International Application No. PCT/US2016/059239, Dec. 23, 2016, 3.

Habib, et al., "Div-Seq: Single-Nucleus RNA-Seq Reveals Dynamics of Rare Adult Newborn Neurons", Science, ePub, vol. 3353, No. 6302, Jul. 28, 2016, 925-928.

Satija, et al., "Spatial Reconstruction of Single-Cell Gene Expression", Nature Biotechnol, vol. 33, No. 5, May 2015, 495-502.

Treutlein, et al., "Reconstructing Lineage Hierarchies of the Distal Lung Epithelium Using Single Cell RNA-Seq", Nature, vol. 509, No. 7500, May 15, 2014, 371-375.

The Broad Institute, Inc., "International Preliminary Report on Patentability issued in International Application No. PCT/US2016/059239", mailed on Oct. 4, 2018, 12 pages.

Anders, et al., "Differential Expression Analysis for Sequence Count Data", Genome Biology, vol. 11, No. 10, Oct. 27, 2010, 12 pages.

Bendall, et al., "Single-cell Trajectory Detection Uncovers Progression and Regulatory Coordination in Human B Cell Development", Cell, vol. 157, No. 3, Apr. 24, 2014, 714-725.

Brennecke, et al., "Accounting for Technical Noise in Single-Cell RNA-seq Experiments", Nature methods, vol. 10, Issue 11, Sep. 22, 2013, 1093-1095.

Cembrowski, et al., "Spatial Gene-Expression Gradients Underlie Prominent Heterogeneity of CA1 Pyramidal Neurons", Neuron, vol. 89, No. 2, Jan. 20, 2016, 351-368.

Chung, et al., "Structural and Molecular Interrogation of Intact Biological Systems", Nature, vol. 497, No. 7449, May 16, 2013, 23 pages.

Darmanis, et al., "A Survey of Human Brain Transcriptome Diversity at the Single Cell Level", Proceedings of the National Academy of Sciences, vol. 112, No. 23, Jun. 9, 2015, 7285-7290.

Datlinger, et al., "Pooled CRISPR Screening with Single-Cell Transcriptome Read-Out", Nature Methods, vol. 14, No. 3, Mar. 2017, 20 pages.

Feliciano, et al., "Noncanonical Sites of Adult Neurogenesis in the Mammalian Brain", Cold Spring Harbor Perspectives in Biology, vol. 7, No. 10, Sep. 18, 2015, 14 pages.

Grindberg, et al., "RNA-sequencing from Single Nuclei", Proceedings of the National Academy of Sciences of the United States of America, vol. 110, No. 49, Dec. 3, 2013, 19802-19807.

Guo, et al., "Droplet Microfluidics for High-throughput Biological Assays", Lab on a Chip, vol. 12, No. 12, Jun. 21, 2012, 10 pages.

Henry, et al., "A Common Pesticide Decreases Foraging Success and Survival in Honey Bees", Science, vol. 336, No. 6079, Apr. 20, 2012, 348-350.

Hu, et al., "Fast-spiking, Parvalbumin(+) Gabaergic Interneurons: from Cellular Design to Microcircuit Function", Science, vol. 345, Issue 6196, Aug. 1, 2014, 1255263-1-1255263-13.

Klein, et al., "Droplet Barcoding for Single-Cell Transcriptomics Applied to Embryonic Stem Cells", Cell, vol. 161, No. 6, May 21, 2015, 24 pages.

Krishnaswami, et al., "Using Single Nuclei for RNA-seq to Capture the Transcriptome of Postmortem Neurons", Nature Protocols, vol. 11, No. 3, Mar. 2016, 51 pages.

Lein, et al., "Genome-wide Atlas of Gene Expression in the Adult Mouse Brain", Nature, vol. 445, No. 7124, Jan. 11, 2007, 168-176.

Llorens-Bobadilla, et al., "Single-Cell Transcriptomics Reveals a Population of Dormant Neural Stem Cells that Become Activated upon Brain Injury", Cell Stem Cell, vol. 17, No. 3, Sep. 3, 2015, 329-340.

Macosko, et al., "Highly Parallel Genome-Wide Expression Profiling of Individual Cells Using Nanoliter Droplets", Cell, vol. 161, No. 5, May 21, 2015, 25 pages.

Maruyama, Yuzo, "An Alternative to Moran's for Spatial Autocorrelation", Center for Spatial Information Science, University of Tokyo, Jan. 26, 2015, 6 pages.

Ming, et al., "Adult Neurogenesis in the Mammalian Brain: Significant Answers and Significant Questions", Neuron, vol. 70, No. 4, May 26, 2011, 687-702.

Moore, et al., "A Mechanism for the Segregation of Age in Mammalian Neural Stem Cells", Science, vol. 349, No. 6254, Sep. 18, 2015, 1334-1338.

Picelli, et al., "Smart-Seq2 for Sensitive Full-Length Transcriptome Profiling in Single Cells", Nature methods, vol. 10, Issue 11, Sep. 22, 2013, 5 pages.

Ryan, et al., "Single-Cell Assays", Biomicrofluidics, vol. 5, No. 021501, Jun. 2011, 9 pages.

Shalek, et al., "Single-Cell RNA-Seq Reveals Dynamic Paracrine Control of Cellular Variation", Nature, vol. 510, Jun. 19, 2014, 363-369.

Shalek, et al., "Single-Cell Transcriptomics Reveals Bimodality in Expression and Splicing in Immune Cells", Nature, vol. 498, No. 7453., Jun. 13, 2013, 236-240.

Shin, et al., "Single-Cell RNA-Seq with Waterfall Reveals Molecular Cascades underlying Adult Neurogenesis", Cell Stem Cell, vol. 17, No. 3, Sep. 3, 2015, 360-372.

Steiner, et al., "Cell-type-specific Nuclei Purification from Whole Animals for Genome-wide Expression and Chromatin Profiling", Genome Research, vol. 22, No. 4, Apr. 2012, 766-777.

(56) References Cited

OTHER PUBLICATIONS

Strange, et al., "Functional Organization of The Hippocampal Longitudinal Axis", Nature Reviews Neuroscience, vol. 15, No. 10, Oct. 2014, 655-669.
Swiech, et al., "In Vivo Interrogation of Gene Function in the Mammalian Brain Using CRISPR-Cas9", Nature Biotechnology, vol. 33, No. 1, Jan. 2015, 102-106.
Tasic, et al., "Adult Mouse Cortical Cell Taxonomy Revealed by Single Cell Transcriptomics", Nature Neuroscience, vol. 19, No. 2, Feb. 2016, 41 pages.
Thomsen, et al., "Fixed Single-cell Transcriptomic Characterization of Human Radial Glial Diversity", Nature Methods, vol. 13, No. 1, Jan. 2016, 24 pages.
Trapnell, et al., "The Dynamics and Regulators of Cell Fate Decisions are Revealed by Pseudotemporal Ordereing of Single Cells", Nature Biotechnology, vol. 32, No. 4, Apr. 2014, 11 pages.
Usoskin, et al., "Unbiased Classification of Sensory Neuron Types by Large-Scale Single-cell RNA Sequencing", Nature Neuroscience, vol. 18, No. 1, Jan. 2015, 145-153.
Zeisel, et al., "Brain Structure. Cell Types in the Mouse Cortex and Hippocampus Revealed by Single-Cell RNA-Seq", Science, vol. 347, No. 6226, Mar. 2015, 1138-1142.
Zhang, et al., "An RNA-Sequencing Transcriptome and Splicing Database of Glia, Neurons, and Vascular Cells Of the Cerebral Cortex", The Journal of Neuroscience, vol. 34, No. 36, Sep. 3, 2014, 11929-11947.
Zhao, et al., "Fluorescent Labeling of Newborn Dentate Granule Cells in Gad67-GFP Transgenic Mice: A Genetic Tool for The Study of Adult Neurogenesis", PLoS One, vol. 5, No. 9, Sep. 2, 2010, 12 pages.

* cited by examiner

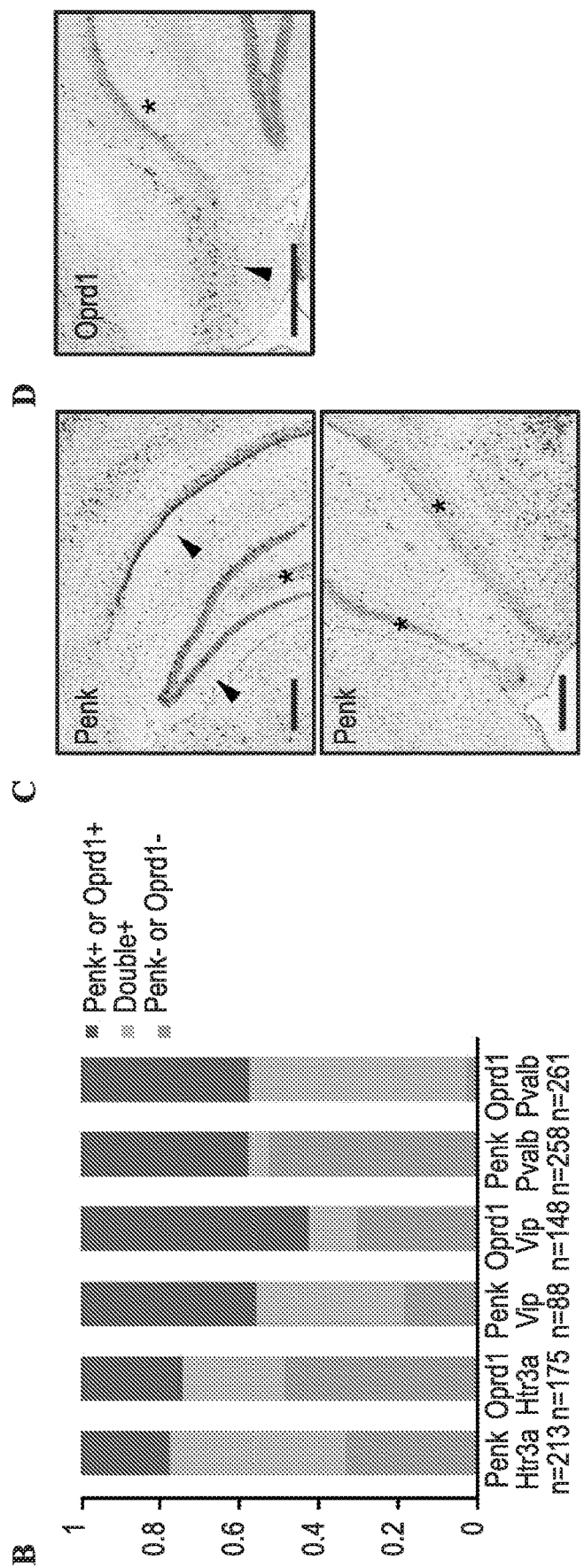
FIG. 21B-D

SEQUENCE LISTING

<160> NUMBER OF SEQ ID NOS: 10

<210> SEQ ID NO 1
<211> LENGTH: 8
<212> TYPE: DNA
<213> ORGANISM: Artificial Sequence
<220> FEATURE:
<223> OTHER INFORMATION: Synthetic Barcode Primer

<400> SEQUENCE: 1 ttgagcct                                                              8

<210> SEQ ID NO 2
<211> LENGTH: 8
<212> TYPE: DNA
<213> ORGANISM: Artificial Sequence
<220> FEATURE:
<223> OTHER INFORMATION: Synthetic Barcode Primer

<400> SEQUENCE: 2 agttgctt                                                              8

<210> SEQ ID NO 3
<211> LENGTH: 8
<212> TYPE: DNA
<213> ORGANISM: Artificial Sequence
<220> FEATURE:
<223> OTHER INFORMATION: Synthetic Barcode Primer

<400> SEQUENCE: 3 ccagttag                                                              8

```
<210> SEQ ID NO 4
<211> LENGTH: 8
<212> TYPE: DNA
<213> ORGANISM: Artificial Sequence
<220> FEATURE:
<223> OTHER INFORMATION: Synthetic Barcode Primer

<400> SEQUENCE: 4 accaactg                                                           8

<210> SEQ ID NO 5
<211> LENGTH: 8
<212> TYPE: DNA
<213> ORGANISM: Artificial Sequence
<220> FEATURE:
<223> OTHER INFORMATION: Synthetic Barcode Primer

<400> SEQUENCE: 5 gtataaca                                                           8

<210> SEQ ID NO 6
<211> LENGTH: 8
<212> TYPE: DNA
<213> ORGANISM: Artificial Sequence
<220> FEATURE:
<223> OTHER INFORMATION: Synthetic Barcode Primer

<400> SEQUENCE: 6 caggagcc                                                           8

<210> SEQ ID NO 7
<211> LENGTH: 57
<212> TYPE: DNA
<213> ORGANISM: Artificial Sequence
<220> FEATURE:
<223> OTHER INFORMATION: Synthetic R T Primer
<220> FEATURE:
<221> NAME/KEY: misc_feature
<222> LOCATION: (57)..(57)
<223> OTHER INFORMATION: n at position 57 is "A", "C" or "G"

<400> SEQUENCE: 7
aagcactggt atcaacgcag agtactttt tttttttttt tttttttttt tttttvn     57

<210> SEQ ID NO 8
<211> LENGTH: 28
<212> TYPE: DNA
<213> ORGANISM: Artificial Sequence
<220> FEATURE:
<223> OTHER INFORMATION: Synthetic TSO Primer

<400> SEQUENCE: 8
aagcagtggt atcaacgcag agtacggg                                    28

<210> SEQ ID NO 9
<211> LENGTH: 23
<212> TYPE: DNA
<213> ORGANISM: Artificial Sequence
<220> FEATURE:
<223> OTHER INFORMATION: Synthetic IS PCR Primer

<400> SEQUENCE: 9
aagcagtggt atcaacgcag agt                                         23

<210> SEQ ID NO 10
<211> LENGTH: 30
<212> TYPE: DNA
```

```
<213> ORGANISM: Artificial Sequence
<220> FEATURE:
<223> OTHER INFORMATION: Synthetic Template Switching Oligonucleotide

<400> SEQUENCE: 10
aagcagtggt atcaacgcag agtacatggg                                      30
```

METHODS FOR DETERMINING SPATIAL AND TEMPORAL GENE EXPRESSION DYNAMICS IN SINGLE CELLS

CROSS-REFERENCE TO RELATED APPLICATIONS

This application claims the benefit of U.S. provisional application 62/311,129 filed Mar. 21, 2016. The entire contents of the above-identified priority application are hereby fully incorporated herein by reference

STATEMENT REGARDING FEDERALLY SPONSORED RESEARCH

This invention was made with government support under grant numbers MH05960 and DK097768 awarded by the National Institutes of Health. The government has certain rights in the invention.

FIELD OF THE INVENTION

The present invention generally relates to methods of determining cell type, subtype, cell state, spatial location and developmental stages of single cells obtained from a sample, preferably a tissue sample. The present invention also relates to a combination of molecular barcoding and emulsion-based microfluidics to isolate, lyse, barcode, and prepare nucleic acids from individual nuclei in a high throughput manner.

BACKGROUND OF THE INVENTION

Single-cell RNA-Seq has greatly extended our understanding of heterogeneous tissues, including the CNS (1-6), and is reshaping the concept of cell type and state. However, some key dynamic processes that occur in dense nervous tissues, such as adult neurogenesis, still remain challenging to study. Transcriptomes of individual neurons provide rich information about cell types and dynamic states. However, it is difficult to capture rare dynamic processes, because isolation from dense adult tissue is challenging. First, single-cell RNA-Seq requires enzymatic tissue dissociation, which damages the integrity of neurons, compromises RNA integrity, and skews data towards easily dissociated cell types. This challenge is exacerbated as animals age, restricting this approach to fetal or young animals (1). Second, rare cells, such as adult newborn neurons found in the adult mouse hippocampus (7), are difficult to capture because they require enrichment using specific tagging and sorting for each phase of the dynamic neurogenesis process and markers for each phase are limited. Thus, there is a need for improved devices and methods to allow for understanding heterogeneous tissues and cell populations.

Citation or identification of any document in this application is not an admission that such document is available as prior art to the present invention.

SUMMARY OF THE INVENTION

It is an object of the present invention to provide for devices and methods to allow for comprehensive analysis of gene expression in single cells obtained from heterogeneous tissues. It is another object of the present invention to identify and characterize different cell types, subtypes and cell states in a heterogeneous tissue. It is a further object of the present invention to provide methods of determining the spatial location of cell types. It is another object of the present invention to determine gene expression in cell populations based on developmental stages. The present invention advantageously provides for improved methods of determining gene expression of single cells in heterogeneous cell populations by isolating single nuclei from cells and sequencing RNA molecules. Cells may further be stained, such that cells of a single cell type and developmental stage are determined. It is further object of the present invention to provide a device or system for high throughput analysis of single nuclei. It is another object of the present invention to provide for high resolution temporal maps based on gene expression profiles.

To study adult neurogenesis in an unbiased manner Applicants developed Div-Seq, a method to analyze single nuclei from recently dividing cells. Div-Seq relies on two advances. Here, Applicants developed Div-Seq, which combines Nuc-Seq, a scalable single nucleus RNA-Seq method, with EdU-mediated labeling of proliferating cells. Applicants first show that Nuc-Seq can sensitively identify closely related cell types within the adult hippocampus. Applicants apply Div-Seq to track transcriptional dynamics of newborn neurons in an adult neurogenic region in the hippocampus. Finally, Applicants find rare adult newborn GABAergic neurons in the spinal cord, a non-canonical neurogenic region. Taken together, Nuc-Seq and Div-Seq open the way for unbiased analysis of any complex tissue.

In one aspect, the present invention provides for a method of producing at least one high resolution map for visualizing different cell subtypes or cell states in a heterogeneous population of cells comprising: performing dimensionality reduction on single cell gene expression data obtained from the heterogeneous population of cells; producing a first set of clusters of cells by a method comprising measuring the dissimilarity between sets of genes in the dimensionality reduced single cell gene expression data and applying a first metric, wherein the clusters are in a dimensionality reduced space and the clusters comprise cells with a continuous trajectory; producing a set of informative genes by a method comprising scoring genes based on their expression across the first set of clusters of cells or a continuous trajectory of cells, wherein the informative genes are uniquely expressed in cells embedded in close proximity in the dimensionality reduced space; and producing at least one second set of clusters of cells or continuous trajectory of cells by a method comprising measuring the dissimilarity between the set of informative genes and applying a second metric, whereby visualization of a map of the second set of clusters or continuous trajectory of cells indicate cell subtypes or cell states.

The method may further comprise mapping the spatial location of the cell subtypes or cells having a cell state by performing RNA in situ hybridization (ISH) on whole tissue sections comprising said cell subtypes using probes specific for genes expressed in the cell subtypes, whereby the spatial location of cell subtypes is visualized in a biological sample. The method may further comprise mapping the spatial location of the cell subtypes or cells having a cell state by comparing gene expression data for each cell type to landmark gene expression patterns in tissue samples, whereby the spatial location of cell subtypes is visualized in a biological sample.

Producing the second set of clusters of cells may comprise producing more than one set of clusters, wherein each set of clusters is produced by using the highest scoring informative gene and each successive cluster is produced by adding the next highest scoring informative gene.

The method may further comprise normalization of the single cell gene expression data, wherein gene expression of one cell is normalized to another using not highly expressed genes. The method may further comprise estimation of missed detection probability, wherein an expectation-maximization algorithm is applied. Scoring informative genes may comprise applying a Moran's I analysis and/or a Manhattan distance analysis. The dimensionality reduction may comprise PCA and/or tSNE.

The heterogeneous population of cells may be derived from a section of a tissue or a tumor from a subject. The section may be obtained by microdissection. The tissue may be nervous tissue. The nervous tissue maybe isolated from the brain, spinal cord or retina. The heterogeneous population of cells may be a population of cells grown in tissue culture. The cells grown in tissue culture may be neurons. The cells grown in tissue culture may be immune cells.

The gene expression data may be obtained from single cell sequencing. The gene expression data may be obtained from single nuclei sequencing. The single nuclei sequencing may comprise: treating the heterogeneous population of cells with a reagent that stabilizes RNA; extracting nuclei from the cells; sorting single nuclei into separate reaction vessels; extracting RNA from the single nuclei; generating a cDNA library; and sequencing the library, whereby gene expression data from single cells is obtained. The single nuclei may be sorted into single wells of a plate by FACS. The sorting single nuclei into separate reaction vessels may comprise microfluidics. The single nuclei may be sorted into individual chambers on a microfluidic chip.

The single nuclei sequencing may comprise a method of high-throughput single nuclei sequencing, said method comprising: treating the heterogeneous population of cells with a reagent that stabilizes RNA; extracting nuclei; generating a suspension of isolated nuclei, wherein the suspension comprises a nuclear pore blocking polymer; optionally, enriching the nuclei suspension by FACS or magnetic-activated cell sorting (MACS); applying the nuclei suspension to a reverse emulsion microfluidic device configured for single nuclei, wherein single nuclei are individually compartmentalized with a single uniquely barcoded capture bead in an emulsion drop; extracting mRNA onto the barcoded capture beads; generating a barcoded cDNA library; and sequencing the library using paired-end sequencing, whereby gene expression data from single nuclei is obtained. The nuclei suspension may comprise 105-106 nuclei. 104-105 nuclei may be sequenced. The nuclear pore blocking polymer may be a poloxamer. The reagent that stabilizes RNA may be a reagent that comprises the properties of RNAlater.

In another aspect, the present invention provides for a method of producing a temporally phased single-cell sequencing library of at least one cell type or subtype, wherein said sequencing library comprises cells along a continuous trajectory of cell developmental stages comprising: treating more than one population of cells of a single cell type or subtype, or optionally a heterogeneous cell type, with a nucleoside analogue, wherein the nucleoside analogue is incorporated into replicating DNA and is configured for labeling with a detectable marker; isolating a first population of cells at one time point and isolating at least one other population of cells at a later time point, optionally, isolating single nuclei from the isolated populations of cells; staining the nucleoside analogue incorporated into replicated DNA with the detectable marker within each population of cells or single nuclei isolated from each population of cells, wherein the DNA is stained with the detectable marker; sorting the stained and/or unstained cells or optionally, sorting the stained and/or unstained single nuclei into separate reaction vessels; and sequencing the RNA from the sorted single cells or optionally, sorted single nuclei, whereby single-cell gene expression data is obtained for cells at different stages of maturation. The treating more than one population of cells of a single cell type or subtype, or optionally a heterogeneous cell type with a nucleoside analogue may be performed in at least one subject. The subject may be a mouse. The isolating one population of cells may comprise dissection of a tissue from the subject. The tissue may be nervous tissue. The nervous tissue may be isolated from the brain, spinal cord or retina. The population of cells may be a population of cells grown in tissue culture. The cells grown in tissue culture may comprise neurons. The cells grown in tissue culture may be immune cells.

The gene expression data may be obtained from single-cell sequencing. The gene expression data may be obtained from single nuclei sequencing. The single nuclei sequencing may comprise: treating the populations of cells with a reagent that stabilizes RNA; extracting nuclei from the cells; sorting single nuclei into separate reaction vessels; extracting RNA from the single nuclei; generating a cDNA library; and sequencing the library, whereby gene expression data from single cells is obtained. The single nuclei may be sorted into single wells of a plate by FACS. The sorting single nuclei into separate reaction vessels may comprise microfluidics. The single nuclei may be sorted into individual chambers on a microfluidic chip.

The single nuclei sequencing may comprise a method of high-throughput single nuclei sequencing, said method comprising: treating the population of cells with a reagent that stabilizes RNA; extracting nuclei; generating a suspension of isolated nuclei, wherein the suspension comprises a nuclear pore blocking polymer; optionally, enriching the nuclei suspension by FACS or magnetic-activated cell sorting (MACS); applying the nuclei suspension to a reverse emulsion microfluidic device configured for single nuclei, wherein single nuclei are individually compartmentalized with a single uniquely barcoded capture bead in an emulsion drop; extracting mRNA onto the barcoded capture beads; generating a barcoded cDNA library; and sequencing the library using paired-end sequencing, whereby gene expression data from single nuclei is obtained. The nuclei suspension may comprise 105-106 nuclei. 104-105 nuclei may be sequenced. The nuclear pore blocking polymer may comprise a poloxamer. The reagent that stabilizes RNA may comprise a reagent with the properties of RNAlater.

The method may further comprise producing at least one high resolution map for visualizing the temporal position or cell developmental stage of cells of a specific cell type, subtype or cell state during proliferation comprising: optionally, performing the method of producing at least one high resolution map for visualizing different cell subtypes or cell states in a heterogeneous population of cells as described herein, whereby heterogeneous cells are clustered by cell type, subtype, or cell state; performing dimensionality reduction on the single-cell gene expression data from the stained cells of a single cell type, subtype or cell state within each population of cells or the stained single nuclei of a single cell type or subtype isolated from each population of cells; measuring the dissimilarity between sets of genes in the dimensionality reduced single-cell gene expression data and applying a first metric, whereby a continuous trajectory is visualized in the dimensionality reduced space from an early time point to a later time point; producing a set of informative genes by a method comprising scoring genes based on their expression across the continuous trajectory, wherein the informative genes are uniquely expressed in cells embedded in close proximity in the dimensionality reduced space, optionally, wherein lowly expressed genes are filtered out; and producing at least one set of clusters of cells by a method comprising measuring the dissimilarity between the set of informative genes and applying a second metric, whereby visualization of the set of clusters in the dimensionality reduced space indicate the gene expression profiles of cells based on a temporal position or developmental stage. The producing the set of clusters of cells may comprise producing more than one set of clusters, wherein the first set of clusters is produced by using the highest scoring informative gene and each successive set of clusters is produced by adding the next highest scoring informative gene. The method may further comprise normalization of the single-cell gene expression data, wherein gene expression of one cell is normalized to another using not highly expressed genes. The method may further comprise estimation of missed detection probability, wherein an expectation-maximization algorithm is applied. The scoring informative genes may comprise applying a Moran's I analysis and/or a Manhattan distance analysis. The dimensionality reduction may comprise PCA and/or tSNE. The nucleoside analogue may comprise EdU (5-ethynyl-2'-deoxyuridine).

In another aspect, the present invention provides for a method for creating a composite single nuclei sequencing library comprising: merging one uniquely barcoded RNA capture microbead with a single nuclei in an emulsion droplet having a diameter from 50 µm to 210 µm, wherein the single nuclei is blocked with a nuclear pore blocking polymer; extracting mRNA onto on the RNA capture microbead; performing a reverse transcription reaction to convert the mRNA to first strand cDNA that is covalently linked to the RNA capture microbead; or conversely reverse transcribing within droplets and thereafter breaking droplets and collecting cDNA-attached beads; preparing and sequencing a single composite RNA-Seq library, containing cell barcodes that record the cell-of-origin of each RNA, and unique molecular identifiers (UMI) that distinguish among RNAs from the same cell.

In another aspect, the present invention provides for a method for creating a composite single-cell sequencing library comprising: merging one uniquely barcoded RNA capture microbead with a with a single nuclei in an emulsion droplet having a diameter from 50 µm to 210 µm, wherein the single nuclei is blocked with a nuclear pore blocking polymer; extracting mRNA onto on the RNA capture microbead; breaking droplets and pooling beads in solution; performing a reverse transcription reaction to convert the RNA to first strand cDNA that is covalently linked to the RNA capture microbead; or conversely reverse transcribing within droplets and thereafter breaking droplets and collecting cDNA-attached beads; preparing and sequencing a single composite RNA-Seq library, containing cell barcodes that record the cell-of-origin of each RNA, and unique molecular identifiers (UMI) that distinguish among RNAs from the same cell.

The methods of amplifying the cDNA-attached beads may be template switch amplification. The method of amplifying the cDNA-attached beads may be T7 linear application. The method of amplifying the cDNA-attached beads may be exponential isothermal amplification. The emulsion droplet may be formed via co-encapsulation comprising RNA capture microbead and composite single nuclei. The RNA may be mRNA. The diameter of the emulsion droplet may be 50-100 µm or 70-90 µm. The diameter of the RNA capture microbeads may be from 10 µm to 95 µm.

The nuclei of any method described herein may further be detectable by a fluorescent signal, whereby individual nuclei may be further sorted. The cells may express a nuclear localized fluorescent protein. The nuclear localized fluorescent protein may comprise a fluorescent protein fused to a KASH protein domain. The single nuclei may be immunostained with an antibody with specific affinity for an intranuclear protein. The antibody may be specific for NeuN. The nuclei may be stained with a nuclear stain. The nuclear stain may comprise DAPI, Ruby red, trypan blue, Hoechst or propidium iodine.

In another aspect, the present invention provides for an apparatus for creating a composite single nuclei sequencing library via a microfluidic system, comprising: a oil-surfactant inlet comprising a filter and a carrier fluid channel, wherein said carrier fluid channel further comprises a resistor; an inlet for an analyte comprising a filter and a carrier fluid channel, wherein said carrier fluid channel optionally further comprises a resistor; an inlet for mRNA capture microbeads and lysis reagent comprising a filter and a carrier fluid channel, wherein said carrier fluid channel optionally further comprises a resistor; said carrier fluid channels have a carrier fluid flowing therein at an adjustable or predetermined flow rate; wherein each said carrier fluid channels merge at a junction; and said junction being connected to a mixer, which contains an outlet for drops. The analyte may comprise a nuclear pore blocking polymer, an enzyme and a nuclei. The junction may be connected to said mixer by a fluid carrier channel with a constriction for droplet pinch-off. The analyte may be a nuclei. The analyte may be a host-pathogen cell or nuclei. The lysis reagent may comprise an anionic surfactant, such as sodium lauroyl sarcosine, or a chaotropic salt, such as guanidinium thiocyanate. The filter may comprise square PDMS. The resistor may be serpentine having a length from 7000-9000, width of 50-75 µm and depth of 100-150 mm. The resistor may have a diameter of 50 µm. The channels may have a length of length of 8000-12,000 µm and width of 125-250 mm, and depth of 100-150 mm. The channel may have a diameter of 125 µm. The channel may have a diameter of 75, 80, 85, or 90 µm. The mixer may have a length of 7000-9000 µm and a width of 80-140 µm or 75-90 µm. The mixer may have a width of 125 µm. The mixer may have a width of 70-90 µm. The oil-surfactant may be a PEG block polymer. The PEG block polymer may be BIORAD™ QX200 Droplet Generation Oil. The carrier fluid may be water-glycerol mixture.

In another aspect, the present invention relates to a method of determining cells responsive to a therapeutic agent. In some embodiments, the invention provides a method of determining cells responsive to a therapeutic agent comprising: (a) contacting a tissue of interest with a therapeutic agent and a nucleoside analogue, wherein the nucleoside analogue is incorporated into replicating DNA and is configured for labeling with a detectable marker; (b) isolating the tissue of interest, optionally, isolating single nuclei from the tissue of interest; (c) staining the nucleoside analogue incorporated into replicated DNA with the detectable marker within the tissue of interest or single nuclei isolated from the tissue of interest, wherein the DNA is stained with the detectable marker; (d) sorting the stained and/or unstained cells or optionally, sorting the stained and/or unstained single nuclei into separate reaction vessels; (e) sequencing the RNA from the sorted single cells or optionally, sorted single nuclei, whereby single-cell gene expression data is obtained; and (f) determining cell subtypes and/or cell subtypes of a specific developmental stage, whereby cells responsive to a therapeutic agent are determined. In some embodiments, the nucleoside analogue is contacted with the tissue of interest before the therapeutic agent. In some embodiments, the nucleoside analogue is contacted with the tissue of interest between 2 and 14 days before the therapeutic agent. In some embodiments, the nucleoside analogue and therapeutic agent is administered from an implantable device. In some embodiments, the tissue of interest is a tumor. In some embodiments, the cell subtypes are determined by a method comprising: (a) performing dimensionality reduction on the single-cell gene expression data obtained from the heterogeneous population of cells; (b) producing a first set of clusters of cells by a method comprising measuring the dissimilarity between sets of genes in the dimensionality reduced single-cell gene expression data and applying a first metric, wherein the clusters are in a dimensionality reduced space and the clusters comprise cells with a continuous trajectory; (c) producing a set of informative genes by a method comprising scoring genes based on their expression across the first set of clusters of cells or a continuous trajectory of cells, wherein the informative genes are uniquely expressed in cells embedded in close proximity in the dimensionality reduced space; and (d) producing at least one second set of clusters of cells or continuous trajectory of cells by a method comprising measuring the dissimilarity between the set of informative genes and applying a second metric, whereby visualization of a map of the second set of clusters or continuous trajectory of cells indicate cell subtypes or cell states. In some embodiments, the cell subtypes of a specific developmental stage are determined by determining the cell subtype of cells that are stained and unstained. In some embodiments, the cell subtypes of a specific developmental stage are determined by a method comprising: (a) performing dimensionality reduction on the single-cell gene expression data from the stained cells of a single cell type, subtype or cell state within each population of cells or the stained single nuclei of a single cell type or subtype isolated from each population of cells; (b) measuring the dissimilarity between sets of genes in the dimensionality reduced single-cell gene expression data and applying a first metric, whereby a continuous trajectory is visualized in the dimensionality reduced space from an early time point to a later time point; (c) producing a set of informative genes by a method comprising scoring genes based on their expression across the continuous trajectory, wherein the informative genes are uniquely expressed in cells embedded in close proximity in the dimensionality reduced space, optionally, wherein lowly expressed genes are filtered out; and (d) producing at least one set of clusters of cells by a method comprising measuring the dissimilarity between the set of informative genes and applying a second metric, whereby visualization of the set of clusters in the dimensionality reduced space indicate the gene expression profiles of cells based on a temporal position or developmental stage. In some embodiments, producing the set of clusters of cells in step (d) comprises producing more than one set of clusters, wherein the first set of clusters is produced by using the highest scoring informative gene and each successive set of clusters is produced by adding the next highest scoring informative gene. In some embodiments, the method further comprises normalization of the single-cell gene expression data, wherein gene expression of one cell is normalized to another using not highly expressed genes. In some embodiments, the method further comprises estimation of missed detection probability, wherein an expectation-maximization algorithm is applied. In some embodiments, scoring informative genes comprises applying a Moran's I analysis and/or a Manhattan distance analysis. In some embodiments, dimensionality reduction comprises PCA and/or tSNE. In some embodiments, the nucleoside analogue comprises EdU (5-ethynyl-2'-deoxyuridine).

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

showing relative expression level of the marker gene across all nuclei. Bottom: histogram quantifying expression level of the marker gene nuclei in the relevant cluster (colored bars) and the distribution across all other nuclei (dashed red line). (D) Single nuclei transcriptional profiles match population RNA-Seq. Heat map showing the expression of top marker genes in the average of single nuclei (left) and in population RNA-Seq [74]. Bottom: Bar plot of the Pearson correlation (R) of each expression signature to the relevant population.

FIG. 11A-11E: BiSNE algorithm. (A) BiSNE algorithm. Top row, left to right: BiSNE takes as input an expression matrix of genes (rows) across nuclei (or cells, columns). It generates a 2-D plot of nuclei by dimensionality reduction using PCA followed by tSNE non-linear embedding, and then scores each gene by their expression across the 2-D plot, such that genes expressed in nuclei in proximity on the 2-D plot (dark blue points, top) are high scoring, whereas those expressed in nuclei scattered across the plot (dark blue points, bottom) are low scoring. Bottom row, right to left: Next, it takes an expression matrix of only high scoring genes (heatmap, genes (rows) across all nuclei (columns)), and repeats the dimensionality reduction. BiSNE is followed by density clustering (colored, bottom left). (B) BiSNE subclustering. Dendrogram of all nuclei clusters along with number of subclusters found by biSNE. NPC: neuronal precursor cells, ODC: oligodendrocytes, ASC: astroglia, OPC: oligodendrocyte precursor cell. (C) Expression of marker genes across 2-D embedded nuclei before and after biSNE. Shown is a panel of the same tSNE 2-D embedding of the GABAergic nuclei (from FIG. 1E), with each panel colored by the expression of a marker genes (denoted on the left). Top: using PCA-tSNE only. Bottom: using biSNE. (D) 2D embedding of cells using genes selected by generalized linear model (GLM) with different thresholds (Top). Cells are grouped in leftmost 2D embedding and denoted by group colors. GLM with less stringent thresholds selects more genes (From left to right), and results in different 2-D embedding without preserving cell grouping (from Left to Right). (E) 2-D embedding of cells using genes selected by biSNE with different thresholds (Top). biSNE with different thresholds results in similar 2-D embedding preserving cell grouping (from Left to Right).

Figure 5:
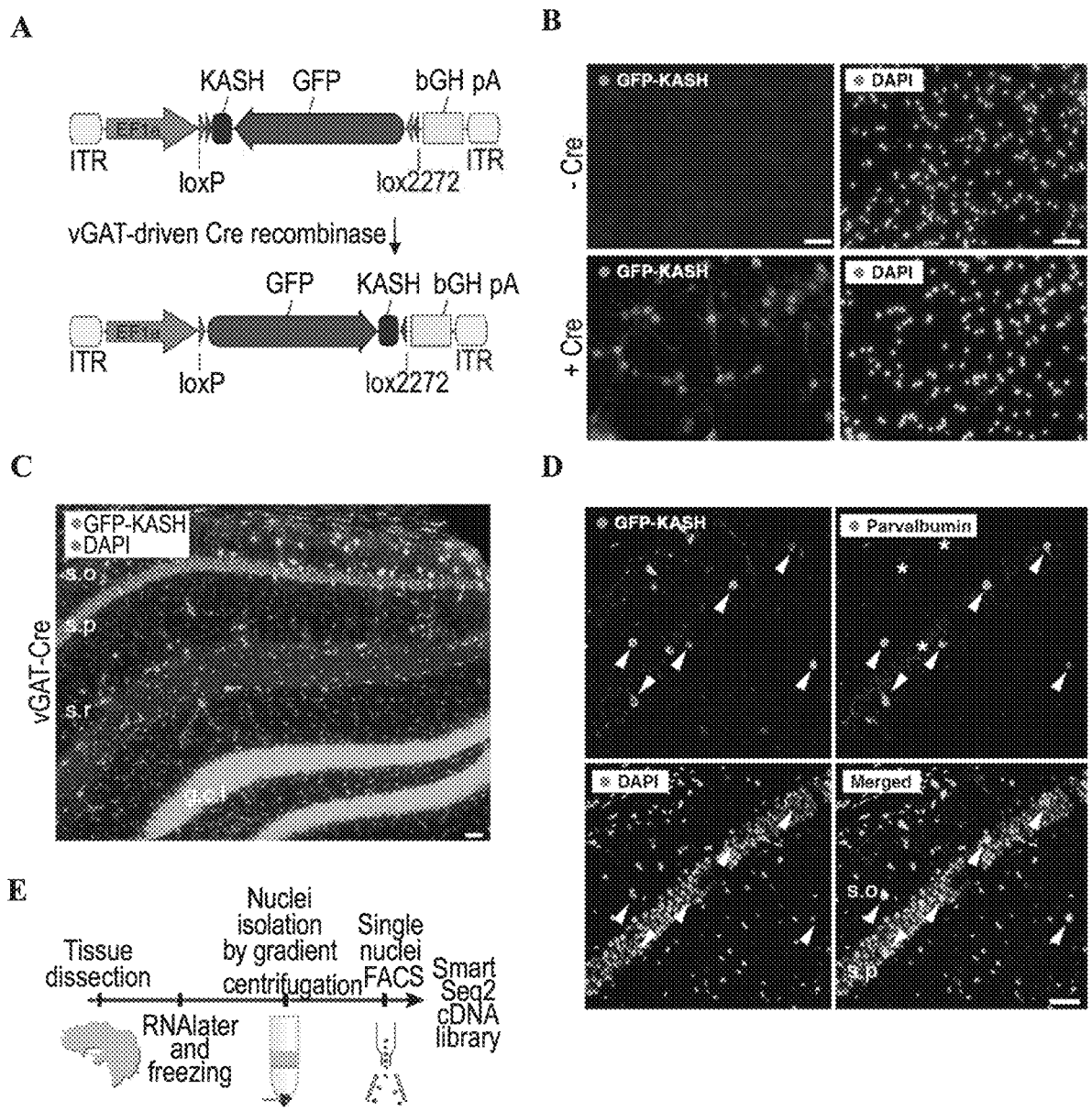
FIG. 5A-5E: Nuc-Seq is compatible with genetic labeling for enrichment of rare cells. (A) Genetic labeling of GABAergic interneurons using AAV expression vectors. Cre-mediated recombination of inverted transgenic cassette flanked by oppositely oriented loxP and lox2272 (Double-floxed Inverted Orientation, DIO) sites drives expression of GFP-KASH. Top: before recombination. Bottom: after cre driven recombination. (B) Primary cortical neurons infected with pAAV-EF1a-DIO-GFP-KASH-bGH-polyA alone (top) or co-infected with pAAV-EF1a-Cre-WPRE-bGH-polyA (bottom). (C) Expression of GFP-KASH in hippocampus of vGAT-Cre mice 14 d after viral delivery of pAAV-EF1a-DIO-GFP-KASH-bGH-polyA into CA1/CA2 stratum pyramidale (s.p.). (D) GFP-KASH labeled parvalbumin positive (arrow) and negative (arrowhead) interneurons in hippocampus of vGAT-Cre mice shown in C. (ITR—inverted terminal repeat; GFP—green fluorescent protein; KASH—Klarsicht, ANC1, Syne Homology nuclear transmembrane domain; hGH pA—human growth hormone polyadenylation signal; WPRE—Woodchuck Hepatitis virus posttranscriptional regulatory element, s.o.—stratum oriens, s.p.—stratum pyramidale, s.r.—stratum radiatum, g.c.l.—granule cell layer). Scale bars: 50 μm (E) Nuc-Seq method overview. Dissected tissue is fixed in RNAlater for 24 hours at 4° C. (and can be subsequently stored in −80° C. or further processed); nuclei are isolated using a gradient centrifugation method [38] (samples kept at 4° C. or on ice), resuspended, and sorted using FACS to a single nucleus per well in plates. Plates are processed using the Smart-Seq2 RNA-Seq protocol [85, 41].

FIG. 12A-12C: Transcriptional profiles of GABAergic interneurons. (A) biSNE clustering of GABAergic interneurons is independent of AAV infection or expression of transgene. Showing tSNE 2-D embedding of the GABAergic nuclei clustered with biSNE (from FIG. 2A) displaying untagged nuclei (blue) and Vgat-tagged nuclei (red) from Vgat-cre mice (FIG. 5). (B) Differentially expressed neuronal functional genes across GABAergic subclusters (FIG. 2A). Average centered expression of differentially expressed (t-test FDR q-value<0.05 with log-ratio>1 in at least one pairwise comparison between subclusters). K+ channels (top left), Ca2+ channels (top right), receptors (bottom right). (C) Differentially expressed neuronal functional genes shown as in (B): synaptic transmission (top left), Neuropeptides (middle left), sodium channels (bottom left), solute carriers (middle, rows), and other neuronal function (right, rows) across GABAergic subclusters (columns, FIG. 2A).

FIG. 13A-13E: Validation of GABAergic interneuron subtypes. (A) double fluorescent RNA in situ hybridization (dFISH) of Calb2 (green) and Vip (red). Expressions of Calb2 and Vip are largely overlapped. Scale bar: 20 µm. (B) dFISH of Calb2 (green) and Htr3a (red). Expressions of Calb2 and Htr3a are partially overlapped. Scale bar: 20 um. (C) dFISH of Calb2 (green) and Pvalb (red). Expressions of Calb2 and Pvalb are not overlapped. Scale bar: 20 µm. (D) Quantification of dFISH images. Bar plots showing the percent of single and double labeled cells in FISH images for each pair of genes. (E) DAPI image showing the entire view of hippocampus. Scale bar 100 µm. g.c.l.—granule cell layer; m.l.—molecular layer; s.l.m.—stratum lacunosum-moleculare; s.r.—stratum radiatum; p.l.—pyramidal layer; s.o.—stratum oriens.

FIG. 14A-14D: Spatial pattern of DG granule cells. (A) DG granule cells subclusters. Shown is a biSNE 2-D embedding of the DG granule nuclei with 3 subclusters denoted by colors. (B) Differential genes between clusters that have a distinct spatial pattern. 2-D embedding of nuclei (as in A), each showing the relative expression level of a gene expressed in the dorsal DG (top) or the ventral DG (bottom). (C) Schematics of hippocampal anatomy in a sagittal plane. DG marked in red. p.l.—pyramidal layer. (D) Spatial pattern of genes in the DG. ISH [64] sagittal image of the genes in (B). Top: Dorsal expression pattern. Bottom: Ventral expression. Scale bar: 400 µm.

FIG. 15A-15E: Spatial assignment method (A) Spatial assignment using landmark gene expression. Nuclei subclusters are assigned to brain regions, by comparing a spatial map of landmark gene expression from ISH data to the expression of the landmark genes in each of the subclusters. An example using the landmark gene Wfs1. Left to right: creating a spatial landmark expression map from ISH data—Wfs1 Allen ISH [64] image data is quantified for its intensity in 15 bin grid (dividing the CA1 region into five grid bins along the dorsal-ventral axis and three grid bins along medial-lateral axis). (B) Left to right: Subcluster expression map—Wfs1 RNA-Seq expression across CA1 pyramidal nuclei (left) is fitted with regression and binarized (middle) to generate a profile (right) of the percentage of Wfs1 expressing nuclei (greyscale) in each of the CA1 pyramidal subclusters. (C) Hippocampus spatial anatomy in a coronal sections. Left: The mouse hippocampus 3-D structure and the coronal section (brown plane) used in this analysis. Right: Schematics of the coronal section shown on the left. CA1 (including subiculum): orange; CA3 (including the hilus): green; DG: dark grey. M: medial, L: lateral, D: dorsal, V: ventral. Sub: Subiculum. (D) Registration of CA1 pyramidal subclusters to CA1 subregions. Left: correlation of each subcluster to CA1 subregions using landmark genes. Right: sub-cluster assignments (numbered arrows and color code). (E) Registration of CA3 pyramidal subclusters to CA3 subregions. Shown as in (D). Dentate gyrus in gray is included in the schematic for spatial reference.

Figure 16:
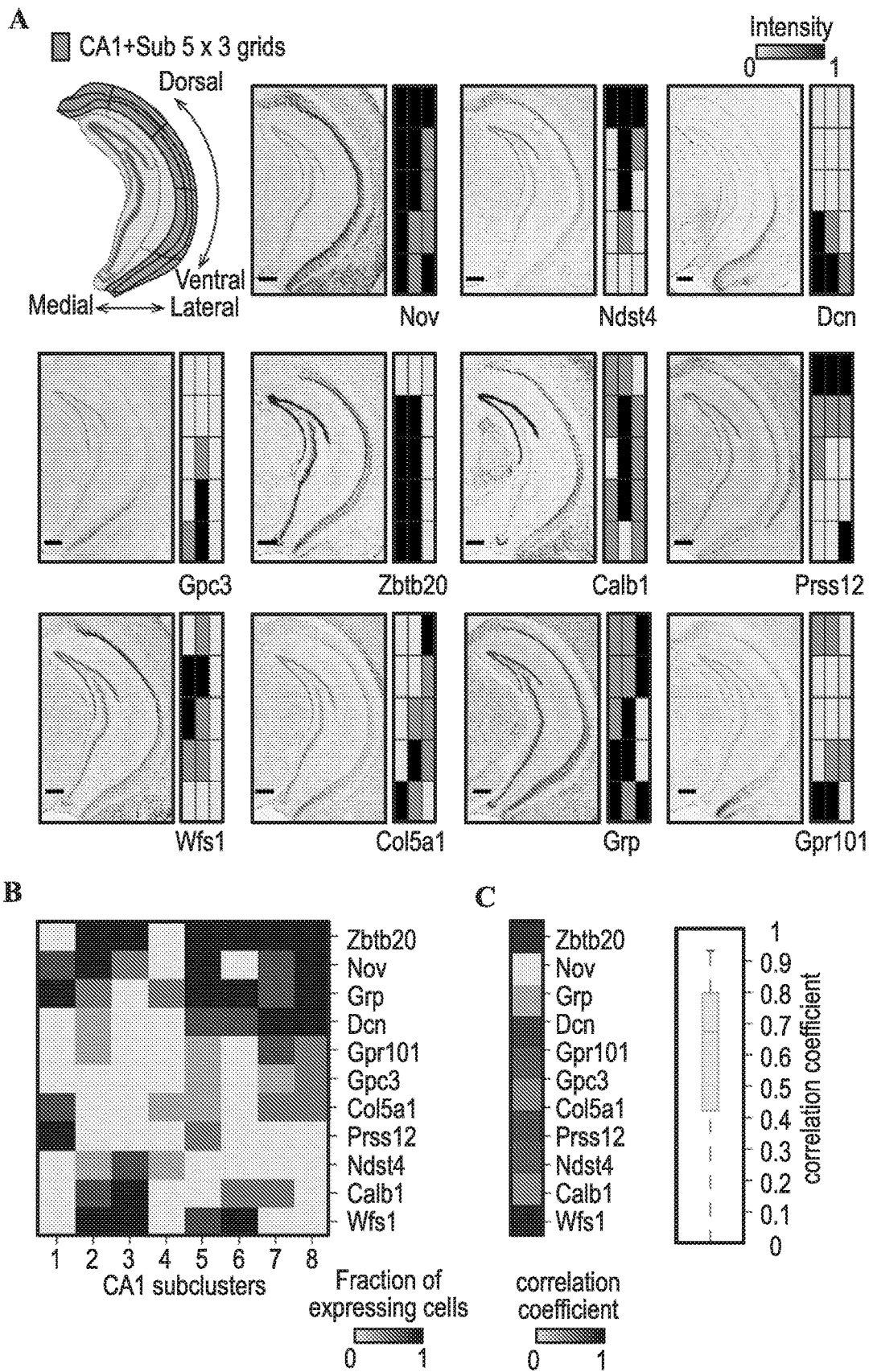

FIG. 16A-16C: Spatial landmark genes in CA1. (A) Spatial landmark genes in the CA1. Top left: Schematics of the hippocampus marking the CA1 and subiculum grid (orange). Displaying for each landmark gene an ISH [64] image showing its expression pattern in CA1 (right) and a heatmap showing the quantification of ISH intensities across the grid (left). Scale bar: 400 µm. (B) Expression of landmark genes across the CA1 pyramidal subclusters. Heatmap showing the fractions of nuclei expressing each landmark genes in each biSNE subcluster. (C) Expression intensity of landmark genes in ISH [64] correlates with expression intensity predicted using Nuc-Seq data. Displayed in heat map (left) and box plot (right). In box plot, the median (red), 75% and 25% quantile (box), error bars (dashed lines).

Figure 17:
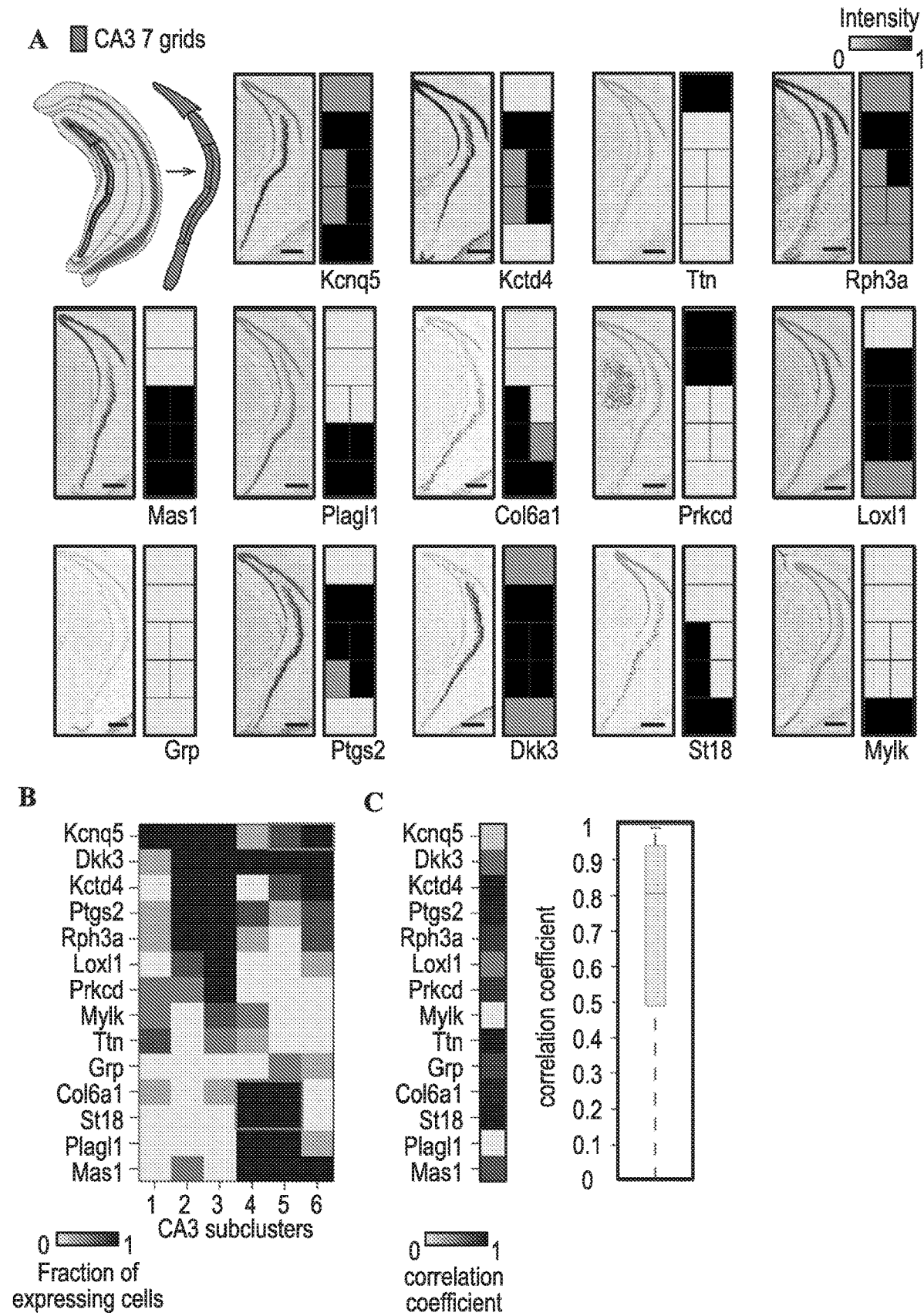

FIG. 17A-17C: Spatial landmark genes in CA3. (A) Spatial landmark genes in the CA3. Top left: Schematics of the hippocampus marking the CA3 grid (green). Displaying for each landmark gene an ISH [64] image showing its expression pattern in CA3 (right) and a heatmap showing the quantification of ISH intensities across the grid (left). Scale bar: 400 μm. (B) Expression of landmark genes across the CA3 pyramidal subclusters. Heatmap showing the fractions of nuclei expressing each landmark genes in each biSNE subcluster. Marking the differentially expressed landmark genes in CA3.4, 5, 6 subclusters (red box). (C) Expression intensity of landmark genes in ISH [64] correlates with expression intensity predicted using Nuc-Seq data. Displayed in heat map (left) and box plot (right). In box plot, the median (red), 75% and 25% quantile (box), error bars (dashed lines).

FIG. 18A-18F: Examples of CA1 and CA3 predicted spatial expression. (A-B) Validation of spatial assignments in the CA1 pyramidal subclusters (denoted as CA1.1, . . . ,CA1.8). Predictions (left illustrations; dark and light boxes showing predicted differential expression regions) match well with Allen ISH [64] images (right; arrowhead: high expression; asterisk: depletion) in pairwise comparison of genes differentially expressed between two subclusters (genes and clusters labeled on top). (C) ISH image [64] of the example genes showing the entire view of dorsal-ventral CA1. Scale bar: 400 μm. (D) ISH image [64] of the example genes showing the entire view of dorsal-ventral CA3. Scale bar: 400 μm. (E) Restricted spatial expression pattern in ventral CA3 of Col6a1 and Kcnq5. Showing ISH [64] images. Top: entire view of CA3. Middle: view of region marked by the upper dashed box. Bottom: view of the region marked by the lower dashed box. (F) Validation of spatial assignments in the CA3 pyramidal subclusters. Shown as in (A).

Figure 19:
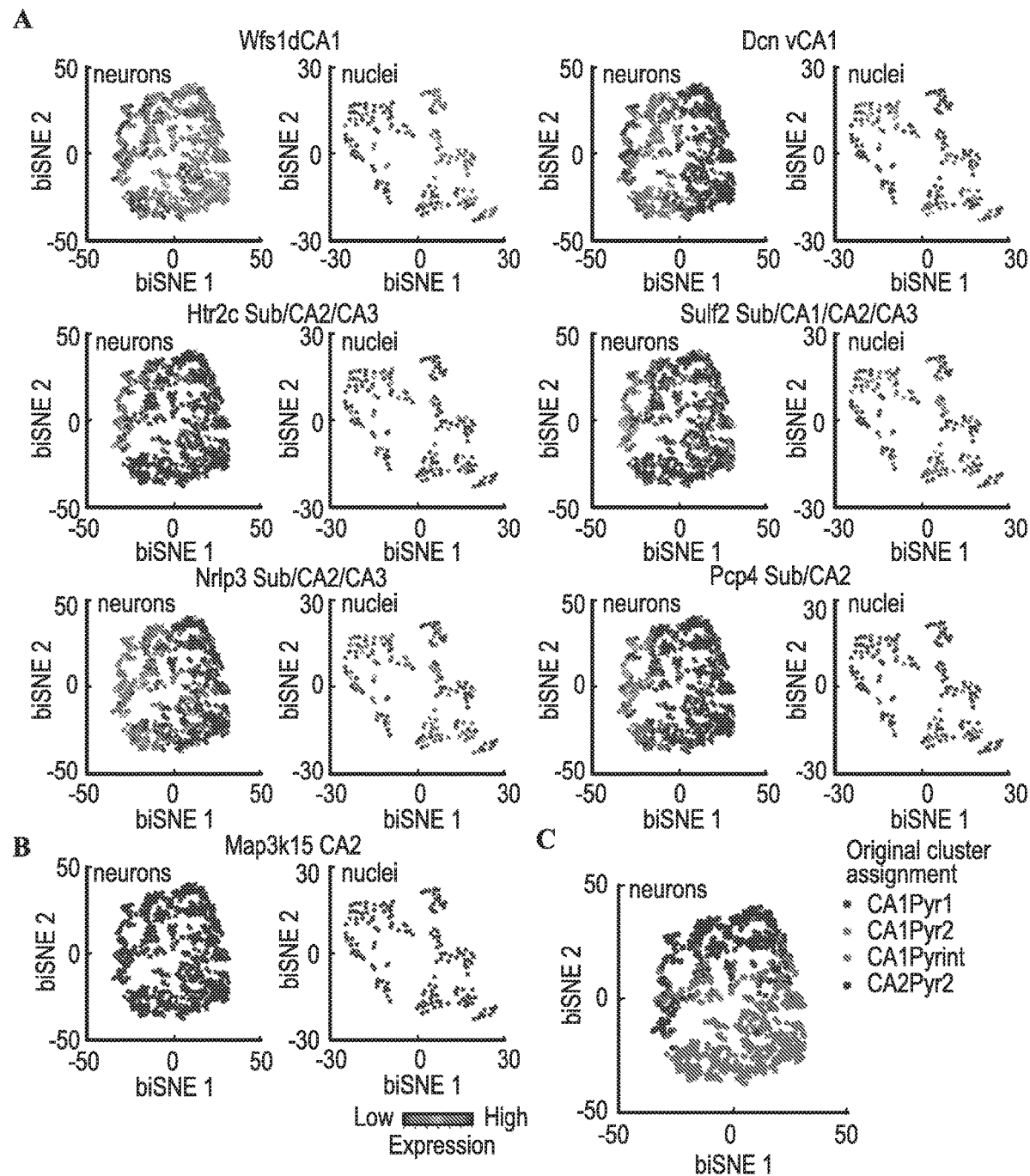

FIG. 19A-19C: Clustering of CA1 pyramidal neurons from published single-cell RNA-Seq data. (A) Nuc-Seq and biSNE improve cell sub-type classification of CA1 pyramidal neurons compared to single neuron RNA-seq. Pairwise comparison of the expression levels of spatial landmark genes across 2-D biSNE embedding of CA1 pyramidal neurons (left, data from single neurons RNA-seq [50]) and Nuc-Seq (right), showing the relative expression level of the gene (color scale). The expression of each gene is not restricted to any subcluster in the single neuron data [50], but is restricted to distinct subclusters in Nuc-Seq data. biSNE identified differential genes that have localized expression pattern the 2-D embedding of the single neuron RNA-Seq data. On top of each pair of plots, the anatomical region where the expression pattern of this gene is restricted to (identified in ISH [64]) is marked on the left, and the gene name on the right. dCA1: dorsal CA1; vCA1: ventral CA1; Sub: Subiculum. (B) A CA2 landmark gene Map3k15 is not selected by biSNE and does not have localized expression pattern in the 2-D embedding of the CA1 pyramidal neurons from the single-cell RNA-Seq data. 2-D embedding of CA1 pyramidal neurons (Left: data from [64]) and nuclei (Right: data from Nuc-Seq) showing the relative expression level of the gene (as in A). (C) 2-D embedding of the CA1 neurons showing the original assignment to 4 subclusters identified in [64] and denoted by colors. CA1Pyr1: CA1 pyramidal neuron type 1; CA2Pyr2: CA1 pyramidal neuron type 2; CA1PyrInt: CA1 pyramidal intermediate; CA2Pyr2: CA2 pyramidal neuron.

FIG. 20A-20G: Expression of Penk/Cck gene signatures in the DG. (A) DG nuclei form a continuum on expressions of Penk/Cck gene signature. Top left: DG cluster (as in FIG. 1E). Bottom left: DG cells form a continuum when mapped only by the gene sets containing Penk or Cck (in B). Cells are color coded by Penk/Cck gene signature expression. (B) Gene signatures expressed across granule cells in DG, marked by Penk and Cck expression (red labels, right). Absolute log(TPM) expression values. Dashed line separates nuclei expressing Penk highly (left) or lowly (right). (C) Distribution of expression (Box plot, Y axis) of Penk (dark grey, facing up) and Cck (light grey, facing down) across each subclusters of GABAergic neurons and DG granule cells (X axis). Box plots show the median (red), 75% and 25% quantile (box), error bars (dashed lines), and outliers (red cross). (D) qPCR validation of two DG subpopulations differentially expressing Penk (Y axis) and Cck genes (X axis), respectively. Proportion of nuclei at each expression quadrant is marked. (E) Schematics of hippocampal anatomy in a sagittal plane. red structure represents DG, same as in FIG. 14. (F) Spatial pattern on the Penk and Col6a1 genes. ISH [64] images of two coexpressed genes Penk and Col6a1 in the sagittal plane with view of the entire DG. scale bar: 400 μm. (G) Inferred transcription factors regulating the Penk/Cck gene signatures. Factors shown have known targets enriched in differentially expressed genes in the Penk/Cck gene signatures (hypergeometric p-value, Ingenuity Pathway Analysis). Edges denote transcription regulation.

FIG. 21A-21D: Continued Double FISH validates mutual exclusive expression of Penk and Oprd1. (A) From Top to Bottom: dFISH Penk/Oprd1 (green) and Htr3a/Vip/Pvalb showing expressions of Penk and Htr3a are partially overlapped. Expressions of Oprd1 and Htr3a are mostly not overlapped. Expressions of Penk and Vip are largely overlapped. Expressions of Oprd1 and Vip are not overlapped. Expressions of Penk and Pvalb are not overlapped. Expressions of Oprd1 and Pvalb are largely overlapped. Scale bar: 20 μm. s.r.—stratum radiatum; p.l.—pyramidal layer. (B) Quantification of dFISH images. Bar plots showing the percent of single and double labeled cells in FISH images for each pair of genes. (C) Allen ISH [64] image of Penk gene with view of the upper DG (top), and the lower DG (bottom). Shows its expression pattern in the CA1 and DG. Scale bar: 400 μm. (D) Allen ISH [64] image of Oprd1 gene (as in B) shows its expression in the subiculum and its depletion in the dorsal CA1 and DG regions. Scale bar: 400 μm.

FIG. 22A-22H: Nuc-seq combined with labeling of dividing cells (Div-Seq) profiles adult newborn precursors and neurons. (A) Cells expressing immature neuronal markers with EdU tagging. Left: heatmap showing 4 nuclei expressing immature neuronal marker genes: Sox4, Dcx, Sox11, and Cd24a. Right: 2-D embedding of the glial cluster of nuclei (from FIG. 1E), clustered as in FIG. 10 colored by the expression level of Sox11 gene. These nuclei are marked in the 2-D embedding of glial-like cells as in FIG. 10 (black dashed circle) (B) EdU labeled cells cluster separately from other cells. Shown is a biSNE 2-D embedding of all nuclei including the EdU labeled nuclei extracted after 2-day and 14-day post labeling. Most labeled nuclei form a distinct cluster. (C) EdU labeling tagged cells in the subgranular zone (SGZ) region. Shown are EdU staining (GFP click chemistry) and DAPI staining (blue) of tissue slice two weeks post EdU injections. (D) FACS sorting of EdU labeled nuclei. Shown is a scatter plot of log GFP intensity (X axis) and the log ruby dye intensity (Y axis) from FACS of nuclei isolated two days after EdU injection (left) and with no EdU injections (right). Both samples were treated with click chemistry as in B. (E) Dcx immature neuronal marker gene is expressed in GABAergic neurons. Box plots showing expression levels of the Dcx gene across mature granule neurons, immature neurons (EdU labeled) and GABAergic neurons. In box plots, the median (red), 75% and 25% quantile (box), error bars (dashed lines), and outliers (red dots). (F) Most of the 14 days EdU labeled nuclei are immature neurons. Shown is the distribution of 14 days EdU labeled nuclei across cell types, assigned to by clustering (as in B) and marker gene expression: Oligodendrocyte precursor cells, OPC; granule cells, DG; Astrocytes, ASC; Oligodendrocytes, ODC. (G) Expression of known marker genes along the trajectory matches the expected dynamics. Left: Heatmap of the expression of the markers and related genes (rows), sorted by their expected pattern, along the neurogenesis trajectory (columns, running average along the trajectory). Data in log(TPM+1), color scale as in (A). Right: Heatmap of the same markers along the neurogenesis trajectory when using Div-Seq libraries at 2.5 days and 1 week post EdU injections, showing a similar dynamic expression pattern. (H) Expression level of known transcription factors across cell types, showing known regulators of each cell type. Shown are the relative average expression levels (bars) across cells.

FIG. 23A-23F: Transcriptional and epigenetic switch during adult neurogenesis and neuronal maturation. (A) Dynamically regulated TFs and chromatin regulator. Heatmap of the running average expression (log(TPM+1)) of the regulators (rows) along the trajectory (columns). Genes are sorted by the cluster they were identified in (as in FIG. 3E). Red lines mark the transition from neuronal precursor cells (NPCs) to neuroblast (NB) and from NB to immature neurons. (B) Examples of dynamic expression patterns of families of regulators. Heatmap as in A with an additional column for the expression (log(TPM+1)) of the same genes in mature granule nuclei (DG cluster). Top: Sox family genes. Middle: Cyclin (Cdk) genes. Bottom: kinesin superfamily. (C) Examples of dynamic expression patterns of families of chromatin remodelers. Presented as in B. Top: Histone deacetylases (HDACs). Middle: Chromatin dehydrogenases. Bottom: histone demethylase protein family. (D) Transcriptional switches in the BAF complex. Top: Schematics of the complex. The positions of each component within the complex are denoted by colors, and below: the heatmap of average expression of complex component genes in NPCs, NB, immature, and mature granule DG cells (log(TPM+1)). (E) Examples of families of actin/cytoskeleton and Semaphorin signaling associated genes. Presented as in B. Top: Semaphorin genes. Middle-top: Rho-associated serine/threonine kinases. Middle-bottom: serine/threonine p21-activating kinases. Bottom: Microtubule Associated Serine/Threonine Kinase 3. (F) Comparison of Div-Seq data to other datasets. Heat maps from right to left: Div-Seq data presented as in (B); RNA-Seq time course of in vitro derived neurons from hES cells, average of replicates per day [84]; Single-cells RNA-Seq of mouse adult neuronal stem cells and progenitors in the DG across pseudotime [79]; Single-cell RNA-Seq of fetal human neuronal precursor cells, hNPCs (Tirosh et al. unpublished);

FIG. 24A-24E: Transcriptional program of neuronal maturation revealed by Div-Seq. (A) Maturation signature. Shown is the expression of genes (rows) differentially expressed (t-test FDR q-value<0.01) between the mature granule cells (orange bar, top) and the immature neurons (14d labeling; grey bar, top). Key markers of immature (Dcx, Sox11, Foxg1) and mature (Calb1) neurons are marked in red. Other genes of interest are marked in black, including receptors, channels, axon guidance molecules and the GABA transporter (Gat1). (B) Differential paralog expression may lead to functional specialization of the semaphorin pathway. Shown is the semaphorin signaling pathway, highlighting genes induced in immature (red) and mature (blue) neurons. (C) Young (1-month-old) mice have a higher fraction of immature cells compared to 12 months and 2 years old animals. Shown is the distribution of maturation scores across granule cells in 2-year old mice (red), 3-months old mice (orange) and adolescent 1-month old mice (green), and immature neurons (gray). Score defined as the difference in accumulated expression levels of up-regulated and down-regulated genes between mature and immature neurons. (D) Gad1 and Gat1 expression in neuronal precursor cells (NPCs), neuroblast (NB), immature and mature granule DG cells. In box plots, the median (red), 75% and 25% quantile (box), error bars (dashed lines), and outliers (red dots). (E) FISH of Gad1 (green) and Gad2 (red). Gad1 is widely expressed throughout cells in DG, whereas Gad2 is sparse. Scale bar: 100 μm.

FIG. 25A-25E: (A) Workflow for microfluidic device for analyzing nuclei (Dronc-Seq.) (B) Microfluidic device design generated using AutoCAD. (C) Bright-field micrographs of droplet generation in Drop-Seq (left), and drops with barcode beads and lysed cellular material (right). (D) Bioanalyzer trace of cDNA library after whole transcriptome amplification. (E) Distribution of number of genes captured for ~500 nuclei.

Figure 26:
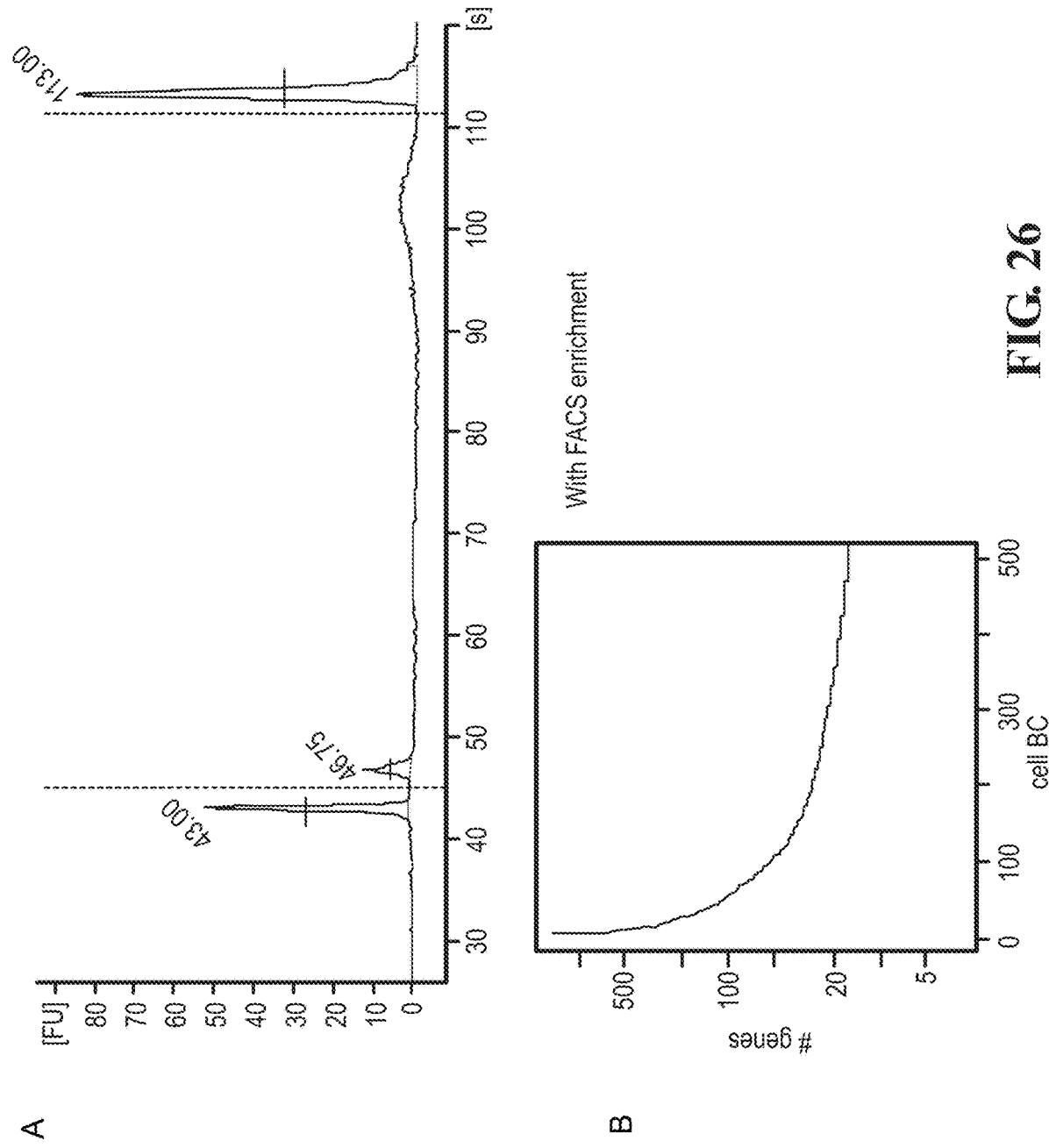

FIG. 26A-26B: (A) Bioanalyzer trace of cDNA library after whole transcriptome amplification with FACS enrichment. (B) Distribution of number of genes captured for ~500 nuclei with FACS enrichment.

Figure 27:
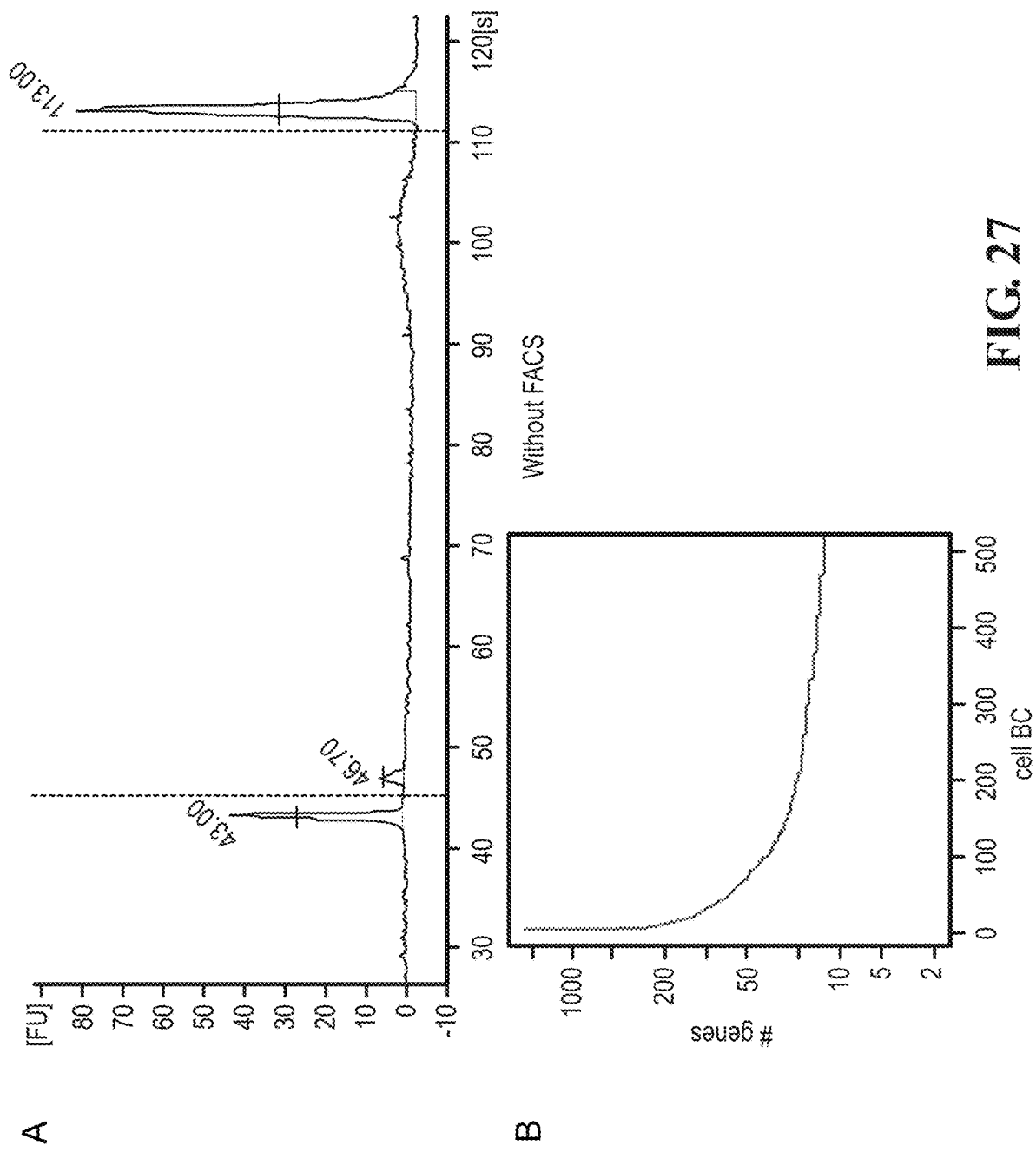

FIG. 27A-27B: (A) Bioanalyzer trace of cDNA library after whole transcriptome amplification without FACS enrichment. (B) Distribution of number of genes captured for 500 nuclei without FACS enrichment.

Figure 28:
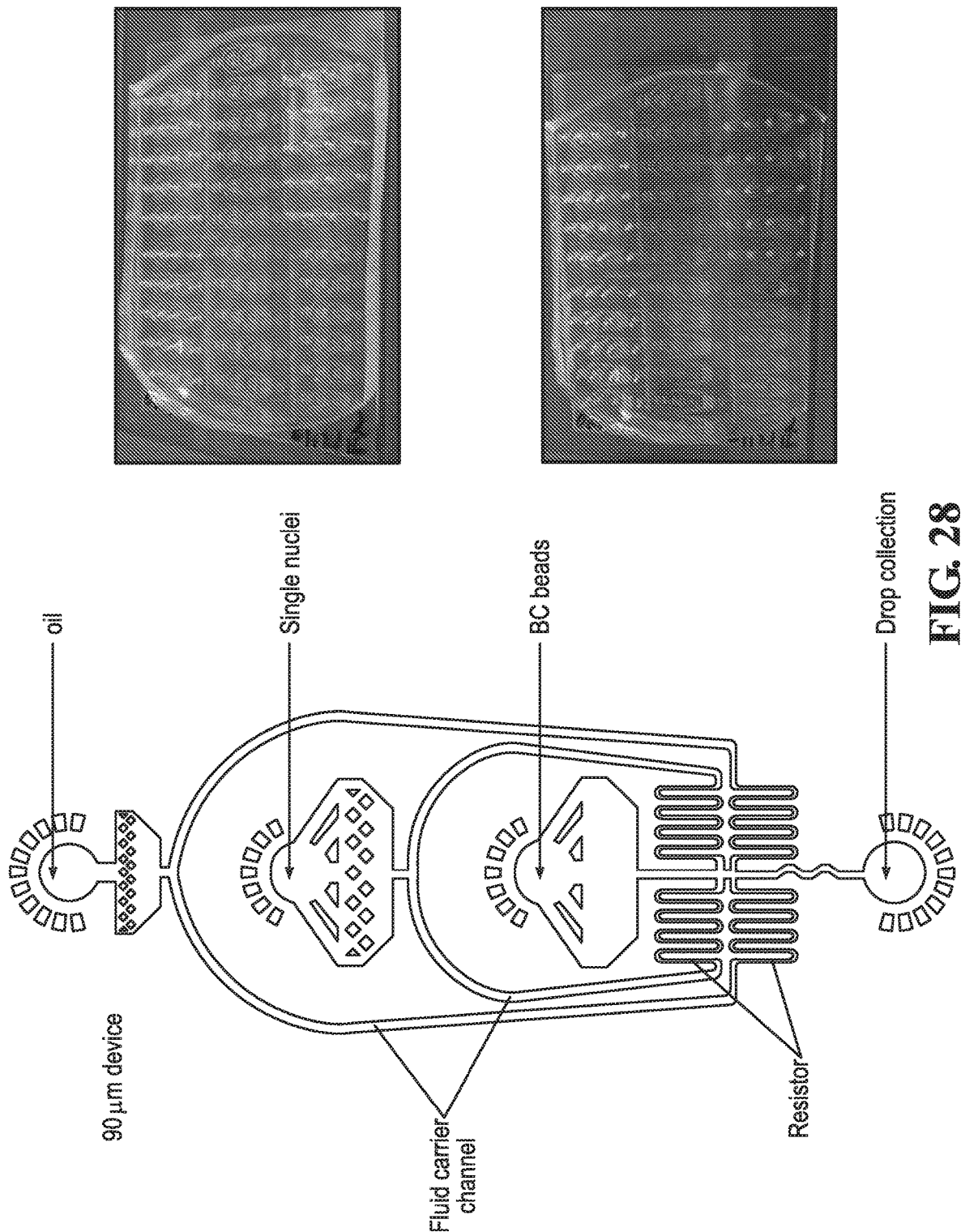

FIG. 28: Schematic representation of a Dronc-Seq device (left) and plates for performing Nuc-Seq (right).

Figure 29:
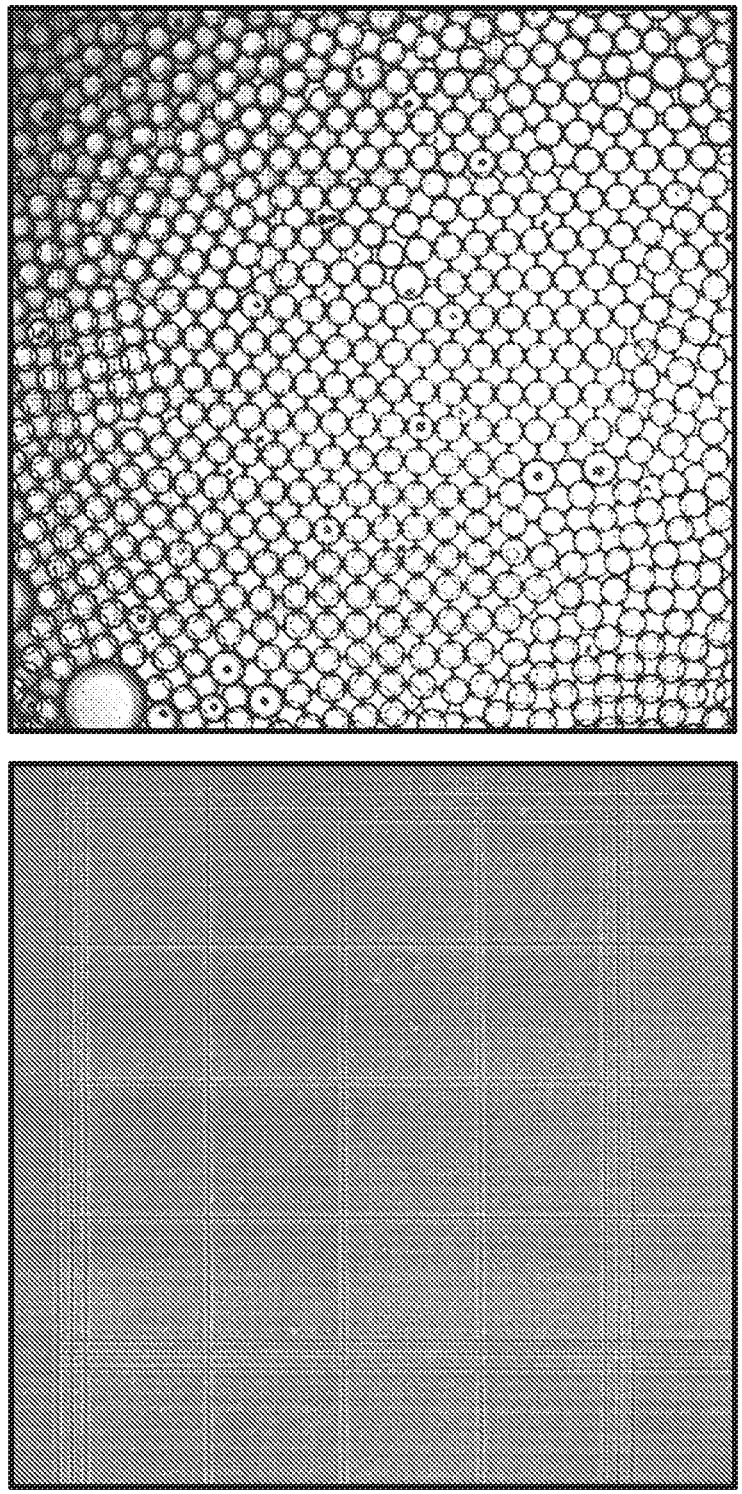

FIG. 29: Staining and photograph of droplets obtained with a Dronc-Seq device. The results were obtained using the nuclei purification protocol (Method A) as described in Example 6.

Figure 30:
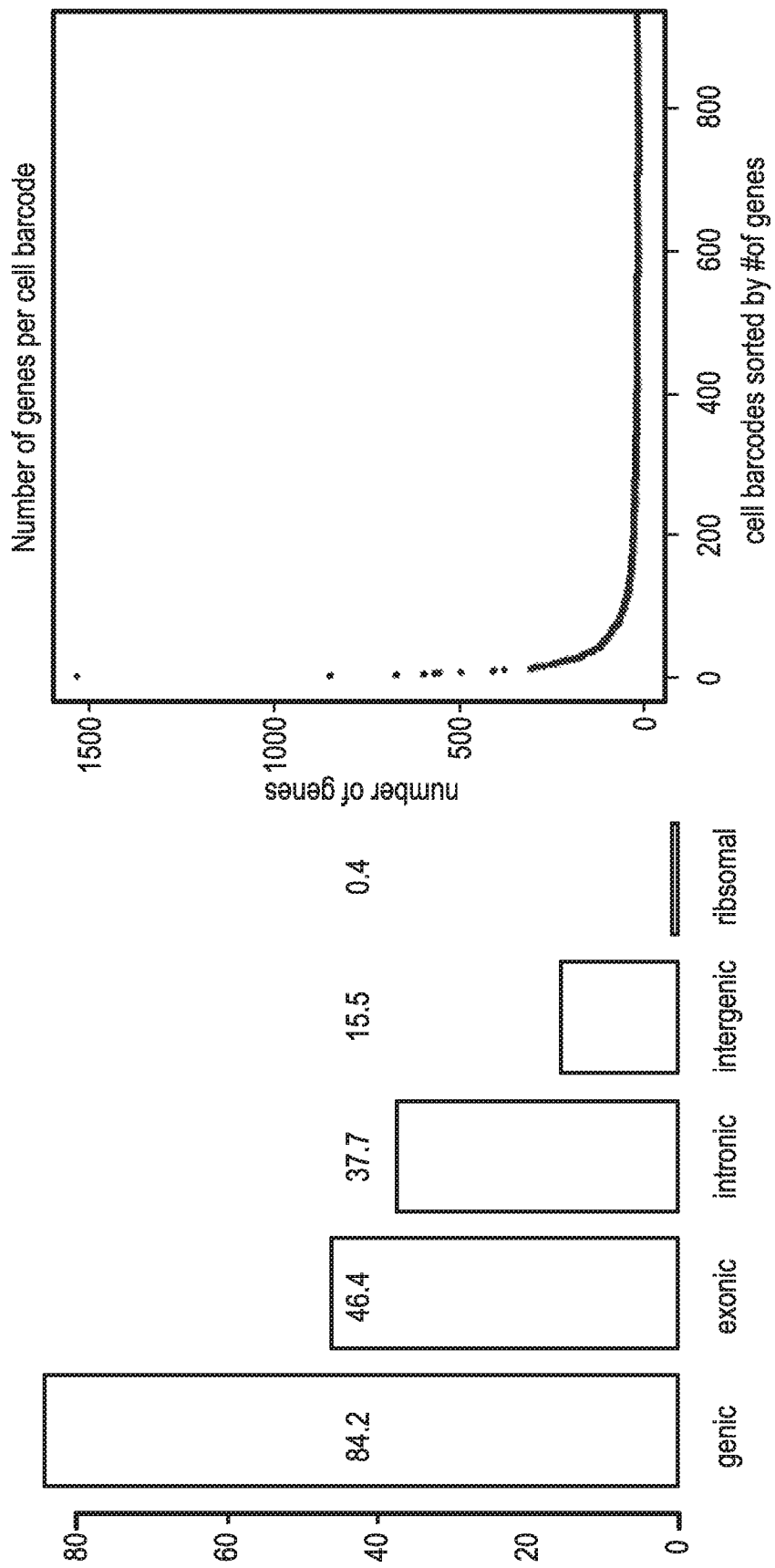

FIG. 30: RNA analysis using Dronc-Seq: single nuclei RNA profiling.

Figure 31:
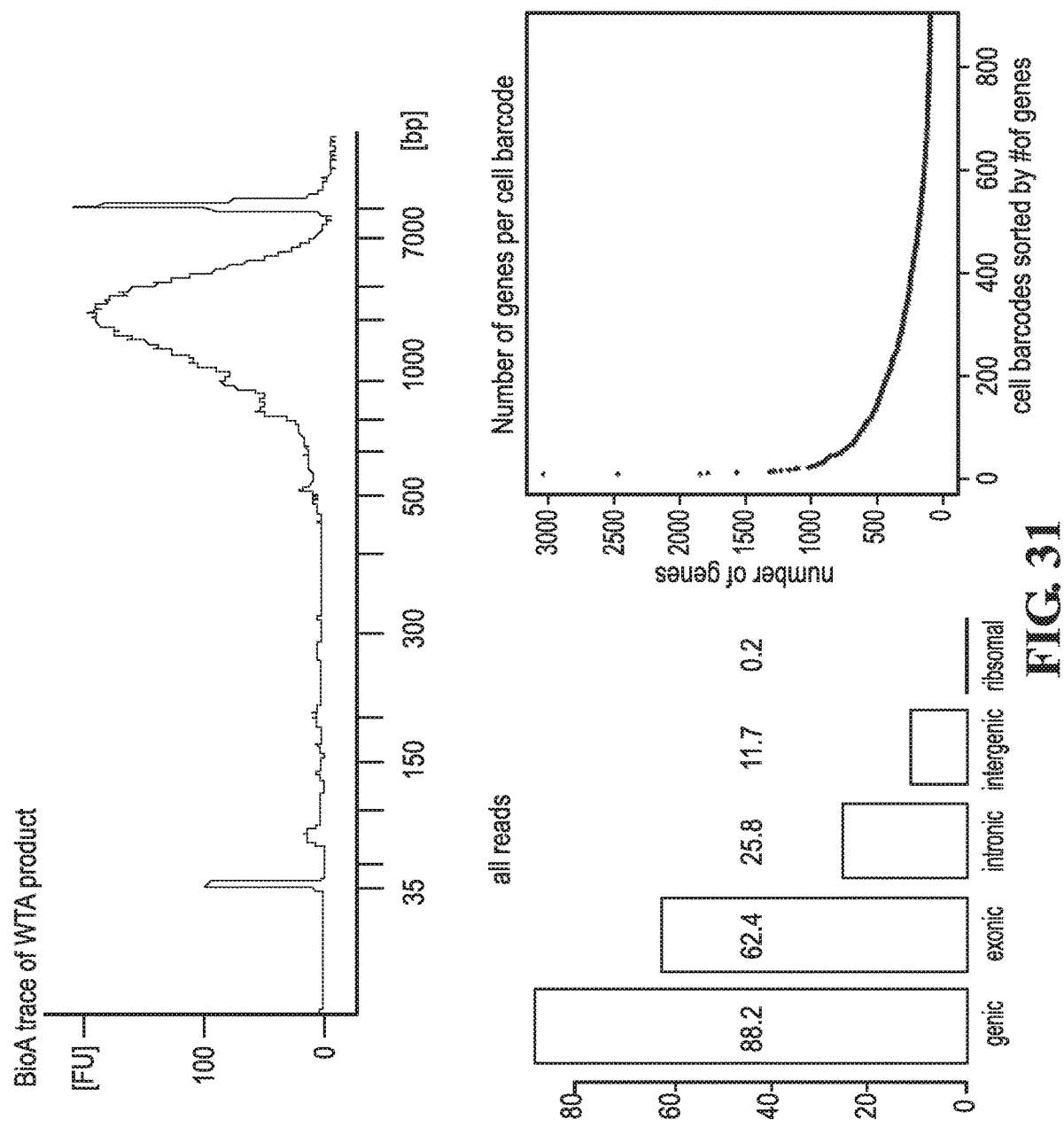

FIG. 31: RNA analysis using Dronc-Seq: single nuclei RNA profiling. WTA: Whole transcriptome analysis, showing integrity of the RNA population retrieved using Dronc-Seq.

Figure 32:
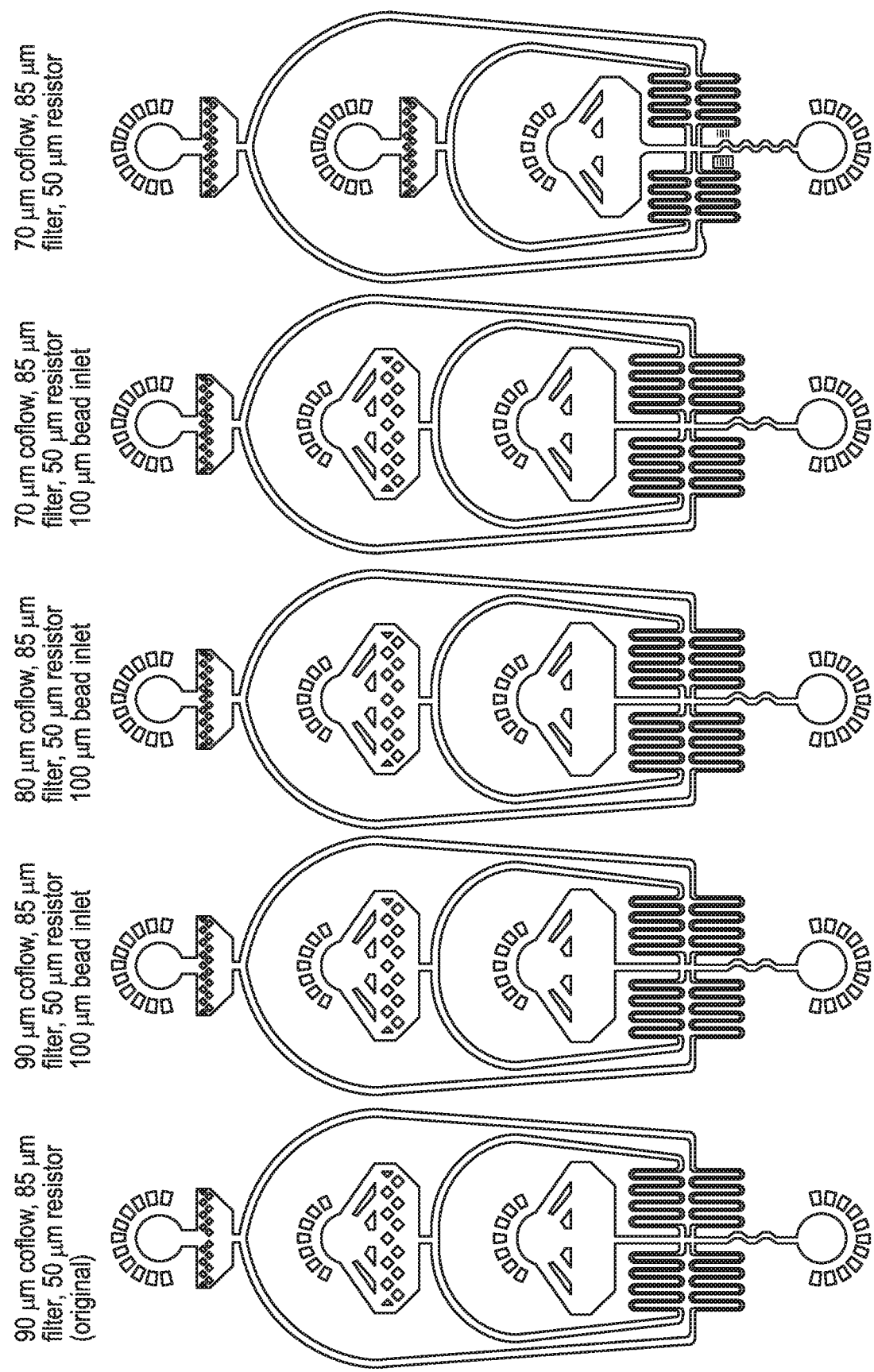

FIG. 32: Schematic representation of Dronc-Seq devices for generating droplets of various sizes. In these designs, both carrier fluid channels comprise a resistor.

Figure 33:
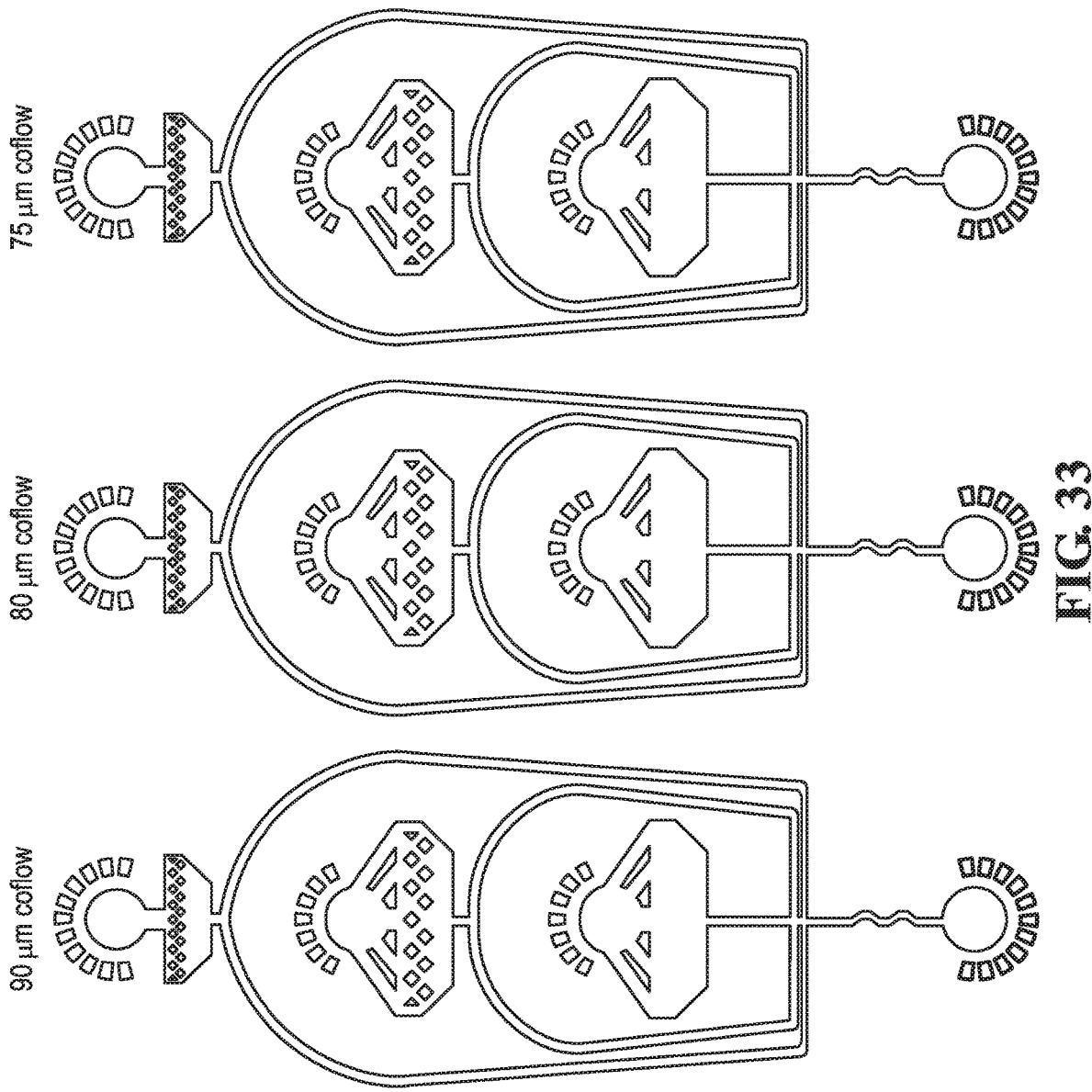

FIG. 33: Schematic representation of Dronc-Seq devices for generating 90, 80 and 75 μm droplets. In these designs, the carrier fluid channels do not comprise a resistor.

Figure 34:
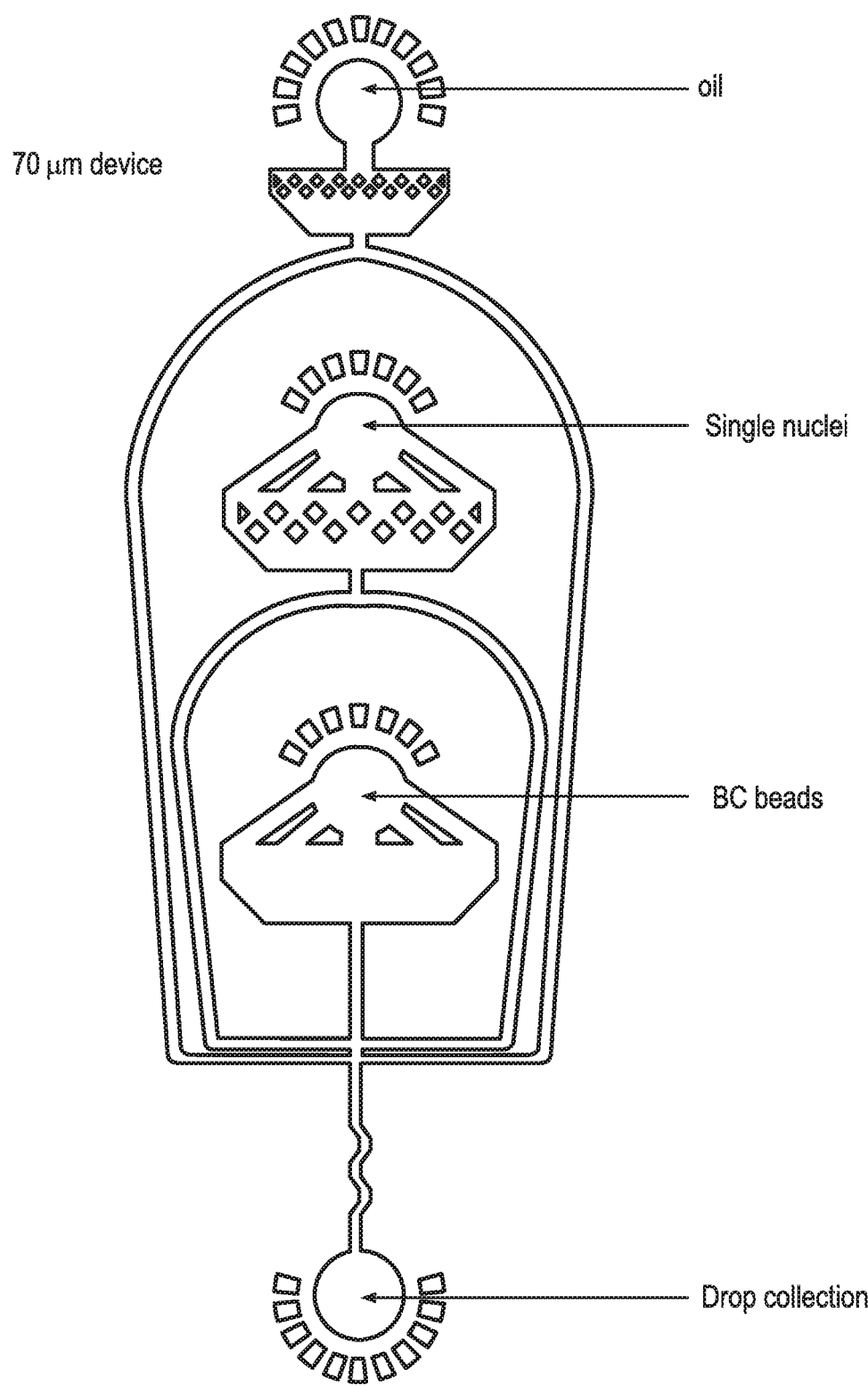

FIG. 34: Schematic representation of a Dronc-Seq device for generating 70 μm droplets.

Figure 35:
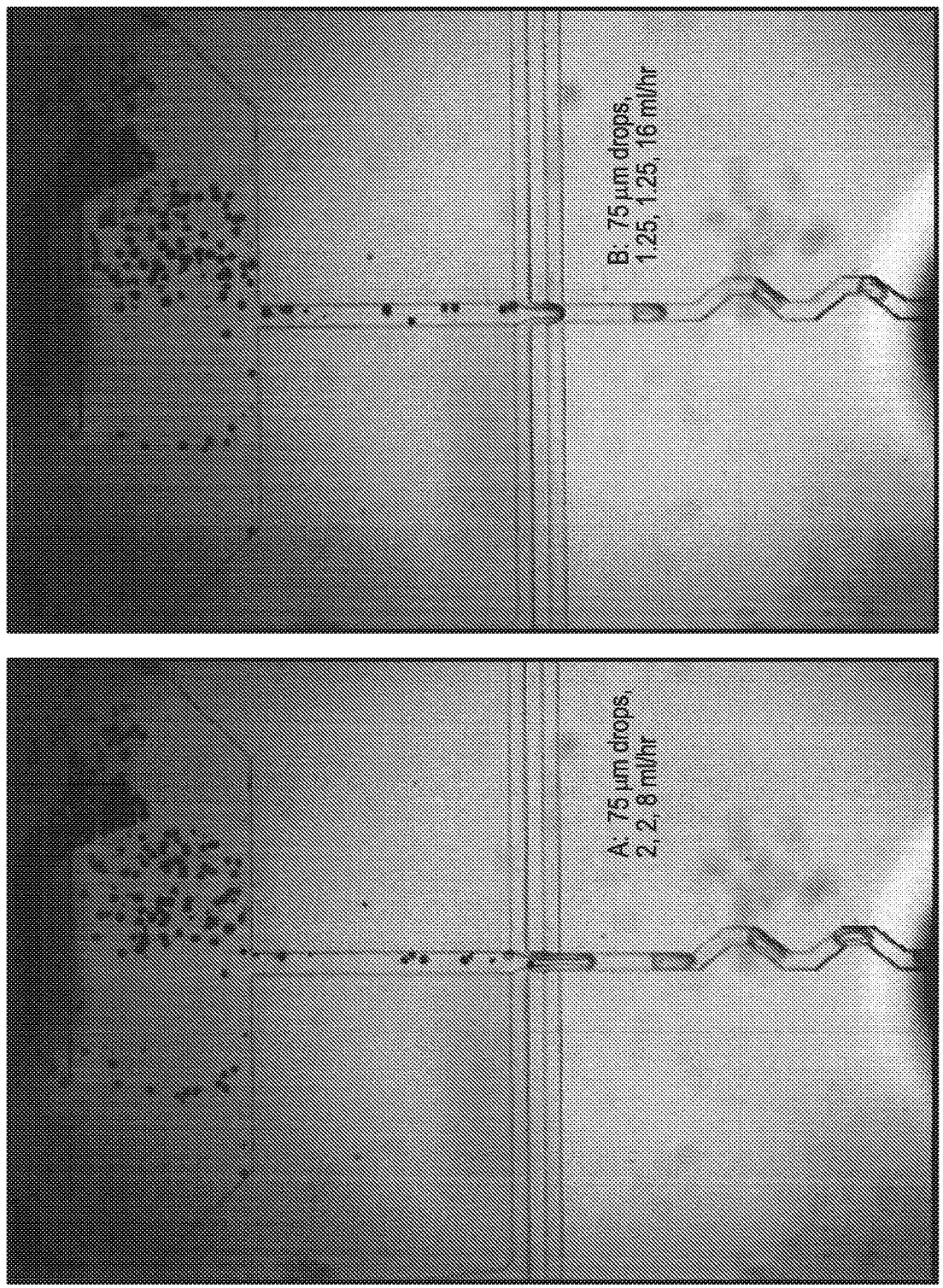

FIG. 35: Photograph of a Dronc-Seq device generating 75 μm droplets. In run A: the flow rates are 2 ml/hr for aqueous suspensions (beads, resp nuclei), and 8 ml/hr for the oilous phase. In run B: the flow rates are 1.25 ml/hr for aqueous suspensions (beads, resp nuclei), and 16 ml/hr for the oilous phase.

Figure 36:
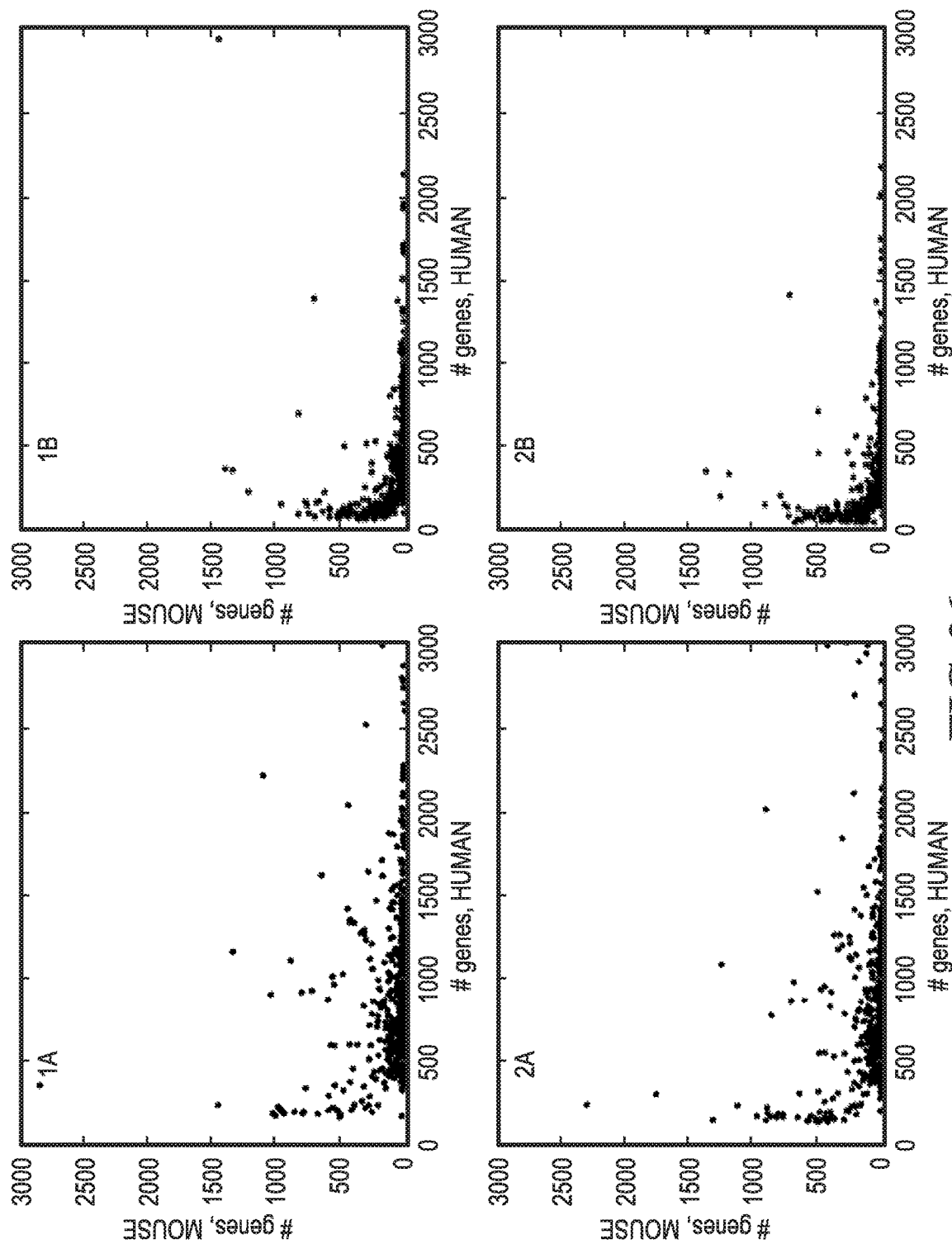

FIG. 36: Species mixing experiments: Dronc-Seq allows to accurately remember the nucleus-of-origin of the RNA. A 70 μm Dronc-Seq device was used to analyze species mixing % using Poisson loading concentrations. Beads were used at 350 k/ml and nuclei at 300k/ml with human (HEK293T cell line) and mouse (frozen brain tissue) at 1:1 number ratio. Runs were performed in duplicate under two conditions (A and B, as depicted in FIG. 35).

Figure 37:
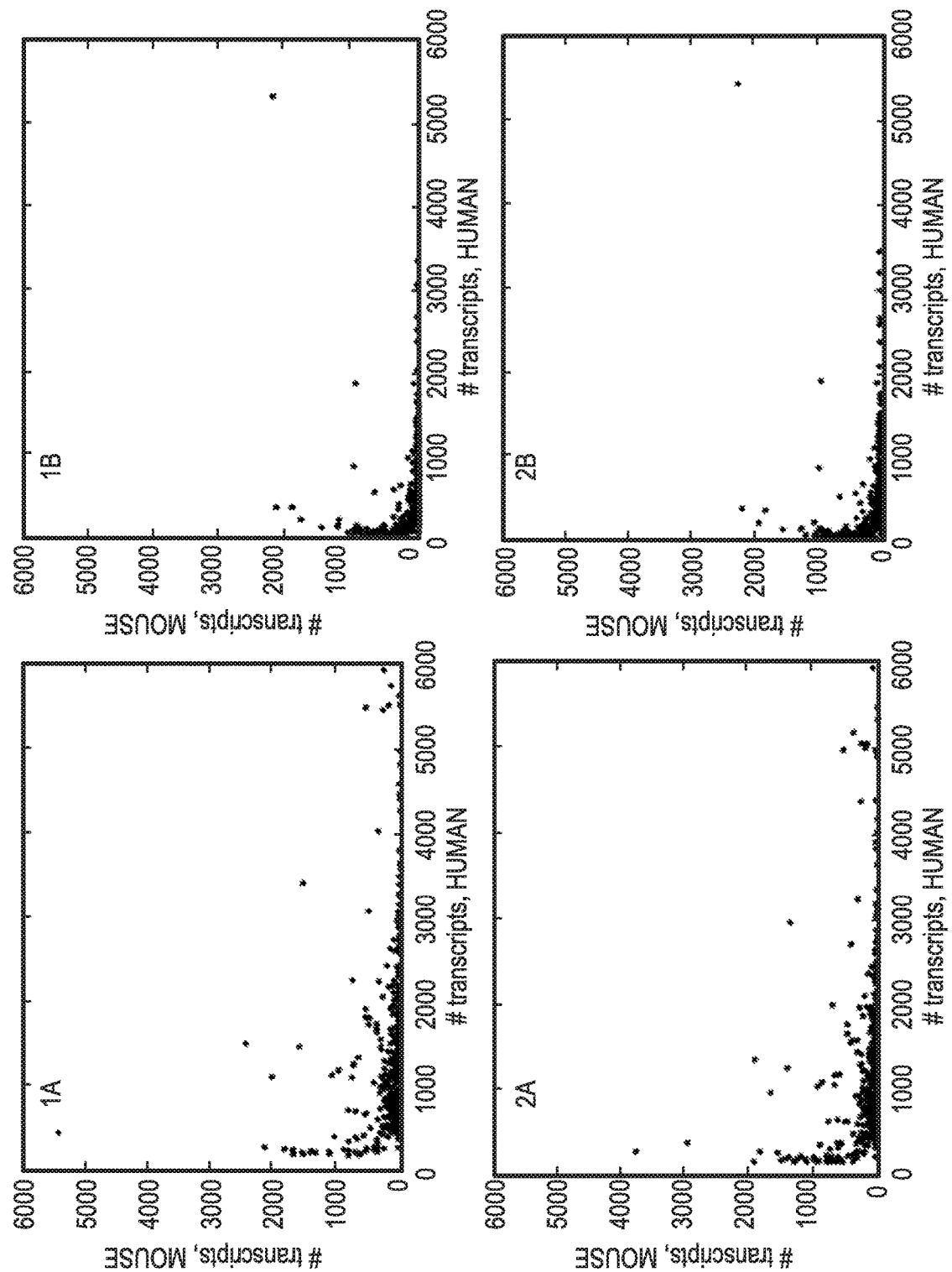

FIG. 37: Species mixing experiments: Dronc-Seq allows to accurately remember the nucleus-of-origin of the RNA. A 70 μm Dronc-Seq device was used to analyze species mixing % using Poisson loading concentrations. Beads were used at 350k/ml and nuclei at 300k/ml with human (HEK293T cell line) and mouse (frozen brain tissue) at 1:1 number ratio. Runs were performed in duplicate under two conditions (A and B, as depicted in FIG. 35).

Figure 38:
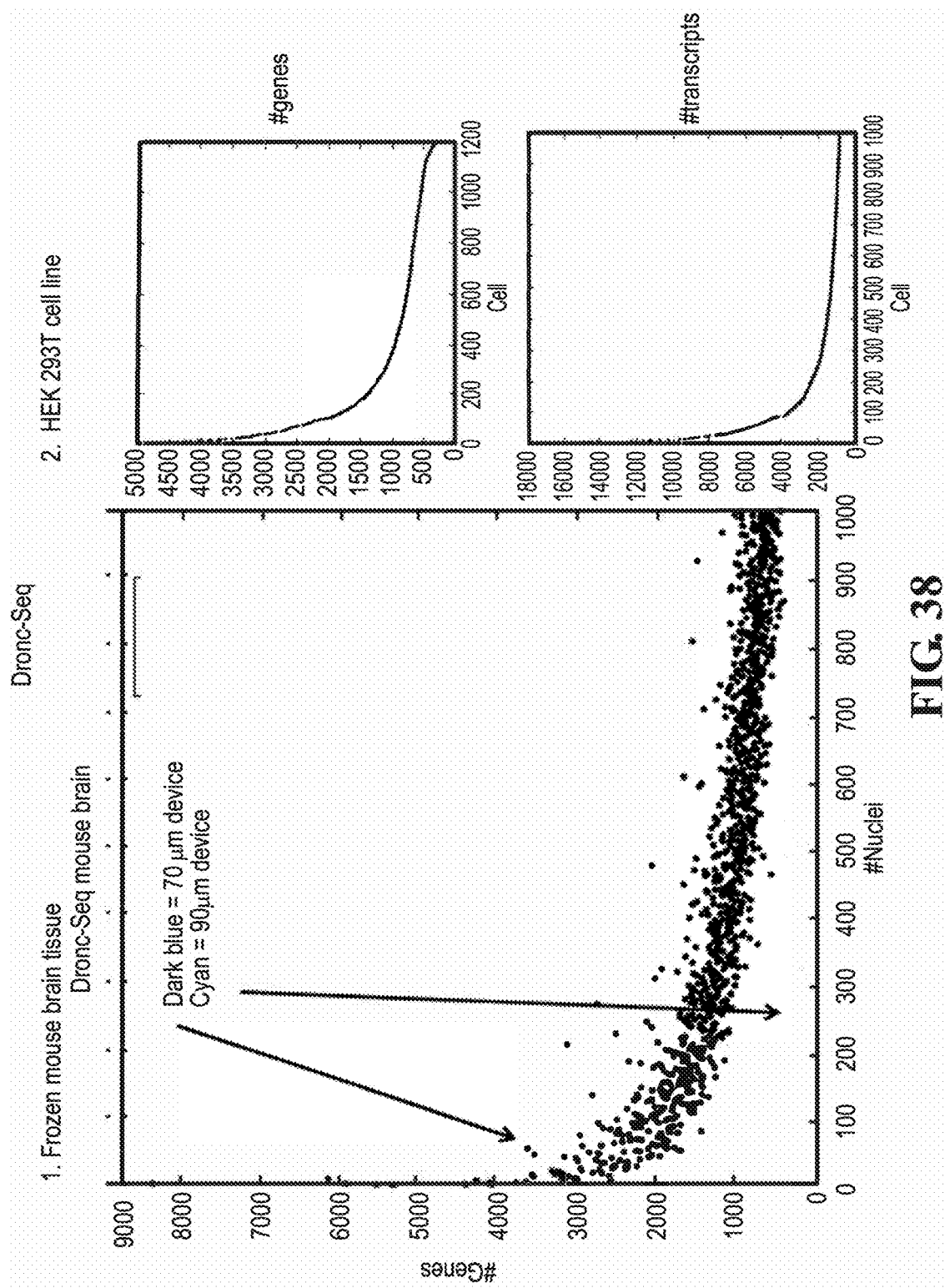

FIG. 38: Results obtained with Dronc-Seq analysis of a frozen sample (1.), and of cells of a human cell line (2.): plots of #genes or #transcripts detected per nucleus for Dronc-Seq.

Figure 39:
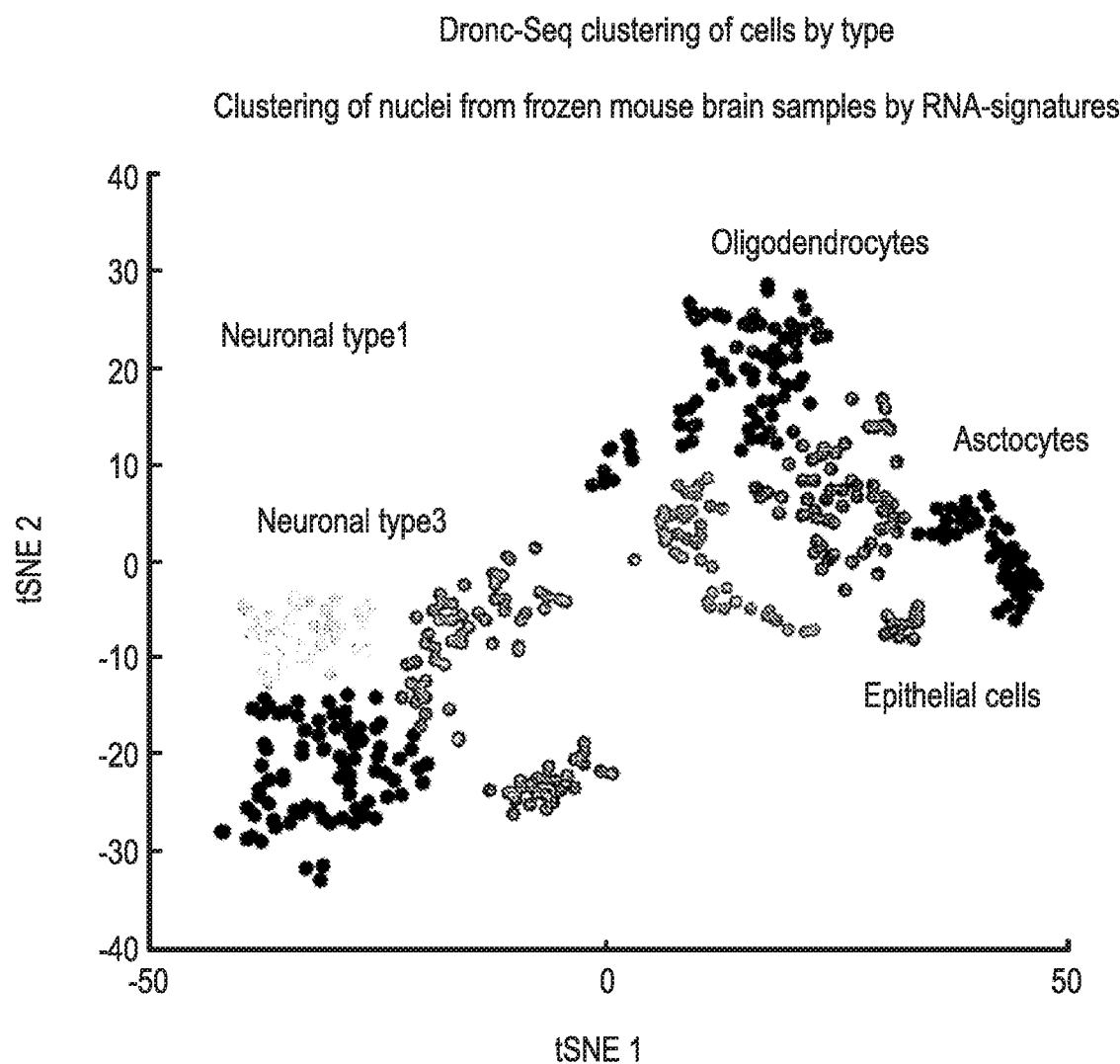

FIG. 39: Dronc-Seq analysis allows clustering of nuclei from frozen mouse brain samples by RNA-signatures.

Figure 40:
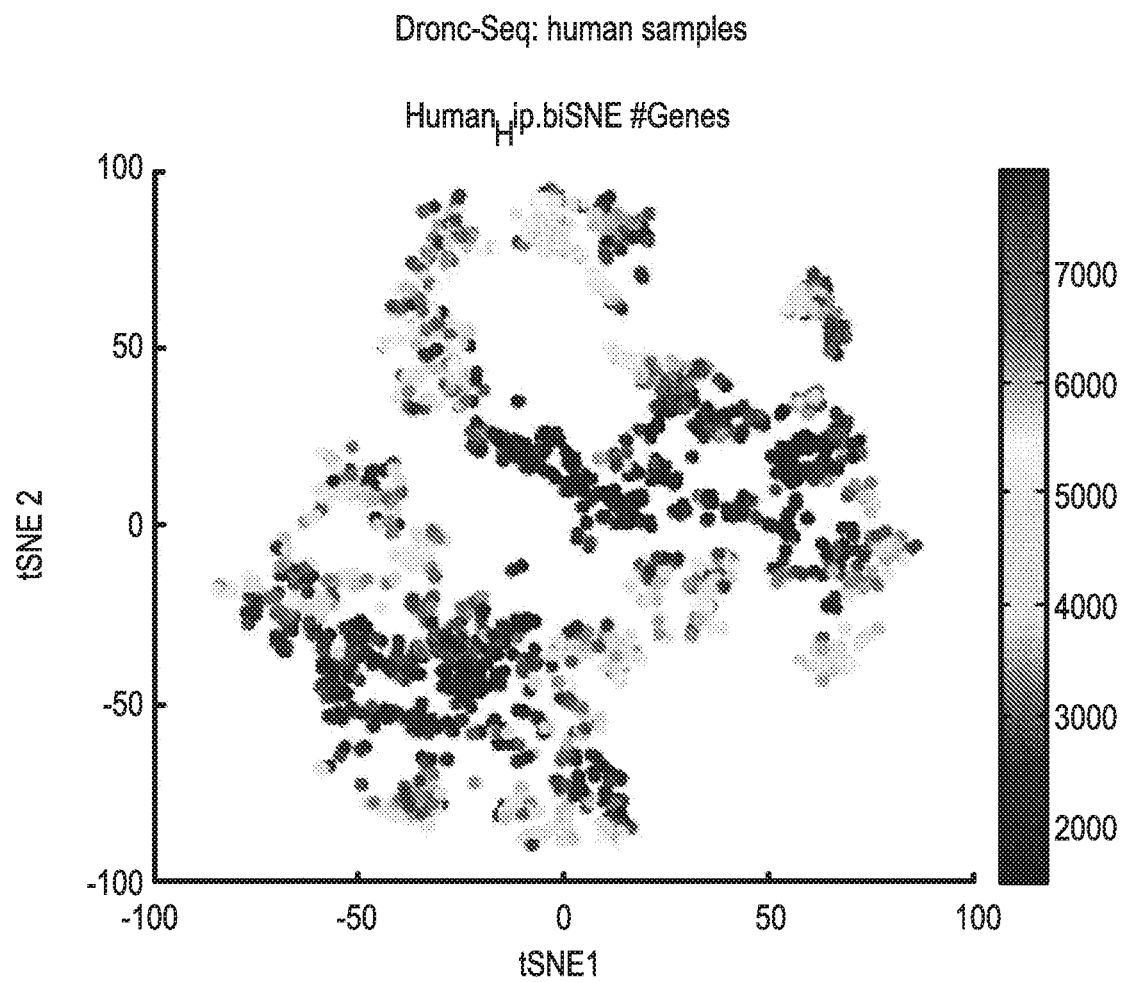

FIG. 40: Dronc-Seq results obtained on human nuclei allows cell clustering (the color indicates the number of genes detected per sample). The cells were from a post-mortem human hippocampus.

DETAILED DESCRIPTION OF THE INVENTION

The term "cell state" refers to a specific state of the cell, such as but not limited to an activated cell, such as activated neuron or immune cell, resting cell, such as a resting neuron or immune cell, a dividing cell, quiescent cell, or a cell during any stages of the cell cycle.

The term "developmental stage" refers to a stage of a cell that may include cell states and may include stages of development from a new born cell to a mature cell, or maturation of a progenitor undifferentiated cell, such as a stem cell, to a mature cell and all stages in between.

The terms "dimensionality reduction" or "dimension reduction" refers to the process of reducing the number of random variables under consideration, via obtaining a set "uncorrelated" principle variables.

The term "metric" refers to a mathematical function that associates a real nonnegative number analogous to distance with each pair of elements in a set such that the number is zero only if the two elements are identical, the number is the same regardless of the order in which the two elements are taken, and the number associated with one pair of elements plus that associated with one member of the pair and a third element is equal to or greater than the number associated with the other member of the pair and the third element.

The present invention may include barcoding. Barcoding may be performed based on any of the compositions or methods disclosed in patent publication WO 2014047561 A1, Compositions and methods for labeling of agents, incorporated herein in its entirety. Not being bound by a theory, amplified sequences from single cells or nuclei can be sequenced together and resolved based on the barcode associated with each cell or nuclei.

The term "barcode" as used herein, refers to any unique, non-naturally occurring, nucleic acid sequence that may be used to identify the originating source of a nucleic acid fragment. Such barcodes may be sequences including but not limited to, TTGAGCCT (SEQ ID NO:1), AGTTGCTT (SEQ ID NO: 2), CCAGTTAG (SEQ ID NO: 3), ACCAACTG (SEQ ID NO:4), GTATAACA (SEQ ID NO: 5) or CAGGAGCC (SEQ ID NO: 6). Although it is not necessary to understand the mechanism of an invention, it is believed that the barcode sequence provides a high-quality individual read of a barcode associated with a viral vector, labeling ligand, shRNA, sgRNA, cDNA, cell or nuclei, such that multiple species can be sequenced together.

DNA barcoding is also a taxonomic method that uses a short genetic marker in an organism's DNA to identify it as belonging to a particular species. It differs from molecular phylogeny in that the main goal is not to determine classification but to identify an unknown sample in terms of a known classification. Kress et al., "Use of DNA barcodes to identify flowering plants" Proc. Natl. Acad. Sci. U.S.A. 102(23):8369-8374 (2005). Barcodes are sometimes used in an effort to identify unknown species or assess whether species should be combined or separated. Koch H., "Combining morphology and DNA barcoding resolves the taxonomy of Western Malagasy Liotrigona Moure, 1961" African Invertebrates 51(2): 413-421 (2010); and Seberg et al., "How many loci does it take to DNA barcode a crocus?" PLoS One 4(2):e4598 (2009). Barcoding has been used, for example, for identifying plant leaves even when flowers or fruit are not available, identifying the diet of an animal based on stomach contents or feces, and/or identifying products in commerce (for example, herbal supplements or wood). Soininen et al., "Analysing diet of small herbivores: the efficiency of DNA barcoding coupled with high-throughput pyrosequencing for deciphering the composition of complex plant mixtures" Frontiers in Zoology 6:16 (2009).

It has been suggested that a desirable locus for DNA barcoding should be standardized so that large databases of sequences for that locus can be developed. Most of the taxa of interest have loci that are sequencable without species-specific PCR primers. CBOL Plant Working Group, "A DNA barcode for land plants" PNAS 106(31):12794-12797 (2009). Further, these putative barcode loci are believed short enough to be easily sequenced with current technology. Kress et al., "DNA barcodes: Genes, genomics, and bioinformatics" PNAS 105(8):2761-2762 (2008). Consequently, these loci would provide a large variation between species in combination with a relatively small amount of variation within a species. Lahaye et al., "DNA barcoding the floras of biodiversity hotspots" Proc Natl Acad Sci USA 105(8): 2923-2928 (2008).

DNA barcoding is based on a relatively simple concept. For example, most eukaryote cells contain mitochondria, and mitochondrial DNA (mtDNA) has a relatively fast mutation rate, which results in significant variation in mtDNA sequences between species and, in principle, a comparatively small variance within species. A 648-bp region of the mitochondrial cytochrome c oxidase subunit 1 (CO1) gene was proposed as a potential 'barcode'. As of 2009, databases of CO1 sequences included at least 620,000 specimens from over 58,000 species of animals, larger than databases available for any other gene. Ausubel, J., "A botanical macroscope" Proceedings of the National Academy of Sciences 106(31):12569 (2009).

Software for DNA barcoding requires integration of a field information management system (FIMS), laboratory information management system (LIMS), sequence analysis tools, workflow tracking to connect field data and laboratory data, database submission tools and pipeline automation for scaling up to eco-system scale projects. Geneious Pro can be used for the sequence analysis components, and the two plugins made freely available through the Moorea Biocode Project, the Biocode LIMS and Genbank Submission plugins handle integration with the FIMS, the LIMS, workflow tracking and database submission.

Additionally, other barcoding designs and tools have been described (see e.g., Birrell et al., (2001) Proc. Natl Acad. Sci. USA 98, 12608-12613; Giaever, et al., (2002) Nature 418, 387-391; Winzeler et al., (1999) Science 285, 901-906; and Xu et al., (2009) Proc Natl Acad Sci USA. February 17; 106(7):2289-94). In one embodiment, the invention provides a method for preparing uniquely barcoded particles. Unique barcoded particles may be generated by a split pool method.

In one embodiment, single-cell or single nuclei analysis is performed by digital polymerase chain reactions (PCR), e.g., Fluidigm C. Digital polymerase chain reaction (digital PCR, DigitalPCR, dPCR, or dePCR) is a refinement of conventional polymerase chain reaction methods that can be used to directly quantify and clonally amplify nucleic acids including DNA, cDNA or RNA. The key difference between dPCR and traditional PCR lies in that PCR carries out one reaction per single sample and dPCR carries out a single reaction within samples separated into a large number of partitions wherein the reactions are carried out in each partition individually. A sample is partitioned so that individual nucleic acid molecules within the sample are localized and concentrated within many separate regions. The capture or isolation of individual nucleic acid molecules may be effected in micro well plates, capillaries, the dispersed phase of an emulsion, and arrays of miniaturized chambers, as well as on nucleic acid binding surfaces.

In a preferred embodiment, single-cell or single nuclei analysis is performed using microfluidics. Microfluidics involves micro-scale devices that handle small volumes of fluids. Because microfluidics may accurately and reproducibly control and dispense small fluid volumes, in particular volumes less than 1 µl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947 and PCT publication No. WO2014085802 A1.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to 10' samples to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

The manipulation of fluids to form fluid streams of desired configuration, discontinuous fluid streams, droplets, particles, dispersions, etc., for purposes of fluid delivery, product manufacture, analysis, and the like, is a relatively well-studied art. Microfluidic systems have been described in a variety of contexts, typically in the context of miniaturized laboratory (e.g., clinical) analysis. Other uses have been described as well. For example, WO 2001/89788; WO 2006/040551; U.S. Patent Application Publication No. 2009/0005254; WO 2006/040554; U.S. Patent Application Publication No. 2007/0184489; WO 2004/002627; U.S. Pat. No. 7,708,949; WO 2008/063227; U.S. Patent Application Publication No. 2008/0003142; WO 2004/091763; U.S. Patent Application Publication No. 2006/0163385; WO 2005/021151; U.S. Patent Application Publication No. 2007/0003442; WO 2006/096571; U.S. Patent Application Publication No. 2009/0131543; WO 2007/089541; U.S. Patent Application Publication No. 2007/0195127; WO 2007/081385; U.S. Patent Application Publication No. 2010/0137163; WO 2007/133710; U.S. Patent Application Publication No. 2008/0014589; U.S. Patent Application Publication No. 2014/0256595; and WO 2011/079176. In a preferred embodiment single-cell analysis is performed in droplets using methods according to WO 2014085802. Each of these patents and publications is herein incorporated by reference in their entireties for all purposes.

Single cells or nuclei may be sorted into separate vessels by dilution of the sample and physical movement, such as micromanipulation devices or pipetting. A computer controlled machine may control pipetting and separation.

Single cells or single nuclei of the present invention may be divided into single droplets using a microfluidic device. The single cells or nuclei in such droplets may be further labeled with a barcode. In this regard reference is made to Macosko et al., 2015, "Highly Parallel Genome-wide Expression Profiling of Individual Cells Using Nanoliter Droplets" Cell 161, 1202-1214 and Klein et al., 2015, "Droplet Barcoding for Single-Cell Transcriptomics Applied to Embryonic Stem Cells" Cell 161, 1187-1201 all the contents and disclosure of each of which are herein incorporated by reference in their entirety. Not being bound by a theory, the volume size of an aliquot within a droplet may be as small as 1 fL.

Single cells or single nuclei may be diluted into a physical multi-well plate or a plate free environment. The multi-well assay modules (e.g., plates) may have any number of wells and/or chambers of any size or shape, arranged in any pattern or configuration, and be composed of a variety of different materials. Preferred embodiments of the invention are multi-well assay plates that use industry standard multi-well plate formats for the number, size, shape and configuration of the plate and wells. Examples of standard formats include 96-, 384-, 1536- and 9600-well plates, with the wells configured in two-dimensional arrays. Other formats include single well, two well, six well and twenty-four well and 6144 well plates. Plate free environments of the present invention utilize a single polymerizable gel containing compartmentalized cells or single nuclei. In one embodiment, extraction of single cells or single nuclei may be by a mechanical punch. Single cells or single nuclei may be visualized in the gel before a punch.

In one embodiment, to ensure proper staining of intracellular and intranuclear proteins and nucleic acids single cells or nuclei are embedded in hydrogel droplets. Not being bound by a theory, the hydrogel mesh provides a physical framework, chemically incorporates biomolecules and is permeable to macromolecules such as antibodies (Chung et al., (2013). Structural and molecular interrogation of intact biological systems. Nature 497, 332-337). In one embodiment, to further improve permeability and staining efficiency, lipids are cleared (Chung et al., 2013). Not being bound by a theory, the clearance of the lipids and the porosity of the hydrogel allow for more efficient washing. This higher accuracy of measurement is important for the high multiplex measurements and computational inference of regulatory mechanisms.

In one embodiment, the nucleic acids of single cells or nuclei are crosslinked to prevent loss of nucleic acids. Not being bound by a theory, leakage of mRNA from nuclei may be prevented by crosslinking. Nucleic acids can be reverse cross-linked after separation of cells or nuclei into separate wells or droplets. The contents of individual wells or droplets may then be sequenced. In one embodiment, crosslinking may be reversed by incubating the cross-linked sample in high salt (approximately 200 mM NaCl) at 65° C. for at least 4 h.

The invention provides a nucleotide- or oligonucleotide-adorned bead wherein said bead comprises: a linker; an identical sequence for use as a sequencing priming site; a uniform or near-uniform nucleotide or oligonucleotide sequence; a Unique Molecular Identifier which differs for each priming site; optionally an oligonucleotide redundant sequence for capturing polyadenylated mRNAs and priming reverse transcription; and optionally at least one other oligonucleotide barcode which provides an additional substrate for identification.

In an embodiment of the invention, the nucleotide or oligonucleotide sequences on the surface of the bead is a molecular barcode. In a further embodiment the barcode ranges from 4 to 1000 nucleotides in length. In another embodiment, the oligonucleotide sequence for capturing polyadenylated mRNAs and priming reverse transcription is an oligo dT sequence.

In an embodiment of the invention, the linker is a non-cleavable, straight chain polymer. In another embodiment, the linker is a chemically-cleavable, straight chain polymer. In a further embodiment, the linker is a non-cleavable, optionally substituted hydrocarbon polymer. In another embodiment, the linker is a photolabile optionally substituted hydrocarbon polymer. In another embodiment, the linker is a polyethylene glycol. In an embodiment, the linker is a PEG-$C_3$ to PEG-$_{24}$.

The invention provides a mixture comprising a plurality of nucleotide- or oligonucleotide-adorned beads, wherein said beads comprises: a linker; an identical sequence for use as a sequencing priming site; a uniform or near-uniform nucleotide or oligonucleotide sequence; a Unique Molecular Identifier (UMI) which differs for each priming site; an oligonucleotide redundant sequence for capturing polyadenylated mRNAs and priming reverse transcription; and optionally at least one additional oligonucleotide sequences, which provide substrates for downstream molecular-biological reactions; wherein the uniform or near-uniform nucleotide or oligonucleotide sequence is the same across all the priming sites on any one bead, but varies among the oligonucleotides on an individual bead.

In an embodiment of the invention, the nucleotide or oligonucleotide sequence on the surface of the bead is a molecular barcode. In a further embodiment the barcode ranges from 4 to 1000 nucleotides in length. In another embodiment, the oligonucleotide sequence for capturing polyadenylated mRNAs and priming reverse transcription is an oligo dT sequence.

In an embodiment of the invention, the mixture comprises at least one oligonucleotide sequences, which provide for substrates for downstream molecular-biological reactions. In another embodiment, the downstream molecular-biological reactions are for reverse transcription of mature mRNAs; capturing specific portions of the transcriptome, priming for DNA polymerases and/or similar enzymes; or priming throughout the transcriptome or genome. In an embodiment of the invention, the additional oligonucleotide sequence comprises a oligo dT sequence. In another embodiment of the invention, the additional oligonucleotide sequence comprises a primer sequence. In an embodiment of the invention, the additional oligonucleotide sequence comprises a oligo dT sequence and a primer sequence.

The invention provides an error-correcting barcode bead wherein said bead comprises: a linker; an identical sequence for use as a sequencing priming site; a uniform or near-uniform nucleotide or oligonucleotide sequence which comprises at least a nucleotide base duplicate; a Unique Molecular Identifier which differs for each priming site; and an oligonucleotide redundant for capturing polyadenylated mRNAs and priming reverse transcription.

In an embodiment of the invention, the error-correcting barcode beads fail to hybridize to the mRNA thereby failing to undergo reverse transcription.

The invention also provides a kit which comprises a mixture of oligonucleotide bound beads and self-correcting barcode beads.

The invention provides a method for creating a single-cell sequencing library comprising: merging one uniquely barcoded RNA capture microbead with a single-cell in an emulsion droplet having a diameter from 50 μm to 210 μm; lysing the cell thereby capturing the RNA on the RNA capture microbead; breaking droplets and pooling beads in solution; performing a reverse transcription reaction to convert the cells' RNA to first strand cDNA that is covalently linked to the RNA capture microbead; or conversely reverse transcribing within droplets and thereafter breaking droplets and collecting cDNA-attached beads; preparing and sequencing a single composite RNA-Seq library, containing cell barcodes that record the cell-of-origin of each RNA, and molecular barcodes that distinguish among RNAs from the same cell..

In an embodiment the diameter of the emulsion droplet is between 50-210 μm. In a further embodiment, the method wherein the diameter of the mRNA capture microbeads is from 10 μm to 95 μm. In a further embodiment the diameter of the emulsion droplet is 90 μm.

The invention provides a method for preparing a plurality of beads with unique nucleic acid sequence comprising: performing polynucleotide synthesis on the surface of the plurality of beads in a pool-and-split process, such that in each cycle of synthesis the beads are split into a plurality of subsets wherein each subset is subjected to different chemical reactions; repeating the pool-and-split process from anywhere from 2 cycles to 200 cycles.

In an embodiment of the invention the polynucleotide synthesis is phosphoramidite synthesis. In another embodiment of the invention the polynucleotide synthesis is reverse direction phosphoramidite chemistry. In an embodiment of the invention, each subset is subjected to a different nucleotide. In another embodiment, each subset is subjected to a different canonical nucleotide. In an embodiment of the invention the method is repeated three, four, or twelve times.

In an embodiment the covalent bond is polyethylene glycol. In another embodiment the diameter of the mRNA capture microbeads is from 10 μm to 95 μm. In an embodiment, wherein the multiple steps is twelve steps.

In a further embodiment the method further comprises a method for preparing uniquely barcoded mRNA capture microbeads, which has a unique barcode and diameter suitable for microfluidic devices comprising: 1) performing reverse phosphoramidite synthesis on the surface of the bead in a pool-and-split fashion, such that in each cycle of synthesis the beads are split into four reactions with one of the four canonical nucleotides (T, C, G, or A); 2) repeating this process a large number of times, at least six, and optimally more than twelve, such that, in the latter, there are more than 16 million unique barcodes on the surface of each bead in the pool.

In an embodiment, the diameter of the mRNA capture microbeads is from 10 μm to 95 μm.

The invention provides a method for simultaneously preparing a plurality of nucleotide- or oligonucleotide-adorned beads wherein a uniform, near-uniform, or patterned nucleotide or oligonucleotide sequence is synthesized upon any individual bead while vast numbers of different nucleotide or oligonucleotide sequences are simultaneously synthesized on different beads, comprising: forming a mixture comprising a plurality of beads; separating the beads into subsets; extending the nucleotide or oligonucleotide sequence on the surface of the beads by adding an individual nucleotide via chemical synthesis; pooling the subsets of beads in (c) into a single common pool; repeating steps (b), (c) and (d) multiple times to produce a combinatorially a thousand or more nucleotide or oligonucleotide sequences; and collecting the nucleotide- or oligonucleotide-adorned beads.

In an embodiment of the invention, the nucleotide or oligonucleotide sequence on the surface of the bead is a molecular barcode. In a further embodiment, the pool-and-split synthesis steps occur every 2-10 cycles, rather than every cycle.

In an embodiment of the invention, the barcode contains built-in error correction. In another embodiment, the barcode ranges from 4 to 1000 nucleotides in length. In embodiment of the invention the polynucleotide synthesis is phosphoramidite synthesis. In a further embodiment, the polynucleotide synthesis is reverse direction phosphoramidite chemistry. In an embodiment of the invention each subset is subjected to a different nucleotide. In a further embodiment, one or more subsets receive a cocktail of two nucleotides. In an embodiment, each subset is subjected to a different canonical nucleotide.

The method provided by the invention contemplates a variety of embodiments wherein the bead is a microbead, a nanoparticle, or a macrobead. Similarly, the invention contemplates that the oligonucleotide sequence is a dinucleotide or trinucleotide.

The invention provides a method for simultaneously preparing a thousand or more nucleotide- or oligonucleotide-adorned beads wherein a uniform or near-uniform nucleotide or oligonucleotide sequence is synthesized upon any individual bead while a plurality of different nucleotide or oligonucleotide sequences are simultaneously synthesized on different beads, comprising: forming a mixture comprising a plurality of beads; separating the beads into subsets; extending the nucleotide or oligonucleotide sequence on the surface of the beads by adding an individual nucleotide via chemical synthesis; pooling the subsets of beads in (c) into a single common pool; repeating steps (b), (c) and (d) multiple times to produce a combinatorically large number of nucleotide or oligonucleotide sequences; and collecting the nucleotide- or oligonucleotide-adorned beads; performing polynucleotide synthesis on the surface of the plurality of beads in a pool-and-split synthesis, such that in each cycle of synthesis the beads are split into a plurality of subsets wherein each subset is subjected to different chemical reactions; repeating the pool-and-split synthesis multiple times.

In an embodiment of the invention, the nucleotide or oligonucleotide sequence on the surface of the bead is a molecular barcode. In an embodiment, the pool-and-split synthesis steps occur every 2 to 10 cycles, rather than every cycle. In an embodiment, the generated barcode contains built-in error correction. In another embodiment, the barcode ranges from 4 to 1000 nucleotides in length. In embodiment of the invention the polynucleotide synthesis is phosphoramidite synthesis. In a further embodiment, the polynucleotide synthesis is reverse direction phosphoramidite chemistry. In an embodiment of the invention each subset is subjected to a different nucleotide. In a further embodiment, one or more subsets receive a cocktail of two nucleotides. In an embodiment, each subset is subjected to a different canonical nucleotide.

The method provided by the invention contemplates a variety of embodiments wherein the bead is a microbead, a nanoparticle, or a macrobead. Similarly, the invention contemplates that the oligonucleotide sequence is a dinucleotide or trinucleotide.

The invention further provides an apparatus for creating a composite single-cell sequencing library via a microfluidic system, comprising: an oil-surfactant inlet comprising a filter and two carrier fluid channels, wherein said carrier fluid channel further comprises a resistor; an inlet for an analyte comprising a filter and two carrier fluid channels, wherein said carrier fluid channel further comprises a resistor; an inlet for mRNA capture microbeads and lysis reagent comprising a carrier fluid channel; said carrier fluid channels have a carrier fluid flowing therein at an adjustable and predetermined flow rate; wherein each said carrier fluid channels merge at a junction; and said junction being connected to a constriction for droplet pinch-off followed by a mixer, which connects to an outlet for drops.

In an embodiment of the apparatus, the analyte comprises a chemical reagent, a genetically perturbed cell, a protein, a drug, an antibody, an enzyme, a nucleic acid, an organelle like the mitochondrion or nucleus, a cell or any combination thereof. In an embodiment of the apparatus the analyte is a cell. In a further embodiment, the analyte is a mammalian cell. In another embodiment, the analyte of the apparatus is complex tissue. In a further embodiment, the cell is a brain cell. In an embodiment of the invention, the cell is a retina cell. In another embodiment the cell is a human bone marrow cell. In an embodiment, the cell is a host-pathogen cell. In an embodiment, the analyte is a nucleus from a cell.

In an embodiment of the apparatus the lysis reagent comprises an anionic surfactant such as sodium lauroyl sarcosinate, or a chaotropic salt such as guanidinium thiocyanate. In an embodiment of the apparatus the filter is consists of square PDMS posts; the filter on the cell channel consists of such posts with sides ranging between 125-135 µm with a separation of 70-100 mm between the posts. The filter on the oil-surfactant inlet comprises square posts of two sizes; one with sides ranging between 75-100 µm and a separation of 25-30 µm between them and the other with sides ranging between 40-50 µm and a separation of 10-15 µm. In an embodiment of the apparatus the resistor is serpentine having a length of 7000-9000 µm, width of 50-75 µm and depth of 100-150 mm. In an embodiment of the apparatus the channels have a length of 8000-12,000 µm for oil-surfactant inlet, 5000-7000 for analyte (cell) inlet, and 900-1200 µm for the inlet for microbead and lysis agent. All channels have a width of 125-250 mm, and depth of 100-150 mm. In another embodiment, the width of the cell channel is 125-250 µm and the depth is 100-150 µm. In an embodiment of the apparatus the mixer has a length of 7000-9000 µm, and a width of 110-140 µm with 35-45° zig-zigs every 150 µm. In an embodiment, the width of the mixer is 125 µm. In an embodiment of the apparatus the oil-surfactant is PEG Block Polymer, such as BIORAD™ QX200 Droplet Generation Oil. In an embodiment of the apparatus the carrier fluid is water-glycerol mixture.

A mixture comprising a plurality of microbeads adorned with combinations of the following elements: bead-specific oligonucleotide barcodes created by the methods provided; additional oligonucleotide barcode sequences which vary among the oligonucleotides on an individual bead and can therefore be used to differentiate or help identify those individual oligonucleotide molecules; additional oligonucleotide sequences that create substrates for downstream molecular-biological reactions, such as oligo-dT (for reverse transcription of mature mRNAs), specific sequences (for capturing specific portions of the transcriptome, or priming for DNA polymerases and similar enzymes), or random sequences (for priming throughout the transcriptome or genome). In an embodiment, the individual oligonucleotide molecules on the surface of any individual microbead contain all three of these elements, and the third element includes both oligo-dT and a primer sequence.

In another embodiment, a mixture comprising a plurality of microbeads, wherein said microbeads comprise the following elements: at least one bead-specific oligonucleotide barcode obtainable by the process outlined; at least one additional identifier oligonucleotide barcode sequence, which varies among the oligonucleotides on an individual bead, and thereby assisting in the identification and of the bead specific oligonucleotide molecules; optionally at least one additional oligonucleotide sequences, which provide substrates for downstream molecular-biological reactions. In another embodiment the mixture comprises at least one oligonucleotide sequences, which provide for substrates for downstream molecular-biological reactions. In a further embodiment the downstream molecular-biological reactions are for reverse transcription of mature mRNAs; capturing specific portions of the transcriptome, priming for DNA polymerases and/or similar enzymes; or priming throughout the transcriptome or genome. In a further embodiment the mixture the additional oligonucleotide sequence comprising a oligo-dT sequence. In another embodiment the mixture further comprises the additional oligonucleotide sequence comprises a primer sequence. In another embodiment the mixture further comprises the additional oligonucleotide sequence comprising a oligo-dT sequence and a primer sequence.

Examples of the labeling substance which may be employed include labeling substances known to those skilled in the art, such as fluorescent dyes, enzymes, coenzymes, chemiluminescent substances, and radioactive substances. Specific examples include radioisotopes (e.g., $^{32}$P, C, $^{125}$I, $^{3}$H, and $^{131}$I), fluorescein, rhodamine, dansyl chloride, umbelliferone, luciferase, peroxidase, alkaline phosphatase, 0-galactosidase, p-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'-disulphonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcoumarin (Coumaran 151); cyanine dyes; cyanosine; 4',6-diamidino-2-phenylindole (DAPI); 5'5"-dibromopyrogallolsulfonaphthalene (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolla Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double-stranded match hybridization complexes. The fluorescent label may be a perylene or a terrylene. In the alternative, the fluorescent label may be a fluorescent bar code.

In an advantageous embodiment, the label may be light sensitive, wherein the label is light-activated and/or light cleaves the one or more linkers to release the molecular cargo. The light-activated molecular cargo may be a major light-harvesting complex (LHCII). In another embodiment, the fluorescent label may induce free radical formation.

In an advantageous embodiment, agents may be uniquely labeled in a dynamic manner (see, e.g., U.S. provisional patent application Ser. No. 61/703,884 filed Sep. 21, 2012). The unique labels are, at least in part, nucleic acid in nature, and may be generated by sequentially attaching two or more detectable oligonucleotide tags to each other and each unique label may be associated with a separate agent. A detectable oligonucleotide tag may be an oligonucleotide that may be detected by sequencing of its nucleotide sequence and/or by detecting non-nucleic acid detectable moieties to which it may be attached.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the nonnucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, one or more other species may be associated with the tags. In particular, nucleic acids released by a lysed cell may be ligated to one or more tags. These may include, for example, chromosomal DNA, RNA transcripts, tRNA, mRNA, mitochondrial DNA, or the like. Such nucleic acids may be sequenced, in addition to sequencing the tags themselves, which may yield information about the nucleic acid profile of the cells, which can be associated with the tags, or the conditions that the corresponding droplet or cell was exposed to.

The invention described herein enables high throughput and high resolution delivery of reagents to individual emulsion droplets that may contain cells, organelles, nucleic acids, proteins, etc. through the use of monodisperse aqueous droplets that are generated by a microfluidic device as a water-in-oil emulsion. The droplets are carried in a flowing oil phase and stabilized by a surfactant. In one aspect single cells or single organelles or single molecules (proteins, RNA, DNA) are encapsulated into uniform droplets from an aqueous solution/dispersion. In a related aspect, multiple cells or multiple molecules may take the place of single cells or single molecules. The aqueous droplets of volume ranging from 1 pL to 10 nL work as individual reactors. Disclosed embodiments provide thousands of single cells in droplets which can be processed and analyzed in a single run.

To utilize microdroplets for rapid large-scale chemical screening or complex biological library identification, different species of microdroplets, each containing the specific chemical compounds or biological probes cells or molecular barcodes of interest, have to be generated and combined at the preferred conditions, e.g., mixing ratio, concentration, and order of combination.

Each species of droplet is introduced at a confluence point in a main microfluidic channel from separate inlet microfluidic channels. Preferably, droplet volumes are chosen by design such that one species is larger than others and moves at a different speed, usually slower than the other species, in the carrier fluid, as disclosed in U.S. Publication No. US 2007/0195127 and International Publication No. WO 2007/089541, each of which are incorporated herein by reference in their entirety. The channel width and length is selected such that faster species of droplets catch up to the slowest species. Size constraints of the channel prevent the faster moving droplets from passing the slower moving droplets resulting in a train of droplets entering a merge zone. Multi-step chemical reactions, biochemical reactions, or assay detection chemistries often require a fixed reaction time before species of different type are added to a reaction. Multi-step reactions are achieved by repeating the process multiple times with a second, third or more confluence points each with a separate merge point. Highly efficient and precise reactions and analysis of reactions are achieved when the frequencies of droplets from the inlet channels are matched to an optimized ratio and the volumes of the species are matched to provide optimized reaction conditions in the combined droplets.

Fluidic droplets may be screened or sorted within a fluidic system of the invention by altering the flow of the liquid containing the droplets. For instance, in one set of embodiments, a fluidic droplet may be steered or sorted by directing the liquid surrounding the fluidic droplet into a first channel, a second channel, etc. In another set of embodiments, pressure within a fluidic system, for example, within different channels or within different portions of a channel, can be controlled to direct the flow of fluidic droplets. For example, a droplet can be directed toward a channel junction including multiple options for further direction of flow (e.g., directed toward a branch, or fork, in a channel defining optional downstream flow channels). Pressure within one or more of the optional downstream flow channels can be controlled to direct the droplet selectively into one of the channels, and changes in pressure can be effected on the order of the time required for successive droplets to reach the junction, such that the downstream flow path of each successive droplet can be independently controlled. In one arrangement, the expansion and/or contraction of liquid reservoirs may be used to steer or sort a fluidic droplet into a channel, e.g., by causing directed movement of the liquid containing the fluidic droplet. In another embodiment, the expansion and/or contraction of the liquid reservoir may be combined with other flow-controlling devices and methods, e.g., as described herein. Non-limiting examples of devices able to cause the expansion and/or contraction of a liquid reservoir include pistons.

Key elements for using microfluidic channels to process droplets include: (1) producing droplet of the correct volume, (2) producing droplets at the correct frequency and (3) bringing together a first stream of sample droplets with a second stream of sample droplets in such a way that the frequency of the first stream of sample droplets matches the frequency of the second stream of sample droplets. Preferably, bringing together a stream of sample droplets with a stream of premade library droplets in such a way that the frequency of the library droplets matches the frequency of the sample droplets.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten pico-liter droplets is driven into an inlet channel on a microfluidic substrate with a drive fluid at a rate of 10,000 pico-liters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example if the nominal droplet volume is expected to be 10 pico-liters in the library, but varies from 9 to 11 pico-liters from library-to-library then a 10,000 pico-liter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

Combinations of surfactant(s) and oils must be developed to facilitate generation, storage, and manipulation of droplets to maintain the unique chemical/biochemical/biological environment within each droplet of a diverse library. Therefore, the surfactant and oil combination must (1) stabilize droplets against uncontrolled coalescence during the drop forming process and subsequent collection and storage, (2) minimize transport of any droplet contents to the oil phase and/or between droplets, and (3) maintain chemical and biological inertness with contents of each droplet (e.g., no adsorption or reaction of encapsulated contents at the oil-water interface, and no adverse effects on biological or chemical constituents in the droplets). In addition to the requirements on the droplet library function and stability, the surfactant-in-oil solution must be coupled with the fluid physics and materials associated with the platform. Specifically, the oil solution must not swell, dissolve, or degrade the materials used to construct the microfluidic chip, and the physical properties of the oil (e.g., viscosity, boiling point, etc.) must be suited for the flow and operating conditions of the platform.

Droplets formed in oil without surfactant are not stable to permit coalescence, so surfactants must be dissolved in the oil that is used as the continuous phase for the emulsion library. Surfactant molecules are amphiphilic—part of the molecule is oil soluble, and part of the molecule is water soluble. When a water-oil interface is formed at the nozzle of a microfluidic chip for example in the inlet module described herein, surfactant molecules that are dissolved in the oil phase adsorb to the interface. The hydrophilic portion of the molecule resides inside the droplet and the fluorophilic portion of the molecule decorates the exterior of the droplet. The surface tension of a droplet is reduced when the interface is populated with surfactant, so the stability of an emulsion is improved. In addition to stabilizing the droplets against coalescence, the surfactant should be inert to the contents of each droplet and the surfactant should not promote transport of encapsulated components to the oil or other droplets.

A droplet library may be made up of a number of library elements that are pooled together in a single collection (see, e.g., US Patent Publication No. 2010002241). Libraries may vary in complexity from a single library element to 1015 library elements or more. Each library element may be one or more given components at a fixed concentration. The element may be, but is not limited to, cells, organelles, virus, bacteria, yeast, beads, amino acids, proteins, polypeptides, nucleic acids, polynucleotides or small molecule chemical compounds. The element may contain an identifier such as a label. The terms "droplet library" or "droplet libraries" are also referred to herein as an "emulsion library" or "emulsion libraries." These terms are used interchangeably throughout the specification.

A cell library element may include, but is not limited to, hybridomas, B-cells, primary cells, cultured cell lines, cancer cells, stem cells, cells obtained from tissue (e.g., retinal or human bone marrow), peripheral blood mononuclear cell, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A variety of analytes may be contemplated for use with the foregoing Drop-Sequencing methods. Examples of cells which are contemplated are mammalian cells, however the invention contemplates a method for profiling host-pathogen cells. To characterize the expression of host-pathogen interactions it is important to grow the host and pathogen in the same cell without multiple opportunities of pathogen infection.

A bead based library element may contain one or more beads, of a given type and may also contain other reagents, such as antibodies, enzymes or other proteins. In the case where all library elements contain different types of beads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids.

Often it is desirable to have exactly one cell or nuclei per droplet with only a few droplets containing more than one cell or nuclei when starting with a plurality of cells or yeast or bacteria, engineered to produce variants on a protein. In some cases, variations from Poisson statistics may be achieved to provide an enhanced loading of droplets such that there are more droplets with exactly one cell per droplet and few exceptions of empty droplets or droplets containing more than one cell.

Examples of droplet libraries are collections of droplets that have different contents, ranging from beads, cells, nuclei, small molecules, DNA, primers, antibodies. Smaller droplets may be in the order of femtoliter (fL) volume drops, which are especially contemplated with the droplet dispensers. The volume may range from about 5 to about 600 fL. The larger droplets range in size from roughly 0.5 micron to 500 micron in diameter, which corresponds to about 1 pico liter to 1 nano liter. However, droplets may be as small as 5 microns and as large as 500 microns. Preferably, the droplets are at less than 100 microns, about 1 micron to about 100 microns in diameter. The most preferred size is about 20 to 40 microns in diameter (10 to 100 picoliters). The preferred properties examined of droplet libraries include osmotic pressure balance, uniform size, and size ranges.

The droplets comprised within the emulsion libraries of the present invention may be contained within an immiscible oil which may comprise at least one fluorosurfactant. In some embodiments, the fluorosurfactant comprised within immiscible fluorocarbon oil is a block copolymer consisting of one or more perfluorinated polyether (PFPE) blocks and one or more polyethylene glycol (PEG) blocks. In other embodiments, the fluorosurfactant is a triblock copolymer consisting of a PEG center block covalently bound to two PFPE blocks by amide linking groups. The presence of the fluorosurfactant (similar to uniform size of the droplets in the library) is critical to maintain the stability and integrity of the droplets and is also essential for the subsequent use of the droplets within the library for the various biological and chemical assays described herein. Fluids (e.g., aqueous fluids, immiscible oils, etc.) and other surfactants that may be utilized in the droplet libraries of the present invention are described in greater detail herein.

The present invention provides an emulsion library which may comprise a plurality of aqueous droplets within an immiscible oil (e.g., fluorocarbon oil) which may comprise at least one fluorosurfactant, wherein each droplet is uniform in size and may comprise the same aqueous fluid and may comprise a different library element. The present invention also provides a method for forming the emulsion library which may comprise providing a single aqueous fluid which may comprise different library elements, encapsulating each library element into an aqueous droplet within an immiscible fluorocarbon oil which may comprise at least one fluorosurfactant, wherein each droplet is uniform in size and may comprise the same aqueous fluid and may comprise a different library element, and pooling the aqueous droplets within an immiscible fluorocarbon oil which may comprise at least one fluorosurfactant, thereby forming an emulsion library.

For example, in one type of emulsion library, all different types of elements (e.g., cells or beads), may be pooled in a single source contained in the same medium. After the initial pooling, the cells or beads are then encapsulated in droplets to generate a library of droplets wherein each droplet with a different type of bead or cell is a different library element. The dilution of the initial solution enables the encapsulation process. In some embodiments, the droplets formed will either contain a single cell or bead or will not contain anything, i.e., be empty. In other embodiments, the droplets formed will contain multiple copies of a library element. The cells or beads being encapsulated are generally variants on the same type of cell or bead. In one example, the cells may comprise cancer cells of a tissue biopsy, and each cell type is encapsulated to be screened for genomic data or against different drug therapies. Another example is that 1011 or 1015 different type of bacteria; each having a different plasmid spliced therein, are encapsulated. One example is a bacterial library where each library element grows into a clonal population that secretes a variant on an enzyme.

In another example, the emulsion library may comprise a plurality of aqueous droplets within an immiscible fluorocarbon oil, wherein a single molecule may be encapsulated, such that there is a single molecule contained within a droplet for every 20-60 droplets produced (e.g., 20, 25, 30, 35, 40, 45, 50, 55, 60 droplets, or any integer in between). Single molecules may be encapsulated by diluting the solution containing the molecules to such a low concentration that the encapsulation of single molecules is enabled. In one specific example, a LacZ plasmid DNA was encapsulated at a concentration of 20 fM after two hours of incubation such that there was about one gene in 40 droplets, where 10 µm droplets were made at 10 kHz per second. Formation of these libraries rely on limiting dilutions.

The present invention also provides an emulsion library which may comprise at least a first aqueous droplet and at least a second aqueous droplet within a fluorocarbon oil which may comprise at least one fluorosurfactant, wherein the at least first and the at least second droplets are uniform in size and comprise a different aqueous fluid and a different library element. The present invention also provides a method for forming the emulsion library which may comprise providing at least a first aqueous fluid which may comprise at least a first library of elements, providing at least a second aqueous fluid which may comprise at least a second library of elements, encapsulating each element of said at least first library into at least a first aqueous droplet within an immiscible fluorocarbon oil which may comprise at least one fluorosurfactant, encapsulating each element of said at least second library into at least a second aqueous droplet within an immiscible fluorocarbon oil which may comprise at least one fluorosurfactant, wherein the at least first and the at least second droplets are uniform in size and comprise a different aqueous fluid and a different library element, and pooling the at least first aqueous droplet and the at least second aqueous droplet within an immiscible fluorocarbon oil which may comprise at least one fluorosurfactant thereby forming an emulsion library.

One of skill in the art will recognize that methods and systems of the invention are not limited to any particular type of sample, and methods and systems of the invention may be used with any type of organic, inorganic, or biological molecule (see, e.g, US Patent Publication No. 20120122714). In particular embodiments the sample may include nucleic acid target molecules. Nucleic acid molecules may be synthetic or derived from naturally occurring sources. In one embodiment, nucleic acid molecules may be isolated from a biological sample containing a variety of other components, such as proteins, lipids and non-template nucleic acids. Nucleic acid target molecules may be obtained from any cellular material, obtained from an animal, plant, bacterium, fungus, or any other cellular organism. In certain embodiments, the nucleic acid target molecules may be obtained from a single cell. Biological samples for use in the present invention may include viral particles or preparations. Nucleic acid target molecules may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid target molecules may also be isolated from cultured cells, such as a primary cell culture or a cell line. The cells or tissues from which target nucleic acids are obtained may be infected with a virus or other intracellular pathogen. A sample may also be total RNA extracted from a biological specimen, a cDNA library, viral, or genomic DNA. Tissues may be freshly dissected, frozen tissue, or fixed tissue.

Generally, nucleic acid may be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loop-structures).

Nucleic acid obtained from biological samples typically may be fragmented to produce suitable fragments for analysis. Target nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydroshear instrument. Generally, individual nucleic acid target molecules may be from about 40 bases to about 40 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent may be up to an amount where the detergent remains soluble in the solution. In one embodiment, the concentration of the detergent is between 0.1% to about 2%. The detergent, particularly a mild one that is nondenaturing, may act to solubilize the sample. Detergents may be ionic or nonionic. Examples of nonionic detergents include triton, such as the Triton™ X series (Triton™ X-100 t-Oct-C6H4—(OCH2—CH2)xOH, x=9-10, Triton™ X-100R, Triton™ X-114 x=7-8), octyl glucoside, polyoxyethylene(9) dodecyl ether, digitonin, IGEPAL™ CA630 octylphenyl polyethylene glycol, n-octyl-beta-D-glucopyranoside (betaOG), n-dodecyl-beta, Tween™. 20 polyethylene glycol sorbitan monolaurate, Tween™ 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

Size selection of the nucleic acids may be performed to remove very short fragments or very long fragments. The nucleic acid fragments may be partitioned into fractions which may comprise a desired number of fragments using any suitable method known in the art. Suitable methods to limit the fragment size in each fragment are known in the art. In various embodiments of the invention, the fragment size is limited to between about 10 and about 100 Kb or longer.

In another embodiment, the sample includes individual target proteins, protein complexes, proteins with translational modifications, and protein/nucleic acid complexes. Protein targets include peptides, and also include enzymes, hormones, structural components such as viral capsid proteins, and antibodies. Protein targets may be synthetic or derived from naturally-occurring sources. In one embodiment of the invention protein targets are isolated from biological samples containing a variety of other components including lipids, non-template nucleic acids, and nucleic acids. In certain embodiments, protein targets may be obtained from an animal, bacterium, fungus, cellular organism, and single cells. Protein targets may be obtained directly from an organism or from a biological sample obtained from the organism, including bodily fluids such as blood, urine, cerebrospinal fluid, seminal fluid, saliva, sputum, stool and tissue. Protein targets may also be obtained from cell and tissue lysates and biochemical fractions. An individual protein is an isolated polypeptide chain. A protein complex includes two or polypeptide chains. Samples may include proteins with post translational modifications including but not limited to phosphorylation, methionine oxidation, deamidation, glycosylation, ubiquitination, carbamylation, S-carboxymethylation, acetylation, and methylation. Protein/nucleic acid complexes include cross-linked or stable protein-nucleic acid complexes.

Extraction or isolation of individual proteins, protein complexes, proteins with translational modifications, and protein/nucleic acid complexes is performed using methods known in the art.

Methods of the invention involve forming sample droplets. The droplets are aqueous droplets that are surrounded by an immiscible carrier fluid. Methods of forming such droplets are shown for example in Link et al. (U.S. patent application numbers 2008/0014589, 2008/0003142, and 2010/0137163), Stone et al. (U.S. Pat. No. 7,708,949 and U.S. patent application number 2010/0172803), Anderson et al. (U.S. Pat. No. 7,041,481 and which reissued as RE41, 780) and European publication number EP2047910 to Raindance Technologies Inc. The content of each of which is incorporated by reference herein in its entirety.

The sample fluid may typically comprise an aqueous buffer solution, such as ultrapure water (e.g., 18 mega-ohm resistivity, obtained, for example by column chromatography), 10 mM Tris HCl and 1 mM EDTA (TE) buffer, phosphate buffer saline (PBS) or acetate buffer. Any liquid or buffer that is physiologically compatible with nucleic acid molecules can be used. The carrier fluid may include one that is immiscible with the sample fluid. The carrier fluid can be a non-polar solvent, decane (e.g., tetradecane or hexadecane), fluorocarbon oil, silicone oil, an inert oil such as hydrocarbon, or another oil (for example, mineral oil).

In certain embodiments, the carrier fluid may contain one or more additives, such as agents which reduce surface tensions (surfactants). Surfactants can include Tween, Span, fluorosurfactants, and other agents that are soluble in oil relative to water. In some applications, performance is improved by adding a second surfactant to the sample fluid. Surfactants can aid in controlling or optimizing droplet size, flow and uniformity, for example by reducing the shear force needed to extrude or inject droplets into an intersecting channel. This can affect droplet volume and periodicity, or the rate or frequency at which droplets break off into an intersecting channel. Furthermore, the surfactant can serve to stabilize aqueous emulsions in fluorinated oils from coalescing.

In certain embodiments, the droplets may be surrounded by a surfactant which stabilizes the droplets by reducing the surface tension at the aqueous oil interface. Preferred surfactants that may be added to the carrier fluid include, but are not limited to, surfactants such as sorbitan-based carboxylic acid esters (e.g., the "Span" surfactants, Fluka Chemika), including sorbitan monolaurate (Span 20), sorbitan monopalmitate (Span 40), sorbitan monostearate (Span 60) and sorbitan monooleate (Span 80), and perfluorinated polyethers (e.g., DuPont Krytox 157 FSL, FSM, and/or FSH). Other non-limiting examples of non-ionic surfactants which may be used include polyoxyethylenated alkylphenols (for example, nonyl-, p-dodecyl-, and dinonylphenols), polyoxyethylenated straight chain alcohols, polyoxyethylenated polyoxypropylene glycols, polyoxyethylenated mercaptans, long chain carboxylic acid esters (for example, glyceryl and polyglyceryl esters of natural fatty acids, propylene glycol, sorbitol, polyoxyethylenated sorbitol esters, polyoxyethylene glycol esters, etc.) and alkanolamines (e.g., diethanolamine-fatty acid condensates and isopropanolamine-fatty acid condensates).

In certain embodiments, the carrier fluid may be caused to flow through the outlet channel so that the surfactant in the carrier fluid coats the channel walls. In one embodiment, the fluorosurfactant can be prepared by reacting the perfluorinated polyether DuPont Krytox 157 FSL, FSM, or FSH with aqueous ammonium hydroxide in a volatile fluorinated solvent. The solvent and residual water and ammonia can be removed with a rotary evaporator. The surfactant can then be dissolved (e.g., 2.5 wt %) in a fluorinated oil (e.g., Fluorinert (3M)), which then serves as the carrier fluid.

Activation of sample fluid reservoirs to produce regent droplets is now described. The disclosed invention is based on the concept of dynamic reagent delivery (e.g., combinatorial barcoding) via an on demand capability. The on demand feature may be provided by one of a variety of technical capabilities for releasing delivery droplets to a primary droplet, as described herein.

An aspect in developing this device will be to determine the flow rates, channel lengths, and channel geometries. Once these design specifications are established, droplets containing random or specified reagent combinations can be generated on demand and merged with the "reaction chamber" droplets containing the samples/cells/substrates of interest.

By incorporating a plurality of unique tags into the additional droplets and joining the tags to a solid support designed to be specific to the primary droplet, the conditions that the primary droplet is exposed to may be encoded and recorded. For example, nucleic acid tags can be sequentially ligated to create a sequence reflecting conditions and order of same. Alternatively, the tags can be added independently appended to solid support. Non-limiting examples of a dynamic labeling system that may be used to bioinformatically record information can be found at US Provisional Patent Application entitled "Compositions and Methods for Unique Labeling of Agents" filed Sep. 21, 2012 and Nov. 29, 2012. In this way, two or more droplets may be exposed to a variety of different conditions, where each time a droplet is exposed to a condition, a nucleic acid encoding the condition is added to the droplet each ligated together or to a unique solid support associated with the droplet such that, even if the droplets with different histories are later combined, the conditions of each of the droplets are remain available through the different nucleic acids. Non-limiting examples of methods to evaluate response to exposure to a plurality of conditions can be found at US Provisional Patent Application entitled "Systems and Methods for Droplet Tagging" filed Sep. 21, 2012.

Applications of the disclosed device may include use for the dynamic generation of molecular barcodes (e.g., DNA oligonucleotides, fluorophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single-cell (or single molecule) level and in a cost effective manner. Disclosed embodiments provide a high throughput and high resolution delivery of reagents to individual emulsion droplets that may contain cells, nucleic acids, proteins, etc. through the use of monodisperse aqueous droplets that are generated one by one in a microfluidic chip as a water-in-oil emulsion. Hence, the invention proves advantageous over prior art systems by being able to dynamically track individual cells and droplet treatments/combinations during life cycle experiments. Additional advantages of the disclosed invention provides an ability to create a library of emulsion droplets on demand with the further capability of manipulating the droplets through the disclosed process(es). Disclosed embodiments may, thereby, provide dynamic tracking of the droplets and create a history of droplet deployment and application in a single-cell based environment. In certain example embodiments, the methods disclosed herein may be used to conduct pooled CRISPR screening such as that disclosed in Datlinger et al. bioRXiv dx.doi.org/10.1101/083774.

Droplet generation and deployment is produced via a dynamic indexing strategy and in a controlled fashion in accordance with disclosed embodiments of the present invention. Disclosed embodiments of the microfluidic device described herein provides the capability of microdroplets that be processed, analyzed and sorted at a highly efficient rate of several thousand droplets per second, providing a powerful platform which allows rapid screening of millions of distinct compounds, biological probes, proteins or cells either in cellular models of biological mechanisms of disease, or in biochemical, or pharmacological assays.

A plurality of biological assays as well as biological synthesis are contemplated for the present invention.

In an advantageous embodiment, polymerase chain reactions (PCR) are contemplated (see, e.g., US Patent Publication No. 20120219947). Methods of the invention may be used for merging sample fluids for conducting any type of chemical reaction or any type of biological assay. In certain embodiments, methods of the invention are used for merging sample fluids for conducting an amplification reaction in a droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. (1991) PNAS 88:189-193; Barany F. (1991) PCR Methods and Applications 1:5-16), ligase detection reaction (Barany F. (1991) PNAS 88:189-193), strand displacement amplification and restriction fragments length polymorphism, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double-stranded target sequence.

To effect amplification, primers are annealed to their complementary sequence within the target molecule. Following annealing, the primers are extended with a polymerase so as to form a new pair of complementary strands. The steps of denaturation, primer annealing and polymerase extension may be repeated many times (i.e., denaturation, annealing and extension constitute one cycle; there may be numerous cycles) to obtain a high concentration of an amplified segment of a desired target sequence. The length of the amplified segment of the desired target sequence is determined by relative positions of the primers with respect to each other, and therefore, this length is a controllable parameter.

Methods for performing PCR in droplets are shown for example in Link et al. (U.S. Patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc. The content of each of which is incorporated by reference herein in its entirety.

The first sample fluid contains nucleic acid templates. Droplets of the first sample fluid are formed as described above. Those droplets will include the nucleic acid templates. In certain embodiments, the droplets will include only a single nucleic acid template, and thus digital PCR may be conducted. The second sample fluid contains reagents for the PCR reaction. Such reagents generally include Taq polymerase, deoxynucleotides of type A, C, G and T, magnesium chloride, and forward and reverse primers, all suspended within an aqueous buffer. The second fluid also includes detectably labeled probes for detection of the amplified target nucleic acid, the details of which are discussed below. This type of partitioning of the reagents between the two sample fluids is not the only possibility. In certain embodiments, the first sample fluid will include some or all of the reagents necessary for the PCR whereas the second sample fluid will contain the balance of the reagents necessary for the PCR together with the detection probes.

Primers may be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers may also be obtained from commercial sources such as Operon Technologies, Amersham Pharmacia Biotech, Sigma, and Life Technologies. The primers may have an identical melting temperature. The lengths of the primers may be extended or shortened at the 5' end or the 3' end to produce primers with desired melting temperatures. Also, the annealing position of each primer pair may be designed such that the sequence and, length of the primer pairs yield the desired melting temperature. The simplest equation for determining the melting temperature of primers smaller than 25 base pairs is the Wallace Rule ($Td=2(A+T)+4(G+C)$). Computer programs may also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

A droplet containing the nucleic acid is then caused to merge with the PCR reagents in the second fluid according to methods of the invention described above, producing a droplet that includes Taq polymerase, deoxynucleotides of type A, C, G and T, magnesium chloride, forward and reverse primers, detectably labeled probes, and the target nucleic acid.

Once mixed droplets have been produced, the droplets are thermal cycled, resulting in amplification of the target nucleic acid in each droplet. In certain embodiments, the droplets are flowed through a channel in a serpentine path between heating and cooling lines to amplify the nucleic acid in the droplet. The width and depth of the channel may be adjusted to set the residence time at each temperature, which may be controlled to anywhere between less than a second and minutes.

In certain embodiments, the three temperature zones are used for the amplification reaction. The three temperature zones are controlled to result in denaturation of double-stranded nucleic acid (high temperature zone), annealing of primers (low temperature zones), and amplification of single-stranded nucleic acid to produce double-stranded nucleic acids (intermediate temperature zones). The temperatures within these zones fall within ranges well known in the art for conducting PCR reactions. See for example, Sambrook et al. (Molecular Cloning, A Laboratory Manual, 3rd edition, Cold Spring Harbor Laboratory Press, Cold Spring Harbor, N.Y., 2001).

In certain embodiments, the three temperature zones are controlled to have temperatures as follows: 95° C. (TH), 55° C. (TL), 72° C. (TM). The prepared sample droplets flow through the channel at a controlled rate. The sample droplets first pass the initial denaturation zone (TH) before thermal cycling. The initial preheat is an extended zone to ensure that nucleic acids within the sample droplet have denatured successfully before thermal cycling. The requirement for a preheat zone and the length of denaturation time required is dependent on the chemistry being used in the reaction. The samples pass into the high temperature zone, of approximately 95° C., where the sample is first separated into single-stranded DNA in a process called denaturation. The sample then flows to the low temperature, of approximately 55° C., where the hybridization process takes place, during which the primers anneal to the complementary sequences of the sample. Finally, as the sample flows through the third medium temperature, of approximately 72° C., the polymerase process occurs when the primers are extended along the single strand of DNA with a thermostable enzyme.

The nucleic acids undergo the same thermal cycling and chemical reaction as the droplets pass through each thermal cycle as they flow through the channel. The total number of cycles in the device is easily altered by an extension of thermal zones. The sample undergoes the same thermal cycling and chemical reaction as it passes through N amplification cycles of the complete thermal device.

In other embodiments, the temperature zones are controlled to achieve two individual temperature zones for a PCR reaction. In certain embodiments, the two temperature zones are controlled to have temperatures as follows: 95° C. (TH) and 60° C. (TL). The sample droplet optionally flows through an initial preheat zone before entering thermal cycling. The preheat zone may be important for some chemistry for activation and also to ensure that double-stranded nucleic acid in the droplets is fully denatured before the thermal cycling reaction begins. In an exemplary embodiment, the preheat dwell length results in approximately 10 minutes preheat of the droplets at the higher temperature.

The sample droplet continues into the high temperature zone, of approximately 95° C., where the sample is first separated into single-stranded DNA in a process called denaturation. The sample then flows through the device to the low temperature zone, of approximately 60° C., where the hybridization process takes place, during which the primers anneal to the complementary sequences of the sample. Finally the polymerase process occurs when the primers are extended along the single strand of DNA with a thermostable enzyme. The sample undergoes the same thermal cycling and chemical reaction as it passes through each thermal cycle of the complete device. The total number of cycles in the device is easily altered by an extension of block length and tubing.

After amplification, droplets may be flowed to a detection module for detection of amplification products. The droplets may be individually analyzed and detected using any methods known in the art, such as detecting for the presence or amount of a reporter. Generally, the detection module is in communication with one or more detection apparatuses. The detection apparatuses may be optical or electrical detectors or combinations thereof. Examples of suitable detection apparatuses include optical waveguides, microscopes, diodes, light stimulating devices, (e.g., lasers), photo multiplier tubes, and processors (e.g., computers and software), and combinations thereof, which cooperate to detect a signal representative of a characteristic, marker, or reporter, and to determine and direct the measurement or the sorting action at a sorting module. Further description of detection modules and methods of detecting amplification products in droplets are shown in Link et al. (U.S. patent application numbers 2008/0014589, 2008/0003142, and 2010/0137163) and European publication number EP2047910 to Raindance Technologies Inc.

In another embodiment, examples of assays are ELISA assays (see, e.g., US Patent Publication No. 20100022414). The present invention provides another emulsion library which may comprise a plurality of aqueous droplets within an immiscible fluorocarbon oil which may comprise at least one fluorosurfactant, wherein each droplet is uniform in size and may comprise at least a first antibody, and a single element linked to at least a second antibody, wherein said first and second antibodies are different. In one example, each library element may comprise a different bead, wherein each bead is attached to a number of antibodies and the bead is encapsulated within a droplet that contains a different antibody in solution. These antibodies may then be allowed to form "ELISA sandwiches," which may be washed and prepared for a ELISA assay. Further, these contents of the droplets may be altered to be specific for the antibody contained therein to maximize the results of the assay.

In another embodiment, single-cell assays are also contemplated as part of the present invention (see, e.g., Ryan et al., Biomicrofluidics 5, 021501 (2011) for an overview of applications of microfluidics to assay individual cells). A single-cell assay may be contemplated as an experiment that quantifies a function or property of an individual cell when the interactions of that cell with its environment may be controlled precisely or may be isolated from the function or property under examination. The research and development of single-cell assays is largely predicated on the notion that genetic variation causes disease and that small subpopulations of cells represent the origin of the disease. Methods of assaying compounds secreted from cells, subcellular components, cell-cell or cell-drug interactions as well as methods of patterning individual cells are also contemplated within the present invention In other embodiments, chemical prototyping and synthetic chemical reactions are also contemplated within the methods of the invention.

In certain embodiments, nucleic acids are labeled with a nucleoside analogue. The nucleoside analogue may be any nucleoside analogue known in the art or developed after the filing of the present invention that is incorporated into replicated DNA and can be detectable by a label. The label may be incorporated into the nucleoside analogue or may include a labeling step after incorporation into DNA with a detectable label. In preferred embodiments, the label is a fluorescent label. In certain embodiments, the nucleoside analogue may be EdU (5-ethynyl-2'-deoxyuridine) or BrdU (5-bromo-2'-deoxyuridine).

In one embodiment of the invention, the method comprises obtaining at least one section from one or more tissue samples. Any suitable tissue sample can be used in the methods described herein. For example, the tissue can be epithelium, muscle, organ tissue, nerve tissue, tumor tissue, and combinations thereof. Samples of tissue can be obtained by any standard means (e.g., biopsy, core puncture, dissection, and the like, as will be appreciated by a person of skill in the art). At least one section may be labeled with a histological stain, to produce a histologically stained section. As used in the invention described herein, histological stains can be any standard stain as appreciated in the art, including but not limited to, alcian blue, Fuchsin, haematoxylin and eosin (H&E), Masson trichrome, toluidine blue, Wright's/Giemsa stain, and combinations thereof. As will be appreciated by a person of skill in the art, traditional histological stains are not fluorescent. At least one other section may be labeled with at least one fluorescently labeled reagent to produce a fluorescently labeled section. As used in the invention described herein, the panel of fluorescently labeled reagents comprises a number of reagents, such as fluorescently labeled antibodies, fluorescently labeled peptides, fluorescently labeled polypeptides, fluorescently labeled aptamers, fluorescently labeled oligonucleotides (e.g. nucleic acid probes, DNA, RNA, cDNA, PNA, and the like), fluorescently labeled chemicals and fluorescent chemicals (e.g., Hoechst 33342, propidium iodide, Draq-5, Nile Red, fluorescently labeled phalloidin), and combinations thereof. Each fluorescently labeled reagent is specific for at least one biomarker. As used herein, a "biomarker" is a molecule which provides a measure of cellular and/or tissue function. For example, and without limitation, a biomarker can be the measure of receptor expression levels, (e.g., estrogen receptor expression levels, Her2/neu expression); transcription factor activation; location or amount or activity of a protein, polynucleotide, organelle, and the like; the phosphorylation status of a protein, etc. In one embodiment, a biomarker is a nucleic acid (e.g., DNA, RNA, including micro RNAs, snRNAs, mRNA, rRNA, etc.), a receptor, a cell membrane antigen, an intracellular antigen, and extracellular antigen, a signaling molecule, a protein, and the like. In one embodiment of the invention, a panel of fluorescently labeled reagents detects at least about four different biomarkers. In another embodiment of the invention, a panel of fluorescently labeled reagents detects at least about four to about six, to about ten, to about twelve different biomarkers or more. In a further embodiment, each fluorescently labeled reagent has different fluorescent properties, which are sufficient to distinguish the different fluorescently labeled reagents in the panel.

A single biomarker can provide a read-out of more than one feature. For example, Hoechst dye detects DNA, which is an example of a biomarker. A number of features can be identified by the Hoechst dye in the tissue sample such as nucleus size, cell cycle stage, number of nuclei, presence of apoptotic nuclei, etc. In one embodiment of the invention, the imaging procedures are automated.

In one embodiment of the invention, the one or more tissue samples are isolated from one or more animals. For example, in one embodiment, the one or more animals are one or more rodents, preferably a mouse. The tissue may be isolated from a human subject. In certain embodiments tissues are isolated post mortem. In a particular embodiment, one or more tissue samples are isolated from an animal at one or more time points.

Methods of dissecting tissues from any organism are well known in the art. One method that may be utilized according to the present invention may be microdissection. Laser Capture Microdissection (LCM) enables separation of clusters of cells or even individual cells of interest from a background of millions of other cells. The collected cells can be directly visualized to verify their identity and purity. LCM is used to select small clusters of cells of interest from frozen sections of tissue by embedding them in a transfer film, e.g., a thermoplastic polymer. An example of a suitable thermoplastic polymer is ethylene vinyl acetate (EVA). The general methods of LCM are well known. See, e.g., U.S. Pat. Nos. 5,985,085; 5,859,699; and 5,843,657; as well as Suarez-Quian et al., "Laser Capture Microdissection of Single Cells from Complex Tissues," BioTechniques, Vol. 26, pages 328-335 (1999); Simone et al., "Laser-capture microdissection: opening the microscopic frontier to molecular analysis," TIG, Vol. 14, pages 272-276 (1998); and Bonner et al., "Laser Capture Microdissection: Molecular Analysis of Tissue," Science, Vol. 278, pages 1481-1483 (1997).

LCM is a process by which cells and portions of biological tissue samples are acquired directly from tissue sections mounted on glass slides or other solid surfaces. Once the cells or tissue portions of interest (tissue targets) are located in the sample, a laser is focused over the tissue targets. When the laser is fired, the thin-film located directly above the tissue targets melts, flows down and adheres to the tissue targets. The tissue targets are now stabilized and ready for molecular analysis.

The present may also be performed on tissue samples isolated from transgenic animals, such as mice. The animal may express a genome editing system such as described in "In vivo interrogation of gene function in the mammalian brain using CRISPR-Cas9" Swiech L., et al., Nat Biotechnol October 19. (2014). The animal may be xenograft. Xenotransplantation of tumor cells into immunocompromised mice is a research technique frequently used in pre-clinical oncology research. The tissue may express a transgene for isolating tissue specifically from a tumor. The tissue may be labeled with a nucleoside analogue in order to isolate cells of a developmental stage.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

Applicants have developed methods of performing a high-throughput single-nucleus isolation and RNA-Seq method compatible with fresh, frozen, or fixed tissue (Nucseq). The uniform shape and fixation of the isolated nuclei (FIG. 1A) combined with nuclei labeling (FIG. 5) enables enrichment of rare cell populations by fluorescent-activated cell sorting (FACS). The method was further developed for temporal analysis of dividing cells by addition of unbiased labeling with 5-ethynyl-2'-deoxyuridine (EdU), which is incorporated into the DNA of dividing cells (8), and using Click-IT to fluorescently tag the isolated EdU labeled nuclei, which can be readily captured by FACS (FIG. 5) (Div-seq).

Figure 6:
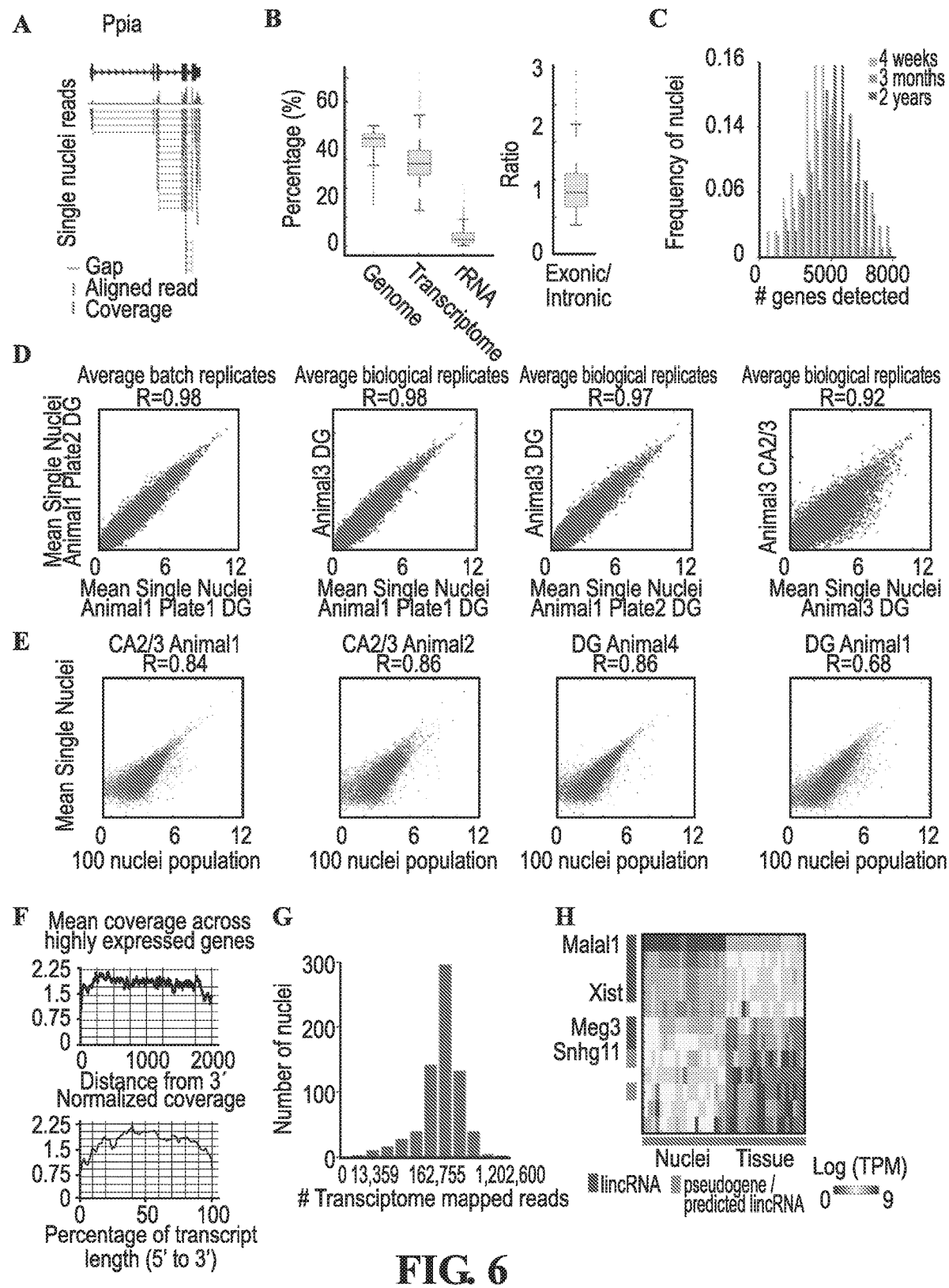
FIG. 6A-6H: Quality measurements of Nuc-Seq libraries. (A) Nuc-Seq detects full-length, spliced transcripts. Alignments of individual spliced reads from one single nucleus at the Ppia genomic locus. Top track: exons/introns, thick and thin lines (as in FIG. 1C). Grey bar: individual read, green line: gapped alignment. (B) Mapping rates of Nuc-Seq data. Left: Box plots showing the mapping rates to the genome, transcriptome, and rRNA. In box plots, the median (red), 75% and 25% quantile (box), error bars (dashed lines), and outliers (red dots). Right: Box plots showing the ratio of the number of reads mapped to introns and exons in Nuc-Seq libraries. (C) Nuc-Seq detects similar number of genes across animal ages, 4 weeks, 3 months and 2 years old (detected gene defined as log(TPM+1)>1.1). (D) Average of dentate gyrus (DG) and CA2/3 Nuc-Seq data correlates between replicates. Scatter plots showing comparison between average of single nuclei across technical and biological replicates. Data is shown in log(TPM+1). Spearman correlation between replicates (R), top. (E) Average of Nuc-Seq data correlates with population samples. Scatter plots showing comparison between average of single nuclei (Y axis) to populations of 100 nuclei (X axis). (F) 3' and 5' bias. Top: Mean read coverage across highly expressed genes per distance from the 3' of the gene. Showing constant coverage with a decrease around 2000 bp from the 3' end. Bottom: Mean read coverage throughout the transcripts, averaged per percentage of the transcript length (3' to 5'). (G) Distribution of number of reads mapped to the transcriptome per Nuc-Seq library. (H) Nuc-Seq libraries are enriched for long non-coding RNAs (lincRNAs). Heatmap showing differentially expressed genes between Nuc-Seq on population of nuclei (columns, pink) and tissue RNA-Seq (columns, blue). t-test FDR q-value<0.05 with log-ratio>1, mean log (TPM)>2 in at least one condition, 21 samples per condition. Left: colorbar showing the classification of genes as lincRNAs (green) and pseudogene/predicted lincRNA (orange). Names of known nuclear localized lincRNAs are marked (left).

Earlier studies have shown the feasibility of single neuronal nuclei RNA-seq (9-11), however, it was previously unclear whether the type and complexity of nuclear mRNA could be effectively used for sensitive classification of cell types and states in the CNS on a large scale. Furthermore, given the relative low total amount and non-uniform distribution of RNA in neurons (nuclei, soma, axons, and dendrites), analysis of nuclei can introduce biases. Applicants thus first tested nuclei RNA-Seq (Nuc-Seq) in bulk. Comparing RNA profiles of bulk tissue and populations of nuclei from the hippocampus dentate gyrus (DG) showed remarkable agreement, with similar RNA complexity and profiles (FIG. 1B, in agreement with the previous observations (9)). Differential expression analysis shows that nuclear RNA enriches for long non-coding RNAs (FIG. 6). Thus, nuclear RNA contains as much information as tissue RNA, suggesting nuclear RNA-Seq does not introduce substantial biological biases.

Figure 7:
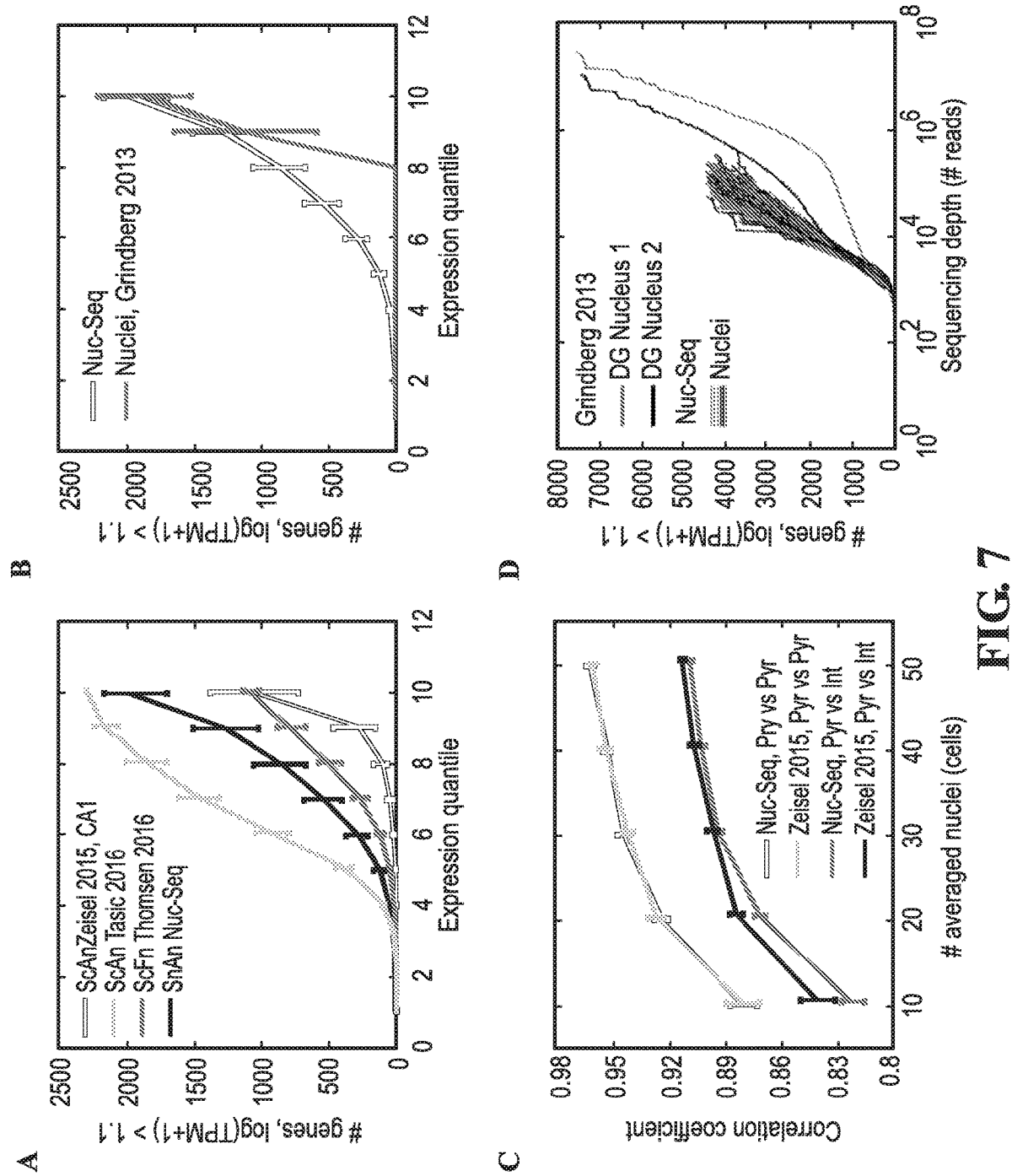
FIG. 7A-7D: Comparison of Nuc-Seq and single-cell RNA-Seq. (A) Nuc-Seq detects more genes than single-cell RNA-Seq across wide expression range. Shown is the distribution of number of genes detected (Y axis, log(TPM+1)>1.1) per nucleus for Nuc-Seq and per cell for Zeisel 2015 (only CA1 neurons) [50], Tasic 2016 [86], and Thomsen 2016 [87] across expression quantiles (X axis). A different threshold (X axis, TPM>1.1) was used in the calculation of number of genes detected for Zeisel 2015, which used unique molecular identifier (UMI) counts. ScAn: Single-cell sequencing of adult neuron; ScFn: Single-cell sequencing of fetal neuron. Error bar: 75% and 25% quantile. (B) Nuc-Seq detects more genes than previously reported single nuclei RNA-Seq (ref) across wide expression range. (C) Transcriptional profiles between different cell types are more distinct in Nuc-Seq than in single-cell RNA-Seq [50]. Plots showing Spearman correlation coefficients (Y axis) between two subsets of averaged pyramidal neurons (Pyr) or between subsets of averaged pyramidal neurons (Pyr) and averaged GABAergic interneurons (Int). A subset of neurons are first randomly sampled from Nuc-Seq and single-cell RNA-Seq. Then Spearman correlation is calculated between the averages of the subsets (see Materials and Methods). (D) Nuc-Seq has significantly improved complexity compared to the previously reported single nuclei RNA-Seq [88]. Shown are rarefaction curves of previously reported two single nuclei RNA-Seq libraries and curves of Nuc-Seq libraries.

Next, Applicants analyzed 1,682 single nuclei from four hippocampal anatomical subregions (DG, CA1, CA2 and CA3) microdissected from adult mice, including genetically labeled and sorted GABAergic neurons nuclei that are of low abundance (~10% of total neuronal population (12), FIG. 5). Nuc-Seq detected 5,100 expressed genes per nucleus on average (FIG. 1C-D), with comparable quality metrics to single-cell (non-neuron) RNA-Seq libraries (FIG. 6) and better library complexity (1.9-fold on average) compared to published single neuron RNA-Seq data (1, 3, 4), across a wide range of expression levels (FIG. 1D, FIG. 7). The range of transcripts detected was significantly improved compared to that of previously analyzed single nuclei (9) (two nuclei, FIG. 7). Finally, the complexity of Nuc-Seq libraries were similar in young (1 month), adult (3 months), and old (2 years) mice (FIG. 6), demonstrating robustness across animal ages. Thus, Nuc-Seq generated high quality data, exceeding the sensitivity of current single neuron RNA-seq.

Example 2

Figure 9:
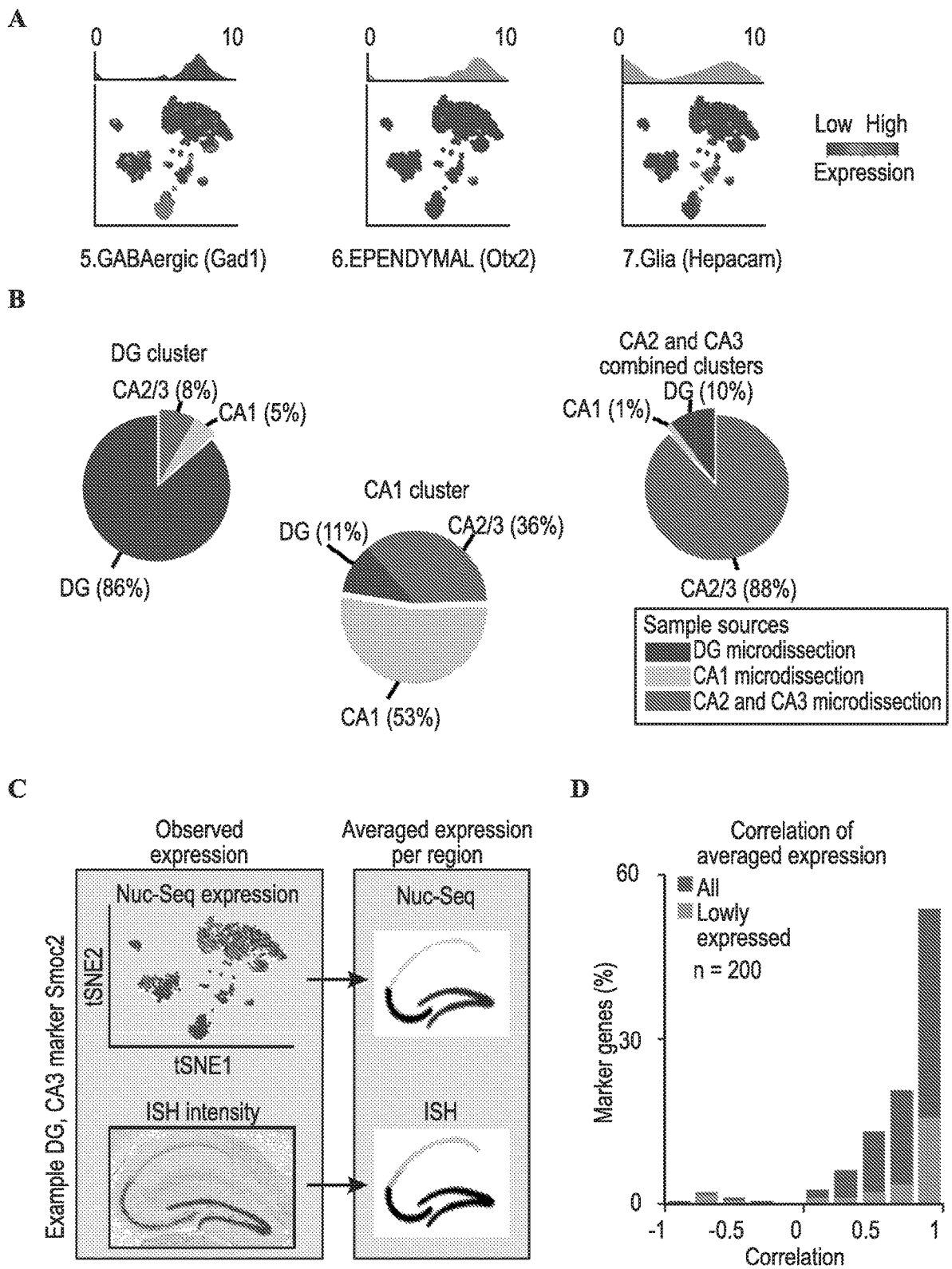
FIG. 9A-9D: Validation of cell type classification based on Nuc-Seq data. (A) Identification of GABAergic, ependymal and glial clusters. For each cluster, marker gene expression is shown in two ways: 1, histogram quantifying expression level of the marker gene across all nuclei in the relevant cluster (top); and 2, 2D embedding of nuclei (as in FIG. 1E) showing relative expression level of the marker gene across all nuclei. (B) Nuc-Seq clusters agree with the anticipated cell types based on the microdissected anatomical regions. Shown are the distributions of nuclei from each microdissection source (DG, CA1, CA2 and CA3) within each of the nuclei clusters identified as DG, CA1, and CA2 and CA3 combined. (C) Computational pipeline for the validation of expression patterns using ISH. An example of comparison of the expression pattern of the Smoc2 gene across CA1, CA2, CA3, and DG Nuc-Seq clusters to its expression in the corresponding regions in ISH data. Top left: scatter plot of 2D embedding of all nuclei (as in FIG. 1E) colored by the expression of Smoc2 across all nuclei (Nuc-Seq data). Top right: the average Nuc-Seq expression levels in the CA1, CA2, CA3, and DG clusters presented in a schematics of the hippocampus (gray scale, high expression in dark grey and low expression in light grey). Bottom left: the expression pattern of Smoc2 in Allen ISH [64] image. Bottom right: the average expression levels in the CA1, CA2, CA3, and DG regions presented in a schematics of the hippocampus (gray scale). (D) Distribution of correlation coefficients of average RNA-Seq expressions and ISH [64] intensities per gene, across all differentially expressed genes between the CA1, CA2, CA3 and DG regions. Shown are all genes (blue) and lowly expressed (red) defined as averaged expression in all regions within bottom 25% quantile.
Figure 10:
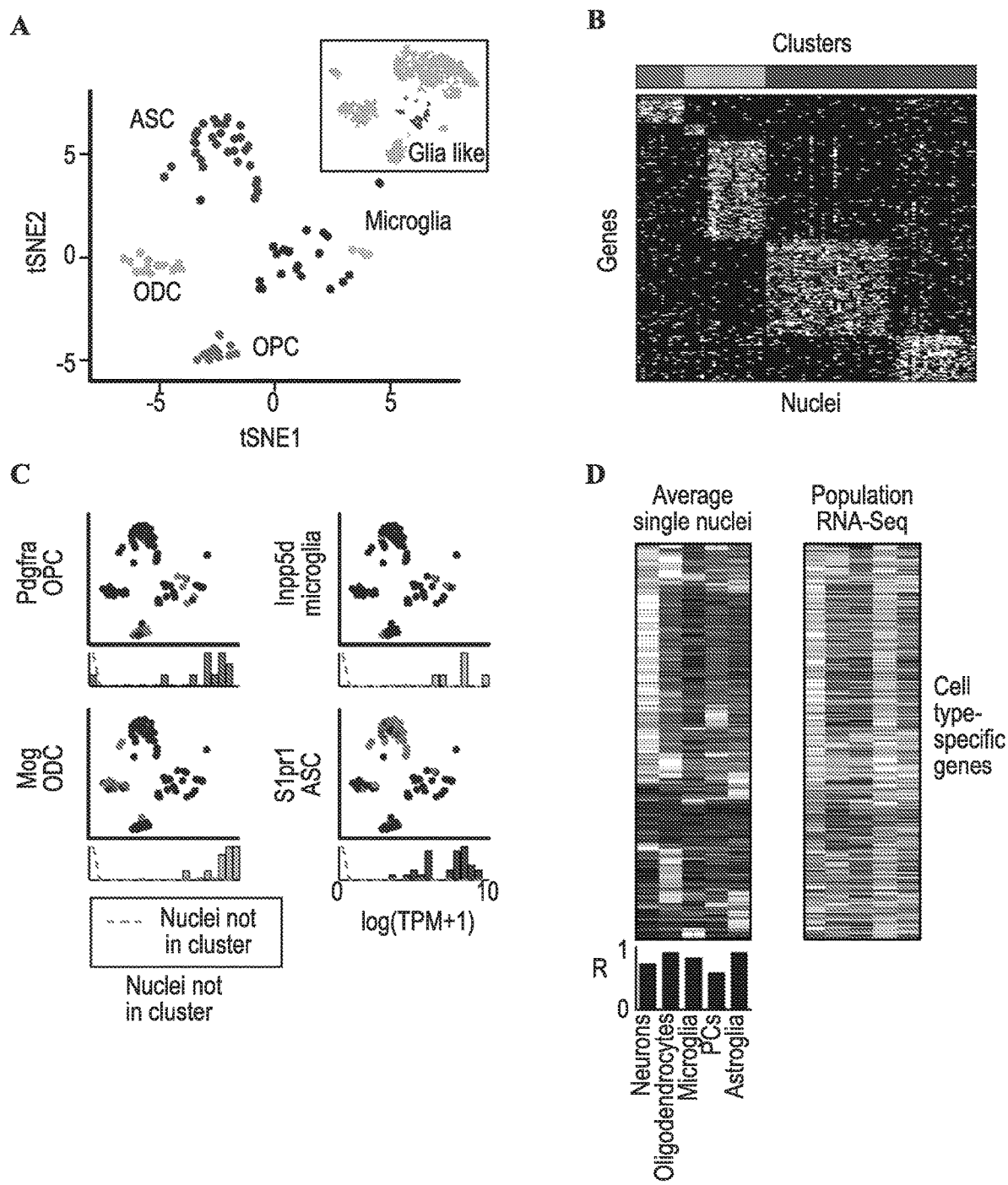
FIG. 10A-10D: Nuc-Seq identifies glial cell types. (A) Clustering of glial nuclei. Top insert: the glial cluster (blue) within all other nuclei from FIG. 1E. The glial nuclei are divided to five clusters by PCA-tSNE: oligodendrocytes (ODC), astroglia (ASC), oligodendrocyte precursor cells (OPC), microglia, and a sparse cluster of diverse cells (grey). (B) Marker genes. Heatmap shows the expression of marker genes (rows, t-test FDR q-value<0.05 with log-ratio>1 across all pairwise comparisons between subclusters) specific for each of the five clusters in (A) (color bar, top, matches cluster color in A) across the single nuclei (columns). (C) Identification of each glial subcluster by marker genes. For each cluster, a marker gene expression is shown in two ways: Top: 2D embedding of nuclei (as in A)

The present invention also provides for novel methods to analyze the Nuc-Seq data and generate high resolution maps (see materials and methods). Nuc-Seq analysis sensitively identified both major cell types and refined sub-types. Cluster analysis of Nuc-Seq data revealed seven major clusters of cells with distinct gene expression patterns (FIG. 1E-G, FIG. 8 and FIG. 9) that clearly correspond to known cell types and major anatomical distinctions in the hippocampus. Cluster identities were consistent with our microdissection scheme, and their gene expression patterns globally agreed with Allen Brain Atlas ISH data (Allen ISH(13), FIG. 9). Iterative re-clustering of the glia nuclei (cluster 7 in FIG. 1E, FIG. 10) recovered five known glial cell sub-types (14), and averaged expressions across each subcluster well-correlated with published population RNA-Seq data (14) (FIG. 10).

Figure 11:
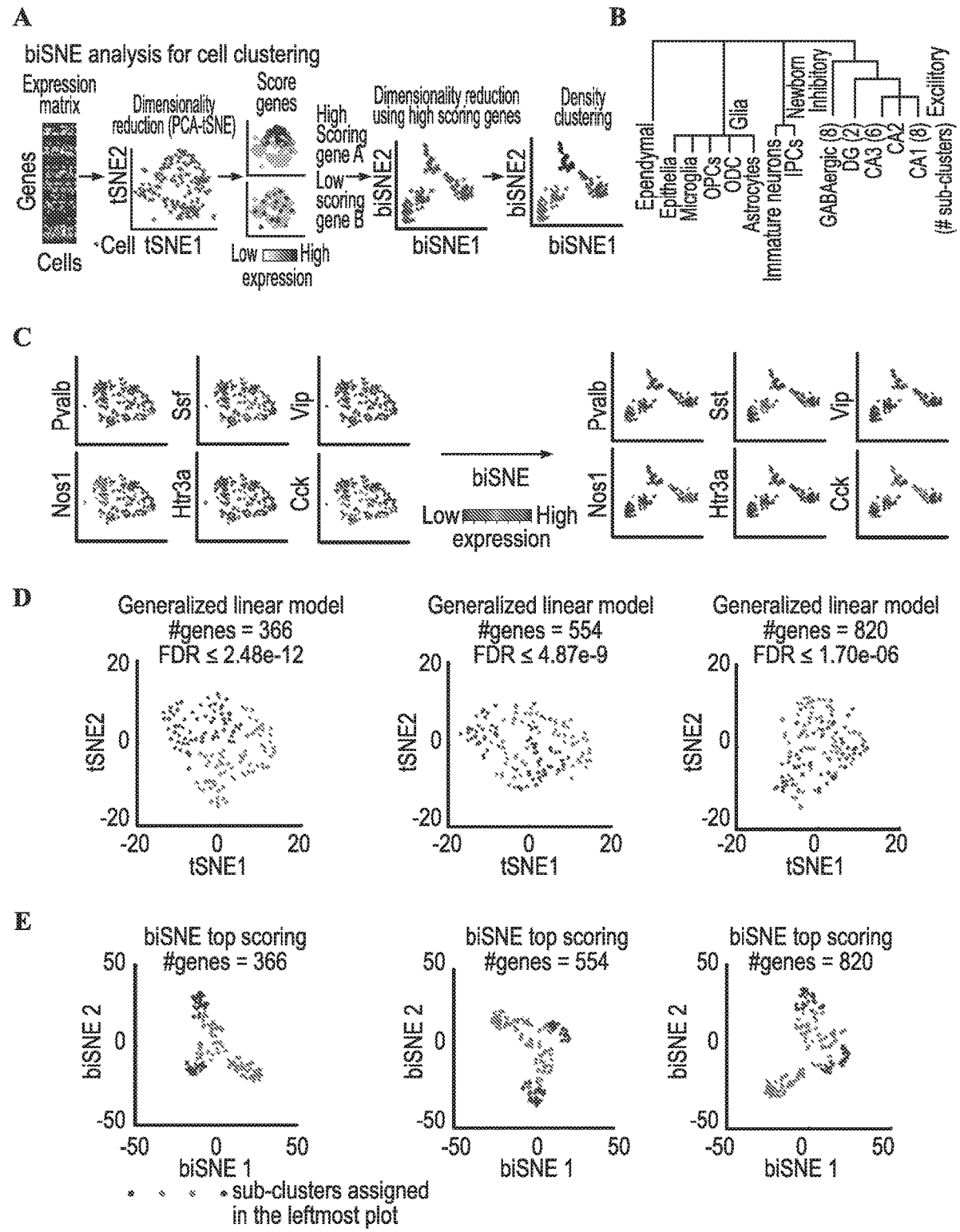
Figure 12:
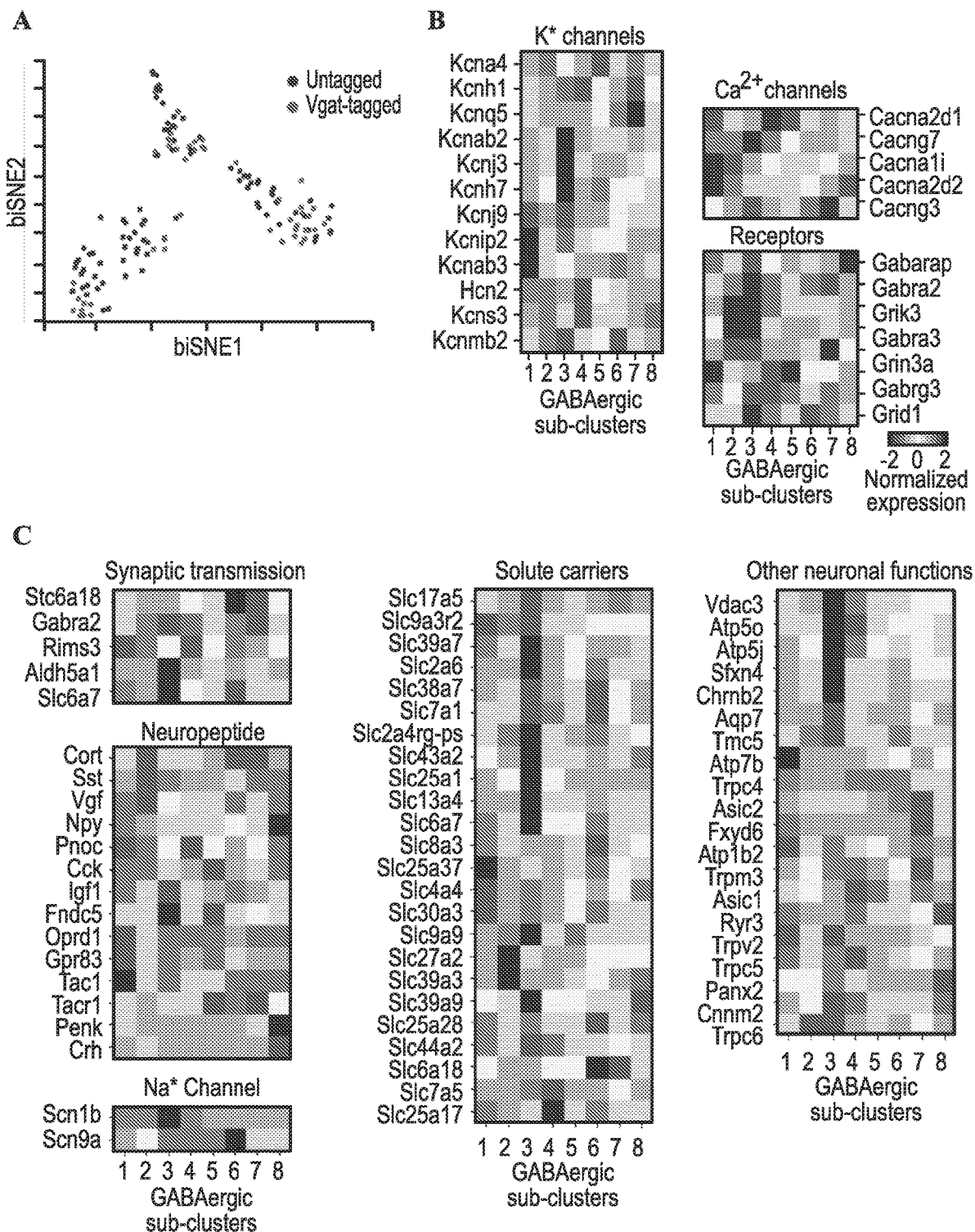
Figure 13:
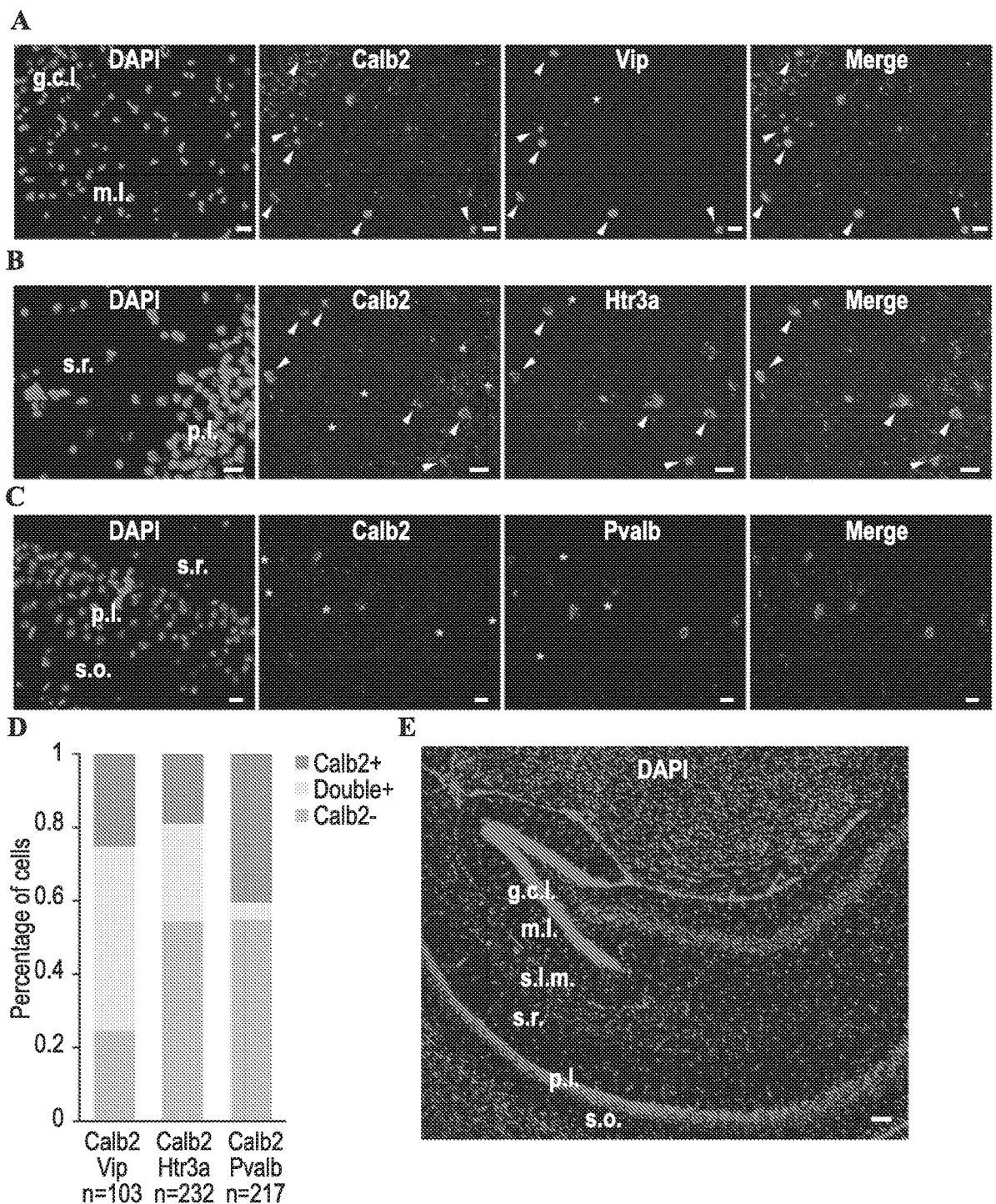

Applicants captured finer distinctions between closely related cell types using a new clustering algorithm, biSNE (biclustering on Stochastic Neighbor Embedding) (FIGS. 11-12), which improved upon current methods (15) (FIG. 11). The biSNE analysis partitioned the GABAergic neurons into eight subclusters (FIG. 2A), each with unique expression of individual or pairs of canonical interneuron marker genes, such as Pvalb and Htr3a (FIG. 2B). Applicants validated the expression patterns of GABAergic markers by double fluorescent RNA in situ hybridization (dFISH) (FIG. 2C, FIG. 13). Applicants further characterized the subclusters by differential gene expression analysis, revealing for example that the calcium channel Canal1 is specifically expressed in Pvalb or Sst positive GABAergic neurons (FIG. 12 and Table S2).

Figure 14:
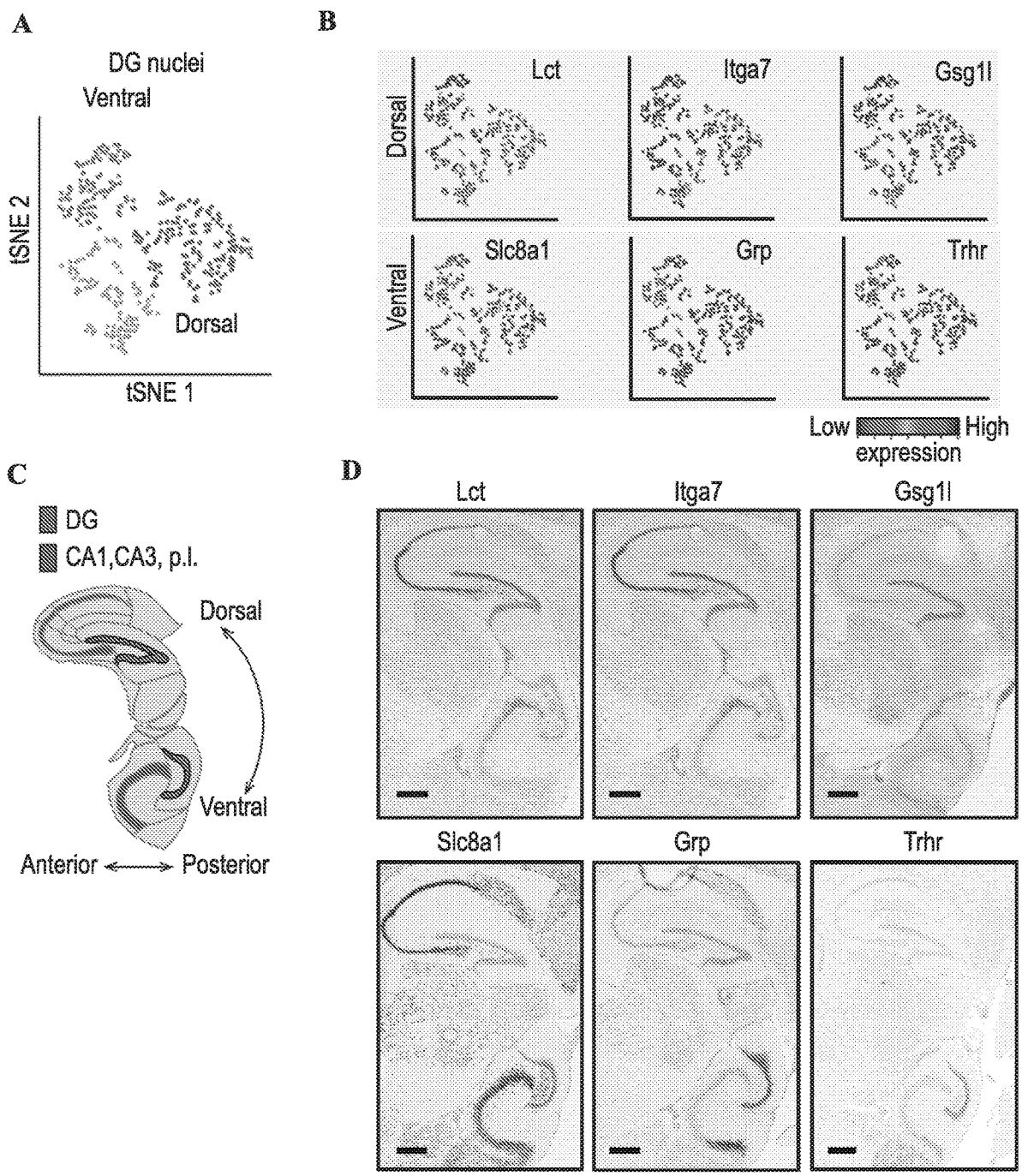
Figure 15:
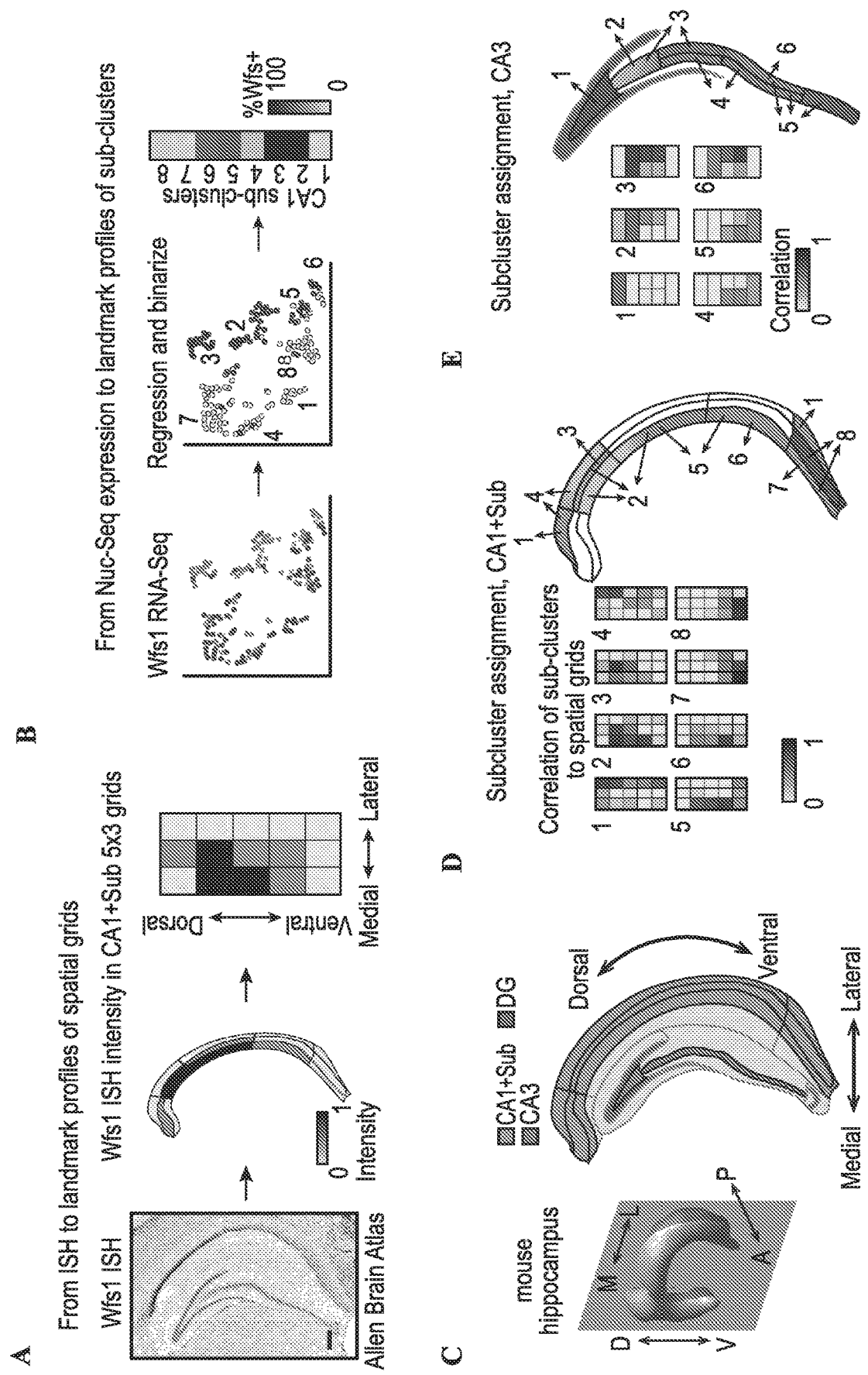
Figure 18:
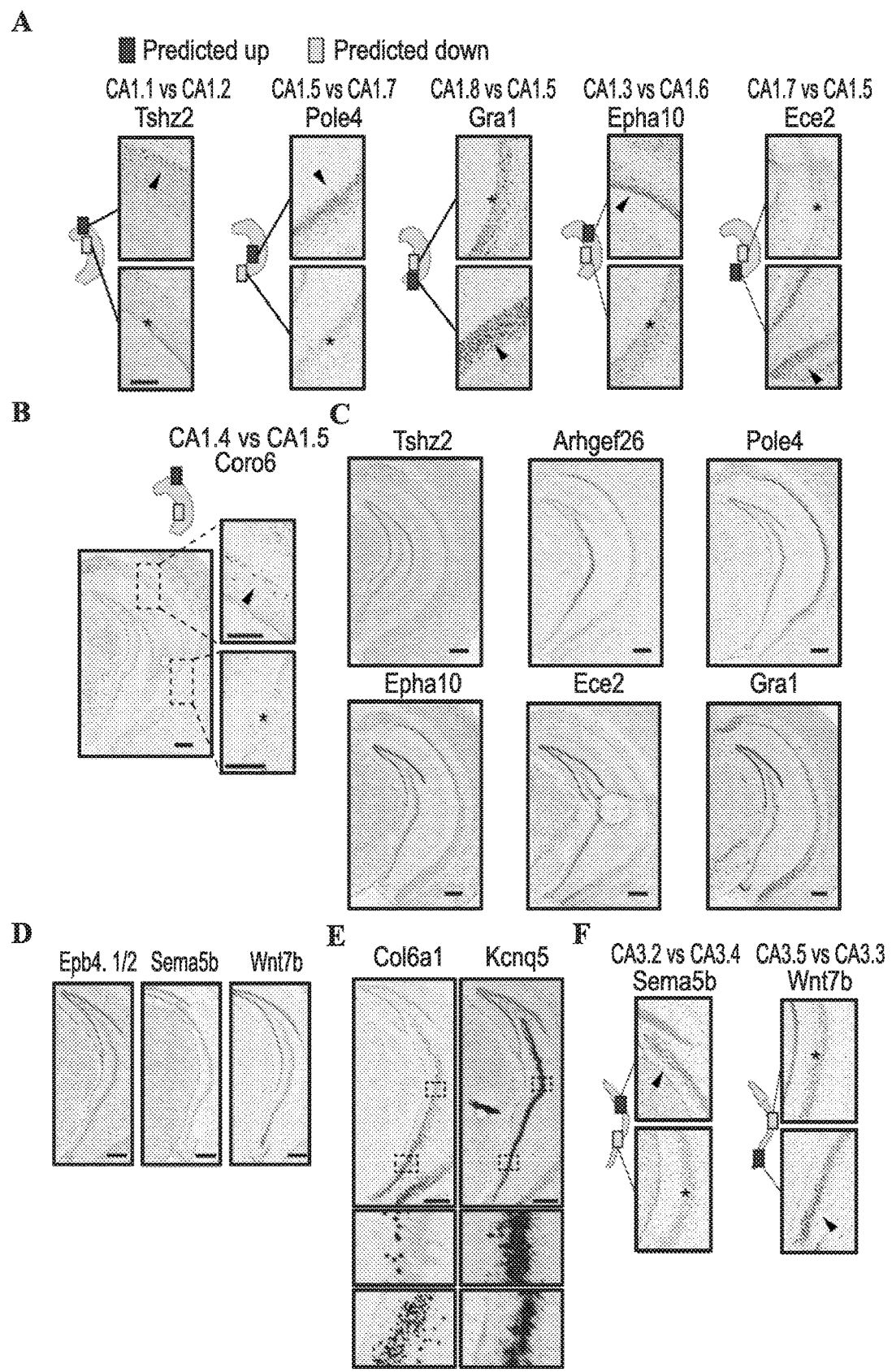

Nuc-Seq also distinguished between spatial subregions with divergent transcriptional profiles. biSNE analysis of Nuc-Seq data partitioned glutamatergic cells from CA1, CA3, and DG into 8, 6, and 2 subclusters, respectively (FIG. 2D and FIG. 14). Analysis of subcluster specific gene expression highlighted several known landmark genes that exhibit spatially restricted expression patters in subregions of the hippocampus, indicating a correspondence between hippocampal subregions and subclusters of glutamatergic nuclei. Applicants then used the spatial expression patterns (13) of these landmark genes to map subclusters in CA1, CA3, and DG to distinct spatial subregions (FIG. 2E and FIGS. 15, 16, 17). Notably, multiple subregions were assigned different, yet partially overlapping, sets of subclusters, indicating a gradual transition of transcriptional profiles between neighboring hippocampal subregions (FIG. 2E). Other subregions were assigned to a single subcluster; in particular, a rare set (7%) of sparse neurons in the dorsal lateral outskirts of the CA1 (FIG. 2E). To validate our mapping, Applicants selected genes that were not used in the spatial mapping, and confirmed their predicted expression patterns in subregions of the hippocampus using the Allen ISH dataset (FIG. 2F and FIG. 18). Previous studies using single-neuron RNA-Seq in CA1 reported two cell clusters that do not match spatial position (1) (FIG. 19), whereas our spatial mapping of Nuc-Seq data corresponds to continual transcriptional transitions within CA1 and CA3 regions, adding to the growing evidence (16, 17) that cellular diversity is not always partitioned into discrete sub-types.

Figure 20:
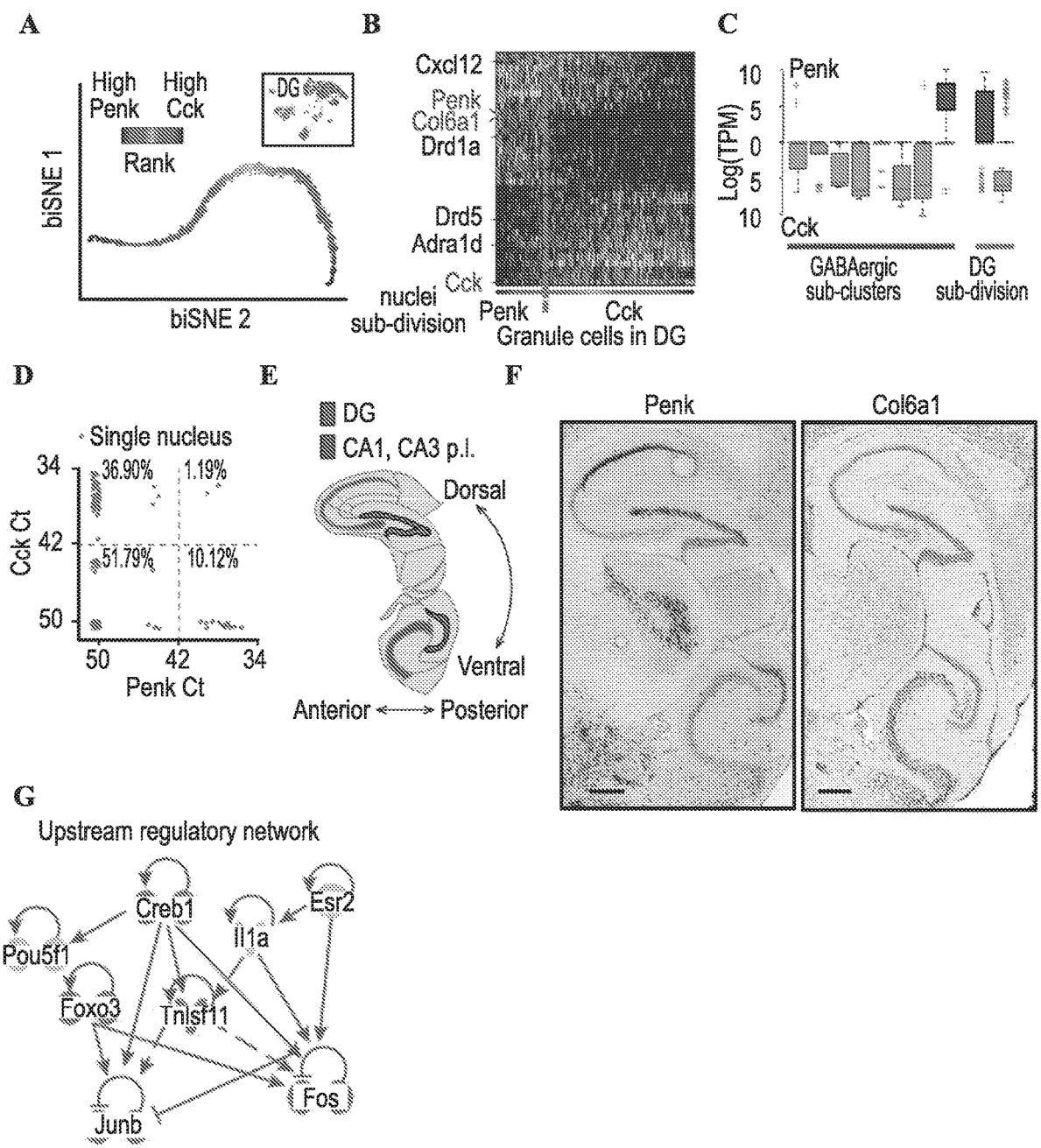
Figure 21A:
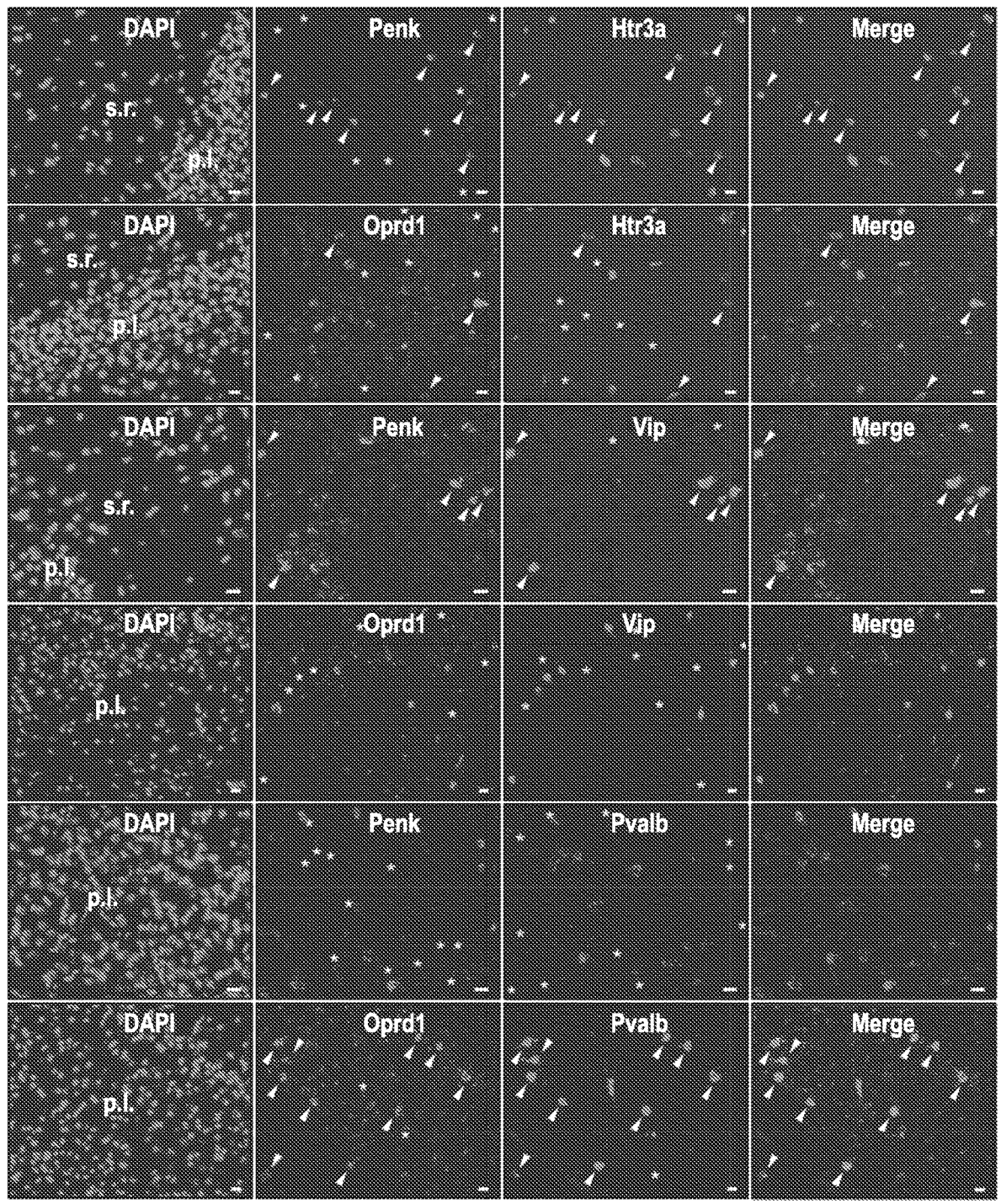

Applicants identified marker genes that are specifically associated with cell type and/or position (Tables S1-S3). For example, Penk, which encodes an opioid neuropeptide (Enkephalin), and its receptor Oprd1 (18), were selectively expressed in mutually exclusive subclusters of cells (FIG. 2G). Applicants validated the mutually exclusive expression pattern of Penk and Oprd1 in GABAergic neurons by dFISH and their spatial expression pattern within the hippocampus by ISH (FIG. 2H, FIGS. 20-21). In DG granule neurons, Applicants found mutually exclusive expression of Penk in a small subset of cells (162/674) (FIG. 20) and of Cck neuropeptide (Cholecystokinin) in all others, which Applicants validated by quantitative PCR (FIG. 20). Previous work showed that Enkephalin is secreted to the extracellular space (18), and its signaling may not require synaptic connection. Thus, the cell-type specific expression of Penk and Oprd1 points to putative cell types and spatial positions involved in the Enkephalin signaling within the hippocampal circuitry.

Example 3

Figure 3:
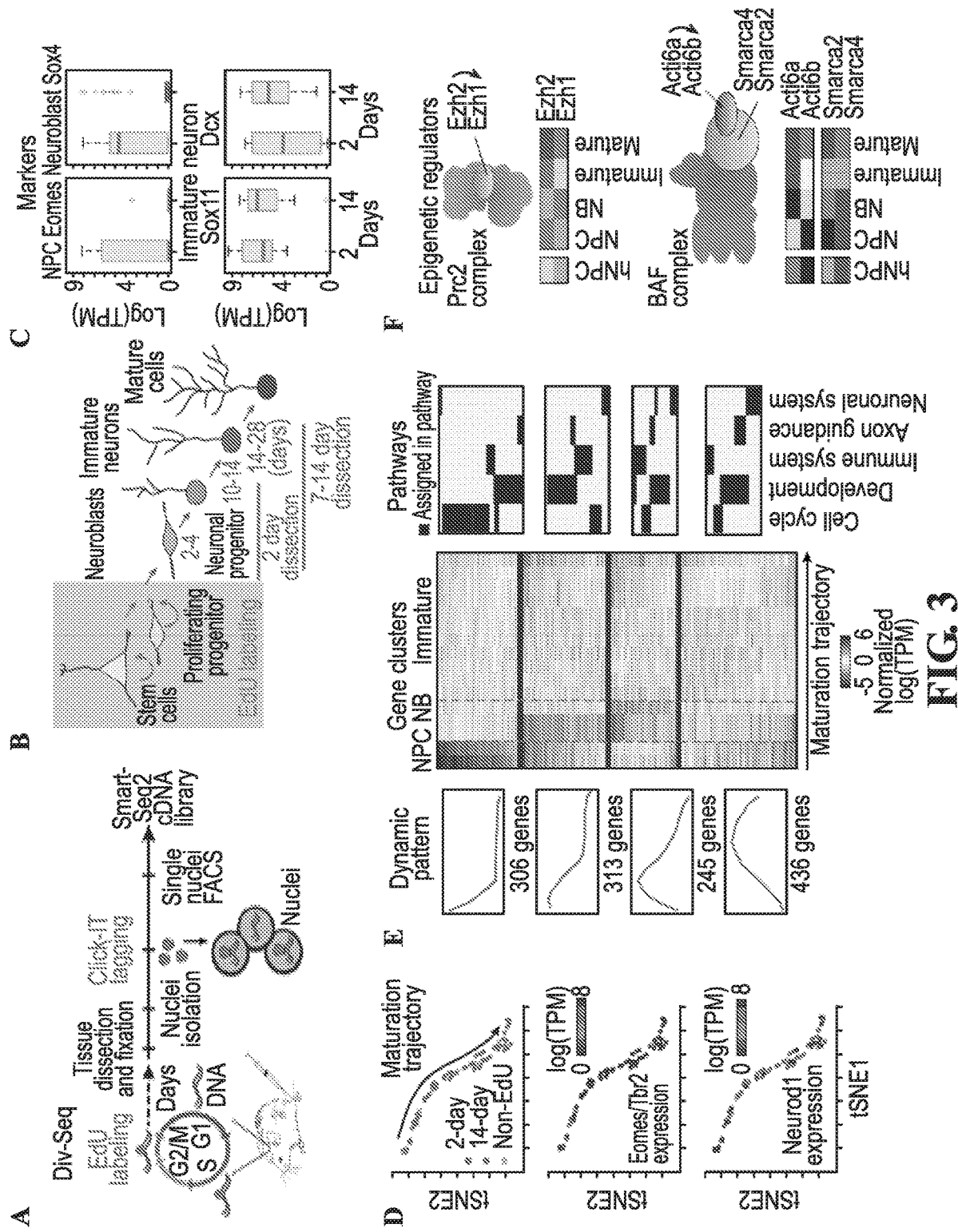
FIG. 3A-3F: Transcriptional dynamics of adult neurogenesis revealed by Div-Seq. (A) Schematics of Div-Seq method. EdU is injected to mice and incorporates into the DNA of dividing cells (8). After isolation, EdU labeled nuclei are fluorescently tagged and captured by FACS for single nuclei RNA-Seq. (B) Schematics of adult neurogenesis in the dentate gyrus(7). Timing of EdU labeling (tan box) and nuclei isolation are marked. (C) Div-Seq captured cells expressing known markers of neuronal precursors, neuroblasts and immature neurons. Box plots for the 2 days (2d) and 14 days (14d) EdU labeled nuclei (excluding nuclei classified as non-neuronal). Boxplots shown as in FIG. 2G. (D) Newborn cells form a continuous trajectory. All panels show 2-D embedding of 2d labeled nuclei, 14d labeled nuclei and nuclei from unbiased survey. Nuclei are colored by source (top), by Eomes/Tbr2 marker gene expression (middle), or by Neurod1 marker expression (bottom). Trajectory directionality is chosen by the position of the 2d labeled neurons and known marker genes. (E) Dynamic gene expression clusters. Four clusters are shown from top to bottom. Left: Running average expression level of the genes in each cluster over the nuclei ordered along the trajectory (as in D). Middle: a heatmap of running average expression of all genes along the trajectory. Red lines mark the transcriptional switches from neuronal precursor cell (NPC) to neuroblast (NB), and from NB to immature neuron. Right: proportions of genes assigned to five major biological pathways (F) Changes in the composition of the Polycomb Complex (Prc2, top) and the BAF (SWI/SNF) complex (bottom). For each complex, schematics of the complex is shown, and the heatmap of average expression of genes in NPC(NP), NB, immature neurons and mature granule DG cells, and compared to human NPCs (hNPC, absolute log (TPM)).
Figure 22:
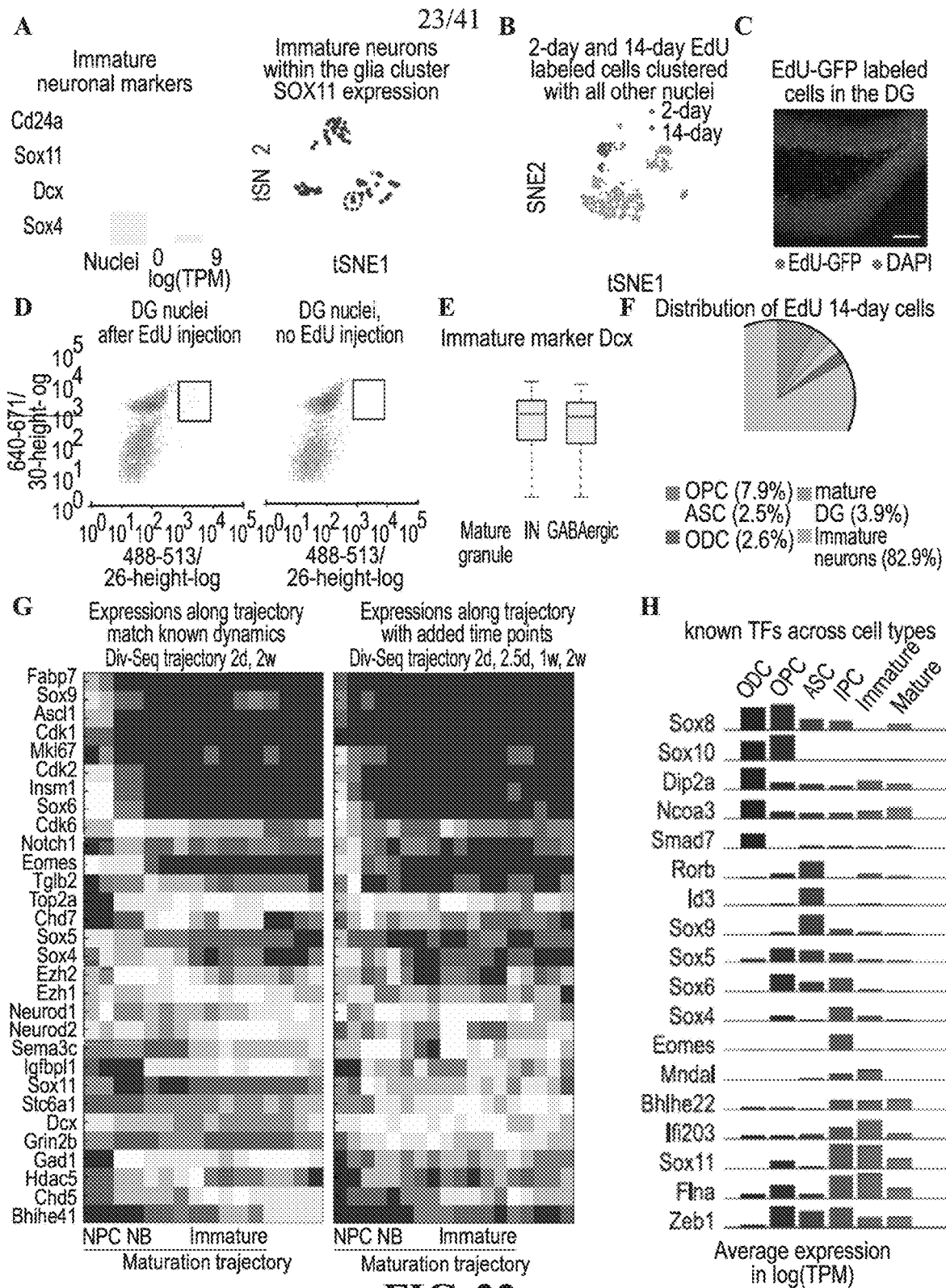

Applicants next combined Nuc-Seq with EdU labeling of dividing cells, in a method Applicants call Div-Seq (FIG. 3A). In contrast to commonly used genetic labeling techniques (3, 19, 20), which might be limited to specific cell types and requires cell types or developmental stage marker genes (3, 19, 20), EdU tags newly synthesized DNA in dividing cells at a given time window, allowing for unbiased isolation of nuclei of neural stem cells and their progeny with high temporal resolution. To study transcriptional dynamics during adult neurogenesis in the DG, one of the canonical neurogenic sites in the mammalian CNS (7), Applicants used Div-Seq to isolate nuclei at 2 and 14 days after cell division, representing neural precursor cells (NPC), neuroblasts, and immature neuronal stages of adult neurogenesis, respectively (7) (FIG. 3B, FIG. 22). Div-Seq enriched for a broad range of newborn cells (FIG. 20). Expression of stage-specific marker genes confirmed that Div-Seq captured cells at distinct stages: 2-day labeled nuclei expressed NPC (Tbr2/Eomes) and neuroblast (Sox4) markers, whereas 7-day and 14-day nuclei expressed immature neuronal markers (Sox11 and Dcx) (FIG. 3C). Of note, Dcx a commonly used marker gene for immature neurons was expressed in all mature GABAergic neurons in the hippocampus (FIG. 22), highlighting the limits of using single marker genes to identify cell types.

Clustering analysis of neuronal lineage nuclei placed the newborn neurons on a continuous trajectory. The order of nuclei along the trajectory matched the EdU labeling time, from 2-day to 14-day labeled nuclei, with partial overlap, and a few nuclei from our unbiased survey of nuclei spread throughout (FIG. 3D). Expression patterns of known neurogenesis genes along the trajectory recapitulated their known dynamics (3, 4, 21) and correctly captured the measured expression of nuclei at an intermediate time point of 7 day post EdU injection (FIG. 22), indicating that the trajectory indeed captured the maturation process.

To further characterize the transcriptional transitions of newborn neurons, Applicants used biSNE to identify genes with dynamic expression patterns along the neurogenesis trajectory (FIG. 3E), clustered genes by their expression patterns, and tested for enriched genetic pathways in each cluster. Applicants found two major coordinated transcriptional switches, involving hundreds of genes and aligning with the known transitions from NPC, through neuroblasts, to immature neurons: (i) from proliferation (cell-cycle exit) to neuronal differentiation (consistent with previous reports (3)), and (ii) from differentiation to neuronal maturation (FIG. 3E).

Figure 23:
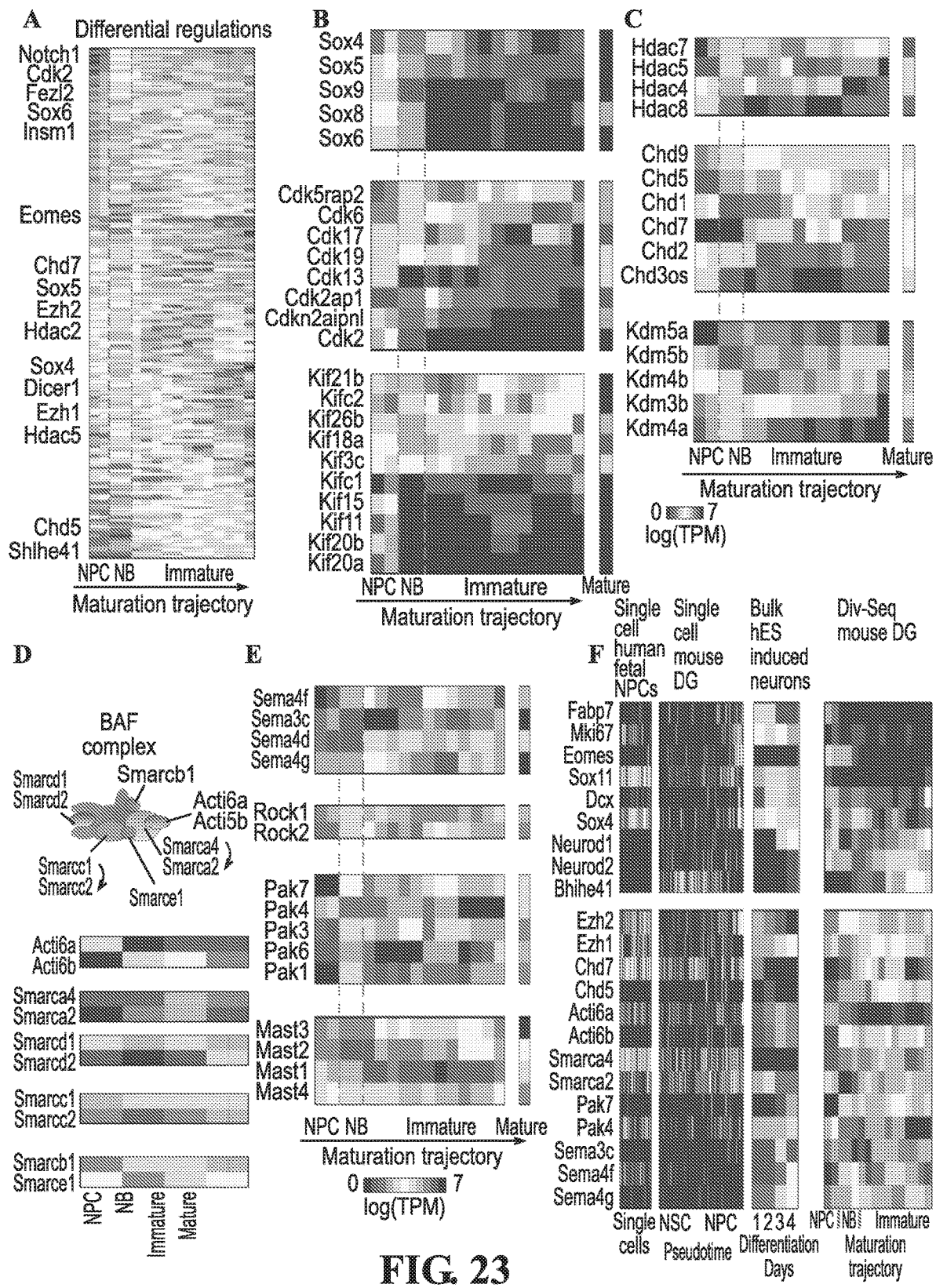

Applicants identified transcription factors (TFs) and chromatin regulators whose expression is coordinated with these two transcriptional switches (FIG. 23). For the Polycomb Complex (Prc2), Applicants observed an expression switch between Ezh2 (expressed in NPCs consistent with previous reports (22)) and its paralog Ezh1 (FIG. 3F); for the BAF (mammalian SWI/SNF) complex, Applicants observed an expression switch of Act16a/Baf53a to its paralog Act16b/Baf53b (23) and a late induction of BAF components (e.g. Smarca2/BAF190b, FIG. 3F, FIG. 23). These expression patterns are consistent with single-cell RNA-Seq of mouse NPCs (3) and human NPCs (24) (FIG. 3F, FIG. 23).

Figure 24:
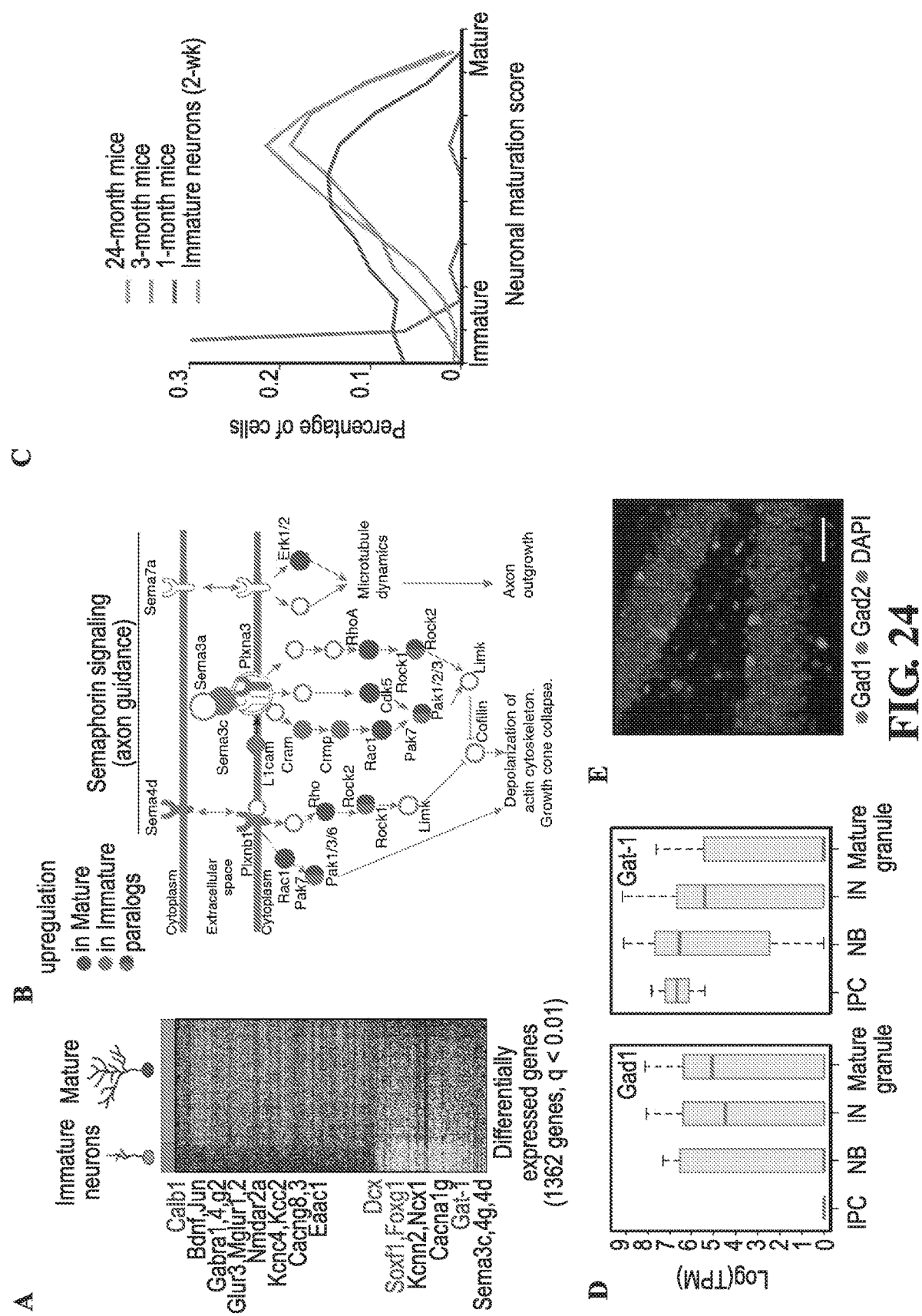

Div-Seq provides a unique opportunity to profile the transcriptional program underlying neuronal maturation. Applicants found differentially expressed genes between immature and mature DG granule neurons (t-test FDR q-value<0.01; FIG. 24, and differentially expressed splice isoforms), enriched for expected molecular pathways (q-value<0.01, FIG. 24), such as semaphorin signaling (25) (FIG. 24) and lipid metabolism (26), supporting our gene signatures. Among the differentially expressed genes Applicants found the chloride/potassium symporter Kcc2, which is pivotal for the GABA switch from excitation to inhibition during neuronal maturation (27), selectively expressed in mature neurons as previously shown (27). Interestingly, immature neurons in DG express genes for both GABA production (one of two GABA synthetase genes, Gad1, as shown (19) and transportation (Gat1, FIG. 24), despite maturing to be primarily glutamatergic neurons (7).

Figure 4:
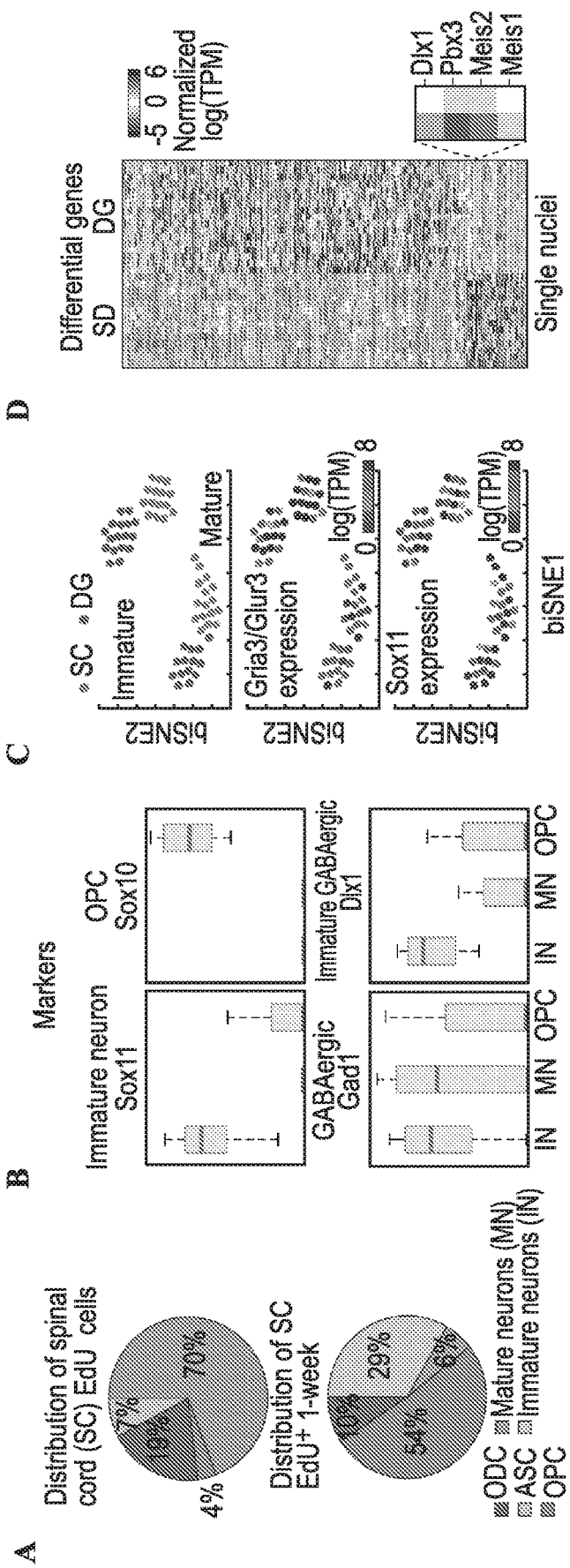
FIG. 4A-4D: Adult newborn GABAergic neurons in the spinal cord revealed by Div-Seq. (A) Div-Seq in the spinal cord (SC) captures oligodendrocyte precursor cells and immature neurons. Shown is the distribution of cell types in the SC in non-EdU-labeled (top) and 7 days EdU labeled nuclei (bottom), assigned by clustering and marker gene expression. Oligodendrocyte precursor cells, OPC; Astrocytes, ASC; Oligodendrocytes, ODC. (B) Div-Seq captured immature neurons expressing marker genes of immature neurons (Sox11), GABAergic (Gad1, Dlx1) or OPCs (Sox10) marker genes. Box plots for immature neurons (IN), mature neurons (MN) and OPCs, shown as in FIG. 2G. (C) Cells cluster primarily by maturation state and secondarily by region. All panels show biSNE 2D embedding of immature and mature neurons from both the SC and the DG. Nuclei are colored by tissue (top), by Gria3/Glur3 mature marker expression levels (middle), or by Sox11 (bottom). (D) Region specific gene expression. Heatmap shows the expression of genes specific to immature neurons in the SC (left) and DG (right), across single nuclei (t-test FDR<0.05, log-ratio>1, across all pairwise comparisons).

Evidence from diverse mammalian systems suggests that adult neurogliogenesis occurs in multiple non-canonical regions of the adult CNS (28). However, traditional methods, such as FISH, are limited in their ability to identify and fully characterize rare newborn cells. In particular, contradicting FISH evidence of a few marker genes suggests that progenitors in the adult spinal cord (SC) give rise either to only glia cells (29) or to both glia cells and neurons (30). To systematically investigate neurogliogenesis in the adult SC, Applicants applied Div-Seq and found a clear signature for dividing cells 7 days after EdU labeling (FIG. 23). Clustering analysis revealed a diverse population of newborn cells, in which the majority (54%) represented oligodendrocyte precursor cells (OPCs) (expressing Sox10), and the second largest population (29%) represented immature neurons (expressing Sox11) (FIG. 4A-B, FIG. 23). Notably, In the non-EdU labeled population Applicants found mainly mature neurons (70%) and glia (30%) with only 4% OPCs and no immature neurons, demonstrating the need for Div-Seq to capture these rare cell types. All newborn neurons Applicants detected expressed the GABA processing genes Gad1 and Gad2, suggesting that newborn neurons in the SC are GABAergic (supporting previous observations (30), FIG. 4B).

Comparison of immature and mature neurons in both the SC and the DG revealed that cells cluster primarily by maturation state and secondarily by region (FIG. 4C), demonstrating genetic similarities between immature neurons independent of their origin within the CNS. However, focusing on immature neurons Applicants identified differentially expressed genes (FIG. 4D) specific to the DG (e.g. Prox1) and the SC (e.g. Rex2), respectively. In particular, Applicants found three transcription factors, Pbx3, Meis2, and Dlx1 co-expressed specifically in the SC but not in DG immature neurons. Previous reports showed that Pbx, Meis, and Dlx super-family factors interact (31) and promote adult neurogenesis in the subventricular zone/olfactory bulb and dopaminergic fate specification (32); our data suggest that these factors may also play a regulatory role in adult neurogenesis in the SC. Taken together, the comparison of RNA signatures of newborn neurons in the SC and DG suggests that common molecular pathways cooperate with cell type-specific fate specifying factors to mediate adult neurogenesis across different brain regions.

In summary, Applicants have shown how Nuc-Seq and Div-Seq open new avenues in the study of neuronal diversity and rare dynamic processes in the adult CNS. Nuc-Seq overcomes the harsh dissociation needed for single-cell RNA-Seq, yet retains rich information required to make fine distinctions between cell types and states. Combined with intra-nuclear tagging, our nuclei profiling method enables the study of rare cell populations, as done in Div-Seq to capture proliferating cells. For increased sensitivity, Nuc/Div-Seq can be integrated with other techniques, for example, integration with droplet-based microfluidics may help to increase throughput, and the use of alternative labeling approaches such as immunostaining of transcription factors (6) or a recently published fluorescent "flash" tagging of dividing cells (33) may broaden the range of cell types possible for investigation. Div-Seq's ability to clearly identify and characterize rare cells in the spinal cord shows its significantly improved sensitivity compared to traditional methods. Nuc-Seq and Div-Seq can be readily applied to diverse biological systems, and may be especially helpful for studying transcriptional dynamics, the aging brain, fixed and frozen tissue including post-mortem biopsy samples or archive samples, and time-sensitive samples such as human biopsies. Overall, our methods will help overcome broad challenges not only in neuroscience, but in many other biological systems as well.

Example 4

Method for sequencing RNA from thousands of nuclei. Drop-seq has previously been developed for generating single-cell libraries. The major advantages are speed, numbers and cost: Applicants can generate libraries from around 10,000 cells per day at a total cost of $600. The cell number is at least 10× greater than was possible with previous methods, and the cost per library is about 100× lower than that of previous methods. The disadvantages include non-biological variation that arises from loss of dendrites and axons and "leakage" of cytoplasm when these processes are sheared. For Nuc-seq, advantages include increased physical stability and structural homogeneity. In addition, nuclear RNAs are enriched for recently transcribed genes, which facilitates detection of transcriptional changes following a stimulus. The current drawback is that the number of nuclei than can be profiled is limited. Applicants therefore developed a hybrid method, Dronc-seq, that combines the strengths of its two parents.

Figure 1:
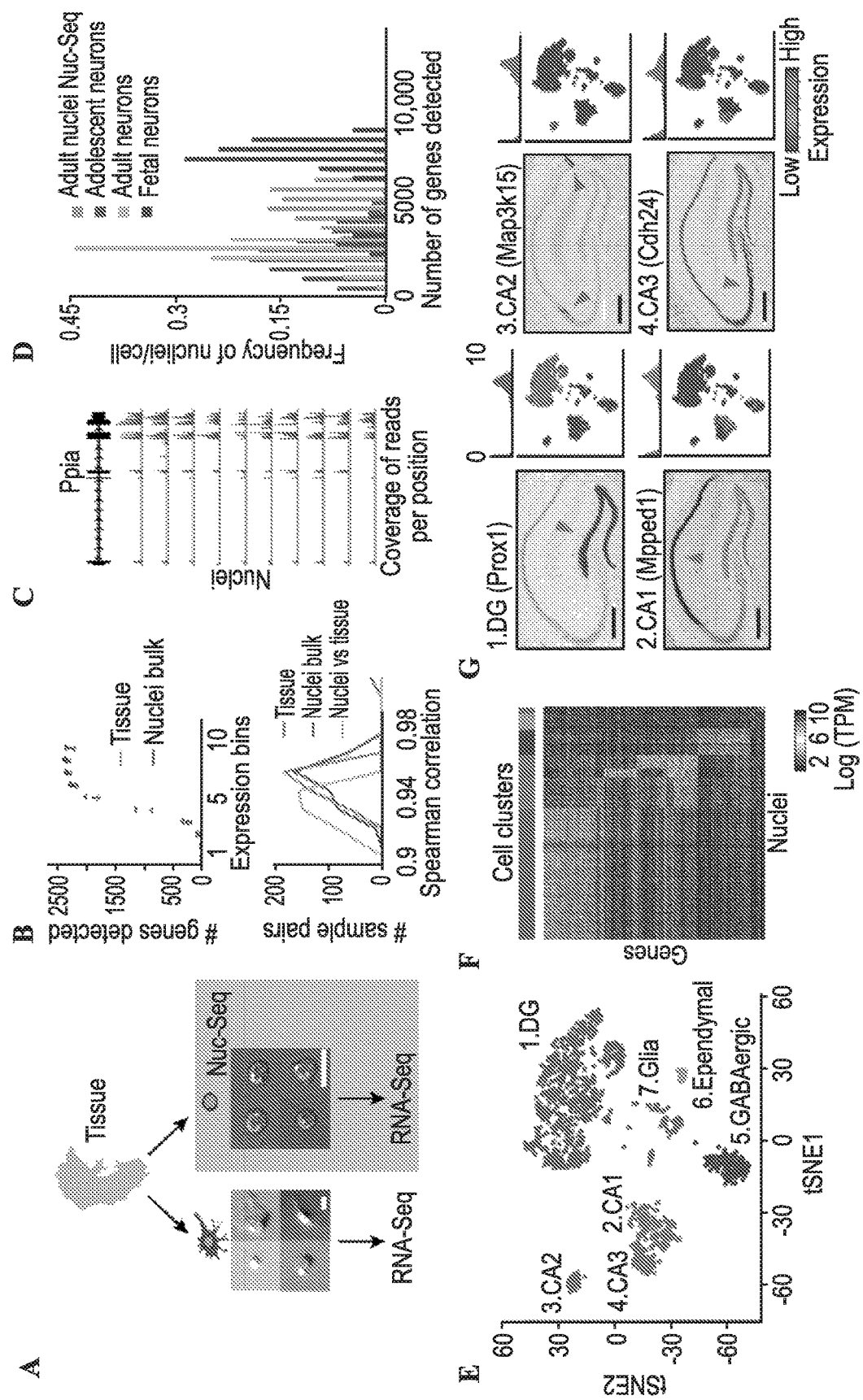
FIG. 1A-1G. Single nuclei RNA-Seq (Nuc-Seq) identifies distinct cell types. (A) Single isolated nuclei (right) are more uniform than enzymatically dissociated single neuronal cell bodies (left) from adult mouse brain tissue. Shown are images of representative examples. Scale=10 μm. Overview of the Nuc-Seq method (right): Dissected tissue is fixed, nuclei are isolated and sorted using FACS, and are then processed using the Smart-Seq2 RNA-Seq protocol(34). (B) Nuc-Seq faithfully captures tissue RNA. Comparing Nuc-Seq on populations of nuclei and RNA-seq on tissue samples from the DG brain region. Shown are number of genes detected (TPM>3) per expression quantile (top) and distribution of pairwise spearman correlations across samples (bottom). (C) Nuc-Seq detects full-length, spliced transcripts in ten individual nuclei (rows). RNA-Seq read coverage at the Ppia genomic locus. (D) Nuc-Seq detects consistently higher number of genes (TPM/FPKM>3 or UMI>=1) compared to published single neuron RNA-seq in adolescent (1) or adult (4) mice, but lower number than in fetal neurons(6). (E) Major cell types identified from Nuc-Seq data reflected by 7 major cell clusters. Shown is a 2-D non-linear embedding with 7 distinct clusters of 1,188 nuclei isolated from adult hippocampus. (F) Heatmap shows the expression of marker genes specific for each of the seven clusters across single nuclei (t-test FDR<0.05, log-ratio>1, across all pairwise comparisons). Top color bar matches cluster color in E. (G) Identification of DG granule cell, CA1, CA2, and CA3 pyramidal cell clusters. For each cluster, expression of marker genes is shown as: 1, ISH image in a coronal section of the hippocampus from (13) (arrowhead indicates high expression levels of marker gene); 2, histogram quantifying expression level across all nuclei in the relevant cluster; and 3, 2-D embedding of nuclei (as in E) showing relative expression level of the marker across all clusters. Scale=400 m.

The Drop-seq method (Macosko et al., 2015) uses a microfluidic device to co-encapsulate individual cells in reverse emulsion aqueous droplets in an oil medium together with one uniquely barcoded mRNA capture bead. The oligonucleotides on the bead are each comprised of four parts: a constant sequence (identical on all primers) for use as a priming site for PCR and sequencing; a "cell barcode" that is the same across all the primers on the surface of any one bead, but different from the cell barcodes on all other beads; a random sequence that enables reads from the same mRNA transcript to be identified computationally (UMI); and an oligo dT sequence for capturing polyadenylated mRNAs. Once the cell and bead are co-encapsulated, the cell lyses and its mRNA is captured on the bead. The emulsion is then broken, and the mRNAs are reverse-transcribed, amplified, and sequenced in a single reaction. The barcodes are used to correct for PCR amplification bias and to infer each transcript's cell of origin. Applicants used Drop-seq to profile 44,808 single cells from the mouse retina, which were clustered by an unsupervised method into 39 cell types. The clusters included all major cell classes and, for several classes, multiple cell types within several of the classes (FIG. 1, from Macasko et al., 2015). The analysis also predicted markers of new types that Applicants validated immunohistochemically. Applicants believe that classification was incomplete because 70-80% of retinal cells are rod photoreceptors, so numbers of the cells in the most heterogeneous classes (bipolar, amacrine and retinal ganglion cells) was limited—for example because ganglion cells comprise<1% of all retinal cells, less than 500 cells are expected among 44,000 analyzed cells, too few to make finer distinctions. Applicants have therefore begun purifying these classes by FACS prior to Drop-Seq. Applicants recently profiled 13,000 bipolar cells, and have been able to double the number of types in the initial dataset.

Figure 2:
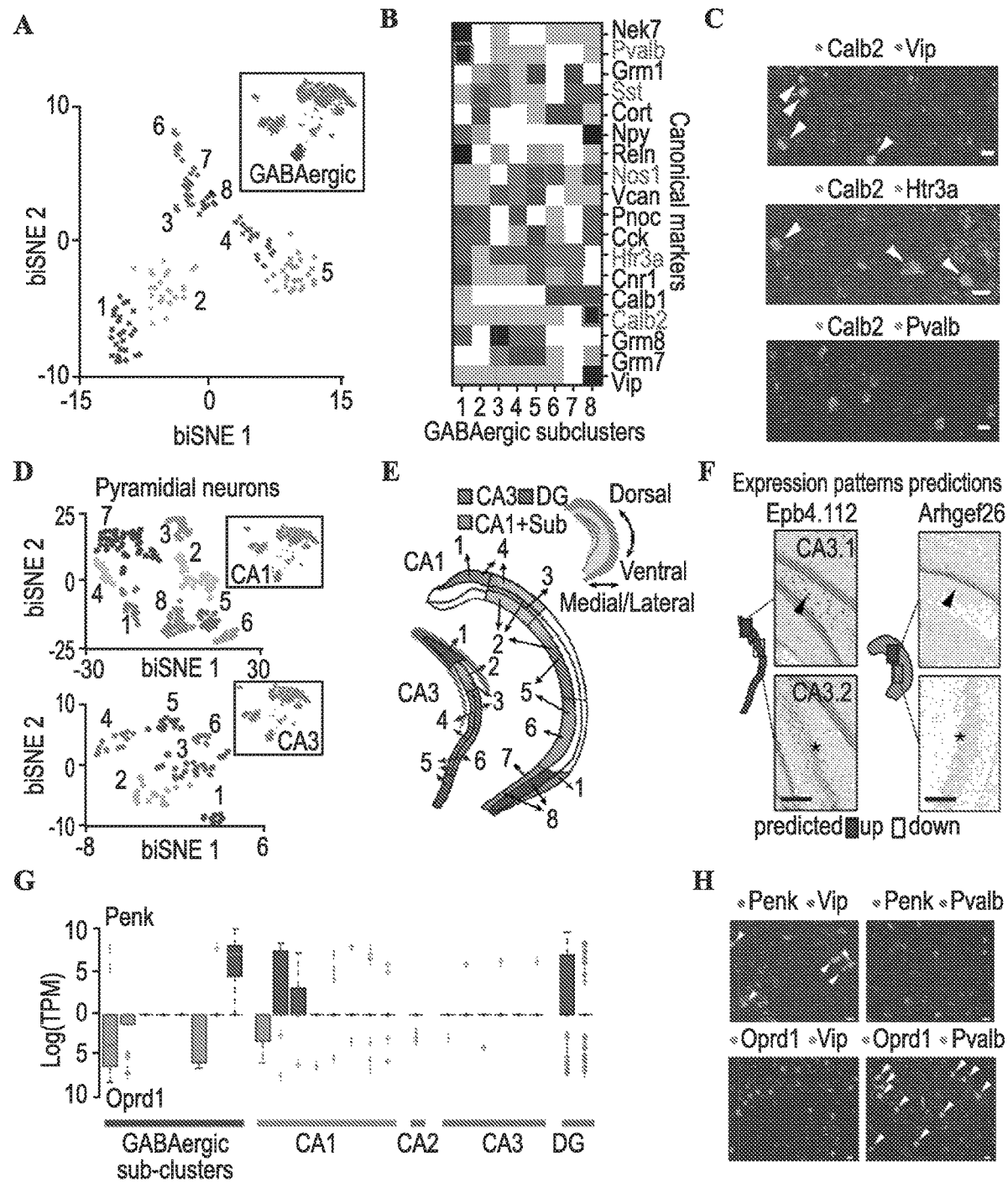
FIG. 2A-2H. Nuc-Seq and biSNE distinguish cell subtypes and transcription patterns. (A) Subclusters of GABAergic interneurons identified by biSNE. Shown is a biSNE 2-D embedding of GABAergic nuclei with 8 subclusters. Top insert: the GABAergic cluster within all other nuclei from FIG. 1E. (B) Subclusters are characterized by a combination of canonical marker genes. Heat map with averaged expression of canonical neuron markers (rows) across GABAergic subclusters (columns). (C) Double fluorescent RNA in situ hybridization (dFISH) of marker genes validating the expression pattern shown in (B). Co-expression of genes indicated by arrowheads. Scale=20 m. (D) Pyramidal CA1 and CA3 biSNE subclusters. Shown is a biSNE 2-D embedding of the CA1 (top) and CA3 (bottom) pyramidal nuclei with 8 and 6 subclusters, respectively. Top insert: the CA1 cluster (orange) within all other nuclei from FIG. 1E. (E) Spatially resolved pyramidal neuron populations in CA1 and CA3. Top: Schematics of hippocampus coronal section with CA1 (including subiculum), CA3 (including the hilus) and DG. Bottom: Registration of CA1 (right) and CA3 (left) pyramidal subclusters to subregions, using a map of landmark gene expression patterns from ISH data. Sub-cluster assignments are numbered and color code as in (D). Scale=200 m. (F) Example of validation of spatial assignments of CA1 and CA3 pyramidal subclusters. Predictions (left illustrations; boxes showing predicted differential expression regions) match with Allen ISH data (13) (right; arrowhead: high expression; asterisk: low expression) in pairwise comparison of genes differentially expressed between two subclusters. (G) Distribution of expression of Penk (facing up) and Oprd1 (facing down) across each neuronal subcluster. Box plots show the median (red), 75% and 25% quantile (box), error bars (dashed lines), and outliers (red cross). (H) dFISH of GABAergic cluster marker genes (Vip and Pvalb) with Penk or Oprd1, validating their mutual exclusive expression across GABAergic subclusters. Co-expression of genes indicated by arrowheads. Scale=20 m.

Recent studies demonstrated the feasibility of sequencing pre-mRNAs from isolated nuclei (Steiner et al., 2012; Henry et al., 2012). Applicants have now adapted these methods for both full-length and 3' directed single-nuclei mRNA-seq of intact nuclei. Our method robustly produces RNA libraries from single nuclei in the adult mammalian brain. The improved RNA libraries, consistently detect 4,000-7,000 genes per cell, while reducing the required sequencing depth. Applicants developed and applied Nuc-Seq to the mouse hippocampus. Applicants selectively tagged neuronal nuclei (Syn promoter) and dissected several hippocampal regions (CA1, CA2/3, Dentate Gyrus [DG]). Focusing on the DG, Applicants prepared Nuc-Seq libraries from 6 animals (~600 nuclei passing filter). Applicants developed new methods for normalization of single cells data and clustering of cell types compatible with Nuc-Seq data. Applicants showed that Nuc-Seq can classify glia vs. neurons, inhibitory vs. excitatory neurons, and neurons from different regions (FIG. 2). Some of the differentially expressed genes were confirmed by available ISH data in the Allen Brain Atlas. Most excitingly, Nuc-Seq shows that inhibitory (GABAergic) neurons in the DG have molecular profiles characteristic of "newly born neurons", consistent with the idea that GABA-related enzymes are transiently expressed during neuronal development. Applicants also found two new cell types/states among DG neurons, which were believed to be homogeneous; Applicants are now validating this with protein staining. Finally, Applicants re-assembled the transcriptome from population libraries and show that our polyA nuclear RNAs are similar to cytoplasmic RNAs in structure (largely spliced), but also reveal new splice isoforms and potential lincRNAs.

Figure 25:
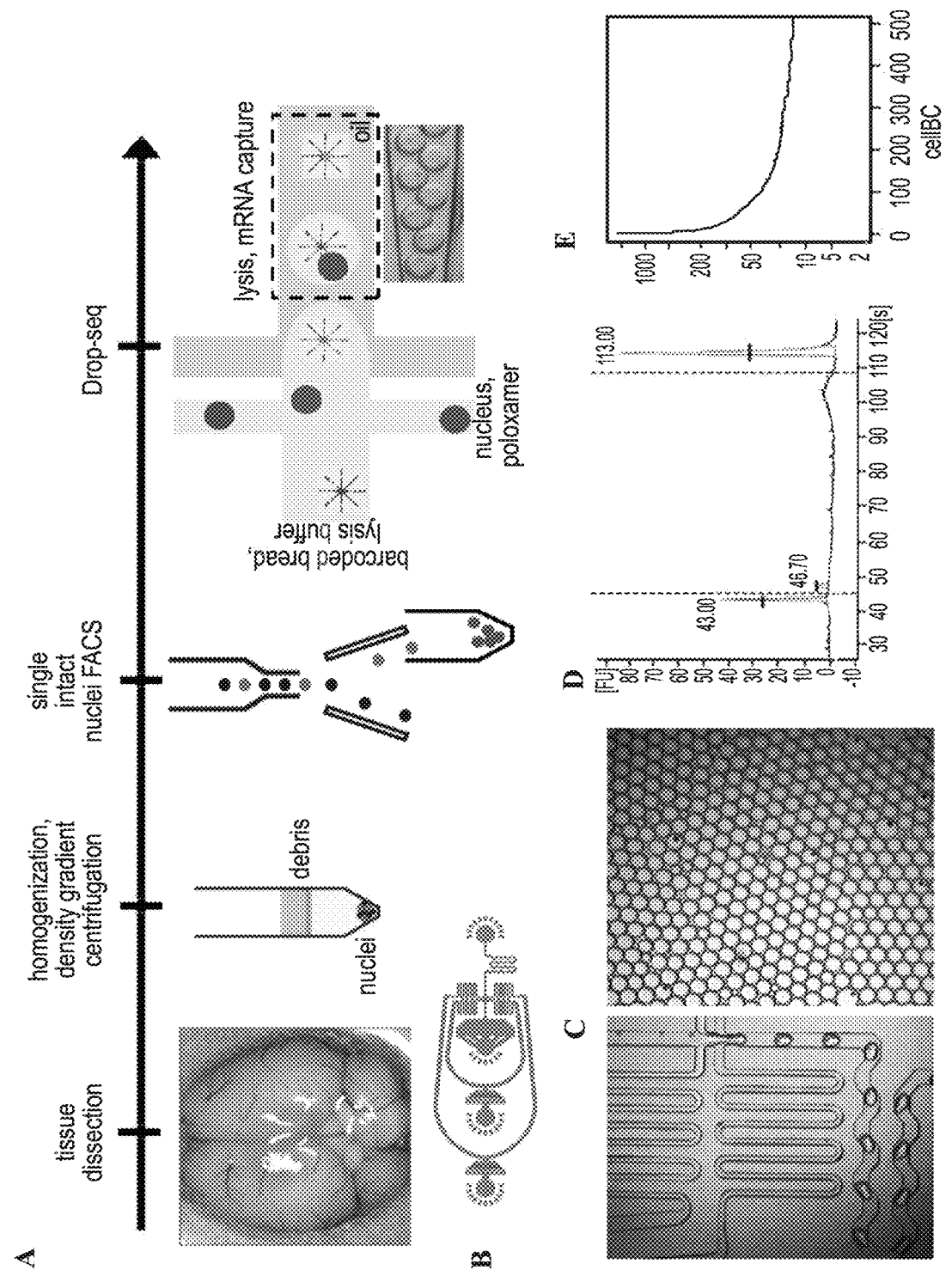

Applicants developed new microfluidic devices and protocols that allow Drop-seq analysis of thousands of isolated nuclei (Dronc-Seq) (FIG. 25, 26, 27). Furthermore, Applicants have recently made important progress with reverse emulsion devices used for other nuclei-based molecular biology applications, such as a droplet version of single-cell ATAC-Seq. To develop Dronc-Seq Applicants combined the nuclei preparation protocol of Nuc-Seq, a new device compatible with nuclei separation, and Drop-Seq reagents (barcoded beads, molecular biology protocols, lysis buffers) for the in-drop and subsequent phases of the protocol. Briefly, as in Nuc-Seq, Applicants rely on our recently published (Sweich et al., 2015) protocols for high quality generation of nuclei suspensions from mouse hippocampus. Unlike Nuc-Seq, where Applicants next sort single nuclei using FACS, in Dronc-Seq Applicants use a new microfluidics device, following on the design principles of Drop-Seq, but optimized for the size and properties of nuclei. The nuclei are lysed in drops, and their mRNA captured on the Drop-Seq beads. Notably, given the smaller quantity of mRNA in nuclei, ensuring efficient capture is key. A complementary modality (Klein et al., 2015) has higher capture but lower throughput than Drop-Seq. Finally, Applicants test for cross-contamination due to 'sticky' RNA from the lysed cytoplasms or leakage from nuclei using the cross-species controls developed for Drop-Seq (Macosko et al., 2015). Nuclei can also be sorted through FACS prior to Drop-Seq encapsulation. Applicants can also use pore-blocking polymers called poloxamers, such as F-68 and F-127 (Sengupta et al., 2015). Applicants can use Dronc-Seq in the hippocampal biological system and compare to the available of Nuc-Seq benchmarking data. Applicants can also generate Nuc-Seq and Dronc-Seq data from the retina, demonstrating its generality.

Example 5

Discusssion

Applicants clustered high scoring biSNE genes into coexpressed gene signatures using cross correlation while taking into account of the proximity of cells expressing these genes. Applicants found two signatures with opposing expression patterns across the DG granule cells. The DG cells span a continuous spectrum of states for the expression of these two modules (FIG. 16), with two neuropeptide genes Penk (Preproenkephalin) and Cck (Cholecystokinin) expressed in largely mutually exclusive cells (18% and 82% of DG cells, respectively). Applicants validated this expression pattern using qPCR and double-ISH. qPCR on an additional 168 single nuclei from DG microdissection shows that all but two express either Penk or Cck, but not both, at a 1:4 ratio, consistent with the Nuc-Seq result (FIG. 20). In single molecule double-ISH, two members of the Penk module (Penk and Col6a1) show overall co-expression in the same cells (FIG. 16), and their expression marks cells sparsely scattered throughout the entire DG. Finally, the genes that are differentially expressed between the Penk and Cck module expressing cells (t-test, p-value FDR q<0.01), are enriched for emotional activity related pathways and seizures (p-value<0.05, hypergeometric test). Among the inferred common upstream regulators (Methods) are several activity dependent factors (Creb1, Jun and Bdnf), consistent with the known regulators of Penk in the brain [37]. This suggests a novel state of granule cells expressing distinct signatures regulated by neuronal activity responses.

(anterior/posterior: −3.52; mediolateral: 2.65; dorsal/ventral: −3), dorsal CA1/2 (anterior/posterior: −1.7; mediolateral: 1.0; dorsal/ventral: −1.35) and ventral CA1/2 (anterior/posterior: −3.52; mediolateral: 3.35; dorsal/ventral: −2.75). After each injection, the pipette was held in place for 5 minutes prior to retraction to prevent leakage. Finally, the incision was sutured and postoperative analgesics (Meloxicam, 1-2 mg/kg) were administered for three days following surgery.

Animal work statement. All animal work was performed under the guidelines of Division of Comparative Medicine (DCM), with protocols (0411-040-14, 0414-024-17 0911-098-11, 0911-098-14 and 0914-091-17) approved by Massachusetts Institute of Technology Committee for Animal Care (CAC), and were consistent with the Guide for Care and Use of Laboratory Animals, National Research Council, 1996 (institutional animal welfare assurance no. A-3125-01).

| Number of animals | Sex & strain | Brain regions | Age | Treatment |
|---|---|---|---|---|
| 4 | Male, C57BL/6 | DG, CA1, CA23 | 12-14 weeks | non |
| 2 | Male, C57BL/6 | DG | 18 weeks | non |
| 2 | Male, C57BL/6 | DG | 12-14 weeks | Sacrificed 2 weeks post pAAV-hSyn-GFP-KASH injection |
| 2 | Male, C57BL/6 | DG | 11-13 weeks | Sacrificed 2 days post EdU injection |
| 3 | Male, C57BL/6 | DG | 11-13 weeks | Sacrificed 2 weeks post EdU injection |
| 2 | Male, C57BL/6 | DG | 2 year | non |
| 2 | Male, VGAT-Cre | DG, CA123 | 12-16 weeks | Sacrificed 2 weeks post pAAV-EF1a-DIO-GFP-KASH |
| 2 | Male, C57BL/6 | DG, SC | 11-13 weeks | Sacrificed 1 week after EdU injection |
| 4 | Male, C57BL/6 | DG, SC | 11-13 weeks | Sacrificed 1 week after EdU injection |
| 4 | Female, C57BL/6 | DG | 11-13 weeks | non |
| 3 | Male, C57BL/6 | DG, SC | 8 weeks | Sacrificed 1 week after EdU injection |
| 3 | Male, C57BL/6 | DG, SC | 8 weeks | Sacrificed 2.5 days after EdU injection |

Materials And Methods

Plasmid and virus production for isolation of GABAergic neurons. EGFP-KASH construct was a generous gift of Prof. Worman (Columbia University, NYC) inverted into pAAV-EF1a-DIO-EYFP-WPRE-hGH-polyA (Addgene, #27056) using AscI and NcoI restriction sites, and WPRE was removed using ClaI restricition sites. pAAV-EF1a-Cre-WPRE-hGH-polA was obtained from Addgene (#27056). The pAAV-hSyn-EGFP-KASH-WPRE-hGH-polyA was described [38]. Concentrated adeno-associated virus 1/2 (AAV1/2) and low titer AAV1 particles in DMEM were produced and titered as described previously [38].

Stereotactic injection of AAV1/2 into the mouse brain. Stereotactic injections were approved by the MIT Committee on Animal Care (MIT CAC). 12-16 week old male vGAT-Cre mice (Slc32a1tm2(cre)Lowl, The Jackson Laboratory, #016962) (Rossi J, Cell Metab 13(2):195-204) were anaesthetized by intraperitoneal (i.p.) injection of 100 mg/kg Ketamine and 10 mg/kg Xylazine and pre-emptive analgesia was given (Buprenex, 1 mg/kg, i.p.). 1 ml of high titer AAV1/2 (≈4×1012 Vg/ml of pAAV-EF1a-DIO-EYFP-WPRE-hGH-polyA) was injected into dorsal and/or ventral hippocampus. The following stereotactic coordinates were used: Dorsal dentate gyBs (anterior/posterior: −1.7; mediolateral: 0.6; dorsal/ventral: −2.15), ventral dentate gyrus Immunohistochemistry and Nissl staining. Mice were sacrificed by a lethal dose of Ketamine/Xylazine 3 weeks post viral injection, and transcardially perfused with PBS followed by 4% PFA. Sagittal sections of 30 μm were cut using vibratome (Leica, VT1000S) and sections were boiled for 2 min in sodium citrate buffer (10 mM tri-sodium citrate dehydrate, 0.05% Tween20, pH 6.0) and cooled down to room temperature (RT) for 30 min. Brain sections were blocked in 5% normal goat serum (NGS) (Cell Signaling Technology, #5425) and 5% donkey serum (DS) (Sigma, #D9663) in PBST (PBS, 0.15% Triton-X) for 1 h at RT and stained with chicken anti-GFP (Aves labs, #GFP-1020, 1:400) and mouse anti-parvalbumin (Sigma, #P3088, 1:500) in 2.5% NGS and 2.5% DS in PBST over night at 4-C. Sections were washed 3 times in PBST and stained with secondary antibodies (Alexa Fluor 488 and 568, 1:1000) at RT for 1 h. After washing with PBST 3 times, sections were mounted using VECTASHIELD HardSet Mounting Medium with DAPI (Vector Laboratories, #H-1500) and imaged using confocal microscopy (Zeiss LSM 710, Ax10 ImagerZ2, Zen 2012 Software). For Nissl staining, mice were perfused with PBS and 4% PFA. Brain samples were dehydrated and paraffin embedded and 7 μm sagittal sections were cut. Nissl staining was performed as described elsewhere [39]. Images were taken with a Zeiss microscope and AxioCam MRm camera. Nuc-Seq.

I. Dissection of Mouse Hippocampal Subregions, Nuclei Isolation and FACS Sorting Freshly dissected mouse brain samples were placed in ice cold PBS and kept cold during microdissection. Microdissections of dentate gyrus, CA1 and CA2/3 regions were performed under a stereomicroscope as described elsewhere [40]. Dissected subregions were placed into ice-cold RNAlater (Ambion, RNAlater, #7020) and stored at 4° C. overnight. Thoracic spinal cord of EdU injected mice were dissected in icecold PBS and fixed in RNAlater at 4° C. overnight. Then samples were processed for nuclei isolation immediately or stored in −80° C. Nuclei were isolated by sucrose gradient centrifugation as described [38] with two modifications: RNAse inhibitor (Clontech, Recombinant Ribonuclease Inhibitor, #2313A, 40 units/µl) was added to the resuspension buffer (final 1U/µl), and nuclei were filtered through a 35 µm cell strainer (Falcon, #352235) before sorting. Nuclei were labeled with ruby dye (Thermo Fisher Scientific, Vybrant DyeCycle Ruby Stain, #V-10309) added to the resuspension buffer at a concentration of 1:800. Nuclei were kept on ice until sorting using Fluorescence Activated Cell Sorting (Harvard University, Bauer Core Facility, Beckman Coulter MoFlo Astrios EQ Cell Sorter) into 96 well plates containing 5 µl of TCL lysis buffer (Qiagen, #1031576) added with 10% 2-Mercaptoethanol. FACS gating was set on FSC, SSC, and on fluorescent channels to include only Ruby+ or Ruby+GFP+ nuclei (for nuclei tagged by GFP-KASH or EdU-GFP). Each 96 well plate included an empty well as a negative control and a population well of 50-100 nuclei as a positive control.

II. Single Nucleus RNA Library Construction and Sequencing

Single nucleus RNA was first purified using RNAClean XP beads (Beckman Coulter, Agencourt RNA-Clean XP, #A63987) at 2.2× beads to sample volume ratio. Single nucleus derived cDNA libraries were generated following a modified Smart-seq2 method [41]. Briefly, beads were eluted into 4 µl elution mix made of 1 µl RT primer (10 µm), 1 µl dNTP mix (10 mM each, Thermo Fisher Scientific, #R0191), 1 µl RNAse inhibitor diluted at 1:10 in water (final 1U/µl), and 1 µl H2O. Eluted samples were incubated at 72° C. for 3 min and immediately placed on ice. Each sample was added with 7 µl reverse transcription (RT) mix made of 0.75 µl H2O, 0.1 µl Maxima RNase-minus RT (Thermo Fisher Scientific, Maxima Reverse Transcriptase, #EP0752), 2 µl 5x Maxima RT buffer, 2 µl Betaine (Sigma Aldrich, 5M, #B0300), 0.9 µl MgCl2 (Sigma Aldrich, 100 mM, #M1028), 1 µl TSO primer (10 µm), 0.25 µl RNase inhibitor (40U/µl). The RT reaction was incubated at 42-C for 90 min and followed by 10 cycles of (50° C. for 2 min, 42° C. for 2 min), then heat inactivated at 70° C. for 15 min. Samples were then amplified with an addition of 14 µl polymerase chain reaction (PCR) mix made of 1 µl H2O, 0.5 µl ISPCR primer (10 µm), 12.5 µl KAPA HiFi HotStart ReadyMix (KAPA Biosystems, #KK2602). The PCR reaction was performed as follows: 98° C. for 3 min, 21 cycles of (98° C. for 15 sec, 67° C. for 20 sec, 72° C. for 6 min), and final extension at 72° C. for 5 min. PCR product was purified using AMPure XP (Beckman Coulter, Agencourt AMPure XP, #A63880) twice and eluted in TE buffer (Thermo Fisher Scientific, #AM9849). Purified cDNA libraries were analyzed on Agilent 2100 Bioanalyzer (Agilent, Agilent High Sensitivity DNA Kit, #5067-4626) and quantified using picogreen (Thermo Fisher Scientific, Quant-iT PicoGreen dsDNA Assay Kit, #P11496) on a plate reader (Biotek, Synergy H4, wavelength at 485 nm, 528 nm with 20 nm bandwidth). Sequencing libraries were prepared using Nextera XT kit (Illumina, #FC-131-1024) as described previously [42]. Single nucleus cDNA libraries were sequenced on an Illumina NextSeq 500 to an average depth of 632,169 reads. Sequences of primers used in single nucleus RNA library construction are shown below (IDT: Integrated DNA Technologies). The following sequences are synthetic.

| Primer | Sequence |
|---|---|
| Rt primer (IDT) | /5BiosG/AAGCAGTGGTATCAACGCAGAGTAC TTTTTTTTTTTTTTTTTTTTTTTTTTTTTTVN |
| TSO primer (Exiqon) | AAGCAGTGGTATCAACGCAGAGTACrGrG + G |
| ISPCR primer (IDT) | /5BiosG/AAGCAGTGGTATCAACGCAG*A*G*T |

Single-cell dissociation and cell picking. Cells were dissociated and hand picked as described [43]. Images were taken on dissociated cells.

Sequencing reads initial processing. Tophat [44] was used to align reads to mouse mm10 UCSC genome with default parameters and the mouse gene annotations (RefSeq mm10 and Ensemble GRCm38 merged using Cufflink [45]). The alignment was visualized using integrated genome browser (IGV) [46]. To estimate gene expression, RSEM v1.27 [47] was run with default parameters on alignments created by Bowtie2 [48] (command line options -q -phred33-quals -n 2 -e 99999999-l 25 -I 1 -X 1000 -a -m 200 -p 4 --chunkmbs 512). Estimated expression levels were multiplied by 106 to obtain transcript per million (TPM) estimates for each gene, and TPM estimates were transformed to log-space by taking log(TPM+1). Genes were considered detected if their transformed expression level equal to or above 1.1 (in log(TPM+1) scale). A library was filtered out if it had less than 2,000 detected genes or more than 8,000 detected genes (threshold set by analysis of 1, 2, 4, and populations of sorted nuclei). 3' and 5' bias was measured using the RNA-SeQC package [49].

Bulk Nuc-Seq and Tissue RNA-Seq. Fresh dorsal and ventral DG tissue was micro-dissected from 4 adult female mice (11-13 weeks) and placed in RNAlater for 24 hours. Each sample was cut in half and used as bulk tissue in RNA-Seq or bulk nuclei populations in Nuc-Seq. Nuclei isolation was done as described for Nuc-Seq protocol, except that at the last stage of the isolation, nuclei were transferred to 300 µl RLT lysis buffer (QIAGEN) instead of the resuspension buffer. Applicants proceeded immediately to extract RNA from nuclei using the RNeasy MinElute kit (QIAGEN, #74204) according to the manufacturer's protocol. For RNA extraction from bulk tissue, the tissue was placed in 300 µl RLT lysis buffer (QIAGEN), and mechanically dissociated using tissue raptor followed by the RNeasy MinElute protocol. For each of the 8 nuclei and 8 tissue samples, libraries were made in triplicates, using the SMART-seq2 protocol, as described for the Nuc-Seq protocol with two modifications: (1) the number of PCR cycles in the whole transcriptome amplification stage was reduced to 14 cycles; (2) 1 µl of the extracted RNA was used as the initial input to the protocol, replacing 1 µl of water in the first RT mix. Libraries were sequenced on the NextSeq 500 to an average read depth of 3 million reads. Correlations were calculated between each pair of samples. Number of genes detected was calculated for each quantile of expression levels by counting the number of genes with expression log(TPM+1)>1.1. Differential expression was analyzed using student's t-test, with FDR<0.01, log-ratio>1, and average expression across all nuclei or tissue samples log (TPM+1)>3.

Comparison of Nuc-Seq and single neuron RNA-Seq. For comparison of correlation of averaged single neuron/nuclei of CA1 pyramidal neurons, the cells labeled as 'CA1Pyr' from the single neuron RNA-Seq dataset [50] were subsampled to get a dataset (referred to as snRNA-Seq CA1Pyr) that has the same number of cells as the CA1 pyramidal nuclei from Nuc-Seq (referred to as Nuc-Seq CA1). To calculate correlations of averaged 10 single neuron/nuclei, snRNA-Seq CA1Pyr and Nuc-Seq CA1 were separately subsampled 20 times, each time to 10 cells with replacement, and the averaged expressions of these 10 cells were calculated. The Spearman correlation was then calculated on the 20 averaged expressions of subsampled snRNA-Seq CA1Pyr data and those of subsampled Nuc-Seq CA1 data. The same procedure was repeated for averaged 20, 30, 40, 50 single neuron/nuclei. For comparison of correlation of averaged single neuron/nuclei of CA1 pyramidal neurons and interneurons, the cells labeled as 'CA1Pyr' and 'Int' from the single neuron RNA-Seq dataset [50] were separately subsampled, each to 100 cells to get two datasets, referred to as snRNA-Seq CA1Pyr and snRNA-Seq Int respectively. The CA1 and GABAergic nuclei from Nuc-Seq were subsampled, each to 100 nuclei to get two datasets, referred to as Nuc-Seq CA1 and Nuc-Seq Int respectively. To calculate correlations of averaged 10 single neuron/ nuclei, snRNA-Seq CA1Pyr, snRNA-Seq Int, Nuc-Seq CA1, and Nuc-Seq Int were separately subsampled 20 times, each time to 10 cells with replacement, and the averaged expressions of these 10 cells were calculated. The Spearman correlation was then calculated between the 20 averaged expressions of subsampled snRNA-Seq CA1Pyr and those of snRNA-Seq Int, and between 20 averaged expressions of subsampled Nuc-Seq CA1 and those of Nuc-Seq Int. The same procedure was repeated for averaged 20, 30, 40, 50 single neuron/nuclei.

Analysis of nuclei clusters. Clustering analysis partitions nuclei into groups, such that nuclei from the same group share more similarity than nuclei from different groups. The quality of the grouping can be measured using the Dunn index [51]

$$DB = \frac{\min_{1 \leq i < j \leq n} d(i,j)}{\max_{1 \leq k \leq n} d'(k)},$$

where d(i, j) represents the inter-group distance between group i and j, and d'(k) represents the intragroup distance of group k.

Applicants expect that the coherent structure in transcriptomes of cells of high similarity generates observations that lie on a low-dimensional manifold in the high-dimensional measurement space [52]. In this case, data points for cells belonging to the same group would lie on a continuous smooth low-dimensional manifold, and data points for cells from different groups would lie on different manifold structures. Applicants confine distances used in calculating the Dunn index to the low-dimensional manifold structure and define the distance d'(k) as $$\hat{\Phi}_{pq} = \underset{\Phi_{pq}}{\operatorname{argmin}} \max \{ d_{mn} \mid d_{mn} \in \Phi_{pq} \}$$

-continued $$d'(k) = \max \left\{ d_{mn} \mid d_{mn} \in \bigcup_{p,q} \hat{\Phi}_{pq} \right\},$$

where p, q, m, and n are data points belonging to the group k, dmn represents the pairwise distance of data points m and n, and _p q represents a path connecting p and q through data points belonging to the group k. Applicants define the distance d(i, j) similarly to d'(k) and confine p, q, m, and n to be data points belonging to the union of the groups i and j.

Here, Applicants describe a pipeline of techniques to obtain nuclei clusters. Applicants first normalize data, then Applicants estimate false negatives and reduce their impact on the calculation of $d_{mn}$. Next, Applicants perform modified PCA and tSNE [53] to map the low-dimensional structures to a 2-D space, where $d_{mn}$ and _p q in the 2-D space represent their high-dimensional counterparts. The mapping transforms each of the low dimensional manifold structures to dense data clouds in the 2-D space, permitting grouping of cells by a density clustering technique [54]. This nonlinear mapping is particularly useful for data sets, where the scales of d'(k) for different cell groups are very different and d'(k) are affected by large noises in the original high dimensional space. Finally, Applicants identify cell subclusters within each cell cluster by the biSNE algorithm. The PCA-tSNE, biSNE, and density clustering are applied hierarchically to each cell clusters to obtain clusters at finer level. In each iteration, the Dunn index with the defined local distances d'(k) can be used to evaluate the quality of the clustering assignment.

Figure 8:
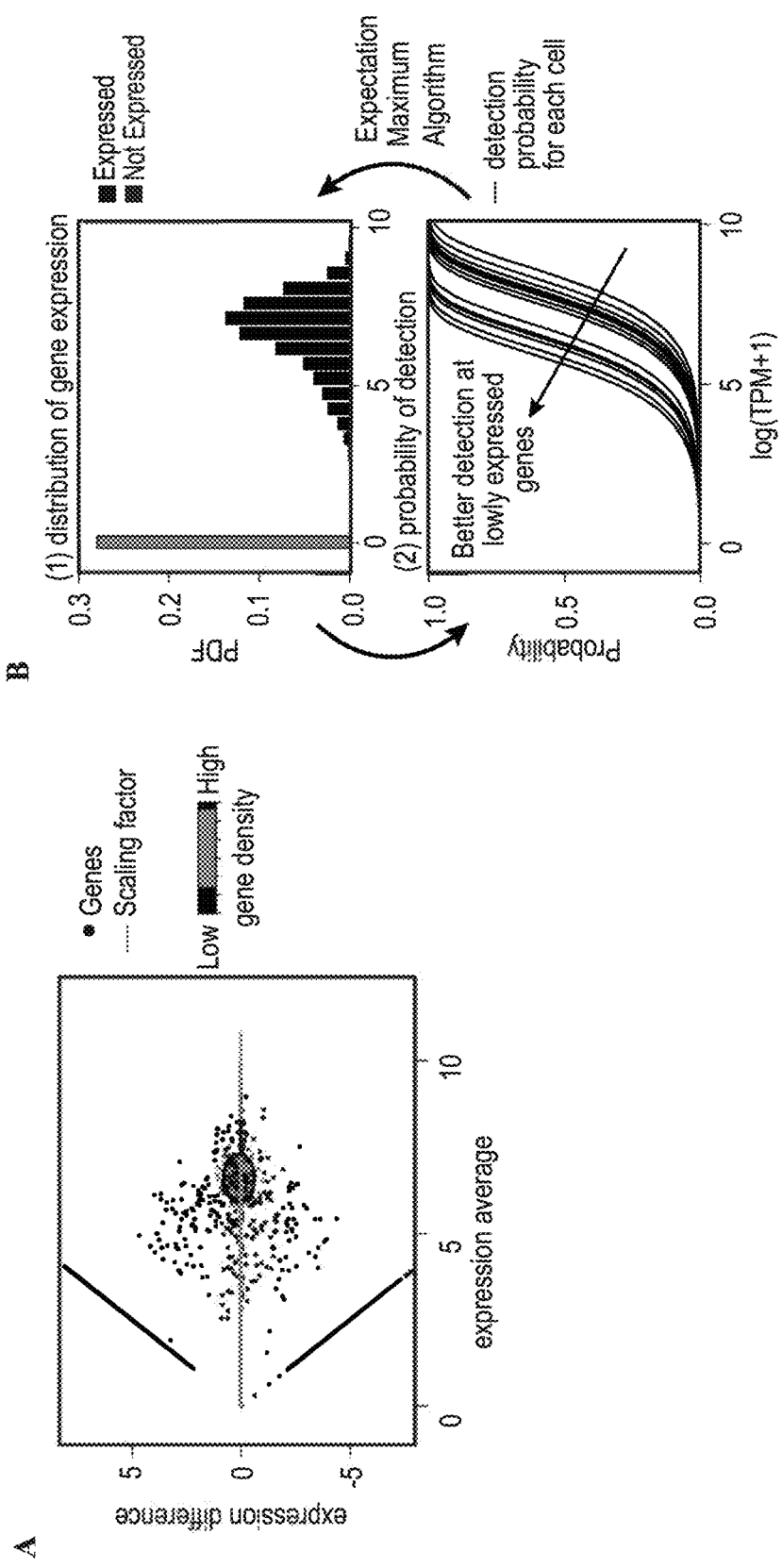
FIG. 8A-8B: Computational methods. (A) Density MA plot normalization method. MA plot showing the average log (X axis) versus the log-ratio (Y axis) of TPM expression of all genes between two single nuclei. High density region marked by a color scale. Genes within the colored density region are used to calculate the scaling factor between libraries for normalization. (B) Illustration of false negative estimation method. An expectation maximization algorithm alternates between estimation of gene expression distribution per gene (top) and the probability of detection (bottom) per cell. Top: histogram shows estimated distribution of expression of an example gene, PDF: probability density function. Bottom: each blue curve represent the probability of successfully detecting genes expressed at different levels in each cell.

Normalization. Each library of single nuclei was prepared individually. Biases exist among libraries due to inevitable differences in lysis efficiency, priming rate at RT, amplification efficiency during the initial PCR, the equalization for tagmentation, and ratios in the final sequencing pooling [55]. Although several experimental methods have been developed to mitigate biases, including, for example, adding spike-in or using unique molecular identifiers, Applicants note that these methods would only help to reduce, at best, the amount of bias introduced after the initial PCR step, however significant amount of bias occurs before that step. Applicants assume that cells of the same type should highly express a set of genes that are tightly regulated and exhibit small "real" intercellular variability. An example of such a gene set includes ribosomal and cytoskeleton genes in stem cells or housekeeping genes in dendritic cells that was previously used to normalize single-cell sequencing data [56]. However, these is no consensus housekeeping gene set for brain cells that consist of both mature neurons, immature neurons, and glia cells. To normalized cells, Applicants developed a computational normalization procedure based on Bland-Altman (MA) plot and density estimation (FIG. 8). For a pair of cells, our procedure normalizes one cell with respect to another so that genes belonging to this gene set are not differentially expressed on average. Using only a small set of highly expressed and lowly variable genes, as opposed to using all genes [55] or genes within the middle quantile, provides robustness against noise, because measurements of highly expressed genes are resistant to sampling noise, and lowly variable measurements unlikely to have been corrupted by large noise. In addition, small intercellular variance enables simple statistical models, such as Gaussian model, to yield good estimates. Similar reasoning underlies previously described normalized methods such as TMM [57], DESeq [58]. However, these methods are designed for population RNA-Seq data, and Applicants empirically found that they not compatible with single-cell data. A modified DESeq normalization which takes into account of massive false negatives common to single-cell data did give comparable performance to our procedure.

Applicants first discuss the case of two cells, and later Applicants show how to generalize to a set of arbitrary size. To identify the set of genes for normalization, Applicants first calculate differences and averages of log transformed expression level of each gene between a given pair of cells, and plot the distribution of differences by averages on an MA plot. Then, gene density in this distribution is estimated [59] and genes within the most densely plotted regions are selected. Applicants calculate a scaling factor as the average of the log expression differences of selected genes. The second cell is normalized with respect to the first cell by dividing gene expressions of the second cell by the scaling factor. Specifically, the log expression difference of gene j between two cells is given by $$r12\_j = \log(e2j) - \log(e1j),$$

and the average of log expression of gene j is given by $$a12\_j = [\log(e1j) + \log(e2j)]2.$$

where eij denotes the expression level of gene j in cell i. Gene j is selected into the gene set SJ, if r12_j and a12_j, coordinates of gene j, are within the region having density above the top 70 percentile in the MA plot. The scaling factor is obtained by $$s = \sum_{j, j \in \mathbb{S}_j} r_{12\_j} / |\mathbb{S}_J|.$$

Then the second cell is normalized as $$e'2j = e2j/s.$$

To normalize single cells of different types, cells are first clustered into separate groups, each of which contains cells of a similar type. This step ensures that normalization complies with our assumption that cells are of the same type. Then normalization is performed for each group separately. Within each group, scaling factors are estimated for each cell with respect to multiple reference cells, which are chosen based on the number of genes detected, for example, cells having number of genes detected around the 80 percentile. Although any particular reference cell could be affected by erroneous measurements to various degrees, using multiple reference cells reduces the effect of these errors in the normalization.

Specifically, for a given group of cells $\{i | i \in C_g$ and $g \in G\}$, a set of cells that have number of genes detected above 80 percentile are selected as reference cells $\{r | r \in C_{gr}$ and $C_{gr} \subset C_g\}$. The scaling factor sir for each cell i with respect to each reference cell r is calculated. To relate sir obtained with different reference cells, Applicants solve the optimization problem $$\{\hat{a}_r \mid r \in \mathbb{C}_{gr}\} = \arg\max_{a_r, r \in C_{gr}} \sum_{i \in C_g} \underset{r \in C_{gr}}{Var} [\log(s_{ir}) - \log(a_r)],$$

and scaling factors are estimated as $$s_i = \underset{r \in \mathbb{C}_{gr}}{\text{median}} \left( \frac{s_{ir}}{\hat{a}_r} \right).$$

To normalize cells from different groups, Applicants use group scaling factors estimated for each group aggregates, which are obtained by averaging all cells within a same group. Cells from a same group are normalized using their group scaling factor. Specifically, for each group g E G, the group aggregate is calculated as $$e_{gj} = \sum_{i \in C_g} e'_{ij},$$

where egj denotes the expression level of gene j in group g, and e' ij is the normalized expression level of gene g in cell i. Multiple reference group aggregates are selected for the estimation of group scaling factors.

Comparison of our normalization method with TMM and DESeq. Applicants consider a model for observed expression level eij given true expression level $$xij, eij = si \cdot \in ij \cdot xij.$$

where si represents the scaling factor of cell i, ∈ij represents the technical noise of gene j measured in cell i, and xij represents the true expression level of gene j measured in cell i. Rewrite eij on log scale, log(eij)=log(si)+log(∈ij)+log(xij). In our normalization, the normalization factor is obtained by averaging, between cell i1 and i2, the differences in the expression of selected subset of genes SJ.

$$\sum_{j \in S_J} (\log(e_{1j}) - \log(e_{2j})) / |\mathbb{S}_J| = \log(s_1) - \log(s_2) +$$

$$\sum_{j \in S_J} (\log(e_{1j}) - \log(e_{2h})) / |\mathbb{S}_J| + \sum_{j \in S_J} (\log(x_{1j}) - \log(2j)) / |\mathbb{S}_J|.$$

As ∈ij for j∈SJ is assumed to be lognormally distributed with zero mean (modeling PCR and sampling noise), and genes within SJ are not differentially expressed on average, it follows that $$\log(s_1) - \log(s_2) = \sum_{j \in \mathbb{S}_J} (\log(e_{1j}) - \log(e_{2j})) / |\mathbb{S}_J|.$$

In TMM normalization, the SJ is replaced by $$\mathbb{S}_Q = \{j | e_{ij} \in [e_{qa}, e_{qb}]\},$$

where eqa and eqb are ath and bth quantiles of eij. Applicants find the assumption that $$\Sigma_{j \in \mathbb{S}_Q} [\log(x_{1j}) - \log(x_{2j})] = 0.$$

might not hold true for single-cell RNA-Seq data. In DESeq normalization, eij is first normalized by its geometric mean across all cells, $$\log(e_{ij}) - \sum_i \log(e_{ij})/|I| =$$

$$\log(s_i) - \sum_i \log(s_i)/|I| + \log(\epsilon_{ij}) - \sum_i \log(\epsilon_{ij})/|I| + \log(x_{ij}) - \sum_i \log(x_{ij})/|I|.$$

Then median is taken over all genes, $$\operatorname*{median}_{j}\left(\log(e_{ij}) - \sum_i \log(e_{ij})/|I|\right) = \log(s_i) - \sum_i \log(s_i)/|I| +$$

$$\operatorname*{median}_{j}\left(\log(\epsilon_{ij}) - \sum_i \log(\epsilon_{ij})/|I|\right) + \operatorname*{median}_{j}\left(\log(x_{ij}) - \sum_i \log(x_{ij})/|I|\right).$$

Assume that the median of $\epsilon_{ij}$ can be replaced by the mean of $\epsilon_{ij}$, $$\operatorname*{median}_{j}\left(\log(\epsilon_{ij}) - \sum_i \log(\epsilon_{ij})/|I|\right) = \sum_j \left(\log(\epsilon_{ij}) - \sum_i \log(\epsilon_{ij})\right)/|I||J| =$$

$$\sum_j \log(\epsilon_{ij})/|J| - \sum_i \frac{1}{|I|} \sum_j \log(\epsilon_{ij})/|J|.$$

It shows that the median of normalized $e_{ij}$ is a good estimator for the scaling factor $s_i$ only if $$\sum_j \log(\epsilon_{ij}) = 0 \text{ and } \operatorname*{median}_{j}\left(\log(x_{ij}) - \sum_i \log(x_{ij})/|I|\right) = 0.$$

However, because single-cell RNA-Seq data contains substantial amount of false negative measurements, as discussed in the next section, these conditions might not hold true generally. Applicants propose a modified DESeq normalization, which gives comparable performance to our normalization method when applied to synthetic test data. In the modified DESeq normalization, the geometric mean and median are taken over only genes whose measured expression level $e_{ij}>0$. This leads to $$\operatorname*{median}_{j,e_{ij}\neq 0}\left(\log(e_{ij}) - \sum_i \log(e_{ij})/|I|\right) = \log(s_i) - \sum_i \log(s_i)/|I| +$$

$$\operatorname*{median}_{j,e_{ij}\neq 0}\left(\log(\epsilon_{ij}) - \sum_i \log(\epsilon_{ij})/|I|\right) + \operatorname*{median}_{j,e_{ij}\neq 0}\left(\log(x_{ij}) - \sum_i \log(x_{ij})/|I|\right).$$

In this formulation, the expression level $\epsilon_{ij}$ for $\{j\ e_{ij}>0\}$ is not subjected to false negative, and is assumed to be lognormally distributed with zero mean. Therefore, the median of $\epsilon_{ij}$ for $\{j|e_{ij}>0\}$ is $$\operatorname*{median}_{j,e_{ij}\neq 0}\left(\log(\epsilon_{ij}) - \sum_i \log(\epsilon_{ij})/|I|\right) =$$

$$\sum_{j,e_{ij}\neq 0} \log(\epsilon_{ij})/|J| - \sum_i \frac{1}{|I|} \sum_{j,e_{ij}\neq 0} \log(\epsilon_{ij})/|J| = 0.$$

And further assume that there exist some genes that are not differentially expressed among all cells, then the median is a robust measure to find one such gene, $$\operatorname*{median}_{j,e_{ij}>0}\left(\log(x_{ij}) - \sum_i \log(x_{ij})/|I|\right) = 0.$$

Therefore, Applicants can obtain the scaling factor by $$\log(s_i) - \sum_i \log(s_i) = \operatorname*{median}_{j,e_{ij}>0}\left(\log(e_{ij}) - \sum_i \log(e_{ij})/|I|\right).$$

Estimation of missed detection probability. Single nuclei transcriptome libraries are amplified from extremely small input materials. As such, Applicants expect that some transcripts that are lowly expressed will not be detected (false negatives). The probability of such missed detection increases for lowly expressed transcripts and lower quality libraries. Such false negatives are detrimental to various analyses. For example, they invalidate the normal distribution assumption underlying typically used Student's t-test, leaving the statistical test unjustified. In addition, false negatives confound the identification of bimodally expressed genes, such as cell type specific markers. Previous studies accounted for such false negatives by combining estimation of cell quality and gene expression [55, 60]. These methods were based on parametric estimation of gene expression distribution. However, distribution of gene expression cannot be readily fitted by a single parametric function. In contrast to these methods, Applicants developed a Bayesian method to estimate the likelihood of an observed zero measurement being a missed detection. Our approach is based on a non-parametric estimation for gene expression distribution.

Our method is based on two observations: a) Detection rates depend on expression level. The higher a gene is expressed, the more likely it can be detected. b) Detection rates depend on library quality. Genes are more likely to be detected in libraries of high quality. Applicants model these two observations as

- prior distributions: distributions of expression levels for each gene in cells of the same type
- sampling probabilities: detection probabilities at different expression levels for each cell For each observed $e_{ij}=0$ of gene j in cell i, Applicants then estimate the posterior distribution for two mutually exclusive hypotheses that $e_{ij}$ is a missed detection or that gene j is not expressed in cell i. Specifically, the distribution of expression level of gene j is calculated as mixture of two distributions. The first one is the probability that gene j is not expressed $$p_j(x=0) = \frac{\Sigma_{i \in \{e_{ij}=0\}} 1}{\Sigma_i 1}.$$

where x denotes the true expression level. The second one is a conditional distribution of expression levels of gene j given that gene j is expressed. This distribution is estimated using a KDE based method [59] using gene expression levels $e_{ij}$ from cells i, $\{i|e_{ij}>0\}$. Combining two parts yields $$p_j(x) = p_j(x=0) + [1 - p_j(x=0)] p_j\_KDE(x),$$

where x denotes the expression level. The detection probability (1—dropout probability) for a cell i is modeled using a geometric distribution parameterized by βi, as it captures the Poisson sampling process, mechanism underlying detection stochasticity $$\Lambda(x, \beta_i) = 1 - e^{-t}, t = \beta_i \begin{bmatrix} 1 \\ x \end{bmatrix} = \beta_{i0} + \beta_{i1} x$$

$$0 \le \Lambda(x, \beta_i) \le 1,$$

where x denotes expression level. Given observed data eij, the expected value of the log likelihood function is given by $$E[L] = \sum_{j \in \{e_{ij} > 0\}} \log(1 \cdot \Lambda(e_{ij}, \beta_i)) + \sum_{j \in \{e_{ij} = 0\}} \sum_x p_j(x) \log(p_j(x)(1 - \Lambda(x, \beta_i))).$$

In each iteration, the log likelihood function is maximized using gradient descent.

$$\hat{\beta}_i = \underset{a_i}{\text{argmax}} \, E[L]$$

$$\frac{\partial E[L]}{\partial \beta_i} = \sum_{j \in \{e_{ij} > 0\}} \frac{1}{\Lambda(e_{ij}, \beta_i)} \frac{\partial \Lambda(e_{ij}, \beta_i)}{\partial \beta_i} +$$

$$\sum_{j \in \{e_{ij} = 0\}} \sum_x p_j(x) \frac{1}{1 - \Lambda(x, \beta_i)} (-1) \frac{\partial \Lambda(x, \beta_i)}{\partial \beta_i}.$$

Because _(x, β) is constrained to be non-negative, its derivative is modified with a rectifier so that _(x, β) is differentiable for any x, $$h(x) = \frac{\log(\exp(x \cdot N) + 1)}{N}, \text{ where } N \text{ is a large number}$$

$$\frac{\partial \Lambda}{\partial \beta} \approx \frac{\partial h}{\partial \Lambda} \frac{\partial \Lambda}{\partial \beta} = \frac{1}{1 + \exp(-\Lambda(x, \beta) \cdot N)} \cdot e^{-t} \begin{bmatrix} 1 \\ x \end{bmatrix}.$$

Then the distribution of expression levels are updated by $$p(e_{ij} = 0 \mid x_{ij} > 0) = \sum_x p_j(x)(1 - \Lambda(x, \hat{\beta}_i))$$

$$p(x_{ij} = 0 \mid e_{ij} = 0) = \frac{p_j(x_{ij} = 0)}{p_j(x_{ij} = 0) + p(e_{ij} = 0 \mid x_{ij} > 0)}$$

$$p_j(x = 0) = \frac{\sum_{j \in \{e_{ij} = 0\}} p(x_{ij} = 0 \mid e_{ij} = 0)}{\sum_{j \in \{e_{ij} = 0\}} p(x_{ij} = 0 \mid e_{ij} = 0) + \sum_{j \in \{e_{ij} > 0\}} 1}$$

$$p_j(x) = p_j(x = 0) + [1 - p_j(x = 0)] p_{j\_KDE}(x),$$

where p (xij|0|eij=0) denotes the probability that gene j is not expressed in cell i. Applicants implemented an expectation-maximization (EM) algorithm that alternates between performing an expectation step for L, and a maximization step for searching the maximizer ^βi of E[L]. The probability p (xij=0|eij=0) is incorporated in calculations of summary statistics and distances to weight zero measurements. The higher the probability, the more likely that an observed zero represents an truly unexpressed gene in a cell, and the more Applicants weight the contribution of the zero. Conversely, the lower the probability, the higher the chance that it is false negative, and the lower Applicants weight its contribution in an analysis.

Specifically, Applicants weight summary statistics, Euclidean distance, Pearson correlation coefficient, and cosine similarity in the following ways.

I. the weighted gene expression mean: where $$u_j = \sum_i e_{ij} w_{ij} / \sum_i w_{ij},$$

$$w_{ij} = \begin{cases} p(x_{ij} = 0 \mid e_{ij} = 0) & \text{if } e_{ij} = 0 \\ 1 & \text{if } e_{ij} > 0. \end{cases}$$

II. the weighted Euclidean distance between two cells x, y:

$$w_j = w_{xj} w_{yj}$$

$$d_{xy} = \frac{\sum_j (e_{xj} - e_{yj})^2 w_j}{\sum_j w_j}.$$

III. the weighted Pearson correlation coefficient between two cells x, y:

$$\hat{e}_x = e_x - u_x, \qquad \hat{e}_y = e_y - u_y$$

$$S_{xy} = \sum_j \hat{e}_{xj} \hat{e}_{yj} w_j, \quad S_{xx} = \sum_j \hat{e}_{xy}^2 w_j, \quad S_{yy} = \sum_j \hat{e}_{yj}^2 w_j$$

$$\rho_{xy} = \frac{S_{xy}}{\sqrt{S_{xx} S_{yy}}}.$$

IV. the weighted cosine similarity is calculated in a similar way except no data centering.
V. the weighted Euclidean distance between two cells x, y under a linear transformation of linear combinations of genes, Y=XA, where X is an i×j matrix, and A is a j×k transformation matrix, is given by $$w_j = w_{xj} w_{yj}$$

$$d_{xy} = \sum_k \left( \frac{\sum_j a_{jk} (e_{xj} - e_{yj}) w_j}{\sum_j w_j} \right)^2.$$

VI. the weighted Pearson correlation coefficient between two cells x, y under a linear transformation of linear combinations of genes as above is given by $$u_x = \frac{1}{|K|} \sum_k \frac{\sum_j a_{jk} e_{xj} w_j}{\sum_j w_j}, \quad u_y = \frac{1}{|K|} \sum_k \frac{\sum_j a_{jk} e_{yj} w_j}{\sum_j w_j}$$

$$\hat{e}_{xk} = \frac{\sum_j a_{jk} w_{xj} w_j}{\sum_j w_j} - u_x, \quad \hat{e}_{yk} = \frac{\sum_j a_{jk} e_{yj} w_j}{\sum_j w_j} - u_y$$

$$S_{xy} = \sum_k \hat{e}_{xk} \hat{e}_{yk}, \qquad S_{xx} = \sum_k c_{xk}^2, \qquad S_{yy} = \sum_k \hat{e}_{yk}^2$$

$$\rho_{xy} = \frac{S_{xy}}{\sqrt{S_{xx} S_{yy}}}.$$

VII. the weighted cosine similarity is calculated similarly as the weighted correlation coefficient except no data centering.

VIII. the weighted covariance between two genes under a linear transformation of linear combinations of genes as above is given by $$u_{xk} = \frac{\Sigma_i \Sigma_j a_{jk} \hat{e}_{ij} w_{ij}}{\Sigma_i \Sigma_j w_{ij}} = \frac{\Sigma_j a_{jk} \Sigma_i \hat{e}_{ij} w_{ij}}{\Sigma_i \Sigma_j w_{ij}} = 0, \hat{e} \text{ is centered along } i$$

$$cov(k, k') = \frac{\Sigma_i (\Sigma_j a_{jk} \hat{e}_{ij} w_{ij})(\Sigma_j a_{jk'} \hat{e}_{ij} w_{ij})}{\Sigma_i (\Sigma_j w_{ij})^2}.$$

PCA and tSNE. To project cells to two dimensional space, Applicants first perform principal component analysis (PCA) to project original data to reduced linear dimensions, where most significant variance of the data is preserved as determined based on the largest eigenvalue gap. Applicants then calculate the cosine distance of cells on the PCA reduced dimensional space. Finally, Applicants use t-distributed Stochastic Neighbor Embedding (tSNE) [53, 61, 62] with the cosine distance to further map cells to two dimensions, where Euclidean distances of closely projected cells represent their cosine distances. The cosine distance depends the angle between two vectors defined by gene expressions in the high dimensional space. It is preferred in our analysis over Euclidean distance and correlation distance, because it is more robust to noise than Euclidean distance and it is invariant under rotational transformations, such as PCA.

I. weighted PCA. The PCA analysis is performed usually using singular value decomposition (SVD) or eigenvalue decomposition (EVD) on the covariance matrix, which scales quadratically with the number of genes. Given large number of genes, more than 25,000, in our data, it is computational costly to directly perform SVD or EVD on the large covariance matrix. In order to get principal components, or the transformation matrix A, while accounting for weights, Applicants first center the original data matrix E across genes to get Ê, where eij is the expression level of gene j in cell i. Next, Applicants perform SVD on centered data matrix Ê to get A*. Applicants calculate the weighted covariance matrix Cw on Ê under the linear transformation defined by the matrix A*. Applicants then perform SVD or EVD on Cw to get A.

II. tSNE with cosine distance. Applicants modified the original tSNE to allow dimensionality reduction based on a weighted cosine similarity. The original tSNE technique projects data in a non-linear way to low dimensional space, such that Euclidean distances between neighboring data points in the low dimensional space overall represent distances between these neighboring data points, or local distances, in the high dimensional space. The input to tSNE is a distance matrix, describing all pairwise distances in the high dimensional space. In order to apply tSNE, Applicants first transform the weighted cosine similarity to cosine distance by exploring relationships between the two measures on the closest data points. Specifically, given a cell and its gene expression measurements denoted by a n dimensional vector x, the measurements of its neighbor y is modeled as $$y = k(x+d),$$

where k is a scaling factor and d denotes the distance between x and y. Under the null hypothesis that x and y are measured from two cells of the same type, d is drawn from a Gaussian distribution with zero mean and variance σ. Our goal is to estimate the distance magnitude |d|, given the measured angle ϕ between x and y. Geometrically, the vector d lies on a hypersphere defined by radius |d|. The volume and surface area of a hypersphere of dimension n (n-sphere) has the following properties $$Sn = (n+1)Vn+1$$

$$dSn = (n+1)dVn+1$$

the volume element is $$dV_{n+1} = |d|^n \sin^{n-1}(\phi_1) \sin^{n-2}(\phi_2) \cdots \sin(\phi_{n-1}) d|d| d\phi_1 d\phi_2 \cdots d\phi_n$$

$$= \sin^{n-1}(\phi_1) d\phi_1 \cdot g(|d|, \phi_2, \ldots, \phi_n)$$

$$dS_n = \sin^{n-1}(\phi_1) d\phi_1 \cdot (n+1) g(|d|, \phi_2, \ldots, \phi_n).$$

The probability of drawing d in a n-sphere of radius |d| with an angle ϕ from x scales as sin-1(Φ). When n is large, most of d lie perpendicular to x, thus there exists a unique mapping between |d| and ϕ.

$$\cos(\phi) = \frac{1}{\sqrt{(1+|d|)^2 + 1}}$$

$$|d| = \sqrt{\frac{1}{\cos^2(\phi)} - 1}$$

Differential gene expression and pathway analysis. Applicants use an adjusted Welch's t-test for identifying differentially expressed genes. Applicants applied weights in the calculation of summary statistics, such as sample mean, sample variance, and effective degrees of freedom, used in Welch's t-test. Specifically, to find the significance level of gene j between cells in group X and cells in group Y, $$n_{xj} = \sum_{i,i \in X} w_{ij}, \qquad n_{yj} = \sum_{i,i \in Y} w_{ij},$$

$$u_{xj} = \sum_{i,i \in X} e_{ij} w_{ij}/n_{xj}, \qquad i_{yj} = \sum_{i,i \in Y} e_{ij} w_{ij}/n_{yj},$$

$$S_{xj} = \sum_{i,i \in X} (e_{ij} - u_{xj})^2 w_{ij}/(n_{xj} - 1), \quad S_{yj} = \sum_{i,i \in Y} (e_{ij} - u_{yj})^2 w_{ij}/(n_{yj} - 1).$$

$$t \text{ statistic } t_j = \frac{u_{xj} - u_{yj}}{\sqrt{\frac{S_{xj}}{n_{xj}} + \frac{S_{yj}}{n_{yj}}}},$$

$$\text{degrees of freedom } v_j \approx \frac{(S_{xj}/n_{xj} + S_{yj}/n_{yj})^2}{S_{xj}^2/[n_{xj}^2(n_{xj}-1)] + S_{yj}^2/[n_{yj}^2(n_{yj}-1)]}.$$

The false discovery rate (FDR) is calculated for each differentially expressed gene in multiple hypothesis testing using Benjamini and Hochberg procedure [63].

Density clustering and selection of the number of clusters. Applicants used a density based clustering method [54] to partition cells embedded in the 2-D space. The method searches cluster centers that are characterized by two quantities. (1) high local density ρi and (2) large distance δi from points of higher density, which are centers of other clusters. Applicants unify the two quantities into a single metric by taking the product of the two quantities, si=ρi·δi.

To select cluster centers, Applicants rank each data points by their si in descending order. For a given n, the number of desired clusters, Applicants select the top ranked n cluster centers, and perform the cluster assignment as described previously [54]. To evaluate the quality of the clustering, Applicants calculate the Dunn index for each n with d(i, j) and d'(k) defined as local distances. The calculation of the Dunn index can be operated in O(N3), where N is the number of total data points.

---

Algorithm: Identification of maximum
steps on shortest paths (MaxStep)

Input: pairwise distance of data points (D)
Output: the pairwise shortest link (D')
D' := D
n := # of data points
for k := 1 to n do
| for i := 1 to n−1 do
| | for j := i+1 to n do
| | | D'(i,j) = min(D'(i,j), max(D'(i,k), D'(k,j)))
| | end
| end
end
return D'

---

Algorithm: Calculation of the Dunn index defined on local distances (DunnLocal)

Input: pairwise distance of data points in the 2-D embedding (D), clustering assignment (Cl)
Output: the Dunn index (θ)
cl_uiq := unique(Cl)
n := # of cl_uiq
d'$_k$ := empty array with a length of n
d$_{ij}$ := empty matrix with a size of (n, n)
for i := 1 to n do
| ii := index of data whose clustering assignment is cl_uiq(i)
| d'$_k$(i) := max(MaxStep(D(ii,ii)))
end
for i := 1 to n−1 do
| for j := i+1 to n do
| | ii := index of data whose clustering assignment is either cl_uiq(i) or el_uiq(j)
| | d$_{ij}$(i,j) := max(MaxStep(D(ii,ii)))
| end
end
θ := min(d$_{ij}$)/ max(d'$_k$)
return θ

---

Large scale comparison between RNA-Seq data and ISH data. Applicants selected genes differentially expressed between any bipartition of DG, CA1, CA2, CA3 clusters in RNA-Seq data. For example, a gene is selected if it is differentially expressed between cells in a combined DG and CA2 cluster, and cells in a combined CA1 and CA3 cluster. Specifically, the differential expression was tested using the adjusted t-test between cells∈C1, C1 ⊂ {DG, CA1, CA2, CA3} and cells∈C2, C2={DG, CA1, CA2, CA3}\C1. Gene j is selected if difference in mean $m\mathbb{C}_{1j} - m\mathbb{C}_{2j} > 1$ mean of cells $\in \mathbb{C}_1$  $m\mathbb{C}_{1j} > 20$ TPM mean of cells $\in \mathbb{C}_2$  $m\mathbb{C}_{2j} < 5$ TPM p values of t-test $p_j < 0.01$.

The quantified ISH data [64] with 200 μm resolution was downloaded from Allen Brain Atlas (Website: 2015 Allen Institute for Brain Science. Allen Mouse Brain Atlas [Internet]. Available from: mouse.brain-map.org.) Mean expression level of ISH data was calculated as averaged energy level for each of the DG, CA1, CA2, CA3 regions. Specifically, averaged energy level eG for grids in a region G is given by $$e_G = \sum_{g \in G} d_g \cdot i_g / |G|,$$

where dg is the quantified expression density for grid g, and ig is the quantified expression intensity for grid g. The Indices for DG, CA1, CA2, CA3 regions are 726, 382, 423, 463. Applicants obtained two vectors e∈R4 comprising averaged expression levels of DG, CA1, CA2, CA3 regions for each gene, one from RNA-Seq data, and another from ISH data. Pearson correlation coefficient was calculated between these two vectors for each selected gene.

BiSNE. Cells positioned in proximity in the tSNE mapping coexpress a set of genes that are not expressed by distal cells. These set of genes could be used to distinguish different cell subpopulations. These genes are coexpressed in the cells grouped in proximity, and therefore they have localized expression patterns in the tSNE mapping.

Statistics for scoring expression patterns. Motivated by this observation, Applicants use two different statistics to identify genes with significantly localized expression patterns in the tSNE mapping and then perform PCA-tSNE using the union of these identified genes to cluster cells.

I. Moran's I. Moran's I [65] scores correlation between a measurement on a set of mapping positions and pairwise distances of these mapping positions. Given tSNE coordinates, the Moran's I for gene k is given by $$I(k) = \frac{\Sigma_i \Sigma_j Q_{ij}(e_{ik} - u_k)(e_{jk} - u_k) w_{ik} w_{jk} / \Sigma_i \Sigma_j Q_{ij} w_{ik} w_{jk}}{\Sigma_i (e_{ik} - u_k)^2 w_{ik} / \Sigma_i w_{ik}},$$

where Qij denotes the pairwise similarity transformed from dij, the Euclidean distances between cell i and j in the tSNE mapping. Applicants obtain Qij from dij using the Gaussian function, $$Q_{ij} = \frac{1}{\sigma\sqrt{2\pi}} \exp\left(-\frac{d_{ij}^2}{2\sigma^2}\right).$$

Applicants choose σ to set the minimal size of localized expressed pattern, as dij≈σweights around 60% and dij≈2σ weights around 13.5%. The statistical significance of the pattern of gene k is tested by converting I(k) to a z score, $$V[I] = \frac{1}{S_0^2(N^2-1)(N^2S_1 - NS_2 + 3S_0^2)} - E[I]^2$$

$$S_0 = 2\sum_i\sum_j Q_{ij}, \quad S_1 = 2\sum_i\sum_j Q_{ij}^2, \quad S_2 = 4\sum_i\left(\sum_j Q_{ij}\right)^2$$

$$z = \frac{I - E[I]}{\sqrt{V[I]}}.$$

Moran's I uses gene expression levels in its calculation. When identifying marker genes, only the information about whether a gene is expressed or not is necessary. Applicants use a modified Moran's I on binarized gene expression levels. Specifically, Applicants binarize gene expression level by a threshold, $$\hat{e}_{ij} = \begin{cases} 1 & \text{if } e_{ij} > 3 \text{ TPM} \\ 0 & \text{if } e_{ij} \leq 3 \text{ TPM} \end{cases}.$$

Applicants then calculate the modified Moran's I by, $$I(k) = \frac{\sum_i\sum_j Q_{ij}(\hat{e}_{ik} - \hat{u}_k)(\hat{e}_{jk} - \hat{u}_k)w_{ik}w_{jk}}{\sum_i\sum_j Q_{ij}w_{ik}w_{jk}}.$$

Moran's I is a global measure. It has biases towards genes that are widely expressed. To reduce false positives, Applicants filtered out genes expressed in more than 80% of cells.

II. Manhattan distance and order statistics. The manhattan distance is an alternative to the Euclidean distance in quantifying proximity. The advantage of using manhattan distance is that x and y coordinates can be tested independently using order statistics. Assume a given set of cells that express gene j and their positions z on a coordinate z, z̄ is defined as the normalized z such that $$\bar{z} = (z_i - \min(z))/(\max(z) - \min(z)), i \in \{i | e_{ij} > TPM\ 3\},$$

and ^z is defined as the ordered list of ⁻z, such that ^zi<^zi+1. The range wz is defined as wz=^zn−^z1. Assume that ^z is a vector of i.i.d. samples from a uniform distribution, the significance level p of wz can be found using order statistics PDF of w $f_w(w) = n(n-1)\int_{-\infty}^{+\infty}[F(x+w) - F(w)]^{(n-2)}f(x)f(x+w)dx$ where $f(x)$ and $F(x)$ are PDF and CDF of z CDF of w $F_w(w) = w^{n-1}[n - (n-1)w]$, under null hypothesis $p_z = F_w(w_z),$ where PDF is the probability density function and CDF is the cumulative density function. To robustly estimate w in the presence of outliers, the distribution of z is fitted using the Gaussian distribution with robust estimators of mean and variance [66].

$u_z = \text{median}(z)$ $S_z = 1.1926\ \text{median}_i(\text{median}_j(|z_i - z_j|))$ $p_i = \Phi\left(-\left|\frac{z_i - u_z}{S_z}\right|\right),$ where Φ denotes the CDF of the standard normal distribution. Samples with pi<∈, a predefined threshold, are considered outliers and are excluded from the estimation of w. A single p value is calculated for each gene by taking the product of px and py, the p values obtained for x and y coordinates, respectively. It measures the overall significance level of each gene in both coordinates.

Selection of significant genes. For each statistic, Applicants rank genes based on their significance. Genes ranked high are likely to be informative for clustering cells, whereas genes ranked low are more likely to be noises that suppress clustering separation. Applicants use a cut off rank to select informative genes, chosen based on the statistic of eigenvalues of random matrices [67], which states that inclusion of a noisy row(gene) in a data matrix would lead to a reduction in the maximum eigenvalue gap of the matrix. Conversely, inclusion of an informative row(gene) would lead to an increase in the maximum eigenvalue gap, as the variance it introduces aligns with variances of some other genes. Therefore, the change in the maximum eigenvalue gap measures the extent a gene being informative. After genes are ranked, Applicants start with a data matrix containing the top ranked genes, and add subsequent genes with lower rank incrementally. For each addition, Applicants calculate the change in the maximum eigenvalue gap before and after adding the gene. Additionally, Applicants randomly permute measurements of this gene across cells and calculate the change in the maximum eigenvalue gap induced by adding this permuted gene. Applicants then select a cut off rank, below which there is no difference in the change of the maximum eigenvalue gap between adding a gene or its permuted counterpart. The selection cut-off can also be formally tested using minimum hypergeometric test [68]. Specifically, for a data matrix E1,j−1 and a gene j, Applicants form a new matrix $$E_{1,j} = \begin{bmatrix} E_{1,j-1} \\ e_j. \end{bmatrix}$$

and we obtain the eigenvalues of $E_{1,j-1}E_{1,j-1}^T$ using weighted SVD. The eigenvalues are normalized and sorted in order.

$$\lambda_1 > \lambda_2 > \ldots > \lambda_n, \text{ and } \sum_i \lambda_i = 1.$$

The distribution density (Marchenko-Pastur distribution) of higher order eigenvalues can be approximated by a linear function [67], and its cumulative distribution can be approximated by a quadratic polynomial. The sorted eigenvalues follow the inverse function of the cumulative distribution, and are fitted by $$\tilde{\lambda}_i = f(i) = \alpha_0 + \alpha_1 \sqrt{\frac{i}{n}}, \alpha_0 \text{ and } \alpha_1 \in \mathbb{R}.$$

The eigenvalue gap is approximated as $$\Delta_j = \sum_{i=1}^{n} (\lambda_i - \tilde{\lambda}_i).$$

For permutation comparison, expression of gene j is permuted,
$\tilde{e}_j : \tilde{e}_{ij} = e_{i'j}$, i' is drawn without replacement from [1,n]

$$\tilde{E}_{1,j} = \begin{bmatrix} E_{1,j-1} \\ \tilde{e}_j \end{bmatrix},$$

where i' denotes randomly permuted cell index. The eigenvalue gap~_j is obtained for the permuted matrix~E 1,j. A cut off rank is chosen at k, if the change in the eigenvalue gap_'~_' is not significant for genes ranked below k. To combine top genes, Applicants take the union of genes selected by different statistics. Clustering of gene signatures using cross correlation to cluster genes into gene signatures while taking into account of the similarity between cells expressing these genes, Applicants compute cross correlations between high scoring genes while taking account of the proximity of cells expressing these genes, convert the correlation coefficient to distances, and cluster these genes using t-SNE and density clustering. Specifically, spatial cross correlation between gene k and k' is given by $$I(k, k') = \frac{\Sigma_i \Sigma_j Q_{ij}(e_{ik} - u_k)(e_{jk'} - u_{k'}) w_{ik} w_{jk'} /}{\sqrt{(\Sigma_i(e_{ik} - u_{k'})^2 w_{ik'}/\Sigma_i w_{ik})} \sqrt{(\Sigma_i(e_{ik'} - u_{k'})^2 w_{ik'}/\Sigma_i w_{ik'})}}.$$

It has been noted that the range of I is not [−1, 1], unlike Pearson's correlation coefficient. Applicants empirically found that I is positively biased in the tSNE mapping. The positive bias may underestimate the strength of anti-correlation genes having complementary patterns. A scalar transformation of I that has the exact range [−1, 1] has been proposed [69].

$\tilde{W}=(n\bar{w})^{-1}H^T WH$, where $\tilde{W}$ is a$(n-1)\times(n-1)$ matrix and $$\tilde{w} = \sum_{i,j=1}^{n} w_{i,j}/n^2$$

$H=(h_1, \ldots, h_{n-1})$ is defined based on Helmert orthogonal matrix $h_i^T = (1_i^T, -i, 0_{n-i-1}^T)/\sqrt{i(i+1)}$, for $i=1, \ldots, n-1$.

The scalar transformation of Moran's I is given by $$I_M = \begin{cases} [(n-1)I + 1]/[[(n-1)\lambda_{(1)} + 1]] & \text{if } (n-1)I + 1 < 0 \\ [(n-1)I + 1]/[(n-1)\lambda_{(n-1)} + 1] & \text{if } (n-1)I + 1 \geq 0, \end{cases}$$

where $\lambda_{(1)}$ and $\lambda_{(n-1)}$ are the smallest and largest eigenvalues of the matrix $\tilde{W}$.

The calculation of spatial cross correlation has a computational complexity that scales quadratically with the number of gene and cells as of O(N2M2), where N is the number of cells and M is the number of genes. When the number of cells and the number of genes are large, it becomes impractical to calculate the spatial cross correlation. However, for clustering genes using tSNE [70], only the information about k nearest neighbor (knn) data points is necessary, requiring a linear complexity as of O(N2MK). The data with knn defined on a metric space can be organized using structures such as vantage point (VP) tree [71] for efficient computation. Applicants develop a conversion between spatial correlation coefficient and a metric.

Theorem For a given similarity $I(k, k')$, $$I(k, k') \in [-B, B], B \in \mathbb{R} \text{ and } B > 0, \text{ define } g(k, k')$$

$$g(k, k') = \begin{cases} 0 & \text{if } k = k' \\ \sqrt{n - I(k, k')} & \text{if } k \neq k' \end{cases}$$

with $a > \frac{5}{3}B$, and $g(I(k, k'))$ is a metric.

Proof: For $k = k'$, the proof is trivial. For $k \neq k'$, 1. non-negativity, $g(k, k') = \sqrt{a - I(k, k')} > \sqrt{\frac{2}{3}B} > 0$ 2. coincidence, $g(k, k') = \sqrt{a - I(k, k')} > 0$ 3. symmetry, $g(k, k') = \sqrt{a - I(k, k')} = \sqrt{a - I(k', k)} = g(k', k)$ 4. triangle inequality, $$g(k, k'') + g(k'', k') \geq 2\sqrt{a - B} > \sqrt{a - (-B)} > g(k, k')$$

Selection of principal components. Applicants choose top principal components (PCs) based on the largest Eigen value gap. Applicants used top 15 PCs for all cells, top 11 PCs for glial cells, top 13 PCs for DG granule cells, top 7 PCs and top 4 PCs before and after biSNE feature selection for GABAergic cells, top 3 PCs and top 4 PCs before and after biSNE feature selection for CA1 pyramidal cells, top 2 PCs and top 5 PCs before and after biSNE feature selection for CA3 pyramidal cells, and top 2 PCs for immature neuronal cells. For GABAergic cells, after biSNE feature selection, two rounds of PCA-tSNE were performed. The first round includes all GABAergic cells, and the second round includes cells belonging to the GABAergic subclusters 3, 6, 7, and 8. The same 4 PCs were used in both rounds.

Comparison of biSNE and generalized linear model. Applicants used an in-house implemented generalized linear model (GLM) [72, 73] to select highly variable genes in the GABAergic nuclei data. Three different set of genes were chosen based on three significance levels. PCA-tSNE embeddings were performed on the nuclei data using each of the chosen sets of genes. The cluster assignments were obtained on the PCA-tSNE embedding that corresponds to the most stringent significance level. Applicants used biSNE to select three sets of correlated highly variable genes in the same nuclei data. Each set contains the same number of genes as that in the corresponding set selected by GLM. PCA-tSNE embedding and the cluster assignments were performed using each of sets of genes.

Validations of glia sub-types expression signatures. Differentially expressed marker genes were found for each of the glia subclusters and for the neuronal clusters. Differential genes were averaged across each glia cluster and averaged across all neuronal clusters combined. Spearman correlation was calculated between these average expression patterns and cell type specific bulk RNA-Seq performed in the cerebral cortex [74]. The published dataset was log transformed.

Identification of nuclei identity based on a single marker gene. Applicants performed in silico cell sorting based on Pvalb expression, and found that the sorted cells constitute a subset of the identified Pvalb interneurons. This demonstrates that cell type identification based on the expression level of a single marker gene can suffer from false negatives, if only because of "drop outs" in single-cell RNA-Seq or Nuc-Seq. Fortunately, the Pvalb expressing interneurons also share similarity in the expression of many other genes, enabling the recovery of genes commonly expressed by Pvalb interneurons, providing a robust way to determine cell type.

Localization of subclusters to anatomical regions. Localizing subclusters requires a spatial reference map of a few landmark genes [42] and the expression level of these landmark genes in each subcluster. Applicants first created a spatial reference map by dividing an anatomical region into a grid. Applicants manually scored the expression levels of known landmark genes [64] in this grid as not expressed, weakly, or highly expressed in these grids. Next, Applicants generated for each subcluster a "landmark profile" by the percentage of cells expressing each landmark in this subcluster. Applicants developed a approach similar to Seurat [42] to infer whether a given landmark gene is expressed in each cell by exploiting information from all non-landmark genes. The technique leverages the fact that many genes that are co-regulated with the landmark genes are measured in Nuc-Seq and that their expression pattern contains information about landmark genes [42]. Our anatomical alignment method is similar to Seurat in concept. Unlike Seurat, however, our method can accommodate situations when far fewer landmark genes are available (a common situation in many system unlike the heavily-studied zebrafish embryo, on which Applicants demonstrated Seurat). Applicants calculated the percentage of inferred expressing cells in each subcluster. To relate the subclusters to the reference map, Applicants evaluated the correlation between each subcluster's landmark profile and the profile of landmark genes in each part of the reference map. Applicants positioned each of the subclusters to the highly correlated parts of the map. The accuracy of this spatial mapping is dependent on the quality of ISH images of landmark genes from the Allan brain atlas. The selected landmark genes for CA1 region are Nov, Ndst4, Dcn, Gpc3, Zbtb20, Calb1, Prss12, Wfs1, Col5a1, Grp, Gpr101. The selected landmark genes for CA3 region are Kcnq5, Kctd4, Ttn, Rph3a, Mas1, Plagl1, Col6a1, Prkcd, Loxl1, Grp, Ptgs2, Dkk3, St18, Mylk. Applicants used a supervised machine learning algorithm to fit and binarize expression of marker genes. To obtain a training data set for a given marker gene j, Applicants ranked subclusters by weighted mean expression of the marker gene, and select cells expressing the marker gene above TPM 8 in the top ranked three subclusters as positive training samples. Applicants selected cells not expressing or lowly (less than TPM 3) expressing the marker gene in the bottom ranked three subclusters as negative training samples. Specifically, Applicants use all genes except marker genes as feature data z in an L1-regularized L2-loss support vector machine $$z_{ik} = \begin{cases} 1 - p(x_{ik} = 0 \mid e_{ik} = 0) & \text{if } e_{ik} = 0 \\ 1 & \text{if } e_{ik} > 0 \end{cases}$$

$$u_{ij} = \begin{cases} 0 & \text{if } i \in \text{negative training samples} \\ 1 & \text{if } i \in \text{positive training samples} \end{cases}.$$

where $k \notin$ markers, and $i \in$ training cells. Applicants solved the unconstrained optimization problem using liblinear package [75]

$$\min_{w_j} \|w_j\|_1 + C \sum_{i=1}^{l} (\max(0, 1 - y_{ij} w_j^T z_i^T))^2$$

where C denotes the penalty parameter. Applicants performed coarse search followed by fine search using 5 fold cross validation for parameter C that yielded the best accuracy for training data. To predict whether the marker gene is expressed in cells not included in the training samples, Applicants used the decision function $$\hat{y}_{ij} = \text{sgn}(w_j^T z_i^T).$$

The fraction of cells expressing marker gene j in a subcluster $\mathbb{C}$ is given by $$f_{\mathbb{C}_j} = \sum_{i, i \in \mathbb{C}} \hat{y}_{ij} / |\mathbb{C}|.$$

Applicants predicted expression of all marker genes in this way and calculate Pearson correlation coefficient between subclusters and subregions using fC and manually quantified expression intensity. To test whether the subclusters were driven by the selected landmark genes, Applicants excluded the landmark genes from PCA-tSNE and biSNE steps, and repeated the clustering. Applicants consistently obtained the same clustering.

Indexing cells along a trajectory on projected continuum. To obtain the ranking of cells along a given trajectory, Applicants treat the indexing as a traveling salesman problem (TSP). Cells at the start and the end points of a given trajectory are manually selected. The Euclidean distances between cells on the projected space are calculated, and normalized to integers $$d = \lceil 10 \ d / \min(d) \rceil$$

The distance between start and points is set to 0. The normalized distances are used in Lin-Kernighan heuristic (LKH) solver [76, 77] for TSP. The obtained ordering of cells is shifted, so that the manually selected start cell is indexed the first.

Pathway and upstream regulator analysis of DG states. The nuclei from the DG cluster (animals of all ages) were mapped to a continuum by the expression of the Penk and Cck gene signature. Applicants selected two discrete sets of nuclei to represent each state: the top 80 nuclei highly expressing the Penk and the top 100 nuclei highly expressing the Cck signature. To find differentially expressed genes between these groups, Applicants used an adjusted t-test (FDR q-value<0.01, log-ratio>1, and mean expression >20 TPM in at least one group). Up-regulated and down-regulated genes were analyzed using Ingenuity Pathway Analysis (IPA, Qiagen) to find enriched canonical pathways, disease and biological functions, (Hypergeometric p-value<0.01), and to infer upstream regulators (by enrichment of target genes, Hypergeometric p-value<0.01).

Single nucleus quantitative PCR. Single nucleus RNA was purified as described for RNA sequencing library construction. Beads were eluted into 5 µl qScript cDNA synthesis reaction (Quanta Biosciences, #95047) made of 1 µl qScript reaction mix, 0.25 µl qScript RT, 3.75 µl water. The RT reactions were performed at 22° C. for 5 min, 42° C. for 90 min, and inactivated at 85° C. for 5 min. After completion of cDNA synthesis, 4 µl samples were combined with 6 µl of quantitative PCR (qPCR) reaction mix made of 5 µl TaqMan 2x Master Mix (Thermo Fisher Scientific, TaqMan Fast Advanced Master Mix 2x, #4444554), 0.5 µl of each 20x TaqMan probe (Thermo Fisher Scientific, custom TaqMan VIC probe Penk Mm01212875_m1 #4448489, TaqMan FAM probe Cck Mm00446170_m1 #4331182). Each sample was split to two technical replicates, and qPCR reactions were performed in 384 well plate using LightCycler 480 II (Roche) as follows: 50° C. for 2 min, 95° C. for 20 sec, 50 cycles of 95° C. for 3 sec with temperature ramping at 4.8° C./s and 60° C. for 30 sec with temperature ramping at 2.5° C./s. The fluorescence filters were selected for FAM at wavelength 465-510 nm and for VIC at wavelength 533-580 nm.

Single molecule in situ hybridization tissue assay. For in situ hybridization (ISH) assay, mice were perfused with PBS and 4% PFA. Brain samples were dehydrated and paraffin-embedded, and 7 µm sagittal sections were cut. ISH assay was performed using QuantiGene ViewRNA ISH Tissue 2-plex Assay Kit (Affymetrix, #QVT0012) with proprietary probes designed for Penk, Col6a1, Gad1, and Gad2. The assay was optimized based on the manufacturer's protocol for FFPE samples with the following modifications: heat pretreatment for 10 min in step 5, protease digestion and fixation for 10 min in step 6, wash slides for 3 times 4 min each wash in step 17 after label probe 6-AP hybridization, in step 19 after applying fast blue substrate, and in step 22 after label probe 1-AP hybridization. For double fluorescent in situ hybridization (dFISH) assay, mice were perfused with PBS. Brain samples were immediately frozen in tissue freezing medium (O.C.T.) and kept in −80° C. overnight. Coronal sections were cut at 15 µm at −15° C.. dFISH assay on O.C.T. embedded sections was performed according to Affymetrix provided protocol for O.C.T. samples, which combines QuantiGene ViewRNA ISH Tissue 2-plex Assay Kit (Affymetrix, #QVT0012) and ViewRNA ISH Cell Assay Kit (Affymetrix, #QVCM0001). Proprietary probes designed for Calb2, Htr3a, Vip, Pvalb, Penk, and Oprd1 were purchased from the vendor (Affymetrix) and used. Images were taken using fluorescent microscopy (Zeiss microscope and Hamamatsu camera C11440-22CU) and were processed in Matlab. Image background due to non-uniform illumination was removed using Matlab function strel('disk',25). The image brightness and contrast were adjusted to obtain the maximum dynamic range.

EdU labeling for staining. Labeling of proliferating cells for staining in mice was performed by intraperitoneal (i.p.) injection of EdU (5-ethynyl-2'-deoxyuridine) (Thermo Fisher Scientific, #A10044) at a dose of 200 mg/kg. Mice were sacrificed by a lethal dose of Ketamine/Xylazine 2 weeks post EdU injection, and transcardially perfused with PBS followed by 4% PFA. Brain coronal sections of 30 µm were cut using vibratome (Leica, VT1000S). Sections were washed twice in PBST with 3% BSA, permeabilized in PBS with 0.5% Triton X-100 for 20 min, and washed three times in PBST with 3% BSA. EdU staining was performed using Click-iT Edu Imaging Kit (Thermo Fisher Scientific, #C10086) according to the manufacturer's protocol. Briefly, Click-iT reaction mix was prepared as follows: 100 µl Click-iT reaction buffer, 800 µl CuSO4, 100 µl 1× Click-iT reaction buffer additive, and Alexa Fluor 488 azide. Sections were incubated with 0.5 ml reaction mix in 6 well plate for 30 min at room temperature covered in dark. Sections were washed twice in PBS 3% BSA post reaction, followed by mounting and imaging.

Div-Seq. Labeling proliferating cells in mice for Div-Seq was performed by intraperitoneal (i.p.) injection of EdU at a dose of 200 mg/kg. Mice were sacrificed 2 days and 2 weeks post EdU injection, fresh tissue was microdissected into RNAlater as described above. 24 hours after dissection nuclei were isolated as described above and resuspended in 100 µl resuspension buffer (with RNAse inhibitor), filtered and transferred to a 15 ml tube. EdU staining was performed immediately using Click-iT Edu Flow Cytometry assay Kit (Thermo Fisher Scientific, #C10086) according to the manufacturer's protocol with the following changes: 500 µl reaction buffer was added directly to the resuspension buffer (mix is made following the manufacturer's protocol), mixed well and left in RT for 30 min; 3 ml of 1% BSA PBS wash solution was added to the resuspended nuclei and mixed well, then nuclei were spun down for 10 min in 4° C., buffer was removed and nuclei were resuspended in 400 µl resuspension buffer with ruby dye (1:800) and FACS sorted immediately.

Clustering of adult newborn cells and reconstructing pseudotime along the maturation trajectory. Applicants clustered EdU labeled nuclei together with non-EdU labeled nuclei. The PCA-tSNE followed by density clustering [54] assigned the majority of the EdU labeled nuclei together with a few non-EdU labeled nuclei to a distinct cluster. Then, Applicants performed second iteration of clustering using nuclei only from this cluster. The clustering positioned these nuclei on a trajectory. Applicants used biSNE to score and select genes differentially expressed along the trajectory (as described in Selection of significant genes) and filtered out lowly expressed genes. The intercellular Euclidean distance on the tSNE embedding reflects the intercellular transcriptional divergence. The embedding of EdU labeled cells forms a trajectory-like distribution. The Euclidean distances along the trajectory reflect transcriptional changes along the underlying biological process. Positions of each cell on that trajectory should indicate how far the cell has progressed along the process. Thus, the position of each cell along the trajectory is correlated with the pseudotime of a cell in the biological process. There is also a considerable cell distribution that makes up the width of the trajectory. The Euclidean distances orthogonal to the longitudinal axis of the trajectory reflect transcriptional divergence due to other cellular variabilities or noises. In order to find the position of each cell along the trajectory, Applicants need to distinguish the distances along the trajectory from the distances orthogonal to the trajectory. Previous methods find the cell positions using minimal spanning tree [78], or shortest possible route (travelling salesman problem) [79], neither of which take into account of the noise or other cellular variabilities. An improved method [80] uses randomization heuristics to mitigate the effect of noises. In contrast to these methods, Applicants model the noise explicitly and find a shortest spanning curve along the trajectory (Occam's razor). Applicants then project cells onto this spanning curve, and find their projected positions. Specifically, Applicants find a curve that minimizes the following objective function, $$f = \sum_i (x_i - SP(\hat{q}_i, cp))^2 + \lambda \int_0^1 \left\| \frac{\partial}{\partial t} SP(t, cp) \right\| dt.$$

where the first term reflects Gaussian noises that model the orthogonal distances, the second term is the total length of the spanning curve, and xi are the coordinates of the tSNE embedding of the cell i. The λ reflects the prior knowledge on the relative amount of noises and the transcriptional changes that align with the trajectory. The SP(^qi, cp) are the coordinates of the projected positions of cell i on the curve, and ^qi is the pseudotime of the cell i along the trajectory. The ^qi is given by $$\hat{q}_i = \underset{0 \leq i \leq 1}{\operatorname{argmax}} (x_i - SP(t, cp))^2.$$

The SP(x, cp) is the b-spline function [81] given by $$SP(x, cp) = \sum_i B_{i,n}(x) \, cp_i,$$

where cp are control points, and Bi,n(x) is the b-spline basis function of degree n given by the following recursion formula $$B_{i,1}(x) := \begin{cases} 1 & \text{if } t_i \leq x < t_{i+1} \\ 0 & \text{otherwise} \end{cases},$$

$$B_{i,k}(x) := \frac{x - t_i}{t_{i+k-1} - t_i} B_{i,k-1}(x) + \frac{t_{i+k} - x}{t_{i+k} - t_{i+1}} B_{i+1,k-1}(x),$$

where t is a knot vector, and k is the degree of the b-spline. Applicants used a knot vector uniformly spaced between 0 and 1, and a third order b-spline. The spanning curve is found by searching for control points that minimize the objective function $f$, $$\hat{cp} = \operatorname{argmax} f.$$

To initialize the curve, Applicants calculated a smoothed shortest path (using Dijkstra's algorithm) that follows the trajectory. The smoothed shortest path contains 16 points spanning from the progenitor cells to immature neurons. These points were used as the initial control points. Applicants then searched for the optimal control points using gradient descent, $$\frac{\partial f}{\partial cp_i} = 2 \sum_i (x_i - SP(\hat{q}_i, cp))(-SP(\hat{q}_i, e_i)) +$$

$$\lambda \int_0^1 \frac{1}{2} \left( \left\| \frac{\partial}{\partial t} SP(t, cp) \right\| \right)^{-1} \left( 2 \frac{\partial}{\partial t} SP(t, cp) \frac{\partial}{\partial t} SP(t, e_i) \right) dt,$$

where ei is a matrix that has the same size as cp, and entries of ei are equal to 1 at column i corresponding to the control point i and zero elsewhere. To quantify the expression of genes along the trajectory, Applicants calculated running averages of gene expressions along the smoothed shortest path that follows the trajectory. Applicants then subtracted the expression along the trajectory by the averaged expression of the first two points to obtain normalized expression pattern. Applicants clustered genes by their normalized expression pattern and chose the top consensus clusters after 5000 iterations of Kmeans clustering. The consensus clusters were found by hierarchically clustering the frequency of pairwise coassignment of genes within the same cluster across all Kmeans iterations (Hamming distance of the cluster assignments matrix).

Pathway and regulator analysis of adult newborn cells. Differentially expressed genes between immature neurons and adult neurons were found using the adjusted t-test. Enriched pathways in dynamic gene clusters and differentially expressed signatures were found (Hypergeometric p-value<0.01) using the MsigDB/GSEA resource (combining Hallmark pathways, REACTOME, KEGG, GO and BIOCARTA) [82]. Dynamically regulated TFs were defined as genes within the genes clusters that are annotated by GO category [83] to be involved in transcription regulation, DNA binding or chromatin remodeling and modification. The gene list for the semaphoring signaling pathway was taken from KEGG mouse axon guidance pathway (mmu04360) and the IPA Semaphoring signaling pathway. Applicants defined a maturation signature as the linear combination of expression levels of the set of up-regulated and down-regulated genes in mature granule cells compared to the immature granule cells in adult mice. The average relative expression of the up-regulated genes minus the average relative expression of the down-regulated genes was used to define a maturation score for each granule DG nuclei, in adult (3 months), adolescent (1 month) and old (2 year) mice.

Comparison of Div-Seq data in the DG to other datasets. Applicants compared dynamically expressed genes along the neurogenesis trajectory to other datasets, including: (1) single-cells RNA-Seq of mouse adult neuronal stem cells and progenitors in the DG [79]; (2) RNA-Seq time course of in vitro derived neurons from hES cells [84]; (3) single-cell RNA-Seq of fetal human neuronal precursor cells, hNPCs (Tirosh et al. unpublished); (4) additional Div-Seq data collected at 7 day post EdU injection; (5) Allen brain atlas ISH data. For each of the published RNA-Seq datasets Applicants log transformed the expression matrix. For the single hNPCs RNA-Seq, paired-end 75 bp reads were mapped to the UCSC human transcriptome (hg19) by Bowtie (version 1.4.1,with parameters -n 0 -e 99999999-I 25 -I 1 -X 2000 -a -m 15 iCS), and expression levels of all genes were estimated by RSEM (version 1.2.3, using the option estimate-rspd and default parameters). To compare gene expression levels between Div-Seq and these datasets Applicants used the relative intensity values per dataset across all genes and samples. For the comparison to the Allen ISH data, Applicants selected genes that have known restricted expression in the early stages of the trajectory, which is spatially restricted to the SGZ and the hilus regions of the DG. Relative expression levels across the DG subregions were manually evaluated.

Differential isoforms. Gene isoform expression levels (TPM) and percent of mapped reads (compared to other all other isoforms of the same gene) were quantified using RSEM (as described in "Sequencing reads initial processing"). Applicants restricted the analysis to highly expressed isoforms only, e.g. genes that have at least two isoforms with expression level of log(TPM)>4 in at least 10% of the analyzed nuclei. Analysis of differentially expressed isoforms between immature and mature granule neurons was done using t-test on the isoform percentage. A pair of isoforms are considered differentially expressed if both are significant in the t-test (FDR<0.01, log-ratio>1) and one is upregulated in immature neuron and the other is down regulated in the immature neuron.

Spinal cord analysis. All the 7 day EdU labeled and unlabeled cells from the spinal cord and DG were clustered by PCA-tSNE and density clustering as described in "Analysis of nuclei clusters". The identities of each clusters were determined based on differentially expressed genes and known marker genes. Immature and mature neurons were clustered by biSNE (top 2 PCs, 2,522 high scoring genes with p<5.4e-5). Differentially expressed genes between immature neurons in the DG and spinal cord were calculated using student's t-test, with FDR<0.05, log(ratio)>1, and the average expression across samples in one region to be log(TPM)>2 and in the other region log(TPM)<3.

REFERENCES

1. A. Zeisel et al., Brain structure. Cell types in the mouse cortex and hippocampus revealed by single-cell RNA-seq. *Science* 347, 1138-1142 (2015).
2. S. Darmanis et al., A survey of human brain transcriptome diversity at the single cell level. *Proc Natl Acad Sci USA* 112, 7285-7290 (2015).
3. J. Shin et al., Single-Cell RNA-Seq with Waterfall Reveals Molecular Cascades underlying Adult Neurogenesis. *Cell Stem Cell* 17, 360-372 (2015).
4. B. Tasic et al., Adult mouse cortical cell taxonomy revealed by single cell transcriptomics. *Nat Neurosci* 19, 335-346 (2016).
5. D. Usoskin et al., Unbiased classification of sensory neuron types by large-scale single-cell RNA sequencing. *Nat Neurosci* 18, 145-153 (2015).
6. E. R. Thomsen et al., Fixed single-cell transcriptomic characterization of human radial glial diversity. *Nat Methods* 13, 87-93 (2016).
7. G. L. Ming, H. Song, Adult neurogenesis in the mammalian brain: significant answers and significant questions. *Neuron* 70, 687-702 (2011).
8. D. L. Moore, G. A. Pilz, M. J. Arauzo-Bravo, Y. Barral, S. Jessberger, A mechanism for the segregation of age in mammalian neural stem cells. *Science* 349, 1334-1338 (2015).
9. R. V. Grindberg et al., RNA-sequencing from single nuclei. *Proc Natl Acad Sci USA* 110, 19802-19807 (2013).
10. S. R. Krishnaswami et al., Using single nuclei for RNA-seq to capture the transcriptome of postmortem neurons. *Nat Protoc* 11, 499-524 (2016).
11. L. Swiech et al., In vivo interrogation of gene function in the mammalian brain using CRISPR-Cas9. *Nat Biotechnol* 33, 102-106 (2015).
12. H. Hu, J. Gan, P. Jonas, Interneurons. Fast-spiking, parvalbumin(+) GABAergic interneurons: from cellular design to microcircuit function. *Science* 345, 1255263 (2014).
13. E. S. Lein et al., Genome-wide atlas of gene expression in the adult mouse brain. *Nature* 445, 168-176 (2007).
14. Y. Zhang et al., An RNA-sequencing transcriptome and splicing database of glia, neurons, and vascular cells of the cerebral cortex. *J Neurosci* 34, 11929-11947 (2014).
15. S. Anders, W. Huber, Differential expression analysis for sequence count data. *Genome Biol* 11, R106 (2010).
16. M. S. Cembrowski et al., Spatial Gene-Expression Gradients Underlie Prominent Heterogeneity of CA1 Pyramidal Neurons. *Neuron*, (2016).
17. B. A. Strange, M. P. Witter, E. S. Lein, E. I. Moser, Functional organization of the hippocampal longitudinal axis. *Nat Rev Neurosci* 15, 655-669 (2014).
18. B. P. Roques, M. C. Fournie-Zaluski, M. Wurm, Inhibiting the breakdown of endogenous opioids and cannabinoids to alleviate pain. *Nat Rev Drug Discov* 11, 292-310 (2012).
19. S. Zhao et al., Fluorescent labeling of newborn dentate granule cells in GAD67-GFP transgenic mice: a genetic tool for the study of adult neurogenesis. *PLoS One* 5, (2010).
20. E. Llorens-Bobadilla et al., Single-Cell Transcriptomics Reveals a Population of Dormant Neural Stem Cells that Become Activated upon Brain Injury. *Cell Stem Cell* 17, 329-340 (2015).
21. M. Schouten, M. R. Buijink, P. J. Lucassen, C. P. Fitzsimons, New Neurons in Aging Brains: Molecular Control by Small Non-Coding RNAs. *Front Neurosci* 6, 25 (2012).
22. J. Zhang et al., Ezh2 regulates adult hippocampal neurogenesis and memory. *J Neurosci* 34, 5184-5199 (2014).
23. J. I. Wu et al., Regulation of dendritic development by neuron-specific chromatin remodeling complexes. *Neuron* 56, 94-108 (2007).
24. I. T. Andrew Venteicher, Mario Suva, Michelle Monje-Diesseroth, Aviv Regev.
25. J. A. Miller et al., Conserved molecular signatures of neurogenesis in the hippocampal subgranular zone of rodents and primates. *Development* 140, 4633-4644 (2013).
26. M. Knobloch et al., Metabolic control of adult neural stem cell activity by Fasn-dependent lipogenesis. *Nature* 493, 226-230 (2013).
27. S. Ge et al., GABA regulates synaptic integration of newly generated neurons in the adult brain. *Nature* 439, 589-593 (2006).
28. D. M. Feliciano, A. Bordey, L. Bonfanti, Noncanonical Sites of Adult Neurogenesis in the Mammalian Brain. *Cold Spring Harb Perspect Biol* 7, a018846 (2015).
29. P. J. Horner et al., Proliferation and differentiation of progenitor cells throughout the intact adult rat spinal cord. *J Neurosci* 20, 2218-2228 (2000).
30. R. Shechter, Y. Ziv, M. Schwartz, New GABAergic interneurons supported by myelin-specific T cells are formed in intact adult spinal cord. *Stem Cells* 25, 2277-2282 (2007).
31. C. A. Rottkamp, K. J. Lobur, C. L. Wladyka, A. K. Lucky, S. O'Gorman, Pbx3 is required for normal locomotion and dorsal horn development. *Dev Biol* 314, 23-39 (2008).
32. M. A. Petryniak, G. B. Potter, D. H. Rowitch, J. L. Rubenstein, Dlx1 and Dlx2 control neuronal versus oligodendroglial cell fate acquisition in the developing forebrain. *Neuron* 55, 417-433 (2007).
33. S. G. Ludovic Telley, Julien Prados, Isabelle Stevant, Serge Nef, Emmanouil Dermitzakis, Alexandre Dayer, Denis Jabaudon, Sequential transcriptional waves direct the differentiation of newborn neurons in the mouse neocortex. *Science* Online.
34. S. Picelli et al., Smart-seq2 for sensitive full-length transcriptome profiling in single cells. *Nat Methods* 10, 1096-1098 (2013).

SUPPLEMENTARY REFERENCES

37. W. Lasón, B. Przewlocka, R. Przewlocki, Molecular brain research 12, 243 (1992).
38. L. Swiech, et al., Nature biotechnology 33, 102 (2015).
39. C. A. Paul, B. Beltz, J. Berger-Sweeney, Cold Spring Harbor Protocols 2008, pdb (2008).
40. H. Hideo, T. Keiko, Y. Nobuyuki, M. Tsuyoshi, Journal of Visualized Experiments (2009).
41. S. Picelli, et al., Nature methods 10, 1096 (2013).
42. R. Satija, J. A. Farrell, D. Gennert, A. F. Schier, A. Regev, Nature biotechnology 33, 495 (2015).
43. C. M. Hempel, K. Sugino, S. B. Nelson, Nature protocols 2, 2924 (2007).
44. C. Trapnell, L. Pachter, S. L. Salzberg, Bioinformatics 25, 1105 (2009).
45. C. Trapnell, et al., Nature biotechnology 28, 511 (2010).
46. J. T. Robinson, et al., Nature biotechnology 29, 24 (2011).
47. B. Li, V. Ruotti, R. M. Stewart, J. A. Thomson, C. N. Dewey, Bioinformatics 26, 493 (2010).
48. B. Langmead, S. L. Salzberg, Nature methods 9, 357 (2012).
49. D. S. DeLuca, et al., Bioinformatics 28, 1530 (2012).
50. A. Zeisel, et al., Science 347, 1138 (2015).
51. J. C. Dunn, Journal of cybernetics 4, 95 (1974).
52. S. T. Roweis, L. K. Saul, Science 290, 2323 (2000).
53. L. Van der Maaten, G. Hinton, Journal of Machine Learning Research 9, 85 (2008).
54. A. Rodriguez, A. Laio, Science 344, 1492 (2014).
55. A. K. Shalek, et al., Nature (2014).
56. A. K. Shalek, et al., Nature 498, 236 (2013).
57. M. D. Robinson, D. J. McCarthy, G. K. Smyth, Bioinformatics 26, 139 (2010).
58. M. I Love, W. Huber, S. Anders, Genome Biol 15, 550 (2014).
59. Z. I. Botev, J. F. Grotowski, D. P. Kroese, et al., The Annals of Statistics 38, 2916 (2010).
60. P. V. Kharchenko, L. Silberstein, D. T. Scadden, Nature methods 11, 740 (2014).
61. E.-a. D. Amir, et al., Nature biotechnology 31, 545 (2013).
62. E. Z. Macosko, et al., Cell 161, 1202 (2015).
63. Y. Benjamini, Y. Hochberg, Journal of the Royal Statistical Society. Series B (Methodological) pp. 289-300 (1995).
64. E. S. Lein, et al., Nature 445, 168 (2007).
65. P. A. Moran, Biometrika pp. 17-23 (1950).
66. P. J. Rousseeuw, C. Croux, Journal of the American Statistical association 88, 1273 (1993).
67. A. Edelman, N. R. Rao, Acta Numerica 14, 233 (2005).
68. E. Eden, D. Lipson, S. Yogev, Z. Yakhini, PLoS Comput Biol 3, e39 (2007).
69. Y. Maruyama, arXiv preprint arXiv:1501.06260 (2015).
70. L. Van Der Maaten, The Journal of Machine Learning Research 15, 3221 (2014).
71. P. N. Yianilos, SODA (1993), vol. 93, pp. 311-321.
72. S. Anders, W. Huber, Genome Biology 11, R106 (2010).
73. P. Brennecke, et al., Nature methods 10, 1093 (2013).
74. Y. Zhang, et al., The Journal of Neuroscience 34, 11929 (2014).
75. R.-E. Fan, K.-W. Chang, C.-J. Hsieh, X.-R. Wang, C.-J. Lin, The Journal of Machine Learning Research 9, 1871 (2008).
76. K. Helsgaun, European Journal of Operational Research 126, 106 (2000).
77. K. Helsgaun, Mathematical Programming Computation 1, 119 (2009).
78. C. Trapnell, et al., Nature biotechnology 32, 381 (2014).
79. J. Shin, et al., Cell stem cell 17, 360 (2015).
80. S. C. Bendall, et al., Cell 157, 714 (2014).
81. C. De Boor, Mathematics of Computation (1978).
82. A. Subramanian, et al., Proceedings of the National Academy of Sciences of the United States of America 102, 15545 (2005).
83. M. Ashburner, et al., Nature genetics 25, 25 (2000).
84. V. Busskamp, et al., Molecular systems biology 10, 760 (2014).
85. J. J. Trombetta, et al., Current Protocols in Molecular Biology pp. 4-22.
86. B. Tasic, et al., Nature neuroscience (2016).
87. E. R. Thomsen, et al., Nature methods 13, 87 (2016).
88. R. V. Grindberg, et al., Proceedings of the National Academy of Sciences 110, 19802 (2013).

Example 6

Nuclei Purification Protocols
Nuclei purification protocol: method A
This method may be used for Nuc-Seq or Div-Seq.
Reference: In vivo interrogation of gene function in the mammalian brain using CRISPR-Cas9. Swiech L, Heidenreich M, Banerjee A, Habib N, Li Y, Trombetta J, Sur M, Zhang F. Nat Biotechnol. 2015 January; 33(1): 102-6. doi: 10.1038/nbt.3055. Epub 2014 Oct. 19.

| | | Buffer 1: | | |
|---|---|---|---|---|
| | Stocks | 25 ml For 2 samples (+spare) | 50 ml For 4 samples (+spare) | 75 ml For 6 samples (+spare) |
| 320 mM Sucrose | 1M | 8 ml | 16 ml | 24 ml |
| 5 mM CaCl | 1M | 125 ul | 250 ul | 375 ul |
| 3 mM Mg(Ac)2 | 1M | 75 ul | 150 ul | 225 ul |
| 10 mM Tris pH 7.8 | 1M | 250 ul | 500 ul | 750 ul |
| 0.1 mM EDTA | 0.5M | 5 ul | 10 ul | 15 ul |
| 0.1 mM PMSF | 100 mM | 25 ul | 50 ul | 75 ul |
| 0.1% NP40 | 10% | 250 ul | 500 ul | 750 ul |
| 1 mM b-mercapto | 500 mM | 50 ul | 100 ul | 150 ul |
| H20 | | 16.2 ml | 32.4 ml | 48.6 ml |

| Working solution (x6): | | | |
| --- | --- | --- | --- |
| | Stocks | 5 ml For 2 samples (+spare) | 10 ml For 4 samples (+spare) |
| 30 mM CaCl | 1M | 150 ul | 300 ul |
| 18 mM Mg(Ac)2 | 1M | 90 ul | 180 ul |
| 60 mM Tris | 1M | 300 ul | 600 ul |
| 0.6 mM PMSF | 100 mM | 30 ul | 60 ul |
| 6 mM b-mercapto | 500 mM | 60 ul | 120 ul |
| H2O | | 4.370 ml | 8.740 ml |

| 50% Optiprep solution: | | | |
| --- | --- | --- | --- |
| 1:6 | 1 sample | 2 samples - 25 ml | 4 samples - 50 ml |
| Working solution | 2 ml | 5 ml | 8.35 ml |
| Optiprep | 8 ml | 25 ml | 41.68 ml |

| 29% Optiprep solution: | | |
| --- | --- | --- |
| | 1 sample | 4 samples - 50 ml |
| 50% Optiprep | 5.8 ml | 29 |
| Buffer 1 | 4.2 ml | 21 |

| Resuspension buffer RB: | | |
| --- | --- | --- |
| | Stocks | 10 ml For 4 samples |
| 340 mM Sucrose | 1M | 3.4 ml |
| 2 mM MgCl2 | 1M | 10 ul |
| 25 mM KCl | 2M | 125 ul |
| 65 mM glycerophosphate | 1M | 650 ul |
| 5% glycerol | 100% | 500 ul |

Before Starting:
1. Make fresh buffers
2. All: buffers, tubes, homogenizer should be on ice at all times Protocol:
1. Dounce homogenize tissue in 2 ml Buffer 1+0.1% NP40 (25 times with a, 25 times with b), transfer to a 15 ml tube
2. Rinse homogenizer with 3 ml Buffer 1 to get final 5 ml, and collect in the same tube
3. Keep on ice 5 min
4. Add 5 ml 50% Optiprep, invert 10x (final volume 10 ml)
5. Keep on ice 5 min
6. While waiting, prepare an ultracentrifuge tube with 10 ml of 29% Optiprep.
7. Transfer the lysate to the ultracentrifuge tube carefully on top of the 10 ml 29% Optiprep solution, to form a gradient
8. Centrifuge at 7500 rpm 4 c for 30 min
9. Carefully remove supernatant
10. Add ~300 ul/hp buffer RB, keep on ice 5-15 min
11. Resuspend carefully by slow vortex & pipette 10x with a 1 ml tip, then transfer to tubes (for FACS, filter through a membrane to get better purity)
12. Counterstain nuclei with Ruby Dye 1:500-1:1000 (check for clumps in the microscope before sorting)

Nuclei Purification Protocol: Method B

This method is particularly suitable for Dronc-Seq.

EZ NUCLEI ISOLATION PROTOCOL FROM TISSUE (using EZ PREP NUC-101, Sigma)

Procedure for Frozen/Fixed Tissue
13. Dounce homogenize tissue in 2 ml of ice-cold Nuclei EZ lysis buffer (25 times with a, 25 times with b), transfer to a 15 ml tube.
1. Rinse homogenizer with 2 ml of ice-cold Nuclei EZ lysis buffer to get final 4 ml, and collect in the same tube.
2. Mix well and set on ice for 5 minutes.
3. Collect the nuclei by centrifugation at 500×g for 5 minutes at 4° C. Carefully aspirate the clear supernatant from each tube and set the nuclei pellet on ice. Note: The supernatant contains cytoplasmic components and can be saved for later analysis or use.
4. Resuspend. Add 1 ml cold Nuclei EZ lysis buffer and mix by pipetting gently with a 1 ml tip to completely suspend nuclei pellet. Add the remaining 3 ml of Nuclei EZ lysis buffer, mix well and set on ice for 5 minutes.
5. Collect washed nuclei by centrifugation as in step 3. Carefully aspirate the clear supernatant and set the nuclei pellet on ice.
6. Optional: Wash. Resuspend in 4 ml 0.01% PBS BSA or Resuspension buffer (RB*). Collect washed nuclei by centrifugation as in step 3.
7. Resuspend with ~500 μl Resuspension buffer (RB*) or 0.01% PBS BSA+RNAse inhibitor carefully by slow vortex & pipette 10x with a 1 ml tip, then transfer to tubes (for FACS, filter through a membrane to get better purity.
8. Counterstain nuclei with Ruby Dye 1:500-1:1000 (check for clumps in the microscope before sorting).

Resuspension Buffer
based on the original nuclei resuspension buffer from Swiech et al. 2015:

| | Stocks | For 10 ml |
| --- | --- | --- |
| 340 mM Sucrose | 1M | 3.4 ml |
| 2 mM MgCl2 | 1M | 10 ul |
| 25 mM KCl | 2M | 125 ul |
| 65 mM glycerophosphate | 1M | 650 ul |
| 5% glycerol | 100% | 500 ul |

Example 7

Div-Seq Labelling Protocol

This protocol is derived from the Click-IT EdU labeling protocol (ThermoFisher, Kit #C10424): https://www.thermofisher.com/us/en/home/references/protocols/cell-and-tissue-analysis/flow-cytometry-protocol/cell-proliferation/standard-click-it-edu-flow-cytometry-cell-proliferation-assay.html Before starting the nuclei isolation thaw reagents for Click-IT EdU labeling (in the dark, at room-temperature).

Follow nuclei isolation protocol (as in Habib et al. Science. 2016), at the last elution step elute in 100 ul of resuspension buffer or PBS with 1% BSA. Follow steps for nuclei resuspension from protocol.
For each sample prepare a reaction mix (as in the Click-IT EdU labeling protocol):

| Reaction mix: | |
|---|---|
| PBS, D-PBS, or TBS | 438 µL |
| CuSO4 | 10 µL |
| Fluorescent dye azide | 2.5 µL |
| Reaction Buffer Additive (10x buffer diluted to 1x with PBS) | 50 µL |
| Total reaction volume | 500 µL |

Transfer 500 ul reaction mix to a 15 ml canonical tube. Add 100 ul of the nuclei resuspension.
Mix by inverting 10 times.
Incubate in the dark for 20-30 minutes.
Add 3-5 ml of PBS with 1% BSA.
Spin at 500 g for 5 minutes, and carefully remove supernatant.
Resuspend with appropriate amount of Resuspension buffer (as in original nuclei isolation protocol) or 0.01% PBS BSA, add RNAse inhibitor. Resuspend carefully by slow vortex & pipette 10x with a 1 ml tip, then transfer to tubes (for FACS, filter through a membrane to get better purity.
Elute in the appropriate amount of resuspension buffer (as in the nuclei isolation protocol) or PBS+0.01% BSA.
Counterstain nuclei with Ruby Dye 1:500-1:1000 (check for clumps in the microscope before sorting).
FACS sort nuclei into 96 well plates for RNA-seq (following the sNuc-Seq SMART-Seq2 protocol).

Example 8

SMART-seq2 protocol Full-length mRNA-seq for single nuclei or small amounts of RNA samples
Tissue, Cells & Nuclei Prep
  Tissue should be stored in RNAlater in 4 c for 24 hours and then moved to the −80 (removing the RNAlater), or immediately frozen and stored at −80 c.
  Prep cells/nuclei short time before sorting. Use RNAse free reagents.
Sorting
  Sort single cells/nuclei into 96-well plate, 5 µL TCL in each well (with bME, and optional RNAse inhibitor)
  Immediately spin for 1-2 min, 2500 RPM
  Snap freeze on dry ice, store at −80°
Prep Work
  RNase-ZAP work surfaces and equipment
  30 minutes prior to purification, let RNA-SPRI beads equilibrate to room temperature
  Thaw cell plates on ice and spin down for 1 min, 2500 RPM
RNA Purification
  Add 11 µL (2.2×) RNA-SPRI beads to each well, mix
  Let at room temp for 10 minutes, place plate on magnet for 5 minutes
  Remove supernatant
  Wash in 100 µL 80% EtOH three times
  Completely remove supernatant, let dry for 8-10 minutes on magnet
  Elute in 4 µL Mix #1
  Continue immediately

| Mix #1 | | | |
|---|---|---|---|
| Reagent | 1 sample (µL) | 96 samples (µL) | 96 for Bravo (µL) |
| RT primer (10 µM) | 1.0 | 115.2 | 120 |
| dNTP mix (10 mM each) | 1.0 | 115.2 | 120 |
| RDil (10% RNase-Inhib, final of 4 U/µL) | 1.0 | 115.2 | 120 |
| H2O | 1.0 | 115.2 | 120 |
| Total | 4.0 | 460.8 | 480 |

RT

Incubate eluted plate at 72° for 3 min, immediately place on ice

| Mix #2 | | |
|---|---|---|
| Reagent | 1 sample (µL) | 96 samples (µL) |
| H2O | 0.75 | 86.4 |
| 5x Maxima RT buffer | 2.0 | 230.4 |
| Betaine (5M) | 2.0 | 230.4 |
| MgCl2 (100 mM) | 0.9 | 103.68 |
| TSO (10 µM) | 1.0 | 115.2 |
| RNase Inhibitor (40 U/µL) | 0.25 | 28.8 |
| Maxima RNaseH-minus RT (200 U/µL) | 0.10 | 11.52 |
| Total | 7.0 | 806.4 |

Add 7 ul of Mix #2 (mix well & spin down)
RT PROGRAM: Incubate at 42° for 90 minutes, followed by 10 cycles of (50° for 2 min, 420 for 2 min), then heat inactivation at 70° for 15 min.
Transfer plate in only when machine is ready at 42 c
PCR Preamplification

| Mix #3 | | | |
|---|---|---|---|
| Reagent | 1 sample (µL) | 96 samples (µL) - x1.2 | x1.1 |
| H2O | 1.0 | 115.2 | 105.6 |
| ISPCR Primer (10 µM) | 0.5 | 57.6 | 52.8 |
| KAPA HiFi HotStart Ready Mix | 12.5 | 1440 | 1320 |
| Total | 14 | 1612.8 | 1478.4 |

Add 14 µL of Mix #3 to each well
Cycle the PCR as follows: 98° for 3 min, 21 cycles of (98° for 15 sec, 67° for 20 sec, 72° for 6 min), final extension at 72° for 5 min.
PCR Pre-Amplification Clean Up
  Purify the PCR products with a 0.8× AMPure XP SPRI cleanup
    Add 20 µL AMPure XP SPRI beads, let sit for 5 min
    place plate on magnet for 6 min
    pipette off supernatant
    Wash beads by adding 100 µL fresh 70% EtOH and magnet switching
    Pipette off supernatant and repeat wash
    remove all EtOH and let dry on magnet for 10 min
  Elute material in 20 µL TE
Post—PCR Pre-Amplification QC
  1. BioAnalyze test quality
  2. PICO-green in the plate reader—QC & quant
Nextera-XT (modified protocol)

Make NTA:
  2.5 µl TD buffer per well
  1.25 µl sample (diluted to 0.15-0.2 ng/µl per well)
  1.25 µl ATM
Put cover, bang to mix & spin down briefly
Incubate 10 min at 55 c ("make NTA" program, hold at 10 c)
Spin down
Neutralize:
  Add 1.25 NT buffer to neutralize
Spin down
Incubate on bench for 5 min
PCR:
  3.75 µl NPM
  2.5 µl of index array primers (1.25 µl of each primer)
Cover & bang to mix & spin down
PCR (NTA PCR program, following the Nextera XT protocol)
  1. Perform PCR using the following program on a thermal cycler (with heated lid, program "Nextera PCR" on machine D):
    a. 72° C. for 3 minutes
    b. 95° C. for 30 seconds
    c. 12 cycles of:
      i. 95° C. for 10 seconds
      ii. 55° C. for 30 seconds
      iii. 72° C. for 30 seconds
      iv. 72° C. for 5 minutes
    d. Hold at 4'C
Pull & Cleanup:
Pull together 2.5 µl from each well and SPRI clean twice (in each SPRI wash twice with ETOH 70%):

1st cleanup: Add 0.9x beads (240 µl samples, 216 I beads), elute in 50 µl TE
2nd cleanup: Add 0.9x beads, elute in 20-25 µl
Post Nextera QC:
BioA/Tape-station and quant pool with qubit
Store at −20
Primers and Oligos:
RT primer:

(SEQ ID NO: 7)
5'-bio-AAGCAGTGGTATCAACGCAGAGTACT30VN-3' where "N" is any base and "V" is either "A", "C" or "G"
Template switching oligo (TSO):

(SEQ ID NO: 10)
5' AAGCAGTGGTATCAACGCAGAGTACATrGrG + G

IS PCR primer;

(SEQ ID NO: 9)
5'-AAGCAGTGGTATCAACGCAG*A*G*T-3'
*: phosphorothioate bond

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

---

What is claimed is:

1. A method of producing a temporally phased single-cell sequencing library of at least one cell type or subtype, wherein said sequencing library comprises cells along a continuous trajectory of cell developmental stages comprising:
   (a) treating more than one population of cells of a single cell type or subtype, or optionally a heterogeneous cell type, with a nucleoside analogue, wherein the nucleoside analogue is incorporated into replicating DNA and is configured for labeling with a detectable marker;
   (b) isolating a first population of cells at one time point and isolating at least one other population of cells at a later time point, and isolating single nuclei from the isolated populations of cells;
   (c) staining the nucleoside analogue incorporated into replicated DNA with the detectable marker within each population of single nuclei isolated from each population of cells, wherein the DNA is stained with the detectable marker;
   (d) sorting stained and/or unstained single nuclei into separate reaction vessels; and
   (e) sequencing RNA from the sorted single nuclei, whereby single cell gene expression data is obtained for cells at different stages of maturation.

2. The method according to claim 1, wherein the treating more than one population of cells of a single cell type or subtype, or optionally a heterogeneous cell type with a nucleoside analogue is performed in at least one subject.

3. The method according to claim 2, wherein the subject is a mouse.

4. The method according to claim 2, wherein isolating one population of cells comprises dissection of a tissue from the subject, or the population of cells is grown in tissue culture, and wherein the tissue is optionally nervous tissue in particular nervous tissue isolated from brain, spinal cord, or retina or immune cells.

5. The method according to claim 1, wherein the gene expression data is obtained from single cell sequencing, or wherein the gene expression data is obtained from single nucleic sequencing.

6. The method according to claim 5, wherein single nuclei sequencing comprises:
   (a) treating the populations of cells with a reagent that stabilizes RNA;
   (b) extracting nuclei from the cells;
   (c) sorting single nuclei into separate reaction vessels;
   (d) extracting RNA from the single nuclei;
   (e) generating a cDNA library; and
   (f) sequencing the library,
   whereby gene expression data from single cells is obtained.

7. The method according to claim 6, wherein single nuclei are sorted into single wells of a plate by FACS or wherein the sorting comprises microfluidics.

8. The method according to claim 5, wherein single nuclei sequencing comprises a method of high-throughput single nuclei sequencing, said method comprising:
   (a) treating the population of cells with a reagent that stabilizes RNA;
   (b) extracting nuclei;
   (c) generating a suspension of isolated nuclei, wherein the suspension comprises a nuclear pore blocking polymer;
   (d) optionally, enriching the nuclei suspension by FACS or magnetic-activated cell sorting (MACS);
   (e) applying the nuclei suspension to a reverse emulsion microfluidic device configured for single nuclei, wherein single nuclei are individually compartmentalized with a single uniquely barcoded capture bead in an emulsion drop;
   (f) extracting mRNA onto the barcoded capture beads;
   (g) generating a barcoded cDNA library; and
   (h) sequencing the library using paired-end sequencing, whereby gene expression data from single nuclei is obtained.

9. The method according to claim 8, wherein the nuclei suspension comprises $10^5$-$10^6$ nuclei or wherein $10^4$-$10^5$ nuclei are sequenced.

10. The method according to claim 8, wherein the nuclear pore blocking polymer comprises a poloxamer, or wherein the reagent comprises an RNA preservation agent, or both.

11. The method according to claim 1, further comprising producing at least one high resolution map for visualizing a temporal position or cell developmental stage of cells of a specific cell type, subtype or cell state during proliferation comprising:
   (a) performing dimensionality reduction on the single cell gene expression data from the stained cells of a single cell type, subtype or cell state within each population of cells or the stained single nuclei of a single cell type or subtype isolated from each population of cells;
   (b) measuring dissimilarity between sets of genes in the dimensionality reduced single cell gene expression data and applying a first metric, whereby a continuous trajectory is visualized in dimensionality reduced space from an early time point to a later time point;
   (c) producing a set of informative genes by a method comprising scoring genes based on their expression across the continuous trajectory, wherein the informative genes are uniquely expressed in cells embedded in close proximity in the dimensionality reduced space, optionally, wherein lowly expressed genes are filtered out; and
   (d) producing at least one set of clusters of cells by a method comprising measuring the dissimilarity between the set of informative genes and applying a second metric, whereby visualization of the set of clusters in the dimensionality reduced space indicate gene expression profiles of cells based on a temporal position or developmental stage.

12. The method according to claim 11, wherein producing the set of clusters of cells in step (d) comprises producing more than one set of clusters, wherein the first set of clusters is produced by using a highest scoring informative gene and each successive set of clusters is produced by adding a next highest scoring informative gene.

13. The method according to claim 11, further comprising a) normalization of the single cell gene expression data, wherein gene expression of one cell is normalized to another using not highly expressed genes, or b) estimation of missed detection probability, wherein an expectation maximization algorithm is applied, or both a) and b)).

14. The method according to claim 11, wherein scoring informative genes comprises applying a Moran's I analysis and/or a Manhattan distance analysis, or wherein dimensionality reduction comprises PCA and/or tSNE, or both.

15. The method according to claim 1, wherein the nucleoside analogue comprises EdU (5-ethynyl-2'-deoxyuridine).

16. The method of claim 11, further comprising first performing a method of producing at least one high resolution map for visualizing different cell subtypes or cell states in a heterogeneous population of cells.

17. The method of claim 16, wherein the step of performing a method of producing at least one high resolution map for visualizing different cell subtypes or cell states in a heterogeneous population of cells comprises:
  (i) performing dimensionality reduction on single cell gene expression data obtained from the heterogeneous population of cells;
  (ii) producing a first set of clusters of cells by a method comprising measuring the dissimilarity between sets of genes in the dimensionality reduced single cell gene expression data and applying a first metric, wherein the clusters are in a dimensionality reduced space and the clusters comprise cells with a continuous trajectory;
  (iii) producing a set of informative genes by a method comprising scoring genes based on their expression across the first set of clusters of cells or a continuous trajectory of cells, wherein the informative genes are uniquely expressed in cells embedded in close proximity in the dimensionality reduced space; and
  (iv) producing at least one second set of clusters of cells or continuous trajectory of cells by a method comprising measuring the dissimilarity between the set of informative genes and applying a second metric, whereby visualization of a map of the second set of clusters or continuous trajectory of cells indicate cell subtypes or cell states, whereby heterogeneous cells are clustered by cell type, subtype, or cell state.

18. The method of claim 11, further comprising mapping a spatial location of the cell subtypes or cells having a cell state by performing RNA in situ hybridization (ISH) on whole tissue sections comprising said cell subtypes using probes specific for genes expressed in the cell subtypes, whereby the spatial location of cell subtypes is visualized in a biological sample.

19. The method of claim 11, The method according to claim 11, further comprising mapping a spatial location of the cell subtypes or cells having a cell state by comparing gene expression data for each cell type to landmark gene expression patterns in tissue samples, whereby the spatial location of cell subtypes is visualized in a biological sample.

20. The method of claim 11, wherein producing the second set of clusters of cells in step (d) comprises producing more than one set of clusters, wherein each set of clusters is produced by using a highest scoring informative gene and each successive cluster is produced by adding a next highest scoring informative gene.

21. The method of claim 11, further comprising normalization of the single cell gene expression data, wherein gene expression of one cell is normalized to another using not highly expressed genes, or estimation of missed detection probability, wherein an expectation-maximization algorithm is applied.

22. The method of claim 11, wherein scoring informative genes comprises applying a Moran's I analysis and/or a Manhattan distance analysis, or wherein dimensionality reduction comprises PCA and/or tSNE or both.

23. The method of claim 11, wherein the heterogeneous population of cells is derived from a section of a tissue or a tumor from a subject, or is a population of cells grown in tissue culture in particular neurons or immune cells.

24. The method of claim 23, wherein the section is obtained by microdissection.

25. The method of claim 23, wherein the tissue is nervous tissue optionally from a brain, spinal cord, or retina.

26. The method of claim 11, wherein the gene expression data is obtained from single cell sequencing or from single nucleic sequencing.

27. The method of claim 26, wherein single nuclei sequencing comprises:
  (a) treating the heterogeneous population of cells with a reagent that stabilizes RNA;
  (b) extracting nuclei from the cells;
  (c) sorting single nuclei into separate reaction vessels;
  (d) extracting RNA from the single nuclei;
  (e) generating a cDNA library; and
  (f) sequencing the library,
  whereby gene expression data from single cells is obtained.

28. The method of claim 27, wherein single nuclei are sorted into single wells of a plate by FACS or wherein the sorting comprises microfluidics.

29. The method of claim 27, wherein single nuclei sequencing comprises a method of high-throughput single nuclei sequencing, said method comprising:
  (a) treating the heterogeneous population of cells with a reagent that stabilizes RNA;
  (b) extracting nuclei;
  (c) generating a suspension of isolated nuclei, wherein the suspension comprises a nuclear pore blocking polymer;
  (d) optionally, enriching the nuclei suspension by FACS or magnetic-activated cell sorting (MACS);
  (e) applying the nuclei suspension to a reverse emulsion microfluidic device configured for single nuclei, wherein single nuclei are individually compartmentalized with a single uniquely barcoded capture bead in an emulsion drop;
  (f) extracting mRNA onto the barcoded capture beads;
  (g) generating a barcoded cDNA library; and
  (h) sequencing the library using paired-end sequencing, whereby gene expression data from single nuclei is obtained.

30. The method of claim 29, wherein the nuclei suspension comprises $10^5$-$10^6$ nuclei or wherein $10^4$-$10^5$ nuclei are sequenced.

31. The method of claim 29, wherein the nuclear pore blocking polymer comprises a poloxamer, or wherein the reagent that stabilized RNA comprises properties of RNAlater, or both.

32. The method of claim 27, wherein nuclei are further detectable by a fluorescent signal, whereby individual nuclei may be further sorted.

33. The method of claim 32, wherein cells express a nuclear localized fluorescent protein.

34. The method of claim 33, wherein the nuclear localized fluorescent protein comprises a fluorescent protein fused to a KASH protein domain.

35. The method of claim 32, wherein single nuclei are immunostained with an antibody with specific affinity for an intranuclear protein.

36. The method of claim 35, wherein the antibody is specific for NeuN.

37. The method of claim 32, wherein nuclei are stained with a nuclear stain optionally comprising DAPI, Ruby red, trypan blue, Hoechst or propidium iodine.

38. The method of claim 8, further comprising:
   (i) in step (e) of merging one uniquely barcoded RNA capture microbead with a single nuclei in an emulsion droplet having a diameter from 50 μm to 210 μm, wherein the single nuclei is blocked with a nuclear pore blocking polymer;
   (ii) after step (f) optionally breaking droplets and pooling beads in solution;
   (iii) performing a reverse transcription reaction to convert the RNA to first strand cDNA that is covalently linked to the RNA capture microbead; or conversely reverse transcribing within droplets and thereafter breaking droplets and collecting cDNA-attached beads;
   (iv) preparing and sequencing a single composite RNA-Seq library, containing cell barcodes that record a cell-of-origin of each RNA, and unique molecular identifiers (UMI) that distinguish among RNAs from a same cell.

39. The method of claim 38, wherein the method of amplifying the cDNA-attached beads is template switch amplification.

40. The method of claim 38, wherein the method of amplifying the cDNA-attached beads is T7 linear application.

41. The method of claim 38, wherein the method of amplifying the cDNA-attached beads is exponential isothermal amplification.

42. The method of claim 38, wherein the emulsion droplet is formed via co-encapsulation comprising RNA capture microbead and composite single nuclei.

43. The method of claim 38, wherein the RNA is mRNA.

44. The method of claim 38, wherein the diameter of the emulsion droplet is 50-100 μm or 70-90 μm.

45. The method of claim 38, wherein the diameter of the RNA capture microbeads is from 10 μm to 95 μm.

46. The method of claim 4, wherein step (a) further comprises contacting a tissue of interest with a therapeutic agent and
   (f) determining cell subtypes and/or cell subtypes of a specific developmental stage, whereby cells responsive to a therapeutic agent are determined.

47. The method of claim 46, wherein the nucleoside analogue is contacted with the tissue of interest before the therapeutic agent, optionally between 2 and 14 days before the therapeutic agent.

48. The method of claim 46, wherein the nucleoside analogue and therapeutic agent is administered from an implantable device or localized injection.

49. The method of claim 46, wherein the tissue of interest is a tumor.

50. The method of claim 46, wherein the cell subtypes are determined by a method comprising:
   (a) performing dimensionality reduction on the single cell gene expression data obtained from the heterogeneous population of cells;
   (b) producing a first set of clusters of cells by a method comprising measuring dissimilarity between sets of genes in the dimensionality reduced single cell gene expression data and applying a first metric, wherein the clusters are in a dimensionality reduced space and the clusters comprise cells with a continuous trajectory;
   (c) producing a set of informative genes by a method comprising scoring genes based on their expression across the first set of clusters of cells or a continuous trajectory of cells, wherein the informative genes are uniquely expressed in cells embedded in close proximity in the dimensionality reduced space; and
   (d) producing at least one second set of clusters of cells or continuous trajectory of cells by a method comprising measuring the dissimilarity between the set of informative genes and applying a second metric, whereby visualization of a map of the second set of clusters or continuous trajectory of cells indicate cell subtypes or cell states; optionally wherein the cell subtypes of a specific developmental stage are determined by determining the cell subtype of cells that are stained and unstained.

51. The method according to claim 50, wherein the cell subtypes of a specific developmental stage are determined by a method comprising:
   (a) performing dimensionality reduction on the single cell gene expression data from the stained cells of a single cell type, subtype or cell state within each population of cells or the stained single nuclei of a single cell type or subtype isolated from each population of cells;
   (b) measuring the dissimilarity between sets of genes in the dimensionality reduced single cell gene expression data and applying a first metric, whereby a continuous trajectory is visualized in the dimensionality reduced space from an early time point to a later time point;
   (c) producing a set of informative genes by a method comprising scoring genes based on their expression across the continuous trajectory, wherein the informative genes are uniquely expressed in cells embedded in close proximity in the dimensionality reduced space, optionally, wherein lowly expressed genes are filtered out; and
   (d) producing at least one set of clusters of cells by a method comprising measuring the dissimilarity between the set of informative genes and applying a second metric, whereby visualization of the set of clusters in the dimensionality reduced space indicate a gene expression profiles of cells based on a temporal position or developmental stage, optionally comprising producing more than one set of clusters, wherein the first set of clusters is produced by using a highest scoring informative gene and each successive set of clusters is produced by adding the a highest scoring informative gene.

52. The method of claim 46, further comprising a) normalization of the single cell gene expression data, wherein gene expression of one cell is normalized to another using not highly expressed genes, or b) estimation of missed detection probability, wherein an expectation maximization algorithm is applied, or both a) and b).

53. The method of claim 46, wherein scoring informative genes comprises applying a Moran's I analysis and/or a Manhattan distance analysis or wherein dimensionality reduction comprises PCA and/or tSNE or both.

54. The method of claim 46, wherein the nucleoside analogue comprises EdU (5-ethynyl-2'-deoxyuridine).

* * * * *